(12) United States Patent
Duggan et al.

(10) Patent No.: US 9,717,736 B2
(45) Date of Patent: *Aug. 1, 2017

(54) PYRIDO-, PYRAZO- AND PYRIMIDO-PYRIMIDINE DERIVATIVES AS MTOR INHIBITORS

(71) Applicant: KuDOS Pharmaceuticals Limited, London (GB)

(72) Inventors: Heather Mary Ellen Duggan, Macclesfield (GB); Frederic Georges Marie Leroux, Macclesfield (GB); Karine Fabienne Malagu, Macclesfield (GB); Niall Morrison Barr Martin, Macclesfield (GB); Keith Menear, Macclesfield (GB); Graeme Cameron Murray Smith, Macclesfield (GB)

(73) Assignee: Kudos Pharmaceuticals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/733,257

(22) Filed: Jun. 8, 2015

(65) Prior Publication Data

US 2016/0067258 A1    Mar. 10, 2016

Related U.S. Application Data

(60) Continuation of application No. 13/859,270, filed on Apr. 9, 2013, now Pat. No. 9,102,670, which is a continuation of application No. 13/307,342, filed on Nov. 30, 2011, now Pat. No. 8,435,985, which is a continuation of application No. 13/014,275, filed on Jan. 26, 2011, now Pat. No. 8,101,602, which is a division of application No. 11/842,930, filed on Aug. 21, 2007, now Pat. No. 7,902,189.

(60) Provisional application No. 60/938,776, filed on May 18, 2007, provisional application No. 60/823,311, filed on Aug. 23, 2006.

(51) Int. Cl.
| | | |
|---|---|---|
| C07D 413/14 | (2006.01) |
| C07D 471/04 | (2006.01) |
| C07D 475/08 | (2006.01) |
| C07D 475/10 | (2006.01) |
| A61K 31/5377 | (2006.01) |
| A61K 31/565 | (2006.01) |
| A61K 45/06 | (2006.01) |

(52) U.S. Cl.
CPC ........ *A61K 31/5377* (2013.01); *A61K 31/565* (2013.01); *A61K 45/06* (2013.01); *C07D 413/14* (2013.01); *C07D 471/04* (2013.01); *C07D 475/08* (2013.01); *C07D 475/10* (2013.01)

(58) Field of Classification Search
CPC .. C07D 413/14; C07D 471/04; C07D 475/08; C07D 475/10; A61K 31/5377; A61K 31/565

See application file for complete search history.

(56) References Cited

U.S. PATENT DOCUMENTS

| | | | |
|---|---|---|---|
| 4,560,685 A | 12/1985 | Roch et al. |
| 5,990,117 A | 11/1999 | Pamukcu et al. |
| 6,894,005 B1 | 5/2005 | Maetzke et al. |
| 7,902,189 B2 | 3/2011 | Duggan et al. |
| 8,101,602 B2 | 1/2012 | Menear et al. |
| 8,435,985 B2 * | 5/2013 | Menear ................ C07D 471/04 514/232.5 |
| 9,102,670 B2 * | 8/2015 | Duggan ............... C07D 471/04 |
| 2003/0187026 A1 | 10/2003 | Li et al. |
| 2008/0194546 A1 | 8/2008 | Hummersone et al. |

FOREIGN PATENT DOCUMENTS

| | | |
|---|---|---|
| AU | 4579072 | 12/1974 |
| CA | 1252783 | 4/1989 |
| DE | 2242162 | 8/1972 |
| EP | 0185259 | 6/1989 |
| EP | 1277738 | 1/2003 |
| WO | WO 97/22596 | 6/1997 |
| WO | WO 97/30035 | 8/1997 |
| WO | WO 97/32856 | 9/1997 |
| WO | WO 98/13354 | 4/1998 |
| WO | WO 98/35985 | 8/1998 |

(Continued)

OTHER PUBLICATIONS

Voskoglou-Nomikos et al., Clinical Cancer Research, vol. 9, 4227-4239.*
ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Abraham, "Phosphatidylinositol 3-kinase Related Kinases", Current Opinion in Immunology 8:412-418 (1996).

(Continued)

*Primary Examiner* — Rebecca Anderson

(57) ABSTRACT

There is provided a compound of formula I:

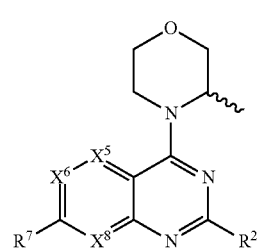

(I)

or a pharmaceutically acceptable salt thereof. There are also provided processes for the manufacture of a compound of Formula 1, and the use of a compound of Formula 1 as a medicament and in the treatment of cancer.

4 Claims, No Drawings

(56) References Cited

FOREIGN PATENT DOCUMENTS

| | | |
|---|---|---|
| WO | WO 99/02166 | 1/1999 |
| WO | WO 00/40529 | 7/2000 |
| WO | WO 00/41669 | 7/2000 |
| WO | WO 00/47212 | 8/2000 |
| WO | WO 01/17972 | 3/2001 |
| WO | WO 01/32651 | 5/2001 |
| WO | WO 01/60814 | 8/2001 |
| WO | WO 01/92224 | 12/2001 |
| WO | WO 02/04434 | 1/2002 |
| WO | WO 02/08213 | 1/2002 |
| WO | WO 2004/052890 | 6/2004 |
| WO | WO 2004/099159 | 11/2004 |
| WO | WO 2006/069805 | 7/2006 |
| WO | WO 2006/135993 | 12/2006 |
| WO | WO 2007/060404 | 5/2007 |

OTHER PUBLICATIONS

Alferez et al., "Selection for Combinational Studies Through Biomarker Stratification in Colorectal Patent-derived Explant Models", AACR-EORTC-NCI, Nov. 12-16, 2011, San Francisco CA; Abstract.

Alferez et al., "Selection for Combinational Studies Through Biomarker Stratification in Colorectal Patent-derived Explant (PTX) Models", AACR-NCRI-NCI Conference Centre, Nov. 6-9, 2011, Liverpool UK; Poster.

Berge et al., "Pharmaceutical Salts", Journal of Pharmaceutical Sciences 66(1):1-19 (1977).

Bernadi, "PML Inhibits HIF-1alpha Translation and Neoangiogenesis Through Repression of mTOR", Nature 442:779-785 (2006).

Bjornsti and Houghton, "The TOR Pathway: A Target for Cancer Therapy", Nature Reviews Cancer 4:335-348 (2004).

Brown et al., "A Mammalian Protein Targeted by G1-arresting Rapamycin-receptor Complex", Letters to Nature 369:756-758 (1994).

Brunn et al., "Direct Inhibition of the Signaling Functions of the Mammalian Target of Rapamycin by the Phosphoinositide 3-kinase Inhibitors, Wortmannin and LY294002", The EMBO Journal 15(19) 5256-5267 (1996).

Burnett et al., "RAFT1 Phosphorylation of the Translational Regulators p70 S6 Kinase and 4E-BP1", Proc. Natl. Acad. Sci. 95:1432-1437 (1998).

Charier et al., "An Efficient Fluorescent Probe for Ratiometric pH Measurements in Aqueous Solutions", Angew. Chem, Int. Ed. 43:4785-4788 (2004).

Chiu et al., "RAPT1, A Mamalian Homolog of Yeast Tor. Interacts with the FKBP12/Rapamycin Complex", Proc. Natl. Acad. Sci. 91:12574-12578 (1994).

Chou and Blenis, "TORgeting Oncogene Addiction for Cancer Therapy", Cancer Cell 77-79 (2006).

Chresta et al., "Characterisation of AZD8055, A Potent Selective Inhibitor of mTORC1 and mTORC2 Kinase", AACR, Denver, USA, Apr. 18-22, 2009; Presentation.

Chresta et al., "AZO8055 is A Potent, Selective, and Orally Bioavailable ATP-competitive Mammalian Target of Rapamycin Kinase Inhibitor with In Vitro and In Vivo Antitumor Activity", Cancer Research 70(1):288-98 (2010).

Churchill "AZD8055: Reaping the Benefits of New Route Development", Organic Process Research & Development Conference, Barcelona, Spain, Sep. 13-15, 2010; Presentation.

Cirstea et al., "Disruption of DEPTOR/mTORC1/mTORC2 Signaling Cascade Using a Novel Selective mTOR Kinase Inhibitor AZD8055 Results in Growth Arrest and Apoptosis in Multiple Myeloma Cells", 52nd ASH Annual Meeting, Orlando, USA, Dec. 4-7, 2010; Abstract.

Cirstea et al., "Deptor Is A Regulator of Response to mTOR inhibitors in Multiple Myeloma", ASH Annual Meeting, Dec. 10-13, 2011, Stockholm, Sweden; Abstract.

Cristofano and Panctolfi, "The Multiple Roles of PTEN in Tumor Suppression", Cell 100:387-390 (2000).

Dahla, "PTEN, A Unique Tumor Suppressor Gene", Endocrine-Related Cancer 7:115-129 (2000).

Dai et al,. "Treatment Effects of the Novel mTOR Kinase Inhibitor AZD8055 in Prostate Cancer Cell Models", American Association for Cancer Research 102nd Annual Meeting' Florida, USA, Apr. 2-6, 2011; Abstract.

Dai and Siemann, "Treatment Effects of the Dual mTORC1 and mTORC2 Inhibitor AZD8055 in Human Prostate Cancer Cell Models", American Association for Cancer Research 102nd Annual Meeting' Florida, USA, Apr. 2-6, 2011; Poster.

Deutsch, "In Vitro and In Vivo Experiences with An Antiaggregating Agent SH-869 SU", International Congress Series (Platelets, Proc. Int. Symp. Blood Platelets, 1974) 357:319-323 (1975).

Dickinson et al., "An Investigation into the Utility of a Multi-compartmental, Dynamic, System of the Upper Gastrointestinal Tract to Support Formulation Development and Establish Bioequivalence of Poorly Soluble Drugs", The AAPS Journal 14(2):196-205 (2012).

Easton and Houghton, "Therapeutic Potential of Target of Rapamycin Inhibitors", Expert Opinion on Therapeutic Targets 8(6):551-564 (2004).

Edinger et al., "Differential Effects of Rapamycin on Mammalian Target of Rapamycin Signaling Functions in Mammalian Cells", Cancer Research 63:8451-8460 (2003).

Eisen et al., "Everolimus for the Prevention of Allograft Rejection and Vasculopathy in Cardiac-transplant Recipients", New England Journal of Medicine 349(9):847-658 (2003).

Eshleman of al., "Inhibition of the Mammalian Target of Rapamycin Sensitizes U87 Xenografts to Fractionated Radiation Therapy", Cancer Research 62:7291-7297 (2002).

Examiner's Search Strategy and Results for U.S. Appl. No. 11/842,927.

Examiner's Search Strategy and Results for U.S. Appl. No. 11/842,930.

Garcia-Martinez et al., "Ku-0063794 is A Specific Inhibitor of the Mammalian Target of Rapamycin (mTOR)", Biochemical Journal 421:29-42 (2009).

Garcia-Martinez et al., "Oral Administration of mTOR and Pl-3 Kinase Inhibitors Reduce the Volume of Pre-formed Tumors in PTEN-deficient Mice", IRB Barcelona BioMed Conferences—Cancer Metabolism, Barcelona, Spain, Nov. 8-10, 2010; Abstract.

Garcia-Martinez et al., "Oral Administration of AZD8055 and GDC-0941 Kinase Inhibitors Reduce the Volume of Pre-formed Tumors in PTEN-deficient Mice", IRB Barcelona BioMed Conferences—Cancer Metabolism, Barcelona, Spain, Nov. 8-10, 2010; Poster.

Gibbs, "New Cancer Drugs in Development: Potential Application to NF1 and NF2", Childrens Tumor Foundation, Annual NF Conference, Baltimore, USA, Jun. 5-8, 2010; Presentation.

Gingras et al., "Regulation of 4E-BP1 Phosphorylation: A Novel Two-step Mechanism", Genes and Development 13:1422-1437 (1999).

Gingras et al., "Regulaton of Translaton Initation by FRAP/mTOR", Genes and Development 15:807-826 (2001).

Griffin et al., "Selective Benzopyranone and Pyrimido[2,1alpha]isoquinolin-4-one Inhibitors of DNA-dependent Protein Kinase: Synthesis, Structure-activity Studies, and Radiosensitization of A Human Tumor Cell Line In Vitro", Journal of Medicinal Chemistry 48(2):569-585 (2005).

Grinsted and Southworth, "Extreme Value Modeling of Liver Related Laboratory Data", 34th Annual PSI (Statisticians in the Pharmaceutical Industry) Conference, May 15-18, 2011, UK; Abstract.

Grinsted and Southworth, "Extreme Value Modeling of Liver Related Laboratory Data to Predict Extreme Values in Future Studies", 34th Annual PSI (Statisticians in the Pharmaceutical Industry) Conference, May 15-18, 2011, UK; Poster.

Grotemeier et al., "AMPK-independent Induction of Autophagy by Cytosolic Ca2+ increase", Cellular Signaling 22(6):914-25 (2010).

(56) References Cited

OTHER PUBLICATIONS

Gu et al., "AZD8055, A Selective mTOR Kinase Inhibitor, Induces Tumor Growth Inhibition in Hepatocellular Carcinoma Models In Vitro and In Vivo", International Liver Cancer Association (ILCA) Fourth Annual Conference, Montreal, Canada, Sep. 10-12, 2010 (Poster and Summary on same document).
Guichard, "Benefits of mTOR Kinase Targeting in Oncology: Preclinical Evidence with AZD8055" Nov. 10, 2010; Presentation.
Guichard et al., "AZD8055, A Potent, Selective and Orally Bioavailable Inhibitor of mTOR Kinase", Manchester Cancer Research Centre (MCRC) Meeting, Manchester, UK, Jan. 17-20, 2010; Presentation.
Guichard et al., "AZD2014, Potent and Selective Inhibitor of mTOR Kinase", AZ Science Day, Japan National Cancer Centre (NCC), Oct. 2, 2011; Congress; Poster.
Gupta et al., "Preclinical Efficacy of AZD8055, An ATP-Competitive Mammalian Target of Rapamycin (mTOR) Kinase Inhibitor, In Vitro in Clear Cell Renal Cell Carcinoma (RCC)", American Association for Cancer Research 102nd Annual Meeting, Florida, USA, Apr. 2-6, 2011; Abstract.
Gupta et al., "Preclinical Efficacy of AZD8055, An ATP-Competitive Mammalian Target of Rapamycin (mTOR) Kinase Inhibitor, In Vitro in Clear Cell Renal Cell Carcinoma (RCC)", American Association for Cancer Research 102nd Annual Meeting, Florida, USA, Apr. 2-6, 2011; Poster.
Hay, "The Akt-mTOR Tango and its Relevance to Cancer", Cancer Cell 8:179-183 (2005).
Hayakawa et al., "Synthesis and Biological Evaluation of 4-morpholino-2-phenylquinazolines and Related Derivatives as Novel Pl3 Kinase p110alpha Inhibitors", Bioorganic & Medicinal Chemistry 14(20):6847-6858 (2006).
Holt et al., "Combining inhibitors of the mTOR (AZD8055) and MEK1/2 (AZD6244; ARRY-142886) Pathways, Demonstrates Enhanced Apoptotic Signalling and Tumour Growth Inhibition in Human Tumour Xenograft Models", NCRI Cancer Conference, Birmingham, UK, Oct. 4-7, 2009; Poster.
Holt et al., "The mTOR Kinase inhibitor AZD8055 Induces Cell Death in Her2+ Tumours Partially or Intrinsically Resistant to ErbB2 Inhibitors", EORTC-NCI-AACR International Symposium on Molecular Targets and Cancer Therapeutics, Berlin, Germany, Nov. 16-19, 2010; Congress Website; Abstract.
Holt et al., "Enhanced Apoptosis and Tumor Growth Suppression Elicited by Combination of MEK (Selumetinib) and mTOR Kinase Inhibitors (AZD8055)", Cancer Research, 72(7):1804-1813 (2012).
Houghton et al., "Pediatric Preclinical Testing Program (PPTP) Stage 1 Evaluation of AZD8055 An Inhibitor of mTOR Kinase", AACR-NCI-EORTC International Conference 'Molecular Targets and Cancer Therapeutics', Nov. 15-19, 2009; Poster.
Houghton et al., "Initial Testing (stage 1) of the mTOR Kinase Inhibitor AZD8055 by the Pediatric 52 Preclinical Testing Program", Pediatr. Blood Cancer, 58:191-199 (2012).
Howard et al., "The Combination of AZD8055 and Selumetinib (AZD6244, ARRY-142886) is Synergistic in a Subset of Non-Small Cell Lung Cancer Lines with Co-dependency to the MEK and mTOR Pathways", NCRI Cancer Conference, Liverpool, UK, Nov. 7-10, 2010; Poster.
Huang et al., "Inhibition of mTOR Kinase by AZD8055 can Antagonize Chemotherapy-induced Cell Death Through Autophagy Induction and Down Regulation of p62/sequestosome 1", Journal of Biological Chemistry 286(46):40002-12 (2011).
Huang and Houghton, "Inhibitors of Mammalian Target of Rapamycin as Novel Antitumor Agents: From Bench to Clinic", Current Opinion in Investigational Drugs 3:295-304 (2002).
Huang and Houghton, "Targeting mTOR Signaling for Cancer Therapy", Current Opinion in Pharmacology 3:371-377 (2003).
Huo et al., "Differing Effects of Rapamycin and mTOR Kinase Inhibitors on Protein Synthesis", Biochemical Society Transactions 39(2):446-50 (2011).
Iadevaia et al., "Roles of the Mammalian Target of Rapamycin, mTOR, in Controlling Ribosome Biogenesis and Protein Synthesis", Biochemical Society Transactions 40(1):168-72 (2012).
Jagtap et al., "The Discovery and Synthesis of Novel Adenosine Substituted 2,3-dihydro-1H-isoindol-1-ones: Potent Inhibitors of Poly (ADP-ribose) Polymerase-1 (PARP-1)", Bioorganic & Medicinal Chemistry Letters 14:81-85 (2004).
Jeffries et al., "Rapamycin Suppresses 5'TOP mRNA Translation Through Inhibition p70s6k", The EMBO Journal 16(12):3693-3704 (1997).
Jiang et al., "Enhanced Anti-tumor Effect of Combination Therapy with Anti-CD40 Antibody and the mTOR Kinase Inhibitor AZD8055", AACR, Washington, USA, Apr. 17-21, 2010; Poster.
Jiang et al., "mTOR Kinase Inhibitor AZD8055 Enhances the Immunotherapeutic Activity of An Agonist CD40 Antibody in Cancer Treatment", Cancer Research 71(12):4074-84 (2011).
Keen et al., "mTOR Kinase Inhibition Modulates 18F-FDG Uptake In Vivo in the Human Glioma Xenograft Model U87-MG", World Molecular Imaging Conference 2009, Montreal, Canada, Sep. 23-26, 2009; Poster.
Keen et al., "The mTOR Kinase Inhibitor AZD8055 Modulates 18F-FDG Uptake In Vivo in the Human Glioma Xenograft Model U87-MG", AACR-NCI-EORTC International Conference 'Molecular Targets and Cancer Therapeutics', Nov. 15-19, 2009; Poster.
Lawrence et al., "Modulation of the Protein Kinase Activity of mTOR", Curr. Top. Microbiol. Immunol., 279:199-213 (2004).
Lellek et al., "Straightforward Synthesis of Axially Chiral 1,4-naphthodiazepine Derivatives", Synlett 11:1616-1618 (2000).
Lin et al., "Preclinical Efficacy of AZD8055, an ATP-Competitive Mammalian Target of Rapamycin (mTOR) Kinase Inhibitor, In Vitro in Urothelial Carcinoma of the Bladder", American Association for Cancer Research 102nd Annual Meeting Florida, USA, Apr. 2-6, 2011; Abstract.
Lin et al., "Preclinical Efficacy of AZD8055, an ATP-Competitive Mammalian Target of Rapamycin (mTOR) Kinase Inhibitor, In Vitro in Urothelial Carcinoma of the Bladder", American Association for Cancer Research 102nd Annual Meeting Florida, USA, Apr. 2-6, 2011; Poster.
Malagu et al,, "The Discovery and Optimisation of Pyrido[2,3-d]pyrimidine-2,4diamines as Potent and Selective Inhibitors of mTOR kinase", Bioorganic & Medicinal Chemistry Letters 19(20):5950-5953 (2009).
Marshall et al., "Benefits of mTOR Kinase Targeting in Oncology: Pre-clinical Evidence with AZD8055", Biochemical Society Transactions 39(2):456-459 (2011).
Menear et al., "Identification and Optimisation of Novel and Selective Small Molecular Weight Kinase Inhibitors of mTOR", Bioorganic & Medicinal Chemistry Letters 19(20):5898-5901 (2009).
Morice et al., "A Randomised Comparison of a Sirolimus-eluting Stent with A Standard Stent for Coronary Revascularization", The New England Journal of Medicine 346(23):1773-1781 (2002).
Naing et al., "First Results from a Phase 1 Trial of AZD8055, A Dual mTORC1 and mTORC2 Inhibitor", AACR-EORTC-NC1, Nov. 12-16, 2011, San Francisco CA; Abstract.
Naing et al., "First Results from a Phase 1 Trial of AZD8055, A Dual mTORC1 and mTORC2 Inhibitor", AACR-EORTC-NC1, Nov. 12-16, 2011, San Francisco CA; Poster.
Neuhaus et al., "mTor inhibitors: An overview", Liver Transplantations 7(6):473-484 (2001).
Nishikawa et al., "Struture-activity Relationship of the Diuretic Activity of Triaza- and Tetraza-naphthalene Compounds", Chem. Pharm. Bull. 24(9):2057-2077 (1976); Abstract.
Office Action for U.S. Appl. No. 11/842,927, mailed Sep. 16, 2009.
Pike, "Identfcation & Optimisation of Selective Small Molecule Inhibitors of mTOR Kinase", 4th Anglo-Swedish Medicinal Chemistry Conference; Lund, Sweden—Mar. 15-16, 2009; Presentation.
Pike, "Identification & Optimisation of Selective Small Molecule Inhibitors of mTOR Kinase", RSC-SCI Protein Kinase 2009; Alderley Park, UK—May 18-19, 2009; Presentation.
Pike, "Identification & Optimisation of Selective Small Molecule Inhibitors of mTOR Kinase", UK-Singapore Symposium on Medicinal Chemistry; Singapore—Jan. 25-26, 2010; Presentation.

(56) References Cited

OTHER PUBLICATIONS

Pike, "Identification & Optimisation of Selective Small Molecule Inhibitors of mTOR Kinase", UK-Malaysia Symposium on Medicinal Chemistry; Penang, Malaysia—Jan. 28-29, 2010; Presentation.
Pike, "The identification of Clinical Candidate, AZD8055: A Potent, Selective Small Molecule Dual Inhibitor of mTOR Kinase", American Chemistry Society (ACS) Kinase symposium, Anaheim, USA, Mar. 27-31, 2011; Presentation.
Proud et al., "Differing Effects of Rapamycin and mTOR Kinase Inhibitors on Protein Synthesis", mTor Signalling in Health Disease, London UK, Nov. 11-12, 2010; Presentation.
Rodrik et al., "AZD8055 is An Effective Inhibitor of mTOR Kinase Signaling and Breast Cancer Growth, While Relieving Feedback Inhibition of HER-kinase Signaling", AACR, Washington, USA, Apr. 17-21, 2010; Poster.
Rodrik-Outmezguine et al., "mTOR Kinase Inhibition Relieves Feedback Inhibition of RTK and PI3K Signaling in Breast Cancer Cells", American Association for Cancer Research 102nd Annual Meeting Florida, USA, Apr. 2-6, 2011; Abstract.
Rodrik-Outmezguine et al., "mTOR Kinase Inhibition Causes Feedback-dependent Biphasic Regulation of AKT Signaling", Cancer Discovery, 1, 248-259, Published OnlineFirst, Jun. 17, 2011; Presentation.
Sabatini et al., "RAFTI: A Mammalian Protein that Binds to FKBP12 in a Rapamycin-dependent Fashion and is Homologous to Yeast TOR's", Cell 78:35-43 (1994).
Sabers et al., "Isolation of A Protein Target of FKBP12-rapamycin Complex in Mammalian Cells", Journal of Biological Chemistry 270(2):815-822 (1995).
Samuels et al., "High Frequency of Mutations of the PIK3CA Gene in Human Cancers", Science 304:554 (2004).
Sarbassov et al., "Rictor, A Novel Binding Partner of mTOR, Defines a Rapamycin-insensitive and Raptor-independent Pathway that Regulates the Cytoskeleton", Current Biology 14:1206-1302 (2004).
Sawyer, "Will mTor Inhibitors Make it as Cancer Drugs?", Cancer Cell 4:343-348 (2003).
Schmelze and Hall, "TOR, A Central Controller of Cell Growth", Cell 103:253-262 (2000).
Sehgal, "Sirolimus: It's Discovery, Biological Properties and Mechanism of Action", Translational Proceedings 35(Suppl 3A):7S-14S (2003).
Serova et al., "Effects of AZD8055, A Novet mTOR Kinase Inhibitor, in Human Cancer Cells Developing Resistance to Rapamycin", AACR-NCI-EORTC International Conference 'Molecular Targets and Cancer Therapeutics', Nov. 15-19, 2009; Poster.
Sini, "Simultaneous Inhibition of mTORC1 and mTORC2 by mTOR Kinase Inhibitor AZD8055 Induces Autophagy and Cell Death in Cancer Cells", Autophagy, May 2, 2010;6(4): Abstract.
Skehan et al., "New Colorimetric Cytotoxicity Assay for Anticancer-drug Screening", J. Natl. Cancer Inst. 82:1107-1112 (1990).
Stocks et al., "Structure-driven HtL: Design and Synthesis of Novel Aminoindazole Inhbitors of c-Jun N-terminal Kinase Activity", Bioorganic & Medicinal Chemistry Letters 15(14)3459-3462 (2005).
Sugimoto and Tanji, "An Improved Method for Chorination of Nitrogen-containing P-deficient Heteroaromatics Using Triphenylphosphine and Trichloroisosycanuric Acid", Heterocycles 65(1):181-185 (2005).
Tanaka et al., "Inhibitors of Acyl CoA: Cholesterol O-acyltransferase 2 Identification and Structure-activity Relationships of A Novel Series of N-akyl-N-(heteroaryl-substituted benzyl)-N-arylureas", Journal of Medicinal Chemistry 41:2390-2410 (1998).
Tee and Blenis, "mTor, Translational Control and Human Disease", Seminars in Cell and Development Biology 16:29-37 (2005).
Terada et al., "Rapamycin Selectively Inhibits Translation of mRNAs Encoding Elongation Factors and Ribosomal Proteins", Proc. Natl. Acad. Sci. 91(24):11477-11481 (1994).
Thomas et al., "Hypoxia-inducible Factor Determines Sensitivity to Inhibitors of mTOR in Kidney Cancer", Nature Medicine 12(1):122-127 (2006).
van der Heijden et al., "Large-scale siRNA-based Screens to Identify Modulators of Sensitivity to mTOR Inhibition in Breast Cancer Cells", AZ/MedI Cross-Alliance Scientific Symposia, Alderley Park, Macclesfield, UK, Jun. 15-16, 2010; Poster.
Vaughan et al., "AZD8055, A Combined TORC1/TORC2 Inhibitor Regulates Mycn Protein Expression and Prevents Neuroblastoma Growth In Vitro and In Vivo", American Association for Cancer Research 102nd Annual Meeting Florida, USA, Apr. 2-6, 2011; Abstract.
Vaughan et al., "MYCN Confers Synthetic Lethality to mTOR Kinase Pathwyay Inhibition and is A Potential Therapy for MYC-driven Tumors", Institute of Cancer Research, Department of Paediatric Oncology, CRUK Centre for Cancer Therapeutics American Association for Cancer Research 102nd Annual Meeting Florida, USA, Apr. 2-6, 2011; Poster.
Willems et al., "The Dual mTORC1 and mTORC2 Inhibitor AZD8055 has Anti-tumor Activity in Acute Myeloid Leukemia", Leukemia doi:10.1038/leu.2011.339:1-8 (2011).
Willems et al., "Targeted Inhibition of mTOR by AZD8055 Blocks Protein Translation and has Anti-leukemic Activity in Acute Myeloid Leukemia", 15th congress of the European Haematology Association Jun. 10-13, 2010, Barcelona, Spain; Abstract.
Woods and Marks, "Drug-eluting Stents", Ann. Rev. Med 55:169-178 (2004).
Yin et al., "Pd-catalysed N-arylation of Heteroarylamines", Organic Letters 4(20):3481-3484 (2002).
Zask et al., "Recent Advances in the Discovery of Small-molecule ATP Competitive mTOR Inhibitors: A Patent Review", Expert Opinion on Therapeutic Patents 21(7):1109-27 (2011).
Zhang et al., "Simultaneous Blockade of MEK and mTOR Kinase Signaling induces Synergistic Pro-apoptotic Effects in AML Cells, which are Further Potentiated by Bcl-2/XL Inhibition", AACR, Washington, USA, Apr. 17-21, 2010; Poster.

* cited by examiner

PYRIDO-, PYRAZO- AND PYRIMIDO-PYRIMIDINE DERIVATIVES AS MTOR INHIBITORS

CROSS-REFERENCE TO RELATED APPLICATIONS

This application is a continuation of U.S. application Ser. No. 13/859,270, filed Apr. 9, 2013 (now U.S. Pat. No. 9,102,670), which is a continuation of U.S. application Ser. No. 13/307,342, filed Nov. 30, 2011 (now U.S. Pat. No. 8,435,985), which is a continuation of U.S. application Ser. No. 13/014,275, filed Jan. 26, 2011 (now U.S. Pat. No. 8,101,602), which is a divisional of U.S. application Ser. No. 11/842,930, filed Aug. 21, 2007 (now U.S. Pat. No. 7,902,189), which claims benefit under 35 U.S.C. §119(e) of U.S. Provisional Application No. 60/823,311 (filed Aug. 23, 2006), and U.S. Provisional Application No. 60/938,776 (filed May 18, 2007). Each of these applications is incorporated by reference in its entirety. This application is also related to U.S. application Ser. No. 13/613,603, filed Sep. 13, 2012 (now abandoned).

The present invention relates to compounds which act as mTOR inhibitors, their use and their synthesis.

BACKGROUND

Growth factor/mitogenic activation of the phosphatidylinositol 3-kinase (PI3K)/AKT signalling pathway ultimately leads to the key cell cycle and growth control regulator mTOR, the mammalian target of rapamycin (alternatively referred to as FRAP (FKBP12 and rapamycin associated protein), RAFT1 (rapamycin and FKBP12 target 1), RAPT1 (rapamycin target 1)—all derived from the interaction with the FK-506-binding protein FKBP12, and SEP (sirolimus effector protein)). mTOR is a mammalian serine/threonine kinase of approximately 289 kDa in size and a member of the evolutionary conserved eukaryotic TOR kinases (refs. 1-4). The mTOR protein is a member of the PI3-kinase like kinase (PIKK) family of proteins due to its C-terminal homology (catalytic domain) with PI3-kinase and the other family members, e.g. DNA-PKcs (DNA dependent protein kinase), ATM (Ataxia-telangiectasia mutated). In addition to a catalytic domain in the C-terminus, mTOR contains a FKBP12/rapamycin complex binding domain (FRB). At the N-terminus up to 20 HEAT (Huntingtin, EF3, alpha regulatory subunit of PP2A and TOR) motifs are found whilst more C-terminal is a FAT (FRAP-ATM-TRRAP) domain, and at the extreme C-terminus of the protein an additional FAT domain is found (FAT-C) (refs. 5,6).

TOR has been identified as a central regulator of both cell growth (size) and proliferation, which is in part governed by translation initiation. TOR dependant phosphorylation of S6-kinase (S6K1) allows translation of ribosomal proteins involved in cell cycle progression (refs. 7-9). Cap-dependant translation is regulated by the phosphorylation of the eukaryotic translation initiation factor 4E (eIF4E)-binding protein 1 (4E-BP1 (PHAS-1)). This modification prevents PHAS-1 binding eIF4E, thereby permitting formation of an active eIF4F translation complex (reviewed in refs. 10, 11, 12). Activation of these signalling elements is dependant on insulin, other growth factors and nutrients suggesting a gatekeeper role for mTOR in the control of cell cycle progression only under favourable environmental conditions. The PI3K/AKT signalling cascade lies upstream of mTOR and this has been shown to be deregulated in certain cancers and results in growth factor independent activation in, for example, PTEN deficient cells. mTOR lies at the axis of control for this pathway and inhibitors of this kinase (e.g. sirolimus (rapamycin or Rapamune™) and everolimus (RAD001 or Certican™)) are already approved for immunosuppression and drug eluting stents (reviewed in refs. 13, 14), and are now receiving particular interest as novel agents for cancer treatment.

Tumour cell growth arises from the deregulation of normal growth control mechanisms such as the loss of tumour suppressor function(s). One such tumour suppressor is the phosphatase and tensin homologue deleted from chromosome ten (PTEN). This gene, also known as mutated in multiple advanced cancers (MMAC), has been shown to play a significant role in cell cycle arrest and is the most highly mutated tumour suppressor after p53. Up to 30% of glioblastoma, endometrial and prostate cancers have somatic mutations or deletions of this locus (refs. 15, 16).

PI3K converts phosphatidylinositol 4,5, bisphosphate (PIP2) to phosphatidylinositol 3,4,5, triphosphate (PIP3) whilst PTEN is responsible for removing the 3' phosphate from PIP3 producing PIP2. PI3-K and PTEN act to maintain an appropriate level of PIP3 which recruits and thus activates AKT (also known as PKB) and the downstream signalling cascade that is then initiated. In the absence of PTEN, there is inappropriate regulation of this cascade, AKT becomes effectively constitutively activated and cell growth is deregulated. An alternative mechanism for the deregulation of this cell signalling process is the recent identification of a mutant form of the PI3K isoform, p110alpha (ref. 17). The apparent increased activity of this mutant is thought to result in increased PIP3 production, presumably in excess of that which the function of PTEN can counteract. Increased signalling from PI3K, thus results in increased signalling to mTOR and consequently, its downstream activators.

In addition to the evidence linking mTOR with cell cycle regulation (from G1 to S-phase) and that inhibition of mTOR results in inhibition of these regulatory events it has been shown that down regulation of mTOR activity results in cell growth inhibition (Reviewed in refs. 7, 18, 19). The known inhibitor of mTOR, rapamycin, potently inhibits proliferation or growth of cells derived from a range of tissue types such as smooth muscle, T-cells as well as cells derived from a diverse range of tumour types including rhabdomyosarcoma, neuroblastoma, glioblastoma and medulloblastoma, small cell lung cancer, osteosarcoma, pancreatic carcinoma and breast and prostate carcinoma (reviewed in ref. 20). Rapamycin has been approved and is in clinical use as an immunosuppressant, its prevention of organ rejection being successful and with fewer side effects than previous therapies (refs. 20, 21). Inhibition of mTOR by rapamycin and its analogues (RAD001, CCI-779) is brought about by the prior interaction of the drug with the FK506 binding protein, FKBP12. Subsequently, the complex of FKBP12/rapamycin then binds to the FRB domain of mTOR and inhibits the downstream signalling from mTOR.

The potent but non-specific inhibitors of PI3K, LY294002 and wortmannin, also have been shown to inhibit the kinase function of mTOR but act through targeting the catalytic domain of the protein (ref. 21). Further to the inhibition of mTOR function by small molecules targeted to the kinase domain, it has been demonstrated that kinase dead mTOR cannot transmit the upstream activating signals to the downstream effectors of mTOR, PHAS-1 or p70S6 kinase (ref. 22). It is also shown that not all functions of mTOR are rapamycin sensitive and this may be related to the observation that rapamycin alters the substrate profile of mTOR rather than inhibiting its activity per se (ref. 23). Analysis of the interactions of mTOR with other cellular factors has revealed that in addition to the mTOR-Raptor complex, there is also an mTOR-Rictor complex representing a rapamycin insensitive activity of mTOR (B) (Sarbassov et al. *Current Biology* (2004) 14, 1296-1302). This activity likely accounts for the discrepancy between kinase dead mTOR and the alteration of mTOR signalling by rapamycin and its derivatives. The discrepancy also identifies the possibility of a therapeutic advantage in inhibiting directly the catalytic activity of mTOR. It has been suggested that a catalytic inhibitor of mTOR may be a more effective antagonist of cancer cell proliferation and survival and that rapamycin may be more useful in combination with agents that can compensate for its failure to completely disrupt pathway signalling (Choo and Blenis, *Cancer Cell* (2006) 9, 77-79; Hay, *Cancer Cell* (2005) 8, 179-183). Therefore, it is proposed that a kinase domain directed inhibitor of mTOR may be a more effective inhibitor of mTOR.

In addition to rapamycin's ability to induce growth inhibition (cytostasis) in its own right, rapamycin and its derivatives have been shown to potentiate the cytotoxicity of a number of chemotherapies including cisplatin, camptothecin and doxorubicin (reviewed in ref. 20). Potentiation of ionising radiation induced cell killing has also been observed following inhibition of mTOR (ref. 24). Experimental and clinical evidence has shown that rapamycin analogues are showing evidence of efficacy in treating cancer, either alone or in combination with other therapies (see refs. 10, 18, 20). These findings suggest that pharmacological inhibitors of mTOR kinase should be of therapeutic value for treatment of the various forms of cancer comprising solid tumours such as carcinomas and sarcomas and the leukaemias and lymphoid malignancies. In particular, inhibitors of mTOR kinase should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

Renal cell carcinoma in particular, has been identified as sensitive to the rapamycin derivative CCI-779, resulting from a loss of VHL expression (Thomas et al. *Nature Medicine* (2006) 12, 122-127). Tumours that have lost the promyelocytic leukaemia (PML) tumour suppressor, have also been shown to be sensitive to inhibition of mTOR by rapamycin as a consequence of disruption of the regulation of the mTOR signalling pathway (Bernadi, *Nature* (2006) 442, 779-785) and the use of an mTOR kinase inhibitor in these diseases should be of therapeutic value. These latter examples in addition to those of PTEN deficiency or PI3K mutation indicate where a targeted approach to the use of mTOR inhibitors may prove particularly effective due to an underlying genetic profile, but are not considered to be exclusive targets.

Recent studies have revealed a role for mTOR kinase in other diseases (Easton & Houghton, *Expert Opinion on Therapeutic Targets* (2004) 8, 551-564). Rapamycin has been demonstrated to be a potent immunosuppressant by inhibiting antigen-induced proliferation of T cells, B cells and antibody production (Sehgal, *Transplantation Proceedings* (2003) 35, 7S-14S) and thus mTOR kinase inhibitors may also be useful immunosuppressives. Inhibition of the kinase activity of mTOR may also be useful in the prevention of restenosis, that is the control of undesired proliferation of normal cells in the vasculature in response to the introduction of stents in the treatment of vasculature disease (Morice et al., *New England Journal of Medicine* (2002) 346, 1773-1780). Furthermore, the rapamycin analogue, everolimus, can reduce the severity and incidence of cardiac allograft vasculopathy (Eisen et al., *New England Journal of Medicine* (2003) 349, 847-858). Elevated mTOR kinase activity has been associated with cardiac hypertrophy, which is of clinical importance as a major risk factor for heart failure and is a consequence of increased cellular size of cardiomyocytes (Tee & Blenis, *Seminars in Cell and Developmental Biology* (2005) 16, 29-37). Thus mTOR kinase inhibitors are expected to be of value in the prevention and treatment of a wide variety of diseases in addition to cancer.

The vast majority of mTOR pharmacology to date has focused on inhibition of mTOR via rapamycin or its analogues. However, as noted above, the only non-rapamycin agents that have been reported to inhibit mTOR's activity via a kinase domain targeted mechanism are the small molecule LY294002 and the natural product wortmannin (ref. 21).

SUMMARY OF THE INVENTION

The present inventors have identified compounds which are ATP-competitive inhibitors of mTOR, and hence are non-rapamycin like in their mechanism of action.

Accordingly, the first aspect of the present invention provides a compound of formula I:

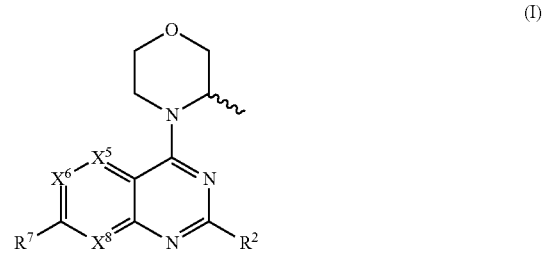

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form an optionally substituted heterocyclic ring containing between 3 and 8 ring atoms;
$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form an optionally substituted heterocyclic ring containing between 3 and 8 ring atoms;

$R^{S2a}$ is selected from H, an optionally substituted $C_{5-20}$ aryl group, an optionally substituted 5- to 20-membered heteroaryl group, or an optionally substituted $C_{1-7}$ alkyl group; $R^{N7a}$ and $R^{N7b}$ are selected from H and a $C_{1-4}$ alkyl group; $R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group, wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form an optionally substituted heterocyclic ring containing between 3 and 8 ring atoms.

According to a second aspect of the present invention there is provided a compound of formula Ia or Ib:

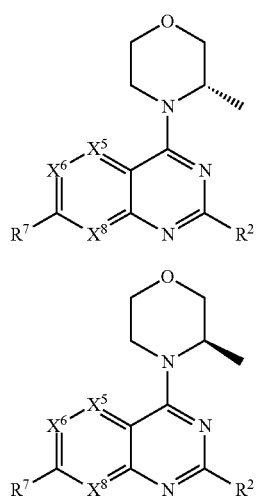

(Ia)

(Ib)

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form an optionally substituted heterocyclic ring containing between 3 and 8 ring atoms;

$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form an optionally substituted heterocyclic ring containing between 3 and 8 ring atoms;

$R^{S2a}$ is selected from H, an optionally substituted $C_{5-20}$ aryl group, an optionally substituted 5- to 20-membered heteroaryl group, or an optionally substituted $C_{1-7}$ alkyl group; $R^{N7a}$ and $R^{N7b}$ are selected from H and a $C_{1-4}$ alkyl group; $R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group, wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form an optionally substituted heterocyclic ring containing between 3 and 8 ring atoms.

According to a third aspect of the present invention there is provided a compound of formula Ia:

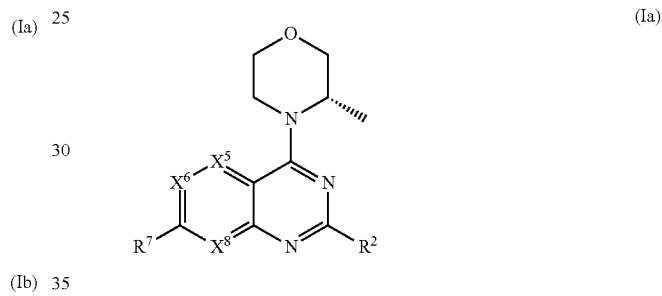

(Ia)

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form an optionally substituted heterocyclic ring containing between 3 and 8 ring atoms;

$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form an optionally substituted heterocyclic ring containing between 3 and 8 ring atoms;

$R^{S2a}$ is selected from H, an optionally substituted $C_{5-20}$ aryl group, an optionally substituted 5- to 20-membered heteroaryl group, or an optionally substituted $C_{1-7}$ alkyl group; $R^{N7a}$ and $R^{N7b}$ are selected from H and a $C_{1-4}$ alkyl group; $R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group, wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form an optionally substituted heterocyclic ring containing between 3 and 8 ring atoms.

According to a further aspect of the present invention there is provided a compound of formula I:

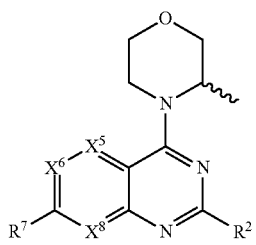

(I)

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form a heterocyclic ring containing between 3 and 8 ring atoms;
$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form a heterocyclic ring containing between 3 and 8 ring atoms;
$R^{S2a}$ is selected from H, an optionally substituted $C_{5-20}$ aryl group, an optionally substituted 5- to 20-membered heteroaryl group, or an optionally substituted $C_{1-7}$ alkyl group;
$R^{N7a}$ and $R^{N7b}$ are selected from H and a $C_{1-4}$ alkyl group;
$R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group,
wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form a heterocyclic ring containing between 3 and 8 ring atoms.

According to a further aspect of the present invention there is provided a compound of formula Ia or Ib:

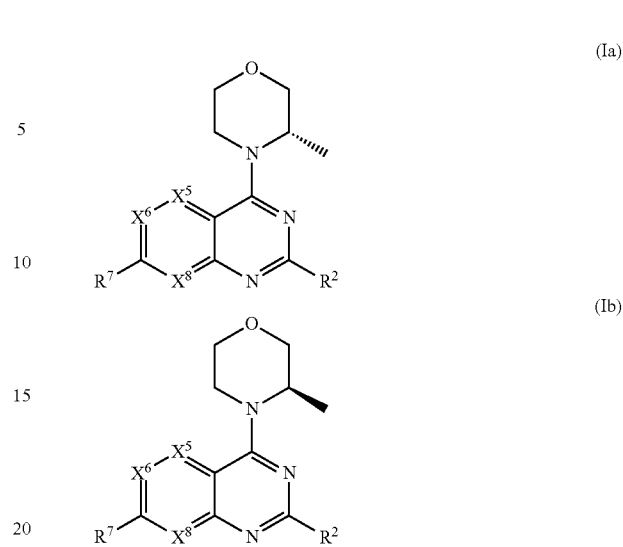

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form a heterocyclic ring containing between 3 and 8 ring atoms;
$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form a heterocyclic ring containing between 3 and 8 ring atoms;
$R^{S2a}$ is selected from H, an optionally substituted $C_{5-20}$ aryl group, an optionally substituted 5- to 20-membered heteroaryl group, or an optionally substituted $C_{1-7}$ alkyl group;
$R^{N7a}$ and $R^{N7b}$ are selected from H and a $C_{1-4}$ alkyl group;
$R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group,
wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form a heterocyclic ring containing between 3 and 8 ring atoms.

According to a further aspect of the present invention there is provided a compound of formula Ia:

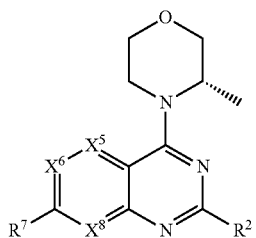
(Ia)

or a pharmaceutically acceptable salt thereof, wherein:
one or two of $X^5$, $X^6$ and $X^8$ is N, and the others are CH;
$R^7$ is selected from halo, $OR^{O1}$, $SR^{S1}$, $NR^{N1}R^{N2}$, $NR^{N7a}C(O)R^{C1}$, $NR^{N7b}SO_2R^{S2a}$, an optionally substituted 5- to 20-membered heteroaryl group, or an optionally substituted $C_{5-20}$ aryl group, where $R^{O1}$ and $R^{S1}$ are selected from H, an optionally substituted $C_{5-20}$ aryl group, an optionally substituted 5- to 20-membered heteroaryl group, or an optionally substituted $C_{1-7}$ alkyl group; $R^{N1}$ and $R^{N2}$ are independently selected from H, an optionally substituted $C_{1-7}$ alkyl group, an optionally substituted 5- to 20-membered heteroaryl group, an optionally substituted $C_{5-20}$ aryl group or $R^{N1}$ and $R^{N2}$ together with the nitrogen to which they are bound form a heterocyclic ring containing between 3 and 8 ring atoms;
$R^{C1}$ is selected from H, an optionally substituted $C_{5-20}$ aryl group, an optionally substituted 5- to 20-membered heteroaryl group, an optionally substituted $C_{1-7}$ alkyl group or $NR^{N8}R^{N9}$, where $R^{N8}$ and $R^{N9}$ are independently selected from H, an optionally substituted $C_{1-7}$ alkyl group, an optionally substituted 5- to 20-membered heteroaryl group, an optionally substituted $C_{5-20}$ aryl group or $R^{N8}$ and $R^{N9}$ together with the nitrogen to which they are bound form a heterocyclic ring containing between 3 and 8 ring atoms;
$R^{S2a}$ is selected from H, an optionally substituted $C_{5-20}$ aryl group, an optionally substituted 5- to 20-membered heteroaryl group, or an optionally substituted $C_{1-7}$ alkyl group; $R^{N7a}$ and $R^{N7b}$ are selected from H and a $C_{1-4}$ alkyl group;
$R^2$ is selected from H, halo, $OR^{O2}$, $SR^{S2b}$, $NR^{N5}R^{N6}$, an optionally substituted 5- to 20-membered heteroaryl group, and an optionally substituted $C_{5-20}$ aryl group,
wherein $R^{O2}$ and $R^{S2b}$ are selected from H, an optionally substituted $C_{5-20}$ aryl group, an optionally substituted 5- to 20-membered heteroaryl group, or an optionally substituted $C_{1-7}$ alkyl group; $R^{N5}$ and $R^{N6}$ are independently selected from H, an optionally substituted $C_{1-7}$ alkyl group, an optionally substituted 5- to 20-membered heteroaryl group, and an optionally substituted $C_{5-20}$ aryl group, or $R^{N5}$ and $R^{N6}$ together with the nitrogen to which they are bound form a heterocyclic ring containing between 3 and 8 ring atoms.

According to a further aspect of the present invention there is provided a pharmaceutical composition comprising a compound of formula (I), (Ia) or (Ib), or a pharmaceutically acceptable salt thereof, and a pharmaceutically acceptable carrier or diluent.

According to a further aspect of the present invention there is provided a compound of formula (I), (Ia) or (Ib), or a pharmaceutically acceptable salt thereof, for use in a method of treatment of the human or animal body.

According to a further aspect of the present invention there is provided the use of a compound of formula (I), (Ia) or (Ib), or a pharmaceutically acceptable salt thereof, in the preparation of a medicament for treating a disease ameliorated by the inhibition of mTOR.

The compounds of formula (I), (Ia) or (Ib), or a pharmaceutically acceptable salt thereof, have activity as pharmaceuticals, in particular as modulators or inhibitors of mTOR activity, and may be used in the treatment of proliferative and hyperproliferative diseases/conditions, examples of which include the following cancers:

(1) carcinoma, including that of the bladder, brain, breast, colon, kidney, liver, lung, ovary, pancreas, prostate, stomach, cervix, colon, endometrium, thyroid and skin;

(2) hematopoietic tumors of lymphoid lineage, including acute lymphocytic leukaemia, B-cell lymphoma and Burketts lymphoma;

(3) hematopoietic tumours of myeloid lineage, including acute and chronic myelogenous leukaemias and promyelocytic leukaemia;

(4) tumours of mesenchymal origin, including fibrosarcoma and rhabdomyosarcoma; and (5) other tumours, including melanoma, seminoma, teratocarcinoma, neuroblastoma and glioma.

Further aspects of the invention provide the use of a compound of formula (I), (Ia) or (Ib), or a pharmaceutically acceptable salt thereof, in the preparation of a medicament for the treatment of: cancer, immuno-suppression, immune tolerance, autoimmune disease, inflammation, bone loss, bowel disorders, hepatic fibrosis, hepatic necrosis, rheumatoid arthritis, restinosis, cardiac allograft vasculopathy, psoriasis, beta-thalassaemia, and ocular conditions such as dry eye. mTOR inhibitors may also be effective as antifungal agents.

Another further aspect of the invention provides for the use of a compound of formula (I), (Ia) or (Ib), or a pharmaceutically acceptable salt thereof, in the preparation of a medicament for use as an adjunct in cancer therapy or for potentiating tumour cells for treatment with ionizing radiation or chemotherapeutic agents.

Thus the compounds of the present invention provide a method for treating cancer characterised by inhibition of mTOR, i.e. the compounds may be used to produce an anti-cancer effect mediated alone or in part by the inhibition of mTOR.

Such a compound of the invention is expected to possess a wide range of anti-cancer properties as activating mutations in mTOR have been observed in many human cancers, including but not limited to, melanoma, papillary thyroid tumours, cholangiocarcinomas, colon, ovarian and lung cancers. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, bladder, prostate, endometrium, breast and pancreas. In particular such compounds of the invention are expected to slow advantageously the growth of primary and recurrent solid tumours of, for example, the skin, colon, thyroid, lungs, endometrium and ovaries. More particularly such compounds of the invention, or a pharmaceutically acceptable salt thereof, are expected to inhibit the growth of those primary and recurrent solid tumours which are associated with mTOR, especially those tumours which are significantly dependent on mTOR for their growth and spread, including for example, certain tumours of the skin, colon, thyroid, endometrium, lungs and ovaries. Particularly the compounds of the present invention are useful in the treatment of melanomas and gliomas.

Thus according to this aspect of the invention there is provided a compound of the formula I or 1(A), or a pharmaceutically acceptable salt thereof, as defined herein for use as a medicament.

According to a further aspect of the invention there is provided the use of a compound of the formula (I), (Ia) or (Ib), or a pharmaceutically acceptable salt thereof, as defined herein in the manufacture of a medicament for use in the production of a mTOR inhibitory effect in a warm-blooded animal such as man.

According to this aspect of the invention there is provided the use of a compound of the formula (I), (Ia) or (Ib), or a pharmaceutically acceptable salt thereof, as defined herein in the manufacture of a medicament for use in the production of an anti-cancer effect in a warm-blooded animal such as man.

According to a further feature of the invention, there is provided the use of a compound of the formula (I), (Ia) or (Ib), or a pharmaceutically acceptable salt thereof, as defined herein in the manufacture of a medicament for use in the treatment of melanoma, papillary thyroid tumours, cholangiocarcinomas, colon cancer, ovarian cancer, lung cancer, leukaemias, lymphoid malignancies, carcinomas and sarcomas in the liver, kidney, bladder, prostate, breast and pancreas, and primary and recurrent solid tumours of the skin, colon, thyroid, lungs and ovaries.

According to a further feature of the invention, there is provided the use of a compound of the formula (I), (Ia) or (Ib), or a pharmaceutically acceptable salt thereof, as defined herein in the manufacture of a medicament for use in the treatment of melanoma, glioma, papillary thyroid tumours, cholangiocarcinomas, colon cancer, ovarian cancer, lung cancer, leukaemias, lymphoid malignancies, carcinomas and sarcomas in the liver, kidney, bladder, prostate, endometrium, breast and pancreas, and primary and recurrent solid tumours of the skin, colon, thyroid, lungs and ovaries.

According to a further aspect of the invention there is provided the use of a compound of the formula (I), (Ia) or (Ib), or a pharmaceutically acceptable salt thereof, as defined herein in the production of a mTOR inhibitory effect in a warm-blooded animal such as man.

According to this aspect of the invention there is provided the use of a compound of the formula (I), (Ia) or (Ib), or a pharmaceutically acceptable salt thereof, as defined herein in the production of an anti-cancer effect in a warm-blooded animal such as man.

According to a further feature of the invention, there is provided the use of a compound of the formula (I), (Ia) or (Ib), or a pharmaceutically acceptable salt thereof, as defined herein in the treatment of melanoma, papillary thyroid tumours, cholangiocarcinomas, colon cancer, ovarian cancer, lung cancer, leukaemias, lymphoid malignancies, carcinomas and sarcomas in the liver, kidney, bladder, prostate, breast and pancreas, and primary and recurrent solid tumours of the skin, colon, thyroid, lungs and ovaries.

According to a further feature of the invention, there is provided the use of a compound of the formula (I), (Ia) or (Ib), or a pharmaceutically acceptable salt thereof, as defined herein in the treatment of melanoma, glioma, papillary thyroid tumours, cholangiocarcinomas, colon cancer, ovarian cancer, lung cancer, leukaemias, lymphoid malignancies, carcinomas and sarcomas in the liver, kidney, bladder, prostate, endometrium, breast and pancreas, and primary and recurrent solid tumours of the skin, colon, thyroid, lungs and ovaries.

According to a further feature of this aspect of the invention there is provided a method for producing a mTOR inhibitory effect in a warm-blooded animal, such as man, in need of such treatment which comprises administering to said animal an effective amount of a compound of formula (I), (Ia) or (Ib), or a pharmaceutically acceptable salt thereof, as defined herein.

According to a further feature of this aspect of the invention there is provided a method for producing an anti-cancer effect in a warm-blooded animal, such as man, in need of such treatment which comprises administering to said animal an effective amount of a compound of formula (I), (Ia) or (Ib), or a pharmaceutically acceptable salt thereof, as defined herein.

According to a further feature of this aspect of the invention there is provided a method of modulting mTOR activity which comprises administering to a patient in need thereof an effective amount of a compound of formula (I), (Ia) or (Ib), or a pharmaceutically acceptable salt thereof, as defined herein.

According to a further feature of this aspect of the invention there is provided a method of treating cancer which comprises administering to a patient in thereof an effective amount of a compound of formula (I), (Ia) or (Ib), or a pharmaceutically acceptable salt thereof, as defined herein.

According to an additional feature of this aspect of the invention there is provided a method of treating melanoma, papillary thyroid tumours, cholangiocarcinomas, colon cancer, ovarian cancer, lung cancer, leukaemias, lymphoid malignancies, carcinomas and sarcomas in the liver, kidney, bladder, prostate, breast and pancreas, and primary and recurrent solid tumours of the skin, colon, thyroid, lungs and ovaries, in a warm-blooded animal, such as man, in need of such treatment which comprises administering to said animal an effective amount of a compound of formula (I), (Ia) or (Ib) or a pharmaceutically acceptable salt thereof as defined herein.

According to an additional feature of this aspect of the invention there is provided a method of treating melanoma, glioma, papillary thyroid tumours, cholangiocarcinomas, colon cancer, ovarian cancer, lung cancer, leukaemias, lymphoid malignancies, carcinomas and sarcomas in the liver, kidney, bladder, prostate, endometrium, breast and pancreas, and primary and recurrent solid tumours of the skin, colon, thyroid, lungs and ovaries, in a warm-blooded animal, such as man, in need of such treatment which comprises administering to said animal an effective amount of a compound of formula (I), (Ia) or (Ib) or a pharmaceutically acceptable salt thereof as defined herein.

In a further aspect of the invention there is provided a pharmaceutical composition which comprises a compound of the formula (I), (Ia) or (Ib), or a pharmaceutically acceptable salt thereof, as defined herein in association with a pharmaceutically-acceptable diluent or carrier for use in the production of a mTOR inhibitory effect in a warm-blooded animal such as man.

In a further aspect of the invention there is provided a pharmaceutical composition which comprises a compound of the formula (I), (Ia) or (Ib), or a pharmaceutically acceptable salt thereof, as defined herein in association with a pharmaceutically-acceptable diluent or carrier for use in the production of an anti-cancer effect in a warm-blooded animal such as man.

In a further aspect of the invention there is provided a pharmaceutical composition which comprises a compound of the formula (I), (Ia) or (Ib), or a pharmaceutically acceptable salt thereof, as defined herein in association with a pharmaceutically-acceptable diluent or carrier for use in the treatment of melanoma, papillary thyroid tumours, cholangiocarcinomas, colon cancer, ovarian cancer, lung cancer, leukaemias, lymphoid malignancies, carcinomas and sarcomas in the liver, kidney, bladder, prostate, breast and pancreas, and primary and recurrent solid tumours of the skin, colon, thyroid, lungs and ovaries in a warm-blooded animal such as man.

In a further aspect of the invention there is provided a pharmaceutical composition which comprises a compound of the formula (I), (Ia) or (Ib), or a pharmaceutically acceptable salt thereof, as defined herein in association with a pharmaceutically-acceptable diluent or carrier for use in the treatment of melanoma, glioma, papillary thyroid tumours, cholangiocarcinomas, colon cancer, ovarian cancer, lung cancer, leukaemias, lymphoid malignancies, carcinomas and sarcomas in the liver, kidney, bladder, prostate, endometrium, breast and pancreas, and primary and recurrent solid tumours of the skin, colon, thyroid, lungs and ovaries in a warm-blooded animal such as man.

Other further aspects of the invention provide for the treatment of disease ameliorated by the inhibition of mTOR, comprising administering to a subject in need of treatment a therapeutically-effective amount of a compound of formula (I), (Ia) or (Ib), or a pharmaceutically acceptable salt thereof, preferably in the form of a pharmaceutical composition and the treatment of cancer, comprising administering to a subject in need of treatment a therapeutically-effective amount of a compound of formula (I), (Ia) or (Ib), or a pharmaceutically acceptable salt thereof, in combination, preferably in the form of a pharmaceutical composition, simultaneously or sequentially with ionizing radiation or chemotherapeutic agents.

DEFINITIONS

The term "aromatic ring" is used herein in the conventional sense to refer to a cyclic aromatic structure, that is, a structure having delocalised π-electron orbitals.

Nitrogen-containing heterocyclic ring having from 3 to 8 ring atoms: The term "Nitrogen-containing heterocyclic ring having from 3 to 8 ring atoms" as used herein refers to a 3 to 8 membered heterocylic ring containing at least one nitrogen ring atom. The term "together with the nitrogen to which they are bound, form a heterocyclic ring containing between 3 and 8 ring atoms" as used herein refers to a 3 to 8 membered heterocylic ring containing at least one nitrogen ring atom. Examples of these groups include, but are not limited to:

$N_1$: aziridine ($C_3$ ie 3 membered), azetidine ($C_4$ ie 4 membered), pyrrolidine (tetrahydropyrrole) ($C_5$ ie 5 membered), pyrroline (e.g., 3-pyrroline, 2,5-dihydropyrrole) ($C_5$ ie 5 membered), 2H-pyrrole or 3H-pyrrole (isopyrrole, isoazole) ($C_5$ ie 5 membered), piperidine ($C_6$ ie 6 membered), dihydropyridine ($C_6$ ie 6 membered), tetrahydropyridine ($C_6$ ie 6 membered), azepine ($C_7$ ie 7 membered);

$N_2$: imidazolidine ($C_5$ ie 5 membered), pyrazolidine (diazolidine) ($C_5$ ie 5 membered), imidazoline ($C_5$ ie 5 membered), pyrazoline (dihydropyrazole) ($C_5$ ie 5 membered), piperazine ($C_6$ ie 6 membered);

$N_1O_1$: tetrahydrooxazole ($C_5$ ie 5 membered), dihydrooxazole ($C_5$ ie 5 membered), tetrahydroisoxazole ($C_5$ ie 5 membered), dihydroisoxazole ($C_5$ ie 5 membered), morpholine ($C_6$ ie 6 membered), tetrahydrooxazine ($C_6$ ie 6 membered), dihydrooxazine ($C_6$ ie 6 membered), oxazine ($C_6$ ie 6 membered);

$N_1S_1$: thiazoline ($C_5$ ie 5 membered), thiazolidine ($C_5$ ie 5 membered), thiomorpholine ($C_6$ ie 6 membered);

$N_2O_1$: oxadiazine ($C_6$ ie 6 membered);

$N_1O_1S_1$: oxathiazine ($C_6$ ie 6 membered).

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes saturated alkyl, alkenyl, alkynyl, saturated cycloalkyl, cycloalkyenyl, cylcoalkynyl, etc., discussed below. Unless otherwise specified, preferable "alkyl" groups are saturated alkyl or saturated cycloalkyl groups, more preferably saturated alkyl groups.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

The term saturated alkyl group includes saturated linear alkyl and saturated branched alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes saturated cycloalkyl, cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds: camphene ($C_{10}$), limonene ($C_{10}$), pinene ($C_{10}$);

polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms. Preferably the ring heteroatoms are selected from O, N and S. The heterocyclic ring may, unless otherwise specified, be carbon or nitrogen linked, and wherein a —$CH_2$— group can optionally be replaced by a —C(O)—, and a ring sulphur atom may be optionally oxidised to form the S-oxides.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl" or "5 to 6 membered heterocyclyl", as used herein, pertains to a heterocyclyl group having 5 or 6 ring atoms. Examples of groups of heterocyclyl groups include $C_{3-20}$ heterocyclyl (ie 3 to 20 membered heterocyclyl), $C_{5-20}$ heterocyclyl (ie 5 to 20 membered heterocyclyl), $C_{3-15}$ heterocyclyl (ie 3 to 15 membered heterocyclyl), $C_{5-15}$ heterocyclyl (ie 5 to 15 membered heterocyclyl), $C_{3-12}$ heterocyclyl (ie 3 to 12 membered heterocyclyl), $C_{5-12}$ heterocyclyl (ie 5 to 12 membered heterocyclyl), $C_{3-10}$ heterocyclyl (ie 3 to 10 membered heterocyclyl), $C_{5-10}$ heterocyclyl (ie 5 to 10 membered heterocyclyl), $C_{3-7}$ heterocyclyl (ie 3 to 7 membered heterocyclyl), $C_{5-7}$ heterocyclyl (ie 5 to 7 membered heterocyclyl), and $C_{5-6}$ heterocyclyl (ie 5 to 6 membered heterocyclyl).

Examples of monocyclic heterocyclyl groups include, but are not limited to, those derived from:

$N_1$: aziridine ($C_3$ ie 3 membered), azetidine ($C_4$ ie 4 membered), pyrrolidine (tetrahydropyrrole) ($C_5$ ie 5 membered), pyrroline (e.g., 3-pyrroline, 2,5-dihydropyrrole) ($C_5$ ie 5 membered), 2H-pyrrole or 3H-pyrrole (isopyrrole, isoazole) ($C_5$ ie 5 membered), piperidine ($C_6$ ie 6 membered), dihydropyridine ($C_6$ ie 6 membered), tetrahydropyridine ($C_6$ ie 6 membered), azepine ($C_7$ ie 7 membered);

$O_1$: oxirane ($C_3$ ie 3 membered), oxetane ($C_4$ ie 4 membered), oxolane (tetrahydrofuran) ($C_5$ ie 5 membered), oxole (dihydrofuran) ($C_5$ ie 5 membered), oxane (tetrahydropyran) ($C_6$ ie 6 membered), dihydropyran ($C_6$ ie 6 membered), pyran ($C_6$ ie 6 membered), oxepin ($C_7$ ie 7 membered);

$S_1$: thiirane ($C_3$ ie 3 membered), thietane ($C_4$ ie 4 membered), thiolane (tetrahydrothiophene) ($C_5$ ie 5 membered), thiane (tetrahydrothiopyran) ($C_6$ ie 6 membered), thiepane ($C_7$ ie 7 membered);

$O_2$: dioxolane ($C_5$ ie 5 membered), dioxane ($C_6$ ie 6 membered), and dioxepane ($C_7$ ie 7 membered);

$O_3$: trioxane ($C_6$ ie 6 membered);

$N_2$: imidazolidine ($C_5$ ie 5 membered), pyrazolidine (diazolidine) ($C_5$ ie 5 membered), imidazoline ($C_5$ ie 5 membered), pyrazoline (dihydropyrazole) ($C_5$ ie 5 membered), piperazine ($C_6$ ie 6 membered);

$N_1O_1$: tetrahydrooxazole ($C_5$ ie 5 membered), dihydrooxazole ($C_5$ ie 5 membered), tetrahydroisoxazole ($C_5$ ie 5 membered), dihydroisoxazole ($C_5$ ie 5 membered), morpholine ($C_6$ ie 6 membered), tetrahydrooxazine ($C_6$ ie 6 membered), dihydrooxazine ($C_6$ ie 6 membered), oxazine ($C_6$ ie 6 membered);

$N_1S_1$: thiazoline ($C_5$ ie 5 membered), thiazolidine ($C_5$ ie 5 membered), thiomorpholine ($C_6$ ie 6 membered);

$N_2O_1$: oxadiazine ($C_6$ ie 6 membered);

$O_1S_1$: oxathiole ($C_5$ ie 5 membered) and oxathiane (thioxane) ($C_6$ ie 6 membered); and, $N_1O_1S_1$: oxathiazine ($C_6$ ie 6 membered).

Examples of substituted (non-aromatic) monocyclic heterocyclyl groups include those derived from saccharides, in cyclic form, for example, furanoses ($C_5$ ie 5 membered), such as arabinofuranose, lyxofuranose, ribofuranose, and xylofuranse, and pyranoses ($C_6$ ie 6 membered), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring (3 to 7 membered) joined to another ring by a single atom common to both rings.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms (or otherwise referred to as a 5 to membered heteroaryl group). Preferably, each ring has from 5 to 7 ring atoms, of which from 1 to 4 are ring heteroatoms. Commonly, heteroatoms are selected from oxygen, nitrogen or sulphur.

Examples of $C_{5-20}$ heteroaryl groups include, but are not limited to, $C_5$ heteroaryl groups (5 membered heteroaryl groups) derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups (6 membered heteroaryl groups) derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{5-20}$ heteroaryl groups which comprise fused rings, include, but are not limited to, $C_9$ heteroaryl groups (9 membered heteroaryl groups) derived from benzofuran, isobenzofuran, benzothiophene, indole, isoindole; $C_{10}$ heteroaryl groups (10 membered heteroaryl groups) derived from quinoline, isoquinoline, benzodiazine, pyridopyridine; $C_{14}$ heteroaryl groups (14 membered heteroaryl groups) derived from acridine and xanthene.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —NO$_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. The cyclic amino groups may be substituted on their ring by any of the substituents defined here, for example carboxy, carboxylate and amido.

Aminosulfonyl —S(=O)$_2$NR$^1$R$^2$, wherein R$^1$ and R$^2$ each independently is an amino substituent, as defined for amino groups. Examples of aminosulfony groups include, but are not limited to, —S(=O)$_2$NH$_2$, —S(=O)$_2$NHCH$_3$, —S(=O)$_2$NHCH$_2$CH$_3$ and —S(=O)$_2$N(CH$_3$)$_2$.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and R$^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

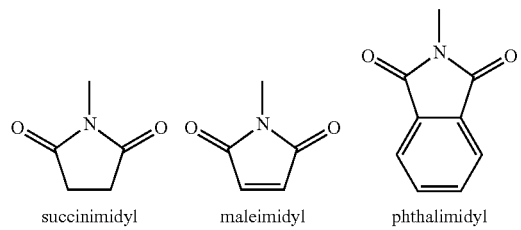

succinimidyl   maleimidyl   phthalimidyl

Ureido: —N(R$^1$)CONR$^2$R$^3$ wherein R$^2$ and R$^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, —OC(=O)C$_6$H$_4$F, and —OC(=O)CH$_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(═O)CH$_3$ and —S(═O)CH$_2$CH$_3$.

Sulfonyl (sulfone): —S(═O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(═O)$_2$CH$_3$ (methanesulfonyl, mesyl), —S(═O)$_2$CF$_3$, —S(═O)$_2$CH$_2$CH$_3$, and 4-methylphenylsulfonyl (tosyl).

Thioamido (thiocarbamyl): —C(═S)NR$^1$R$^2$, wherein R$^1$ and R$^2$ are independently amino substituents, as defined for amino groups. Examples of amido groups include, but are not limited to, —C(═S)NH$_2$, —C(═S)NHCH$_3$, —C(═S)N(CH$_3$)$_2$, and —C(═S)NHCH$_2$CH$_3$.

Sulfonamino: —NR$^1$S(═O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(═O)$_2$CH$_3$, —NHS(═O)$_2$Ph and —N(CH$_3$)S(═O)$_2$C$_6$H$_5$.

In addition, two or more adjacent substituents may be linked such that together with the atoms to which they are attached from a $C_{3-7}$ cycloalkyl, $C_{3-20}$ heterocyclyl or $C_{5-20}$ aryl ring.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

According to a further aspect of the present invention there is provided a compound of formula I:

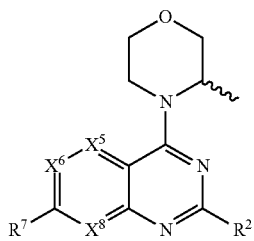

(I)

or a pharmaceutically acceptable salt thereof, wherein:
one or two of $X^5$, $X^6$ and $X^8$ is N, and the others are CH;
$R^7$ is halo, OR$^{O1}$, SR$^{S1}$, NR$^{N1}$R$^{N2}$, NR$^{N7a}$C(═O)R$^{C1}$, NR$^{N7b}$SO$_2$R$^{S2a}$, a $C_{5-20}$ heteroaryl group optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino),
where R$^{O1}$ and R$^{S1}$ are H, a $C_{5-20}$ aryl group, a $C_{5-20}$ heteroaryl group, or a $C_{1-7}$ alkyl group where each $C_{1-7}$ alkyl, $C_{5-20}$ heteroaryl, or $C_{5-20}$ aryl is optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino);

R$^{N1}$ and R$^{N2}$ are independently H, a $C_{1-7}$ alkyl group, a $C_{5-20}$ heteroaryl group, a $C_{5-20}$ aryl group or R$^{N1}$ and R$^{N2}$ together with the nitrogen to which they are bound form a heterocyclic ring containing between 3 and 8 ring atoms, where each $C_{1-7}$ alkyl, $C_{5-20}$ heteroaryl, $C_{5-20}$ aryl or heterocyclic is optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino);

R$^{C1}$ is H, a $C_{5-20}$ aryl group, a $C_{5-20}$ heteroaryl group, a $C_{1-7}$ alkyl group or NR$^{N8}$R$^{N9}$ where R$^{N8}$ and R$^{N9}$ are independently selected from H, a $C_{1-7}$ alkyl group, a $C_{5-20}$ heteroaryl group, a $C_{5-20}$ aryl group or R$^{N8}$ and R$^{N9}$ together with the nitrogen to which they are bound form a heterocyclic ring containing between 3 and 8 ring atoms, where each $C_{1-7}$ alkyl, $C_{5-20}$ heteroaryl, $C_{5-20}$ aryl or heterocyclic ring is optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino);

R$^{S2a}$ is H, a $C_{5-20}$ aryl group, a $C_{5-20}$ heteroaryl group, or a $C_{1-7}$ alkyl group where each $C_{1-7}$ alkyl, $C_{5-20}$ heteroaryl or $C_{5-20}$ aryl is optionally substituted by one or more groups selected from halo, hydroxyl, nitro, cyano, carboxy, and thiol, or $C_{1-7}$ alkyl, $C_{2-7}$ alkenyl, $C_{2-7}$ alkynyl, $C_{3-7}$ cycloalkyl, $C_{3-7}$ cycloalkenyl, $C_{3-20}$ heterocyclyl, $C_{5-20}$ aryl, $C_{5-20}$ heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N7a}$ and $R^{N7b}$ are H or a $C_{1-4}$alkyl group;

$R^2$ is H, halo, $OR^{O2}$, $SR^{S2b}$, $NR^{N5}R^{N6}$, a $C_{5-20}$ heteroaryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), wherein $R^{O2}$ and $R^{S2b}$ are H, a $C_{5-20}$ aryl group, a $C_{5-20}$ heteroaryl group, or a $C_{1-7}$ alkyl group where each $C_{1-7}$alkyl, $C_{5-20}$heteroaryl or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N5}$ and $R^{N6}$ are independently H, a $C_{1-7}$ alkyl group, a $C_{5-20}$ heteroaryl group, a $C_{5-20}$ aryl group, or $R^{N5}$ and $R^{N6}$ together with the nitrogen to which they are bound form a heterocyclic ring containing between 3 and 8 ring atoms where each $C_{1-7}$alkyl, $C_{5-20}$heteroaryl, $C_{5-20}$aryl or heterocyclic ring is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino).

According to a further aspect of the present invention there is provided a compound of formula Ia or Ib:

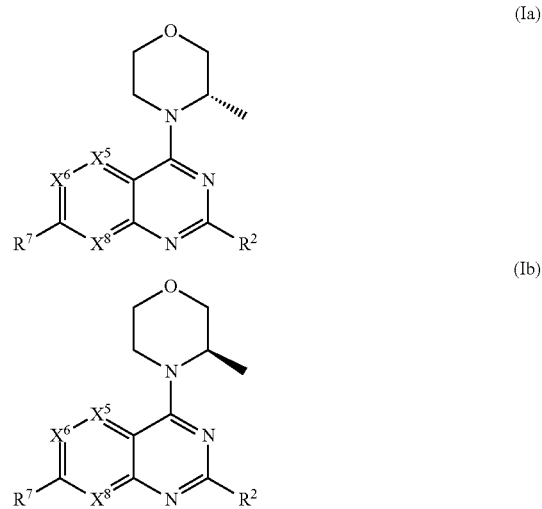

or a pharmaceutically acceptable salt thereof, wherein:

one or two of $X^5$, $X^6$ and $X^8$ is N, and the others are CH;

$R^7$ is halo, $OR^{O1}$, $SR^{S1}$, $NR^{N1}R^{N2}$, $NR^{N7a}C(=O)R^{C1}$, $NR^{N7b}SO_2R^{S2a}$, a $C_{5-20}$ heteroaryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), where $R^{O1}$ and $R^{S1}$ are H, a $C_{5-20}$ aryl group, a $C_{5-20}$ heteroaryl group, or a $C_{1-7}$ alkyl group where each $C_{1-7}$alkyl, $C_{5-20}$heteroaryl, or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N1}$ and $R^{N2}$ are independently H, a $C_{1-7}$ alkyl group, a $C_{5-20}$heteroaryl group, a $C_{5-20}$ aryl group or $R^{N1}$ and $R^{N2}$ together with the nitrogen to which they are bound form a heterocyclic ring containing between 3 and 8 ring atoms, where each $C_{1-7}$alkyl, $C_{5-20}$heteroaryl, $C_{5-20}$aryl or heterocyclic is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{C1}$ is H, a $C_{5-20}$ aryl group, a $C_{5-20}$ heteroaryl group, a $C_{1-7}$ alkyl group or $NR^{N8}R^{N9}$ where $R^{N8}$ and $R^{N9}$ are independently selected from H, a $C_{1-7}$ alkyl group, a $C_{5-20}$ heteroaryl group, a $C_{5-20}$ aryl group or $R^{N8}$ and $R^{N9}$ together with the nitrogen to which they are bound form a heterocyclic ring containing between 3 and 8 ring atoms, where each $C_{1-7}$alkyl, $C_{5-20}$heteroaryl, $C_{5-20}$aryl or heterocyclic ring is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{S2a}$ is H, a $C_{5-20}$ aryl group, a $C_{5-20}$ heteroaryl group, or a $C_{1-7}$ alkyl group where each $C_{1-7}$alkyl, $C_{5-20}$heteroaryl or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N7a}$ and $R^{N7b}$ are H or a $C_{1-4}$ alkyl group;

$R^2$ is H, halo, $OR^{O2}$, $SR^{S2b}$, $NR^{N5}R^{N6}$, a $C_{5-20}$ heteroaryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), wherein $R^{O2}$ and $R^{S2b}$ are H, a $C_{5-20}$ aryl group, a $C_{5-20}$ heteroaryl group, or a $C_{1-7}$ alkyl group where each $C_{1-7}$alkyl, $C_{5-20}$heteroaryl or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$ cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N5}$ and $R^{N6}$ are independently H, a $C_{1-7}$ alkyl group, a $C_{5-20}$ heteroaryl group, a $C_{5-20}$ aryl group, or $R^{N5}$ and $R^{N6}$ together with the nitrogen to which they are bound form a heterocyclic ring containing between 3 and 8 ring atoms where each $C_{1-7}$alkyl, $C_{5-20}$heteroaryl, $C_{5-20}$aryl or heterocyclic ring is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino).

According to a further aspect of the present invention there is provided a compound of formula Ia:

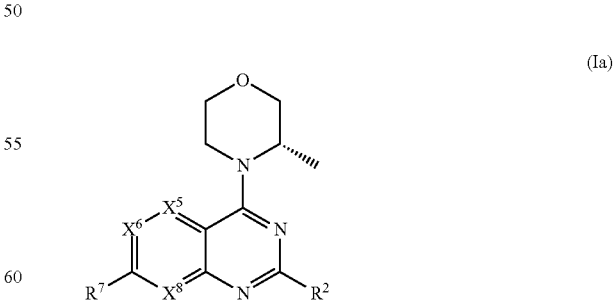

(Ia)

or a pharmaceutically acceptable salt thereof, wherein:
one or two of $X^5$, $X^6$ and $X^8$ is N, and the others are CH;
$R^7$ is halo, $OR^{O1}$, $SR^{S1}$, $NR^{N1}R^{N2}$, $NR^{N7a}C(=O)R^{C1}$, $NR^{N7b}SO_2R^{S2a}$, a $C_{5-20}$ heteroaryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), where $R^{O1}$ and $R^{S1}$ are H, a $C_{5-20}$ aryl group, a $C_{5-20}$ heteroaryl group, or a $C_{1-7}$ alkyl group where each $C_{1-7}$alkyl, $C_{5-20}$heteroaryl, or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N1}$ and $R^{N2}$ are independently H, a $C_{1-7}$ alkyl group, a $C_{5-20}$heteroaryl group, a $C_{5-20}$ aryl group or $R^{N1}$ and $R^{N2}$ together with the nitrogen to which they are bound form a heterocyclic ring containing between 3 and 8 ring atoms, where each $C_{1-7}$alkyl, $C_{5-20}$heteroaryl, $C_{5-20}$aryl or heterocyclic is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{C1}$ is H, a $C_{5-20}$ aryl group, a $C_{5-20}$ heteroaryl group, a $C_{1-7}$ alkyl group or $NR^{N8}R^{N9}$ where $R^{N8}$ and $R^{N9}$ are independently selected from H, a $C_{1-7}$ alkyl group, a $C_{5-20}$ heteroaryl group, a $C_{5-20}$ aryl group or $R^{N8}$ and $R^{N9}$ together with the nitrogen to which they are bound form a heterocyclic ring containing between 3 and 8 ring atoms, where each $C_{1-7}$alkyl, $C_{5-20}$heteroaryl, $C_{5-20}$aryl or heterocyclic ring is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{S2a}$ is H, a $C_{5-20}$ aryl group, a $C_{5-20}$ heteroaryl group, or a $C_{1-7}$ alkyl group where each $C_{1-7}$alkyl, $C_{5-20}$heteroaryl or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N7a}$ and $R^{N7b}$ are H or a $C_{1-4}$ alkyl group;

$R^2$ is H, halo, $OR^{O2}$, $SR^{S2b}$, $NR^{N5}R^{N6}$, a $C_{5-20}$ heteroaryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), or a $C_{5-20}$ aryl group optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino), wherein $R^{O2}$ and $R^{S2b}$ are H, a $C_{5-20}$ aryl group, a $C_{5-20}$ heteroaryl group, or a $C_{1-7}$ alkyl group where each $C_{1-7}$alkyl, $C_{5-20}$heteroaryl or $C_{5-20}$aryl is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino);

$R^{N5}$ and $R^{N6}$ are independently H, a $C_{1-7}$ alkyl group, a $C_{5-20}$ heteroaryl group, a $C_{5-20}$ aryl group, or $R^{N5}$ and $R^{N6}$ together with the nitrogen to which they are bound form a heterocyclic ring containing between 3 and 8 ring atoms where each $C_{1-7}$alkyl, $C_{5-20}$heteroaryl, $C_{5-20}$aryl or heterocyclic ring is optionally substituted by one or more groups selected from halo, hydroxyl, nitro, cyano, carboxy, and thiol, or $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino (each optionally substituted with one or more groups selected from halo, hydroxyl, nitro, cyano, carboxy, thiol, $C_{1-7}$alkyl, $C_{2-7}$alkenyl, $C_{2-7}$alkynyl, $C_{3-7}$cycloalkyl, $C_{3-7}$cycloalkenyl, $C_{3-20}$heterocyclyl, $C_{5-20}$aryl, $C_{5-20}$heteroaryl, ether, acyl, ester, amido, amino, acylamido, ureido, acyloxy, thioether, sulfoxide, sulfonyl, thioamido and sulfonamino).

Further Preferences

The following preferences can apply to each aspect of the present invention, where applicable. The preferences for each group may be combined with those for any or all of the other groups, as appropriate.

$X^5$, $X^6$, and $X^8$

When two of $X^5$, $X^6$ and $X^8$ are N, preferably $X^5$ and $X^8$ are N.

It is preferred that only one of $X^5$, $X^6$ and $X^8$ is N. More preferably one of $X^5$ and $X^8$ is N, and most preferably $X^8$ is N.

$R^7$ $R^7$ is preferably selected from an optionally substituted $C_{5-20}$ aryl group, $OR^{O1}$, $SR^{S1}$, $NR^{N1}R^{N2}$, $NR^{N7a}C(O)R^{C1}$ and $NR^{N7b}SO_2R^{S2a}$, where $R^{O1}$, $R^{S1}$, $R^{N1}$, $R^{N2}$, $R^{N7a}$, $R^{N7b}$, $R^{C1}$ and $R^{S2a}$ are as previously defined. It is further preferred that $R^7$ is preferably selected from an optionally substituted $C_{5-20}$ aryl group, $OR^{O1}$, $NR^{N1}R^{N2}$, $NR^{N7a}C(O)R^{C1}$ and $NR^{N7b}SO_2R^{S2a}$.

If $R^7$ is $OR^{O1}$, then preferably $R^{O1}$ is a $C_{1-7}$ alkyl group, which may be substituted.

If $R^7$ is $NR^{N1}R^{N2}$, then preferably $R^{N2}$ is selected from H and $C_{1-4}$ alkyl (e.g. methyl) and more preferably is H. If $R^N$ is $C_{1-7}$ alkyl, it is preferably selected from $C_{3-7}$ cycloalkyl. If $R^{N1}$ is $C_{5-20}$ aryl, it is preferably selected from $C_{5-10}$ aryl (e.g. phenyl, pyrrolyl, pyridyl, pyrazolyl, furanyl, thiophenyl, pyrazinyl, pyrimidinyl, tetrazolyl, thiazolyl, indazolyl, imidazolyl, triazolyl, oxadiazolyl) and more preferably $C_{5-6}$ aryl (e.g. phenyl, pyrrolyl, pyridyl, pyrazolyl, furanyl, thiophenyl, pyrazinyl, pyrimidinyl, tetrazolyl, thiazolyl, imidazolyl, triazolyl, oxadiazolyl). Particularly preferred groups include furyl, phenyl, pyridyl, pyrrolyl, pyrazolyl and thiophenyl. The aforementioned groups are optionally substituted, and in some embodiments are preferably substituted. Substituent groups may include, but are not limited to, $C_{1-7}$ alkyl, $C_{3-20}$ heterocyclyl, $C_{5-20}$ aryl, carboxy, ester, ether (eg $C_{1-7}$alkoxy), hydroxy, aryloxy, cyano, halo, nitro, amido, sulfonyl, sulfonylamino, amino sulfonyl and amino.

If $R^7$ is $NR^{N7a}C(O)R^{C1}$, then $R^{N7a}$ is preferably H. $R^{C1}$ may be an optionally substituted $C_{5-20}$ aryl group (e.g. phenyl, imadazolyl, quinoxalinyl), $C_{3-20}$ heterocyclyl, $C_{1-7}$ alkyl (e.g. propenyl, methyl (substituted with thiophenyl)) or $NR^{N8}R^{N9}$. $R^{N8}$ is preferably hydrogen, and $R^{N9}$ is preferably $C_{1-7}$ alkyl (e.g. ethyl).

If $R^7$ is $NR^{N7b}SO_2R^{S2a}$, then $R^{N7b}$ is preferably H. $R^{S2a}$ is preferably $C_{1-7}$ alkyl (e.g. methyl).

If $R^7$ is a $C_{5-20}$ aryl group, it is more preferably an optionally substituted $C_{5-10}$ aryl and more preferably an optionally substituted $C_{5-6}$ aryl group. Most preferably it is an optionally substituted phenyl group, wherein the optional substituents are preferably selected from halo, hydroxyl, $C_{1-7}$ alkyl, $C_{1-7}$ alkoxy, $C_{5-6}$arylamino and $C_{1-7}$ alkylamino and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino and $C_{1-7}$ alkylamino.

If $R^7$ is a 5 to 20 membered heteroaryl group, it is preferably an optionally substituted 5 to 10 membered heteroaryl and more preferably an optionally substituted 5 or 6 membered heteroaryl group.

In one embodiment, $R^7$ is an optionally substituted $C_{5-20}$ aryl group or an optionally substituted 5 to 20 membered heteroaryl group, wherein the optional substituents are preferably selected from halo, hydroxyl, cyano, $C_{1-7}$ alkyl, $C_{1-7}$ alkoxy, sulfonamino (for example $-NHS(=O)_2C_{1-7}$alkyl) amino (for example $-NH_2$, $C_{5-6}$arylamino, $C_{1-7}$alkylamino, and di-($C_{1-7}$alkyl)amino), and amido (for example $-CONH_2$, $-CONHC_{1-7}$alkyl, $-CON(C_{1-7}$alkyl$)_2$ and $-CONH$heterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $-NHS(=O)_2C_{1-7}$alkyl, $C_{5-6}$arylamino, di-($C_{1-7}$alkyl)amino and $C_{1-7}$alkylamino.

In one embodiment, $R^7$ is an optionally substituted phenyl group, wherein the optional substituents are preferably selected from halo, hydroxyl, cyano, $C_{1-7}$ alkyl, $C_{1-7}$ alkoxy, sulfonamino (for example $-NHS(=O)_2C_{1-7}$alkyl) amino (for example $-NH_2$, $C_{5-6}$arylamino, $C_{1-7}$alkylamino, and di-($C_{1-7}$alkyl)amino), and amido (for example $-CONH_2$, $-CONHC_{1-7}$alkyl, $-CON(C_{1-7}$alkyl$)_2$ and $-CONH$heterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $-NHS(=O)_2C_{1-7}$alkyl, $C_{5-6}$arylamino, di-($C_{1-7}$alkyl)amino and $C_{1-7}$alkylamino.

In one embodiment, $R^7$ is an optionally substituted phenyl group, wherein the optional substituents are preferably selected from halo, hydroxyl, cyano, $C_{1-7}$ alkyl, $C_{1-7}$ alkoxy, amino (for example $-NH_2$, $C_{5-6}$arylamino, $C_{1-7}$alkylamino, and di-($C_{1-7}$alkyl)amino), and amido (for example $-CONH_2$, $-CONHC_{1-7}$alkyl, $-CON(C_{1-7}$alkyl$)_2$ and $-CONH$heterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl) amino and $C_{1-7}$alkylamino.

In one embodiment, $R^7$ is an optionally substituted phenyl group, wherein the optional substituents are preferably selected from fluoro, hydroxyl, cyano, nitro, methyl, methoxy, $-OCH_2CH_3$, $-NH_2$, $-NHSO_2CH_3$, $-CH_2NHSO_2CH_3$, $-OCHF_2$, $-CH_2OH$, $-CO_2H$, $-CONH_2$, $-CONHMe$, $-CONHEt$, $-CONHCH(CH_3)_2$, $-CONHCH_2CH_2F$, $-CONHCH_2CHF_2$, $-CONHCH_2CH_2OH$, $-CONMeEt$, $-CONMe_2$, N-methylpiperazinylcarbonyl and 4-hydroxypiperidinylcarbonyl.

In one embodiment, $R^7$ is an optionally substituted phenyl group, wherein the optional substituents are preferably selected from fluoro, hydroxyl, cyano, nitro, methyl, methoxy, $-CH_2OH$, $-CO_2H$, $-CONH_2$, $-CONHMe$, $-CONHEt$, $-CONHCH_2CH_2F$, $-CONHCH_2CHF_2$, $-CONHCH_2CH_2OH$, $-CONMeEt$, $-CONMe_2$, N-methylpiperazinylcarbonyl and 4-hydroxypiperidinylcarbonyl.

In one embodiment, $R^7$ is an optionally substituted phenyl group, wherein the optional substituents are preferably selected from methoxy, $-OCH_2CH_3$, $-NH_2$, $-NHSO_2CH_3$, $-CH_2NHSO_2CH_3$, $-OCHF_2$, $-CH_2OH$, $-CONH_2$, $-CONHMe$ and $-CONHCH(CH_3)_2$.

In one embodiment R$^7$ is an optionally substituted 5 or 6 membered nitrogen containing heteroaryl group such as a pyridine group, wherein the optional substituents are selected from halo, hydroxyl, cyano, C$_{1-7}$ alkyl, C$_{1-7}$ alkoxy, amino (for example —NH$_2$, C$_{5-6}$arylamino, C$_{1-7}$ alkylamino, and di-(C$_{1-7}$alkyl)amino), and amido (for example —CO$_2$NH$_2$, —CO$_2$NHC$_{1-7}$alkyl, —CO$_2$N(C$_{1-7}$alkyl)$_2$ and —CONHheterocycyl) and wherein the substitutent alkyl, alkoxy, or aryl groups may be further optionally substituted by one or more groups selected from halo, hydroxyl, C$_{1-7}$ alkyl, C$_{1-7}$ alkoxy, C$_{5-6}$aryl, C$_{5-6}$arylamino, di-(C$_{1-7}$alkyl)amino and C$_{1-7}$alkylamino.

In one embodiment, R$^7$ is a pyridinyl group optionally substituted halo, hydroxyl, cyano, C$_{1-7}$ alkyl, C$_{1-7}$ alkoxy, amino (for example —NH$_2$, C$_{5-6}$arylamino, C$_{1-7}$alkylamino, and di-(C$_{1-7}$alkyl)amino), and amido (for example —CO$_2$NH$_2$, —CO$_2$NHC$_{1-7}$alkyl, —CO$_2$N(C$_{1-7}$alkyl)$_2$ and —CONHheterocycyl) and wherein the substitutent alkyl, alkoxy, or aryl groups may be further optionally substituted by one or more groups selected from halo, hydroxyl, C$_{1-7}$ alkyl, C$_{1-7}$ alkoxy, C$_{5-6}$aryl, C$_{5-6}$arylamino, di-(C$_{1-7}$alkyl)amino and C$_{1-7}$alkylamino.

In one embodiment, R$^7$ is a pyridinyl group optionally substituted with NH$_2$.

In one embodiment, R$^7$ is an optionally substituted phenyl group selected from

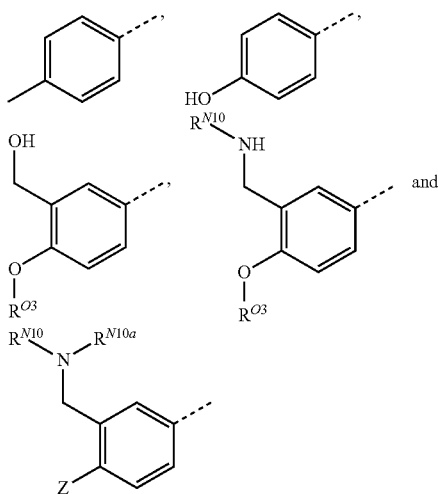

wherein
Z is H, F or OR$^{O3}$;
R$^{O3}$ is selected from hydrogen or an optionally substituted C$_{1-6}$ alkyl group;
R$^{N10}$ is selected from hydrogen, C(O)R$^{C2}$, C(S)R$^{C3}$, SO$_2$R$^{S3}$, an optionally substituted C$_{5-20}$ heterocyclyl group, an optionally substituted C$_{5-20}$ aryl group, or an optionally substituted C$_{1-10}$ alkyl group where R$^{C2}$ and R$^{C3}$ are selected from H, an optionally substituted C$_{5-20}$ aryl group, an optionally substituted C$_{5-20}$ heterocyclyl group, an optionally substituted C$_{1-7}$ alkyl group or NR$^{N1}$R$^{N12}$, where R$^{N11}$ and R$^{N12}$ are independently selected from H, an optionally substituted C$_{1-7}$ alkyl group, an optionally substituted C$_{5-20}$ heterocyclyl group, an optionally substituted C$_{5-20}$ aryl group or R$^{N11}$ and R$^{N12}$ together with the nitrogen to which they are bound form a heterocyclic ring containing between 3 and 8 ring atoms; and R$^{S3}$ is selected from H, an optionally substituted C$_{5-20}$ aryl group, an optionally substituted C$_{5-20}$ heteroaryl group, or an optionally substituted C$_{1-7}$ alkyl group;
R$^{N10a}$ is selected from hydrogen or an optionally substituted C$_{1-10}$ alkyl group; or
R$^{N10}$ and R$^{N10a}$ together with the nitrogen to which they are bound form an optionally substituted heterocyclic ring containing between 3 and 8 ring atoms.

In one embodiment, R$^7$ is an optionally substituted phenyl group selected from

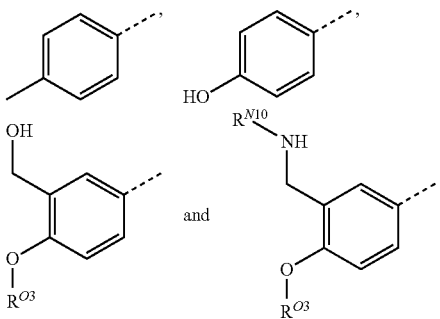

wherein
R$^{O3}$ is selected from hydrogen or an optionally substituted C$_{1-6}$ alkyl group; and
R$^{N10}$ is selected from C(O)R$^{C2}$, C(S)R$^{C3}$, SO$_2$R$^{S3}$, an optionally substituted C$_{5-20}$ heteroaryl group, an optionally substituted C$_{5-20}$ aryl group, or an optionally substituted C$_{1-10}$ alkyl group where R$^{C2}$ and R$^{C3}$ are selected from H, an optionally substituted C$_{5-20}$ aryl group, an optionally substituted C$_{5-20}$ heteroaryl group, an optionally substituted C$_{1-7}$ alkyl group or NR$^{N11}$R$^{N12}$, where R$^{N11}$ and R$^{N12}$ are independently selected from H, an optionally substituted C$_{1-7}$ alkyl group, an optionally substituted C$_{5-20}$ heteroaryl group, an optionally substituted C$_{5-20}$ aryl group or R$^{N11}$ and R$^{N12}$ together with the nitrogen to which they are bound form a heterocyclic ring containing between 3 and 8 ring atoms; and R$^{S3}$ is selected from H, an optionally substituted C$_{5-20}$ aryl group, an optionally substituted C$_{5-20}$ heteroaryl group, or an optionally substituted C$_{1-7}$ alkyl group.

In one embodiment, R$^7$ is

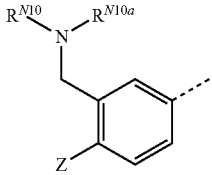

wherein
Z is H, F or OR$^{O3}$;
R$^{N10}$ is selected from hydrogen, C(O)R$^{C2}$, an optionally substituted C$_{5-20}$ heteroaryl group, an optionally substituted C$_{5-20}$ aryl group, or an optionally substituted C$_{1-10}$ alkyl group where R$^{C2}$ are selected from H, an optionally substituted C$_{5-20}$ aryl group, an optionally substituted C$_{5-20}$ heterocyclyl group, an optionally substituted C$_{1-7}$ alkyl group or NR$^{N11}$R$^{N12}$, where R$^{N11}$ and R$^{N12}$ are independently selected from H, an optionally substituted C$_{1-7}$ alkyl group, an optionally substituted C$_{5-20}$ heterocyclyl group, an optionally substituted C$_{5-20}$ aryl group or R$^{N11}$ and R$^{N12}$ together with the nitrogen to which they are bound form a heterocyclic ring containing between 3 and 8 ring atoms;
$R^{N10a}$ is selected from hydrogen or an optionally substituted $C_{1-10}$ alkyl group; or
$R^{N10}$ and $R^{N10a}$ together with the nitrogen to which they are bound form an optionally substituted heterocyclic ring containing between 3 and 8 ring atoms.

In one embodiment, $R^7$ is

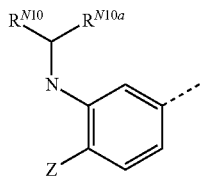

wherein
Z is H, F or $OR^{O3}$;
$R^{N10}$ is selected from hydrogen, $C(O)R^{C2}$, an optionally substituted $C_{5-6}$ heteroaryl group, an optionally substituted $C_6$ aryl group, or an optionally substituted $C_{1-10}$ alkyl group where $R^{C2}$ are selected from $CH_3$ or $CH_2OH$;
$R^{N10a}$ is selected from hydrogen or an optionally substituted $C_{1-10}$ alkyl group; or
$R^{N10}$ and $R^{N10a}$ together with the nitrogen to which they are bound form an optionally substituted heterocyclic ring containing between 3 and 8 ring atoms;
and where the optional substitutents are selected from cyano, halo, hydroxyl, $C_{1-7}$ alkyloxy, $C_{1-7}$ alkylamino and di-$C_{1-7}$ alkylamino.

In one embodiment, $R^7$ is

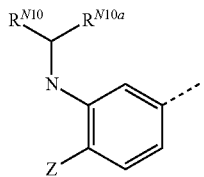

wherein
Z is H, F or $OR^{O3}$;
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyclopropyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms;
and where the optional substitutents are selected from halo, hydroxyl, $C_{1-7}$ alkyloxy.

In a further embodiment of the invention $R^7$ is selected from

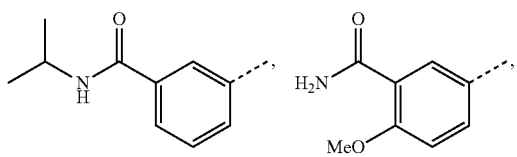

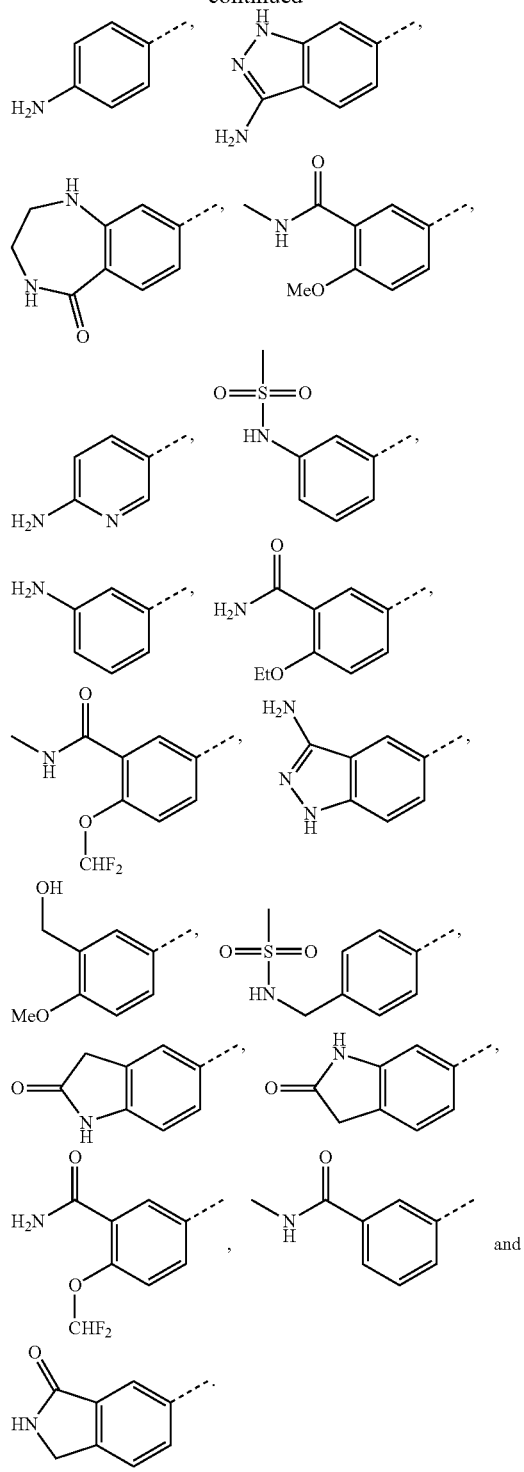

$R^2$

In one embodiment $R^2$ is $OR^{O2}$ where $R^{O2}$ is an optionally substituted $C_{1-7}$ alkyl group.

In one embodiment $R^2$ is $OR^{O2}$ where $R^{O2}$ is —CH$_3$, —CH$_2$CH$_3$, —CH$_2$CH$_2$OH, —CH$_2$CH$_2$OCH$_3$, or —CH(CH$_3$)CH$_2$N(CH$_3$)$_2$.

Preferably $R^2$ is $NR^{N5}R^{N6}$, where $R^{N5}$ and $R^{N6}$ are as previously defined, and more preferably $R^{N5}$ and $R^{N6}$ together with the nitrogen to which they are bound form a heterocyclic ring containing between 3 and 8 ring atoms, which may optionally be substituted. The ring preferably has from 5 to 7 ring atoms. Preferred optionally substituted groups include, but are not limited to, imidazolyl, morpholino, thiomorpholino, piperadinyl, homopiperadinyl, piperazinyl (preferably N-substituted), homopiperazinyl (preferably N-substituted) and pyrrolidinyl.

Preferred N-substituents for the piperazinyl and homopiperazinyl groups include esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$.

Preferred N-substituents for the piperazinyl and homopiperazinyl groups include $C_{1-7}$ alkyl groups or esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$.

Preferred C-substituents for the groups include $C_{1-4}$ alkyl, preferably methyl. The groups may bear one or more substituents, for example one or two substituents.

Preferred C-substituents for the groups include phenyl, ester, amide and $C_{1-4}$ alkyl, preferably methyl, aminomethyl, hydroxymethyl or hydroxyethyl. The groups may bear one or more substituents, for example one or two substituents.

In one embodiment $R^2$ is $NR^{N5}R^{N6}$ where $R^{N5}$ and $R^{N6}$ together with the nitrogen to which they are bound form a heterocyclic ring containing 5 to 7 ring atoms which may be optionally be substituted, wherein the optional substituents are selected from amino, cyano, halo, hydroxyl, ester, a $C_{3-7}$ cycloalkyl ring, a $C_6$carboaryl ring, a heterocyclic ring containing 5 to 7 ring atoms and $C_{1-7}$ saturated alkyl and $C_{1-7}$ saturated alkoxy (wherein the heterocyclic ring, the cycloalkyl ring, the carboaryl ring, the saturated alkyl and alkoxy groups may be optionally substituted by one or more groups selected from halo, hydroxyl, $C_{1-7}$ alkoxy, amino and $C_{5-6}$ aryl)

In one embodiment $R^2$ is $NR^{N5}R^{N6}$ where $R^{N5}$ and $R^{N6}$ together with the nitrogen to which they are bound form a heterocyclic ring containing between 5 to 7 ring atoms which may be optionally be substituted, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl)

In one embodiment $R^2$ is $NR^{N5}R^{N6}$, where $R^{N5}$ is an optionally substituted $C_{1-7}$ alkyl group or an optionally substituted phenyl group, and $R^{N6}$ is hydrogen.

In one embodiment $R^2$ is $NR^{N5}R^{N6}$, where $R^{N5}$ is —CH(CH$_3$)CH$_2$OCH$_3$, cyclopentyl or a phenyl group, and $R^{N6}$ is hydrogen.

Preferred $R^2$ groups are pyrrolidinyl, morpholino, piperadinyl and homopiperadinyl groups. More preferred groups are morpholino and piperadinyl. These are preferably substituted with one or more alkyl substituents, for example methyl or ethyl substituents. More preferably these are substituted with one or two methyl substituents. If these groups bear two methyl substituents, these are preferably on separate carbon atoms. The alkyl substituents may also be optionally substituted. Examples of optional substituents of the alkyl substitutents include halo, hydroxy, ether or amino. Particularly preferred groups include methylmorpholino groups, dimethylmorpholino groups and methyl piperidinyl groups, for example:

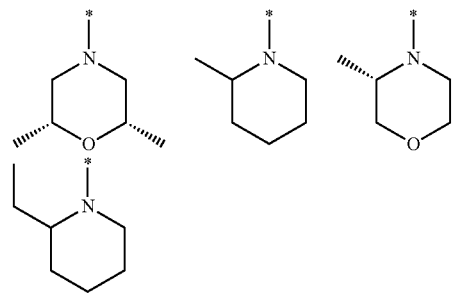

More preferred groups are morpholino and piperadinyl. These are preferably substituted with one or more alkyl substituents, for example methyl or ethyl substituents. More preferably these are substituted with one or two methyl substituents. If these groups bear two methyl substituents, these are preferably on separate carbon atoms. Particularly preferred groups include methylmorpholino groups, dimethylmorpholino groups and methyl piperidinyl groups, for example:

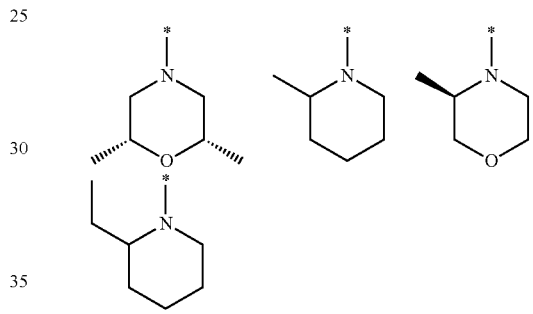

Preferred $R^2$ groups are pyrrolidinyl, morpholino, piperadinyl and homopiperadinyl groups. More preferred groups are morpholino and piperadinyl. These are preferably substituted with one or more alkyl substituents, for example methyl or ethyl substituents. More preferably these are substituted with one or two methyl substituents. If these groups bear two methyl substituents, these are preferably on separate carbon atoms. The alkyl substituents may also be optionally substituted. Examples of optional substituents of the alkyl substitutents include halo, hydroxy, ether or amino. Particularly preferred groups include methylmorpholino groups, dimethylmorpholino groups and methyl piperidinyl groups, for example:

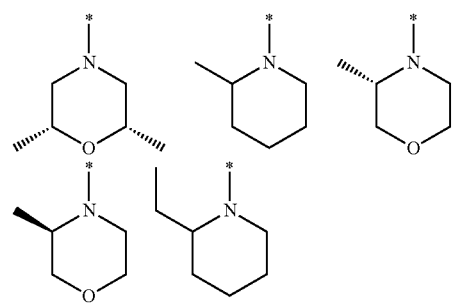

Further preferred $R^2$ groups are optionally substituted pyrrolidinyl, morpholino, piperadinyl and homopiperadinyl wherein the optional substituents are selected from hydroxyl, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), amido (for example —$CONH_2$, —$CONHC_{1-7}$alkyl, —$CON(C_{1-7}alkyl)_2$), ester (for example —$CO_2C_{1-7}$alkyl), $C_6$aryl and 3 to 7 membered heterocyclyl group and wherein the substitutent alkyl, alkoxy, aryl or heterocyclyl groups may be further optionally substituted by one or more groups selected from halo, hydroxyl, $C_{1-7}$ alkyl, $C_{1-7}$ alkoxy, —$NH_2$, di-($C_{1-7}$alkyl)amino and $C_{1-7}$alkylamino. More preferred groups are morpholino, piperadinyl and homopiperadinyl which may be optionally substituted by one or more groups selected from hydroxyl, methyl, ethyl, —$CO_2Me$, —$CO_2Et$, —$CH_2OH$, —$CH_2Ome$, —$CH_2NMe_2$, —$CONH_2$, —$CONHMe$, —$CONMe_2$, phenyl, pyrrolidinyl, morpholino and piperadinyl.

In a further embodiment of the invention $R^2$ is selected from

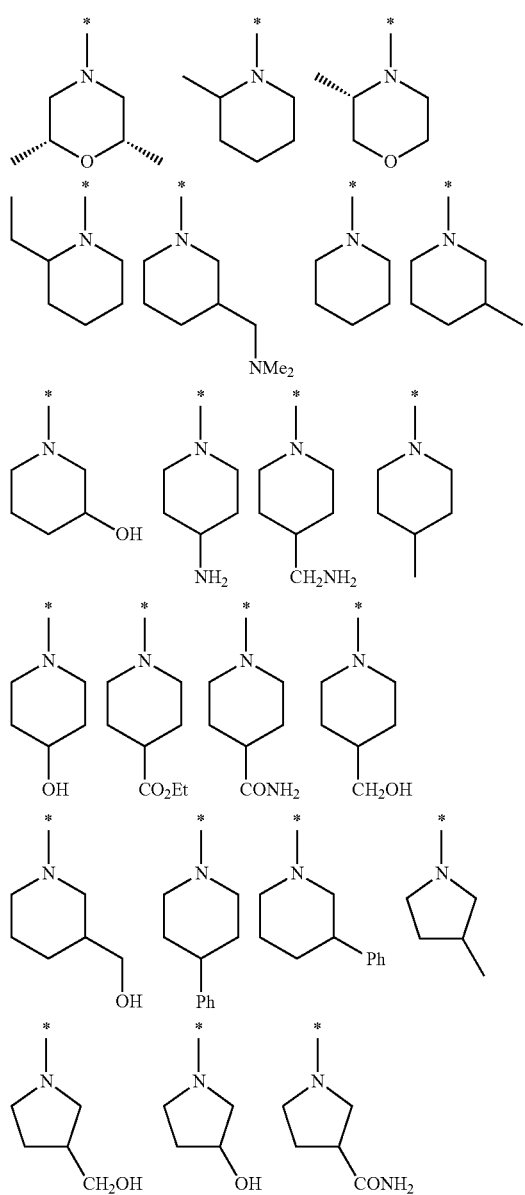
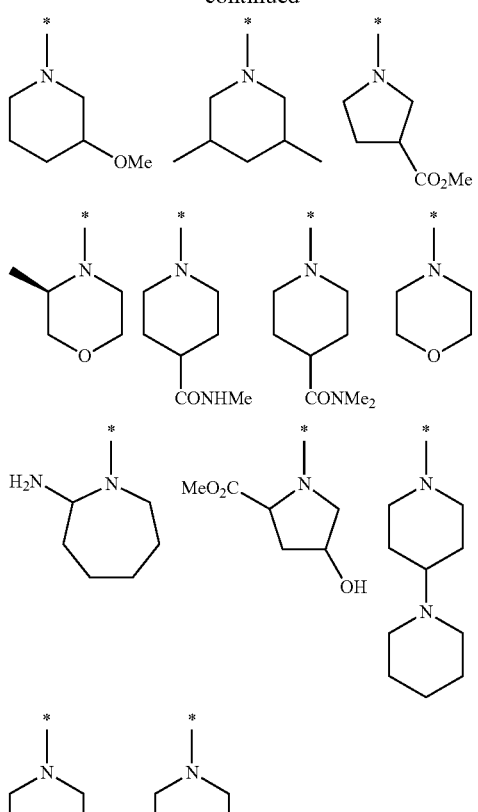

In a further embodiment of the invention $R^2$ is selected from

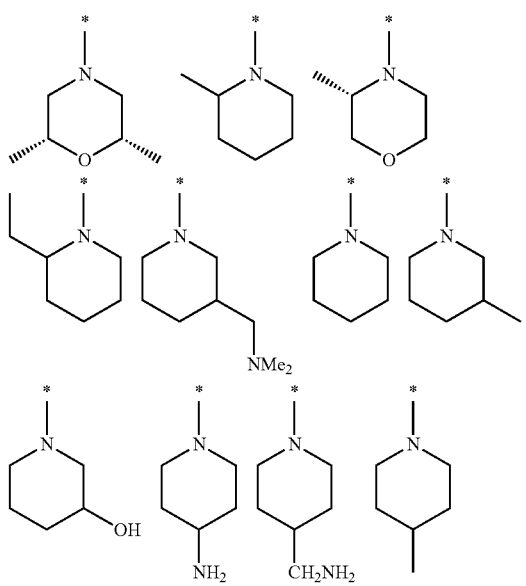

-continued

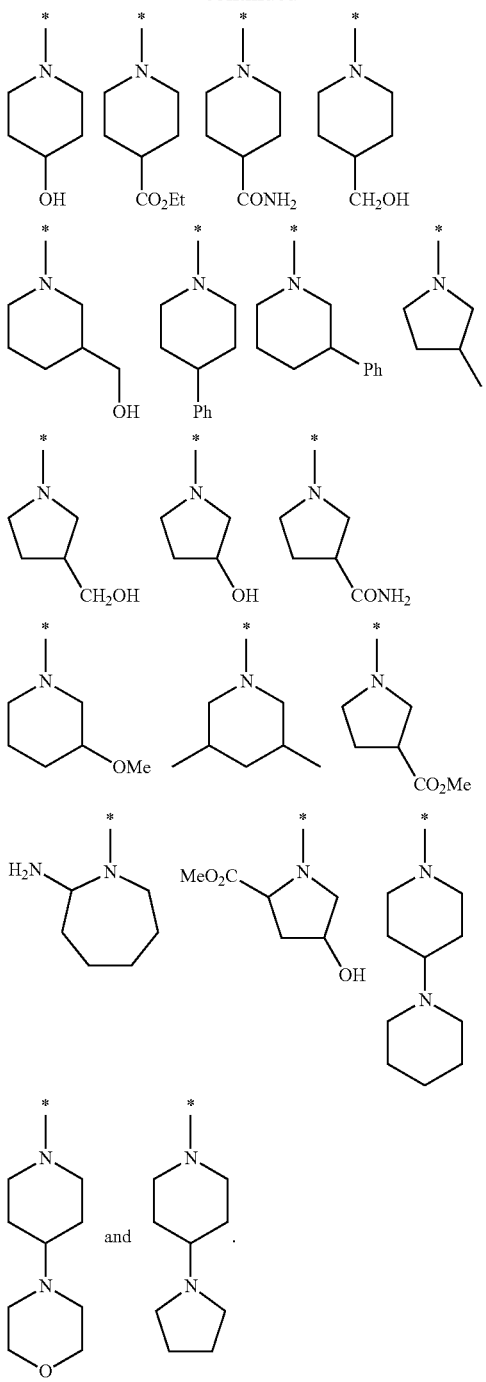

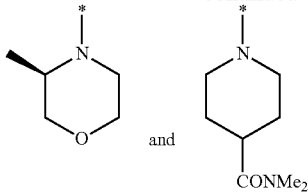

In an embodiment of the invention, there is provided a subset of compounds of formula (I) or (Ia), and pharmaceutically acceptable salts thereof, in which:

only one of $X^5$, $X^6$ and $X^8$ is N;

$R^7$ is selected from an optionally substituted $C_{5-20}$ aryl group, an optionally substituted 5- to 20-membered heteraryl group, $OR^{O1}$, $NR^{N1}R^{N2}$, $NR^{N7a}C(=O)R^{C1}$ and $NR^{N7b}SO_2R^{S2a}$; and $R^2$ is selected from $OR^{O2}$, $NR^{N5}R^{N6}$, an optionally substituted $C_{5-20}$ heteroaryl group, and an optionally substituted $C_{5-20}$ aryl group.

In another embodiment, there is provided a subset of compounds of formula (I) or (Ia), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is selected from $OR^{O2}$, $NR^{N5}R^{N6}$, an optionally substituted $C_{5-6}$heteroaryl group, and an optionally substituted $C_6$ aryl group.

In another embodiment, there is provided a subset of compounds of formula (I) or (Ia), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is $NR^{N5}R^{N6}$ where $R^{N5}$ and $R^{N6}$ together with the nitrogen to which they are bound form a heterocyclic ring containing between 5 to 7 ring atoms which may be optionally be substituted, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment of the invention $R^2$ is selected from

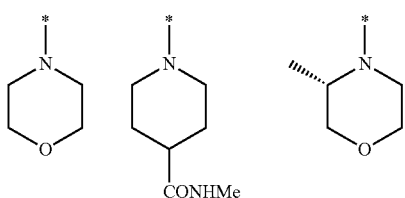

In a further embodiment, there is provided a subset of compounds of formula (I) or (Ia), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is $NR^{N5}R^{N6}$ where $R^{N5}$ and $R^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include $C_{1-7}$ alkyl groups or esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and $C_{1-4}$ alkyl, preferably methyl, aminomethyl, hydroxymethyl or hydroxyethyl.

In an embodiment of the invention, there is provided a subset of compounds of formula (I), (Ia) or (Ib), and pharmaceutically acceptable salts thereof, in which:

only one of $X^5$, $X^6$ and $X^8$ is N;

$R^7$ is selected from an optionally substituted $C_{5-20}$ aryl group, an optionally substituted 5- to 20-membered heteraryl group, $OR^{O1}$, $NR^{N1}R^{N2}$, $NR^{N7a}C(=O)R^{C1}$ and $NR^{N7b}SO_2R^{S2a}$; and $R^2$ is selected from $OR^{O2}$, $NR^{N5}R^{N6}$, an optionally substituted $C_{5-20}$ heteroaryl group, and an optionally substituted $C_{5-20}$ aryl group.

In another embodiment, there is provided a subset of compounds of formula (I), (Ia) or (Ib), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is selected from $OR^{O2}$, $NR^{N5}R^{N6}$, an optionally substituted $C_{5-6}$ heteroaryl group, and an optionally substituted $C_6$ aryl group.

In another embodiment, there is provided a subset of compounds of formula (I), (Ia) or (Ib), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is $NR^{N5}R^{N6}$ where $R^{N5}$ and $R^{N6}$ together with the nitrogen to which they are bound form a heterocyclic ring containing between 5 to 7 ring atoms which may be optionally be substituted, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment, there is provided a subset of compounds of formula (I), (Ia) or (Ib), and pharmaceutically acceptable salts thereof, in which:

only one of $X^5$, $X^6$ and $X^8$ is N;

$R^7$ is an optionally substituted $C_{5-6}$ aryl group or an optionally substituted 5 or 6 membered heteraryl group, wherein the optional substituents are selected from halo, hydroxyl, cyano, $C_{1-7}$ alkyl, $C_{1-7}$ alkoxy, amino (for example —$NH_2$, $C_{5-6}$arylamino, $C_{1-7}$alkylamino, and di-($C_{1-7}$alkyl)amino), and amido (for example —$CONH_2$, —$CONHC_{1-7}$alkyl, —$CON(C_{1-7}$alkyl$)_2$ and —CONHheterocycyl) and wherein the substitutent alkyl, alkoxy, or aryl groups may be further optionally substituted by one or more groups selected from halo, hydroxyl, $C_{1-7}$ alkyl, $C_{1-7}$ alkoxy, $C_{5-6}$aryl, $C_{5-6}$arylamino, di-($C_{1-7}$alkyl)amino and $C_{1-7}$alkylamino; and $R^2$ is $NR^{N5}R^{N6}$ where $R^{N5}$ and $R^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include $C_{1-7}$ alkyl groups or esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and $C_{1-4}$ alkyl, preferably methyl, aminomethyl, hydroxymethyl or hydroxyethyl.

In a further embodiment, there is provided a subset of compounds of formula (I), (Ia) or (Ib), and pharmaceutically acceptable salts thereof, in which:

$X^5$ and $X^6$ are each CH;

$X^8$ is N;

$R^7$ is an optionally substituted phenyl or pyridinyl group, wherein the optional substituents are preferably selected from fluoro, hydroxyl, cyano, nitro, methyl, methoxy, —OCH$_2$CH$_3$, —NH$_2$, —NHSO$_2$CH$_3$, —CH$_2$NHSO$_2$CH$_3$, —OCHF$_2$, —CH$_2$OH, —CO$_2$H, —CONH$_2$, —CONHMe, —CONHEt, —CONHCH(CH$_3$)$_2$, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and R$^2$ is NR$^{N5}$R$^{N6}$ where R$^{N5}$ and R$^{N6}$ together with the nitrogen to which they are bound form a heterocyclic ring containing 5 to 7 ring atoms which may be optionally be substituted, wherein the optional substituents are selected from amino, cyano, halo, hydroxyl, ester, a C$_{3-7}$ cycloalkyl ring, a C$_6$carboaryl ring, a heterocyclic ring containing 5 to 7 ring atoms and C$_{1-7}$ saturated alkyl and C$_{1-7}$ saturated alkoxy (wherein the heterocyclic ring, the cycloalkyl ring, the carboaryl ring, the saturated alkyl and alkoxy groups may be optionally substituted by one or more groups selected from halo, hydroxyl, C$_{1-7}$ alkoxy, amino and C$_{5-6}$ aryl).

In a further embodiment, there is provided a subset of compounds of formula (I), (Ia) or (Ib), and pharmaceutically acceptable salts thereof, in which:

X$^5$ and X$^6$ are each CH;

X$^8$ is N;

R$^7$ is an optionally substituted phenyl or pyridinyl group, wherein the optional substituents are preferably selected from fluoro, hydroxyl, cyano, nitro, methyl, methoxy, —OCH$_2$CH$_3$, —NH$_2$, —NHSO$_2$CH$_3$, —CH$_2$NHSO$_2$CH$_3$, —OCHF$_2$, —CH$_2$OH, —CO$_2$H, —CONH$_2$, —CONHMe, —CONHEt, —CONHCH(CH$_3$)$_2$, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and R$^2$ is NR$^{N5}$R$^{N6}$ where R$^{N5}$ and R$^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include C$_{1-7}$ alkyl groups or esters, in particular, esters bearing a C$_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and C$_{1-4}$ alkyl, preferably methyl, aminomethyl, hydroxymethyl or hydroxyethyl.

In a further embodiment, there is provided a subset of compounds of formula (I) or (Ia), and pharmaceutically acceptable salts thereof, in which:

X$^5$ and X$^6$ are each CH;

X$^8$ is N;

R$^7$ is an optionally substituted phenyl or pyridinyl group, wherein the optional substituents are preferably selected from —NH$_2$, fluoro, hydroxyl, cyano, nitro, methyl, methoxy, —CH$_2$OH, —CO$_2$H, —CONH$_2$, —CONHMe, —CONHEt, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and R$^2$ is NR$^{N5}$R$^{N6}$ where R$^{N5}$ and R$^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include C$_{1-7}$ alkyl groups or esters, in particular, esters bearing a C$_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and C$_{1-4}$ alkyl, preferably methyl, aminomethyl, hydroxymethyl or hydroxyethyl.

In a further embodiment, there is provided a subset of compounds of formula (I), (Ia) or (Ib), and pharmaceutically acceptable salts thereof, in which:

X$^5$ and X$^6$ are each CH;

X$^8$ is N;

R$^7$ is an optionally substituted phenyl or pyridinyl group, wherein the optional substituents are preferably selected from —NH$_2$, fluoro, hydroxyl, cyano, nitro, methyl, methoxy, —CH$_2$OH, —CO$_2$H, —CONH$_2$, —CONHMe, —CONHEt, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and R$^2$ is NR$^{N5}$R$^{N6}$ where R$^{N5}$ and R$^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include C$_{1-7}$ alkyl groups or esters, in particular, esters bearing a C$_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and C$_{1-4}$ alkyl, preferably methyl, aminomethyl, hydroxymethyl or hydroxyethyl.

In a further embodiment, there is provided a subset of compounds of formula (I), (Ia) or (Ib), and pharmaceutically acceptable salts thereof, in which:

X$^5$ and X$^6$ are each CH;

X$^8$ is N;

R$^7$ is an optionally substituted phenyl or pyridinyl group, wherein the optional substituents are preferably selected from fluoro, hydroxyl, cyano, nitro, methyl, methoxy, —OCH$_2$CH$_3$, —NH$_2$, —NHSO$_2$CH$_3$, —CH$_2$NHSO$_2$CH$_3$, —OCHF$_2$, —CH$_2$OH, —CO$_2$H, —CONH$_2$, —CONHMe, —CONHEt, —CONHCH(CH$_3$)$_2$, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and R$^2$ is a group selected from

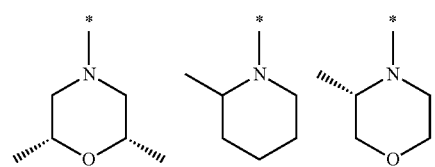

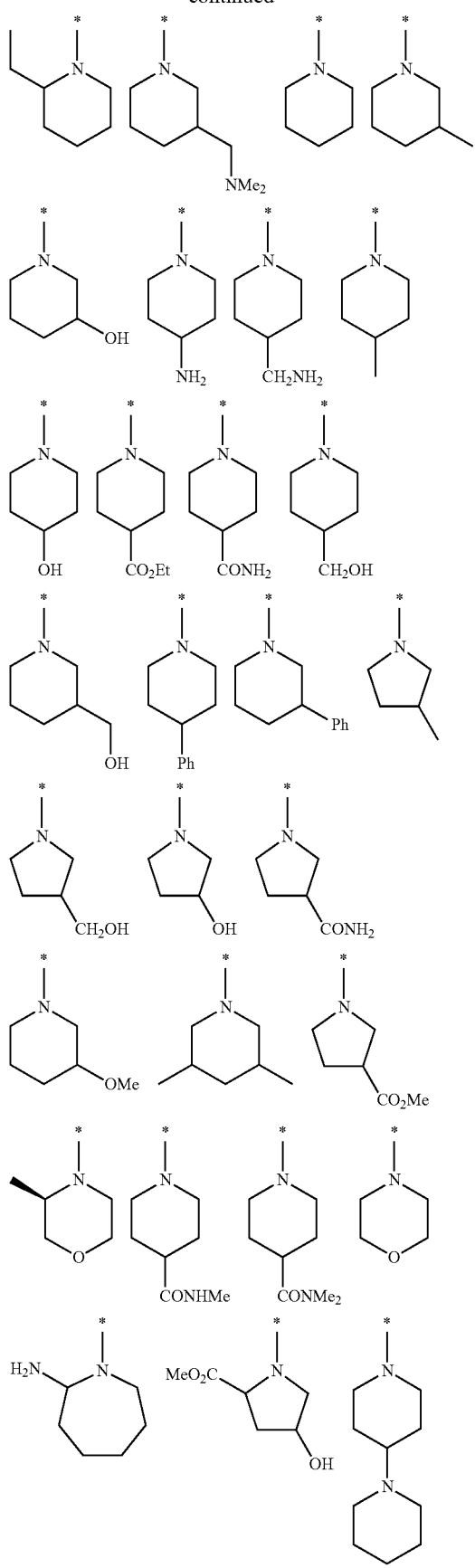

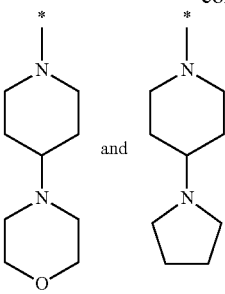

In a further embodiment, there is provided a subset of compounds of formula (I) or (Ia), and pharmaceutically acceptable salts thereof, in which:

$X^5$ and $X^6$ are each CH;

$X^8$ is N;

$R^7$ is an optionally substituted phenyl or pyridinyl group, wherein the optional substituents are preferably selected from —$NH_2$, fluoro, hydroxyl, cyano, nitro, methyl, methoxy, —$CH_2OH$, —$CO_2H$, —$CONH_2$, —CONHMe, —CONHEt, —$CONHCH_2CH_2F$, —$CONHCH_2CHF_2$, —$CONHCH_2CH_2OH$, —CONMeEt, —$CONMe_2$, N-methylpiperazinylcarbonyl and 4-hydroxypiperidinylcarbonyl; and $R^2$ is a group selected from

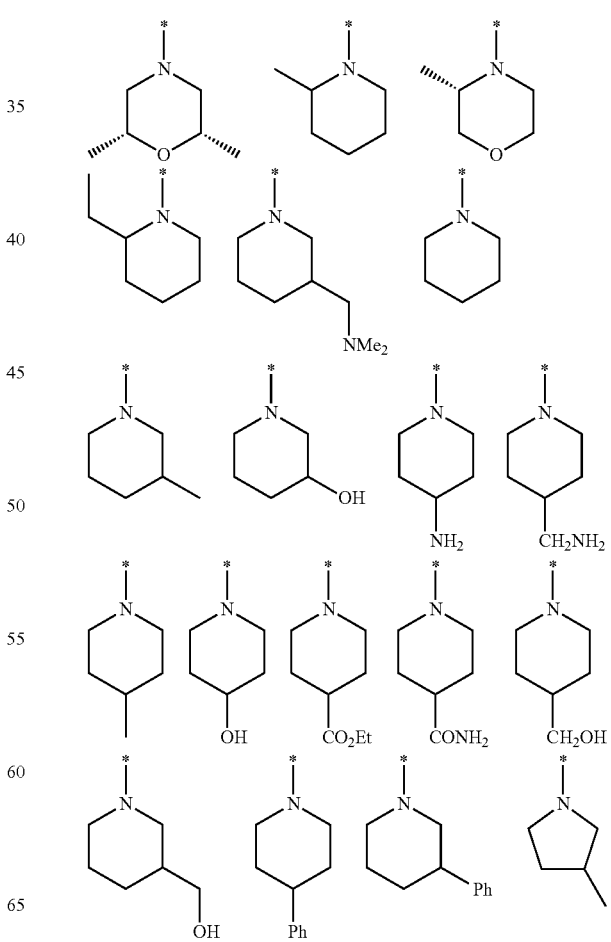

-continued

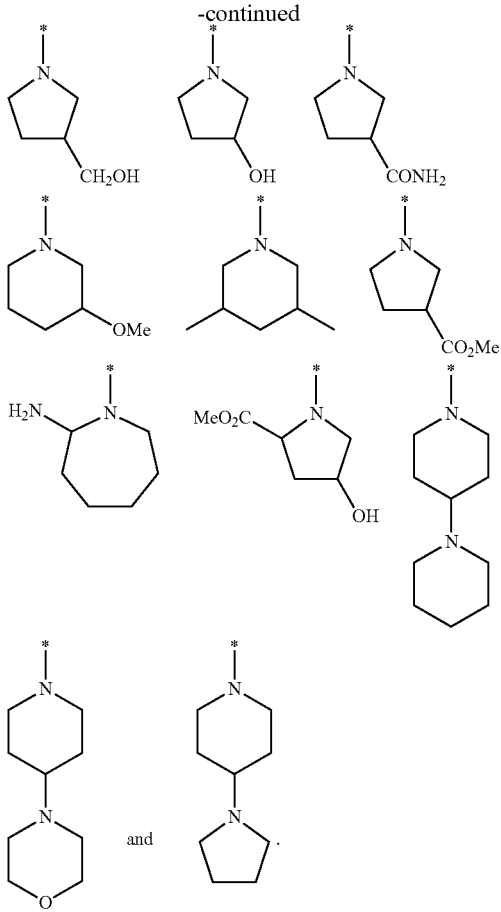

In a further embodiment, there is provided a subset of compounds of formula (I), (Ia) or (Ib), and pharmaceutically acceptable salts thereof, in which:
X$^5$ and X$^6$ are each CH;
X$^8$ is N;
R$^7$ is an optionally substituted phenyl or pyridinyl group, wherein the optional substituents are preferably selected from —NH$_2$, fluoro, hydroxyl, cyano, nitro, methyl, methoxy, —CH$_2$OH, —CO$_2$H, —CONH$_2$, —CONHMe, —CONHEt, —CONHCH$_2$CH$_2$F, —CONHCH$_2$CHF$_2$, —CONHCH$_2$CH$_2$OH, —CONMeEt, —CONMe$_2$, N-methylpiperazinylcarbonyl and 4-hydroxypiperidinylcarbonyl; and
R$^2$ is a group selected from

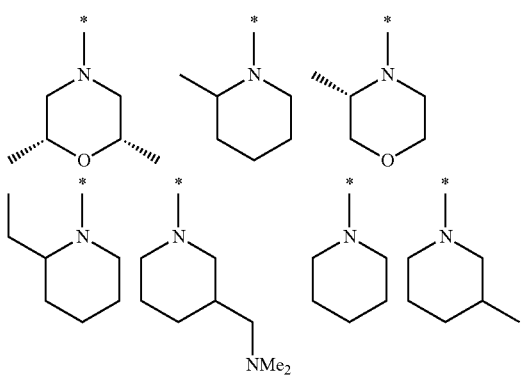

-continued

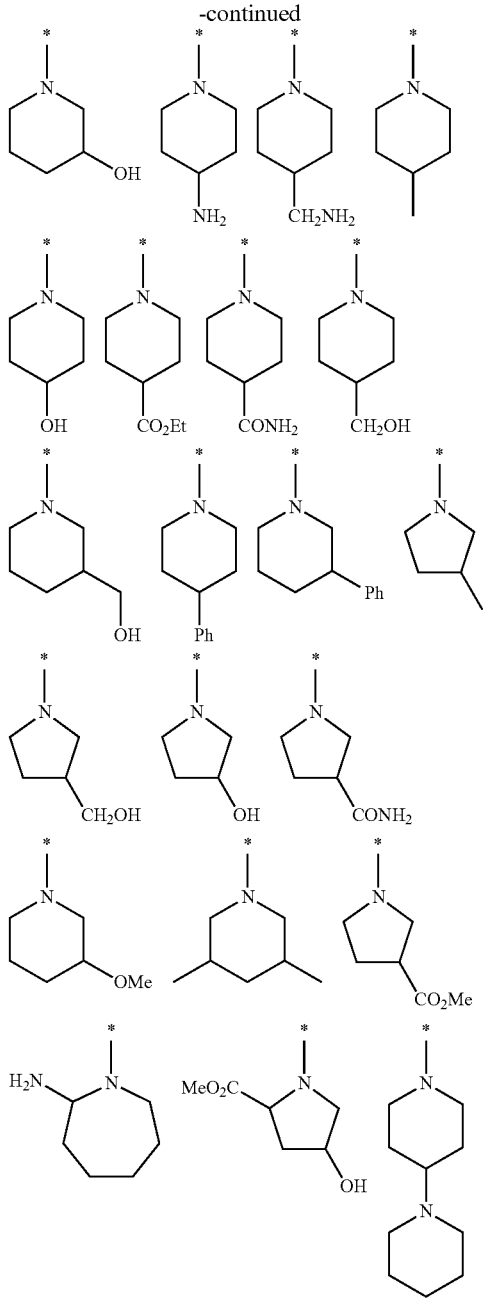

In a further embodiment, there is provided a subset of compounds of formula (I), (Ia) or (Ib), and pharmaceutically acceptable salts thereof, in which:
X$^5$ and X$^6$ are each CH;
X$^8$ is N;

R[7] is a 4-chlorophenyl, 4-methylphenyl, 4-methoxyphenyl, 3-hydroxymethyl-4-methoxy-phenyl, 3,5-dimethoxy-4-hydroxyphenyl, 4-hydroxyphenyl, 3-hydroxyphenyl or a 3-hydroxymethylphenyl group; and R[2] is NR[N5]R[N6] where R[N5] and R[N6] together with the nitrogen to which they are bound form a

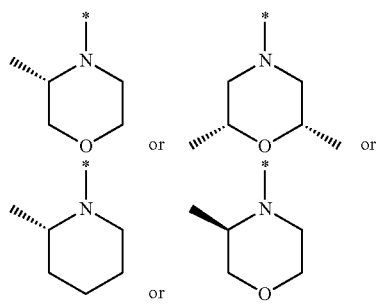

group.

In a further embodiment, there is provided a subset of compounds of formula (I) or (Ia), and pharmaceutically acceptable salts thereof, in which:

X[5] and X[6] are each CH;

X[8] is N;

R[7] is a 4-chlorophenyl, 4-methylphenyl, 4-methoxyphenyl, 3-hydroxymethyl-4-methoxy-phenyl, 3,5-dimethoxy-4-hydroxyphenyl, 4-hydroxyphenyl, 3-hydroxyphenyl or a 3-hydroxymethylphenyl group; and R[2] is NR[N5]R[N6] where R[N5] and R[N6] together with the nitrogen to which they are bound form a

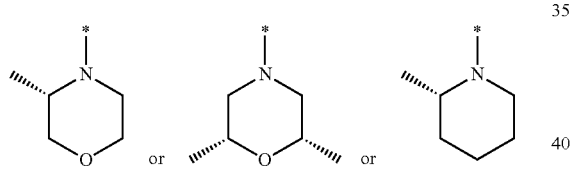

group.

In a further embodiment, there is provided a subset of compounds of formula (I), (Ia) or (Ib), and pharmaceutically acceptable salts thereof, in which:

X[5] and X[6] are each CH;

X[8] is N;

R[7] is a 4-chlorophenyl, 4-methylphenyl, 4-methoxyphenyl, 3-hydroxymethyl-4-methoxy-phenyl, 3,5-dimethoxy-4-hydroxyphenyl, 4-hydroxyphenyl, 3-hydroxyphenyl or a 3-hydroxymethylphenyl group; and R[2] is NR[N5]R[N6] where R[N5] and R[N6] together with the nitrogen to which they are bound form a

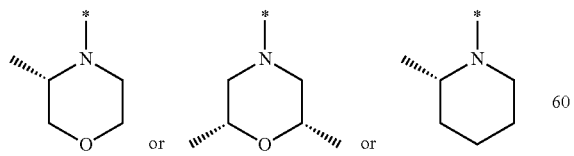

group.

In a further embodiment, there is provided a subset of compounds of formula (I), (Ia) or (Ib), and pharmaceutically acceptable salts thereof, in which:

X[5] and X[6] are each CH;

X[8] is N;

R[7] is a

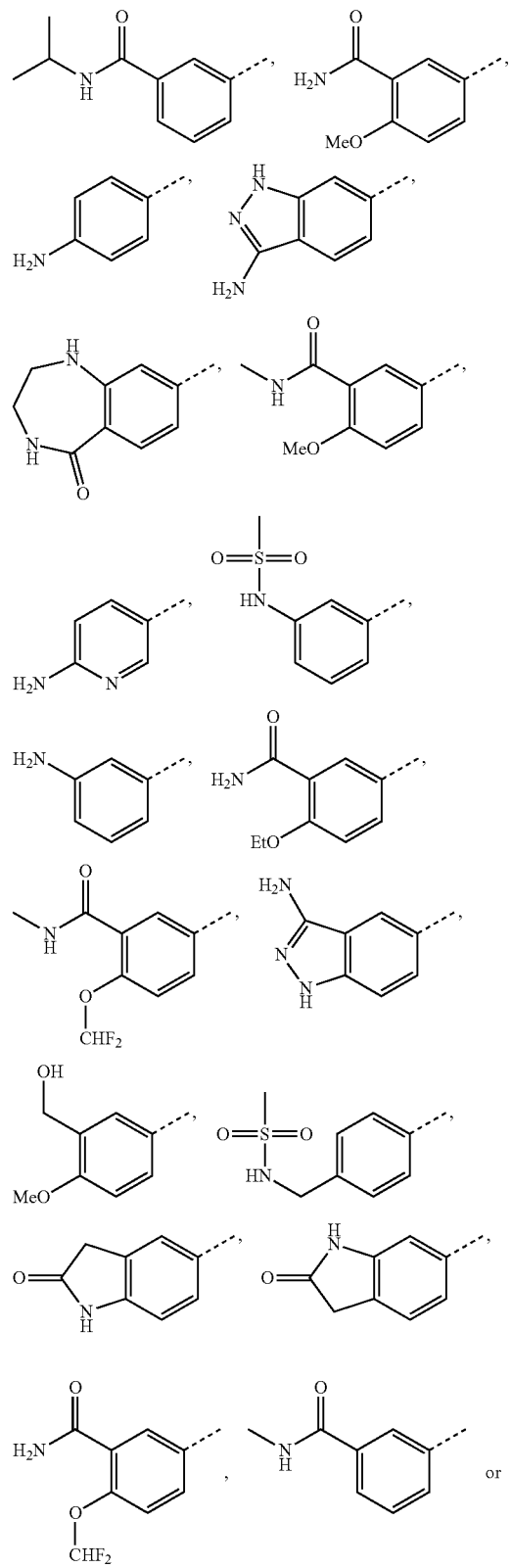

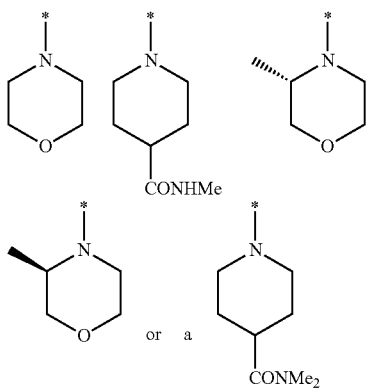

group; and

R² is NR^{N5}R^{N6} where R^{N5} and R^{N6} together with the nitrogen to which they are bound form a

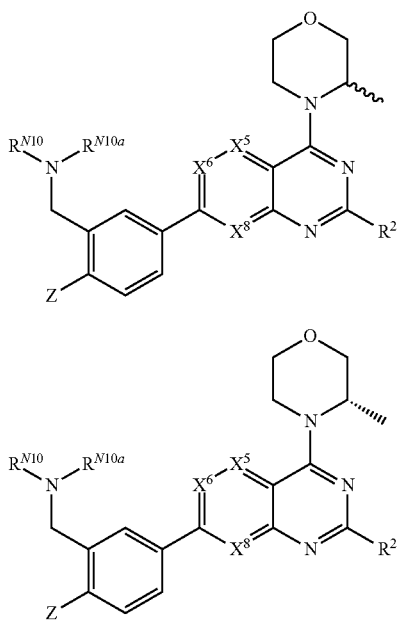

group.

In an embodiment of the invention, there is provided a subset of compounds of formula (II) or (IIa), and pharmaceutically acceptable salts thereof, (II)

(IIa)

wherein:
only one of $X^5$, $X^6$ and $X^8$ is N, and the others are CH;
Z is H, F or $OR^{O3}$;
$R^{N10}$ is selected from hydrogen, $C(O)R^{C2}$, an optionally substituted $C_{5-20}$ heteroaryl group, an optionally substituted $C_{5-20}$ aryl group, or an optionally substituted $C_{1-10}$ alkyl group where $R^{C2}$ are selected from H, an optionally substituted $C_{5-20}$ aryl group, an optionally substituted $C_{5-20}$ heterocyclyl group, an optionally substituted $C_{1-7}$ alkyl group or $NR^{N11}R^{N12}$, where $R^{N11}$ and $R^{N12}$ are independently selected from H, an optionally substituted $C_{1-7}$ alkyl group, an optionally substituted $C_{5-20}$ heterocyclyl group, an optionally substituted $C_{5-20}$ aryl group or $R^{N11}$ and $R^{N12}$ together with the nitrogen to which they are bound form a heterocyclic ring containing between 3 and 8 ring atoms;
$R^{N10a}$ is selected from hydrogen or an optionally substituted $C_{1-10}$ alkyl group; or
$R^{N10}$ and $R^{N10a}$ together with the nitrogen to which they are bound form an optionally substituted heterocyclic ring containing between 3 and 8 ring atoms;
$R^{O3}$ is an optionally substituted $C_{1-6}$ alkyl group; and
R² is selected from $NR^{N5}R^{N6}$, an optionally substituted $C_{5-20}$ heteroaryl group, and an optionally substituted $C_{5-20}$ aryl group.

In another embodiment, there is provided a subset of compounds of formula (II) or (IIa), and pharmaceutically acceptable salts thereof, in which:
only one of $X^5$, $X^6$ and $X^8$ is N, and the others are CH;
Z is H, F or $OR^{O3}$
$R^{N10}$ is $R^{N10}$ is selected from hydrogen, $C(O)R^{C2}$, an optionally substituted $C_{5-6}$ heteroaryl group, an optionally substituted $C_6$ aryl group, or an optionally substituted $C_{1-10}$ alkyl group where $R^{C2}$ are selected from $CH_3$ or $CH_2OH$ where the optional substitutents are selected from cyano, halo, hydroxyl, $C_{1-7}$ alkyloxy, $C_{1-7}$alkylamino and di-$C_{1-7}$alkylamino;
$R^{N10a}$ is selected from hydrogen or an optionally substituted $C_{1-10}$ alkyl group where the optional substitutents are selected from cyano, halo, hydroxyl, $C_{1-7}$ alkyloxy, $C_{1-7}$alkylamino and di-$C_{1-7}$alkylamino; or
$R^{N10}$ and $R^{N10a}$ together with the nitrogen to which they are bound form an optionally substituted heterocyclic ring containing between 3 and 8 ring atoms, where the optional substitutents are selected from cyano, halo, hydroxyl, $C_{1-7}$alkyloxy, $C_{1-7}$alkylamino and di-$C_{1-7}$alkylamino;
$R^{O3}$ is an unsubstituted $C_{1-3}$alkyl group; and
R² is selected from $NR^{N5}R^{N6}$, an optionally substituted $C_{5-6}$heteroaryl group, and an optionally substituted $C_6$ aryl group.

In another embodiment, there is provided a subset of compounds of formula (II) or (IIa), and pharmaceutically acceptable salts thereof, in which:
only one of $X^5$, $X^6$ and $X^8$ is N, and the others are CH;
Z is H, F or $OR^{O3}$
$R^{N10}$ is selected from hydrogen, —C(O)CH₃, —C(O)CH₂OH, —CH₃, —CH₂CH₃, —CH₂CH₂OH, —CH(CH₃)₂, —CH₂CH₂OMe, —CH₂C(CH₃)₂, —CH₂CH₂C(CH₃)₂, —CH(CH₃)CH₂C(CH₃)₂, —CH₂CH₂CH₂N(CH₃)₂, cyproyl, cyclopentyl, cyclohexyl, cycloheptyl, —CH₂cyclopropyl, methylcyclohexyl, cyanocyclohexyl, pyrazolyl, hydroxypyrrolidinyl, —CH₂imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$ alkyloxy;
$R^{O3}$ is a methyl group; and
R² is $NR^{N5}R^{N6}$ where $R^{N5}$ and $R^{N6}$ together with the nitrogen to which they are bound form a heterocyclic ring containing between 5 to 7 ring atoms which may be optionally be substituted, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment, there is provided a subset of compounds of formula (II) or (IIa), and pharmaceutically acceptable salts thereof, in which:

only one of $X^5$, $X^6$ and $X^8$ is N, and the others are CH; Z is H, F or $OR^{O3}$ $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyploroyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;

$R^{O3}$ is a methyl group; and $R^2$ is $NR^{N5}R^{N6}$ where $R^{N5}$ and $R^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include $C_{1-7}$ alkyl groups or esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and $C_{1-4}$ alkyl, preferably methyl, aminomethyl, hydroxymethyl or hydroxyethyl.

In a further embodiment, there is provided a subset of compounds of formula (II) or (IIa), and pharmaceutically acceptable salts thereof, in which:

$X^5$ and $X^6$ are each CH;

$X^8$ is N;

Z is H, F or $OR^{O3}$ $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyploroyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;

$R^{O3}$ is a methyl group; and $R^2$ is $NR^{N5}R^{N6}$ where $R^{N5}$ and $R^{N6}$ together with the nitrogen to which they are bound form an optionally substituted morpholino, thiomorpholino, piperidinyl, homopiperidinyl, piperazinyl (preferably N-substituted), homopiperazinyl (preferably N-substituted) or pyrrolidinyl group, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment, there is provided a subset of compounds of formula (II) or (IIa), and pharmaceutically acceptable salts thereof, in which:

$X^5$ and $X^6$ are each CH;

$X^8$ is N;

Z is H, F or $OR^{O3}$ $R^{N10}$ is a $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyploroyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$ alkyloxy;

$R^{O3}$ is a methyl group; and $R^2$ is a group selected from

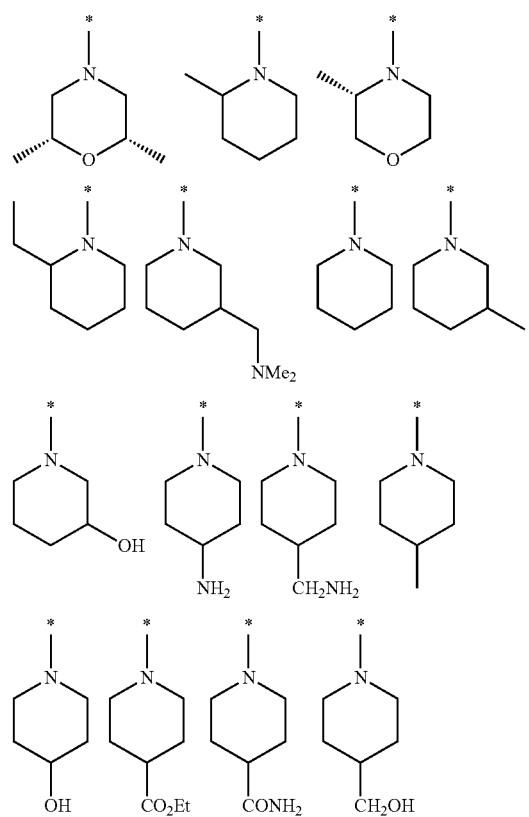

-continued

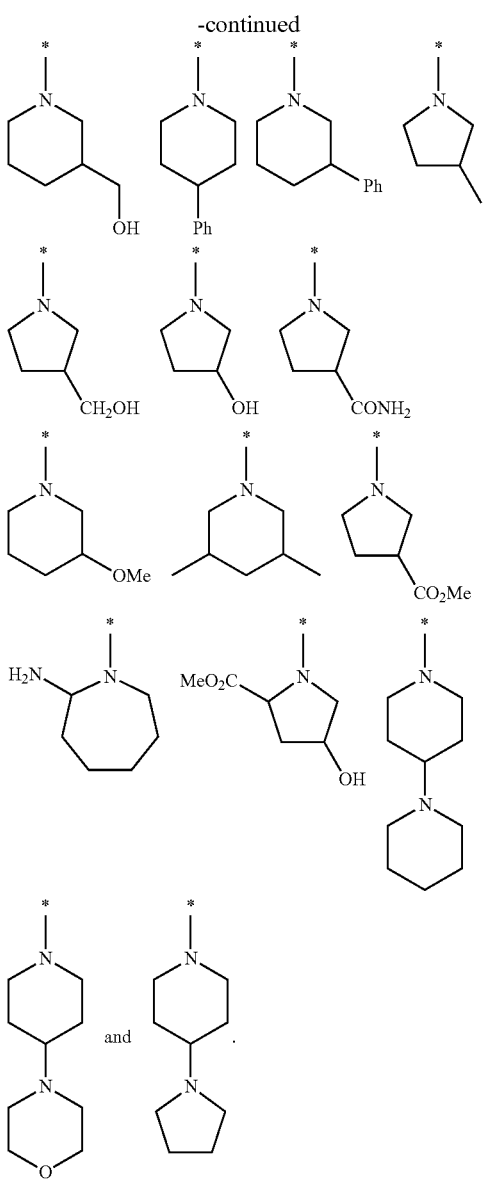

In a further embodiment, there is provided a subset of compounds of formula (II) or (IIa), and pharmaceutically acceptable salts thereof, in which:

$X^5$ and $X^6$ are each CH;

$X^8$ is N;

Z is H, F or $OR^{O3}$ $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyploroyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;

$R^{O3}$ is a methyl group; and $R^2$ is $NR^{N5}R^{N6}$ where $R^{N5}$ and $R^{N6}$ together with the nitrogen to which they are bound form a

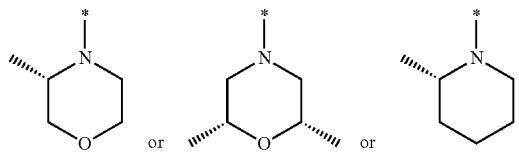

group.

In a further embodiment, there is provided a subset of compounds of formula (II) or (IIa), and pharmaceutically acceptable salts thereof, in which:

$X^5$ and $X^6$ are each CH;

$X^8$ is N;

Z is H, F or $OR^{O3}$ $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyploroyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$ alkyloxy;

$R^{O3}$ is a methyl group; and $R^2$ is $NR^{N5}R^{N6}$ where $R^{N5}$ and $R^{N6}$ together with the nitrogen to which they are bound form a

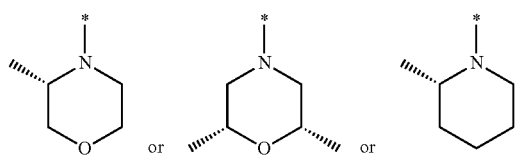

group.

In an embodiment of the invention, there is provided a subset of compounds of formula (I), (Ia) or (Ib) wherein the compound is a compound of formula (II), (IIa) or (IIb), and pharmaceutically acceptable salts thereof,

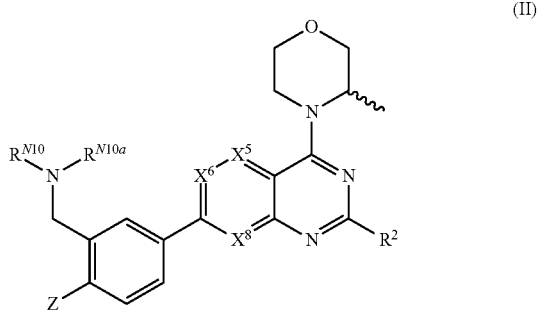

(II)

-continued (IIa)

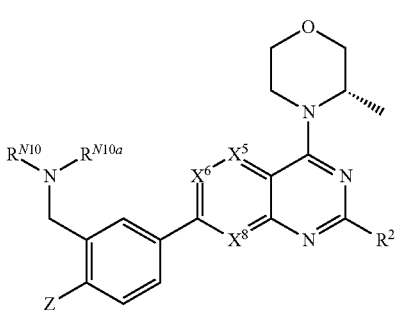

(IIb)

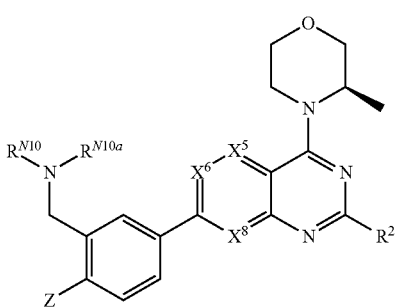

wherein:
only one of $X^5$, $X^6$ and $X^8$ is N, and the others are CH;
Z is H, F or $OR^{O3}$;
$R^{N10}$ is selected from hydrogen, $C(O)R^{C2}$, an optionally substituted $C_{5-20}$ heteroaryl group, an optionally substituted $C_{5-20}$ aryl group, or an optionally substituted $C_{1-10}$ alkyl group where $R^{C2}$ are selected from H, an optionally substituted $C_{5-20}$ aryl group, an optionally substituted $C_{5-20}$ heterocyclyl group, an optionally substituted $C_{1-7}$ alkyl group or $NR^{N11}R^{N12}$, where $R^{N11}$ and $R^{N12}$ are independently selected from H, an optionally substituted $C_{1-7}$ alkyl group, an optionally substituted $C_{5-20}$ heterocyclyl group, an optionally substituted $C_{5-20}$ aryl group or $R^{N11}$ and $R^{N12}$ together with the nitrogen to which they are bound form a heterocyclic ring containing between 3 and 8 ring atoms;
$R^{N10a}$ is selected from hydrogen or an optionally substituted $C_{1-10}$ alkyl group; or
$R^{N10}$ and $R^{N10a}$ together with the nitrogen to which they are bound form an optionally substituted heterocyclic ring containing between 3 and 8 ring atoms;
$R^{O3}$ is an optionally substituted $C_{1-6}$ alkyl group; and
$R^2$ is selected from $NR^{N5}R^{N6}$, an optionally substituted $C_{5-20}$ heteroaryl group, and an optionally substituted $C_{5-20}$ aryl group.

In another embodiment, there is provided a subset of compounds of formula (II), (IIa) or (IIb), and pharmaceutically acceptable salts thereof, in which:
only one of $X^5$, $X^6$ and $X^8$ is N, and the others are CH;
Z is H, F or $OR^{O3}$
$R^{N10}$ is $R^{N10}$ is selected from hydrogen, $C(O)R^{C2}$, an optionally substituted $C_{5-6}$ heteroaryl group, an optionally substituted $C_6$ aryl group, or an optionally substituted $C_{1-10}$ alkyl group where $R^{C2}$ are selected from $CH_3$ or $CH_2OH$ where the optional substituents are selected from cyano, halo, hydroxyl, $C_{1-7}$ alkyloxy, $C_{1-7}$alkylamino and di-$C_{1-7}$alkylamino;
$R^{N10a}$ is selected from hydrogen or an optionally substituted $C_{1-10}$ alkyl group where the optional substituents are selected from cyano, halo, hydroxyl, $C_{1-7}$alkyloxy, $C_{1-7}$alkylamino and di-$C_{1-7}$alkylamino; or
$R^{N10}$ and $R^{N10a}$ together with the nitrogen to which they are bound form an optionally substituted heterocyclic ring containing between 3 and 8 ring atoms, where the optional substituents are selected from cyano, halo, hydroxyl, $C_{1-7}$alkyloxy, $C_{1-7}$alkylamino and di-$C_{1-7}$alkylamino;
$R^{O3}$ is an unsubstituted $C_{1-3}$ alkyl group; and
$R^2$ is selected from $NR^{N5}R^{N6}$, an optionally substituted $C_{5-6}$ heteroaryl group, and an optionally substituted $C_6$ aryl group.

In another embodiment, there is provided a subset of compounds of formula (II), (IIa) or (IIb), and pharmaceutically acceptable salts thereof, in which:
only one of $X^5$, $X^6$ and $X^8$ is N, and the others are CH;
Z is H, F or $OR^{O3}$
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substituents are selected from halo, hydroxyl, $C_{1-7}$alkyloxy;
$R^{O3}$ is a methyl group; and
$R^2$ is $NR^{N5}R^{N6}$ where $R^{N5}$ and $R^{N6}$ together with the nitrogen to which they are bound form a heterocyclic ring containing between 5 to 7 ring atoms which may be optionally be substituted, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment, there is provided a subset of compounds of formula (II), (IIa) or (IIb), and pharmaceutically acceptable salts thereof, in which:
only one of $X^5$, $X^6$ and $X^8$ is N, and the others are CH;
Z is H, F or $OR^{O3}$
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substituents are selected from halo, hydroxyl, $C_{1-7}$alkyloxy;
$R^{O3}$ is a methyl group; and
$R^2$ is $NR^{N5}R^{N6}$ where $R^{N5}$ and $R^{N6}$ together with the nitrogen to which they are bound form an optionally substituted imidazolyl, morpholino, thiomorpholino, piperadinyl, homopiperadinyl, piperazinyl (preferably N-substituted), homopiperazinyl (preferably N-substituted) or pyrrolidinyl, wherein optional N-substituents on the piperazinyl and homopiperazinyl groups include $C_{1-7}$ alkyl groups or esters, in particular, esters bearing a $C_{1-7}$ alkyl group as an ester substituent, e.g. —C(=O)OCH$_3$, —C(=O)OCH$_2$CH$_3$ and —C(=O)OC(CH$_3$)$_3$, and optional C-substituents for the imidazolyl, morpholino, thiomorpholino, piperadinyl, homopiperadinyl, piperazinyl, homopiperazinyl or pyrrolidinyl groups include phenyl, ester, amide and $C_{1-4}$ alkyl, preferably methyl, aminomethyl, hydroxymethyl or hydroxyethyl.

In a further embodiment, there is provided a subset of compounds of formula (II), (IIa) or (IIb), and pharmaceutically acceptable salts thereof, in which:

$X^5$ and $X^6$ are each CH;

$X^8$ is N;

Z is H, F or OR$^{O3}$ $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;

$R^{O3}$ is a methyl group; and $R^2$ is NR$^{N5}$R$^{N6}$ where R$^{N5}$ and R$^{N6}$ together with the nitrogen to which they are bound form an optionally substituted morpholino, thiomorpholino, piperidinyl, homopiperidinyl, piperazinyl (preferably N-substituted), homopiperazinyl (preferably N-substituted) or pyrrolidinyl group, wherein the optional substituents are selected from cyano, halo, hydroxyl, and $C_{1-7}$ saturated alkyl and $C_{1-7}$ saturated alkoxy (wherein the saturated alkyl and alkoxy groups may be optionally substituted by one or more groups selected from halo, hydroxyl, $C_{1-7}$ alkoxy, amino and $C_{5-6}$ aryl).

In a further embodiment, there is provided a subset of compounds of formula (II), (IIa) or (IIb), and pharmaceutically acceptable salts thereof, in which:

$X^5$ and $X^6$ are each CH;

$X^8$ is N;

Z is H, F or OR$^{O3}$ $R^{N10}$ is a $R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N1}$ is hydrogen; or $R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;

$R^{O3}$ is a methyl group; and $R^2$ is a group selected from

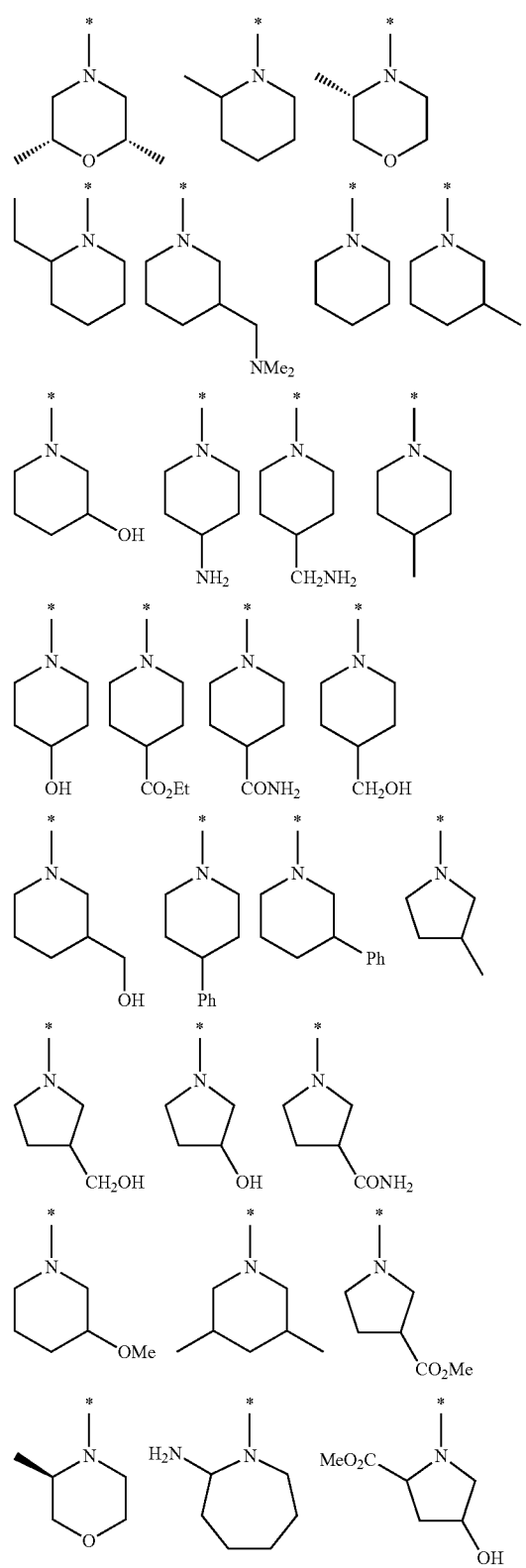

-continued

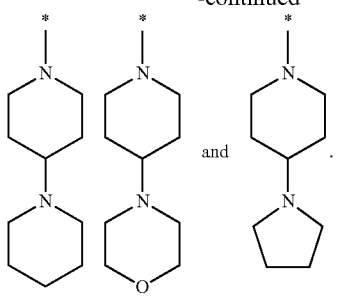

and

In a further embodiment, there is provided a subset of compounds of formula (II), (IIa) or (IIb), and pharmaceutically acceptable salts thereof, in which:

$X^5$ and $X^6$ are each CH;
$X^8$ is N;
Z is H, F or $OR^{O3}$
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;
$R^{O3}$ is a methyl group; and
$R^2$ is $NR^{N5}R^{N6}$ where $R^{N5}$ and $R^{N6}$ together with the nitrogen to which they are bound form a

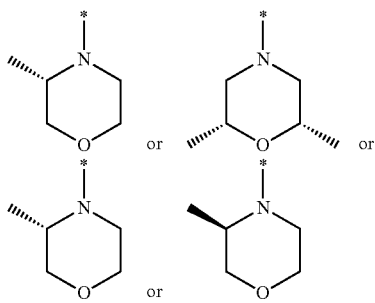

group.

In a further embodiment, there is provided a subset of compounds of formula (II), (IIa) or (IIb), and pharmaceutically acceptable salts thereof, in which:

$X^5$ and $X^6$ are each CH;
$X^8$ is N;
Z is H, F or $OR^{O3}$
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;

$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;
$R^{O3}$ is a methyl group; and
$R^2$ is $NR^{N5}R^{N6}$ where $R^{N5}$ and $R^{N6}$ together with the nitrogen to which they are bound form a

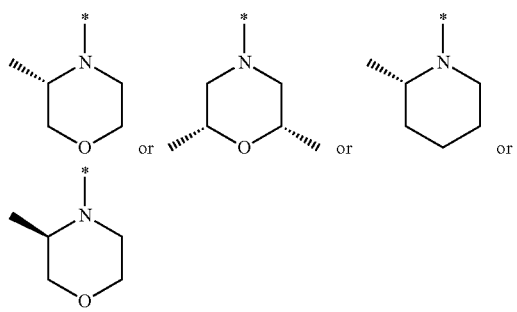

group.

In a further embodiment, there is provided a subset of compounds of formula (II), (IIa) or (IIb), and pharmaceutically acceptable salts thereof, in which:

$X^5$ and $X^6$ are each CH;
$X^8$ is N;
Z is H, F or $OR^{O3}$
$R^{N10}$ is selected from hydrogen, —C(O)CH$_3$, —C(O)CH$_2$OH, —CH$_3$, —CH$_2$CH$_3$, —CH$_2$CH$_2$OH, —CH(CH$_3$)$_2$, —CH$_2$CH$_2$OMe, —CH$_2$C(CH$_3$)$_2$, —CH$_2$CH$_2$C(CH$_3$)$_2$, —CH(CH$_3$)CH$_2$C(CH$_3$)$_2$, —CH$_2$CH$_2$CH$_2$N(CH$_3$)$_2$, cyproyl, cyclopentyl, cyclohexyl, cycloheptyl, —CH$_2$cyclopropyl, methylcyclohexyl, cyanocyclohexyl, pyrazolyl, hydroxypyrrolidinyl, —CH$_2$imidazole;
$R^{N10a}$ is hydrogen; or
$R^{N10}$ and $R^{N10a}$ together with the nitrogen to which they are bound form an optionally substituted heterocyclic ring containing between 5 or 6 ring atoms, where the optional substitutents are selected from halo, hydroxyl, $C_{1-7}$alkyloxy;
$R^{O3}$ is a methyl group; and
$R^2$ is $NR^{N5}R^{N6}$ where $R^{N5}$ and $R^{N6}$ together with the nitrogen to which they are bound form a

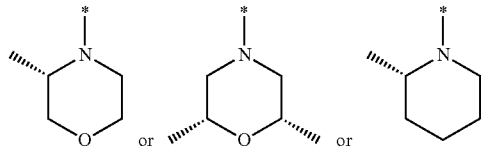

group.

In another aspect of the invention, there is provided a compound, or a pharmaceutical salt thereof, selected from any one of the Examples.

In a further aspect of the invention, there is provided a compound, or a pharmaceutical salt thereof, selected from Examples 1bu, 1ce, 12b, 18de, 18dg, 18j, 1ar, 19e, 19 h, 19i, 19l, 19m, 19n, 19o, 18n, 18o, 18z, 18aa, 18ag, 18ai, 18al, 1v, 18az, 1ah, 7e, 7i, 7j, 5d, 5f, 4v, 4ab, 4aj, 5t, 5u, 5w, 5x, 5y, 5z, 3f, 3g, 18 bp, 18bs, 18bv, 18by, 18cb, 18cv, 1aw, 3u, 1bf, 18ct, 19q, 19s, 19u, 19v, 19w, 1au, 5r, 4t, 18dj, 1cl, 2d, 2e, 1cs, 2 h, 2j, 1cw, 1bo, 1bp, 1j, 1bx, 1by, 1cf, 1ci, 1cj, 4an, 4ap, 4av, 12d, 18dh, 18di, 6a, 1n, 1p, 1q, 18e, 18 h, 19b, 19c, 19f, 19k, 18p, 1bd, 18w, 18ab, 18af, 18aj, 18aq, 18as, 18av, 18ay, 18bb, 18bc, 18bf, 18bl, 1ab, 4p, 9a, 1av, 3a, 5b, 5c, 5e, 5g, 4aa, 4ad, 4ah, 5v, 3e, 18bq, 18bt, 18bz, 18ca, 18cd, 18cg, 18ci, 18bx, 5n, 1am, 1ao, 18cn, 18cx, 1bk, 13b, 4g, 5s, 4q, 18dd, 1cp, 1cq, 2f, 2g, 13g, 1cy, 1ct, 1b, 1a, 1c, 1d, 1bl, 1bm, 1f, 1i, 1g, 1h, 1br, 1bs, 1bv, 1e, 1bz, 1cc, 1k, 1cg, 1l, 4al, 4am, 4ao, 4aq, 4as, 4at, 4au, 4aw, 4ax, 4ay, 4az, 4ba, 4bb, 4bc, 4bd, 4be, 4bf, 12c, 12a, 18a, 1as, 1s, 18c, 18d, 18f, 18g, 18i, 18k, 19j, 18m, 18q, 18r, 18s, 18t, 18u, 18v, 18x, 18y, 18ac, 18ad, 18ae, 18ah, 18ak, 18am, 18an, 18ap, 18ar, 18au, 18aw, 18ax, 18ba, 18bd, 18be, 18bg, 18bi, 18bk, 18bh, 18bj, 18bm, 1bg, 8b, 4 h, 1ba, 8a, 1aa, 1ac, 1ae, 1af, 1ag, 14b, 1bc, 4i, 4j, 4k, 4l, 4m, 4n, 4o, 18bn, 18bo, 4u, 1bb, 1at, 7b, 7c, 7d, 7f, 7g, 7k, 5a, 4w, 4x, 4y, 4z, 4ac, 4af, 4ai, 18br, 18bw, 18cc, 18cf, 18ch, 18cj, 18ck, 18cl, 4ak, 18cm, 4a, 3i, 3y, 1ak, 1al, 1ap, 1be, 18co, 18cr, 18cs, 18db, 19p, 3l, 1u, 4b, 5q, 4c, 4e, 4f, 4d, 1az, 4r, 4s, 1cn, 1co, 3ad, 1cr, 1cw, 1cy, 1dv, 15c, 1cl, 1cm, 1cn, 1cq, 1cy, 1cx, 1di, 1dj, 1eb, 1cj, 1ck, 1ct, 1cu, 1cz, 1db, 1dc, 1dd, 1de, 1dg, 1dh, 1dk, 1dl, 1dm, 1dn, 1do, 1dp, 1dq, 1dt, 1du, 1dw, 1dy, 1dz, 1ea, 1ec, 1ed, 1ee, 18dm, 18dn and 18do.

In a further aspect of the invention, there is provided a compound, or a pharmaceutical salt thereof, selected from Examples 1bo, 1bp, 1j, 1bx, 1by, 1cf, 1ci, 1cj, 4an, 4ap, 4av, 12d, 18dh, 18di, 6a, 1n, 1p, 1q, 18e, 18 h, 19b, 19c, 19f, 19k, 18p, 1bd, 18w, 18ab, 18af, 18aj, 18aq, 18as, 18av, 18ay, 18bb, 18bc, 18bf, 18bl, 1ab, 4p, 9a, 1av, 3a, 5b, 5c, 5e, 5g, 4aa, 4ad, 4ah, 5v, 3e, 18bq, 18bt, 18bz, 18ca, 18cd, 18cg, 18ci, 18bx, 5n, 1am, 1ao, 18cn, 18cx, 1bk, 13b, 4g, 5s, 4q, 18dd, 1cp, 1cq, 2f, 2g, 13g, 1cy, 1ct, 1b, 1a, 1c, 1d, 1bl, 1bm, 1f, 1i, 1g, 1h, 1br, 1bs, 1bv, 1e, 1bz, 1cc, 1k, 1cg, 1l, 4al, 4am, 4ao, 4aq, 4as, 4at, 4au, 4aw, 4ax, 4ay, 4az, 4ba, 4bb, 4bc, 4bd, 4be, 4bf, 12c, 12a, 18a, 1as, 1s, 18c, 18d, 18f, 18g, 18i, 18k, 19j, 18m, 18q, 18r, 18s, 18t, 18u, 18v, 18x, 18y, 18ac, 18ad, 18ae, 18ah, 18ak, 18am, 18an, 18ap, 18ar, 18au, 18aw, 18ax, 18ba, 18bd, 18be, 18bg, 18bi, 18bk, 18bh, 18bj, 18bm, 1bg, 8b, 4 h, 1ba, 8a, 1aa, 1ac, 1ae, 1af, 1ag, 14b, 1bc, 4i, 4j, 4k, 4l, 4m, 4n, 4o, 18bn, 18bo, 4u, 1bb, 1at, 7b, 7c, 7d, 7f, 7g, 7k, 5a, 4w, 4x, 4y, 4z, 4ac, 4af, 4ai, 18br, 18bw, 18cc, 18cf, 18ch, 18cj, 18ck, 18cl, 4ak, 18cm, 4a, 3i, 3y, 1ak, 1al, 1ap, 1be, 18co, 18cr, 18cs, 18db, 19p, 3l, 1u, 4b, 5q, 4c, 4e, 4f, 4d, 1az, 4r, 4s, 1cn, 1co, 3ad, 1cl, 1cm, 1cn, 1cq, 1cyv, 1cx, 1di, 1dj, 1eb, 1cj, 1ck, 1ct, 1cu, 1cz, 1db, 1dc, 1dd, 1de, 1dg, 1dh, 1dk, 1dl, 1dm, 1dn, 1do, 1dp, 1dq, 1dt, 1du, 1dw, 1dy, 1dz, 1ea, 1ec, 1ed, 1ee, 18dm, 18dn and 18do.

In a further aspect of the invention, there is provided a compound, or a pharmaceutical salt thereof, selected from Examples 1b, 1a, 1c, 1d, 1bl, 1bm, 1f, 1i, 1g, 1h, 1br, 1bs, 1bv, 1e, 1bz, 1ce, 1k, 1cg, 1l, 4al, 4am, 4ao, 4aq, 4as, 4at, 4au, 4aw, 4ax, 4ay, 4az, 4ba, 4bb, 4bc, 4bd, 4be, 4bf, 12c, 12a, 18a, 1as, 1s, 18c, 18d, 18f, 18g, 18i, 18k, 19j, 18m, 18q, 18r, 18s, 18t, 18u, 18v, 18x, 18y, 18ac, 18ad, 18ae, 18ah, 18ak, 18am, 18an, 18ap, 18ar, 18au, 18aw, 18ax, 18ba, 18bd, 18be, 18bg, 18bi, 18bk, 18bh, 18bj, 18bm, 1bg, 8b, 4 h, 1ba, 8a, 1aa, 1ac, 1ae, 1af, 1ag, 14b, 1bc, 4i, 4j, 4k, 4l, 4m, 4n, 4o, 18bn, 18bo, 4u, 1bb, 1at, 7b, 7c, 7d, 7f, 7g, 7k, 5a, 4w, 4x, 4y, 4z, 4ac, 4af, 4ai, 18br, 18bw, 18cc, 18cf, 18ch, 18cj, 18ck, 18cl, 4ak, 18cm, 4a, 3i, 3y, 1ak, 1al, 1ap, 1be, 18co, 18cr, 18cs, 18db, 19p, 3l, 1u, 4b, 5q, 4c, 4e, 4f, 4d, 1az, 4r, 4s, 1cn, 1co, 3ad, 1cj, 1ck, 1ct, 1cu, 1cz, 1db, 1dc, 1dd, 1de, 1dg, 1dh, 1dk, 1dl, 1dm, 1dn, 1do, 1dp, 1dq, 1dt, 1du, 1dw, 1dy, 1dz, 1ea, 1ec, 1ed, 1ee, 18dm, 18dn and 18do.

In a further aspect of the invention, there is provided a compound, or a pharmaceutical salt thereof, selected from Examples 1a, 1u, 1al, 1ap, 1at, 1az, 1co, 1de, 1dg, 1dh, 1dk, 1dl, 1dp, 1dq, 1dr, 1ds, 1dt, 1du, 1dy, 1ec, 1ee, 12d, 14b, 18dn and 18do.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms. For example, for Example 1a was isolated as Form A: 2-Theta° 6.9 (46%), 8.53 (100%), 10.1 (21%), 10.86 (24%), 11.65 (11%), 13.31 (14%), 13.75 (7%), 14.37 (54%), 15.21 (5%), 16.19 (13%), 16.81 (39%), 17.19 (40%), 17.97 (21%), 18.41 (65%), 18.78 (80%), 20.66 (8%), 21.07 (89%), 22.05 (19%), 22.36 (42%), 24 (7%), 24.36 (33%), 25.25 (31%), 25.54 (16%), 26.92 (18%), 27.26 (8%), 28.03 (8%), 28.39 (21%), 29 (8%), 29.91 (13%), 30.62 (23%), 31.48 (9%), 32.72 (5%), 33.27 (11%), 34.88 (4%), 35.48 (5%), 36.16 (4%), 36.88 (4%), 37.37 (4%), 37.91 (6%), 38.65 (4%) and 39.83 (4%). A less stable form, Form B, has also been isolated from water/THF: 2-Theta° 3.67 (7%), 7.28 (7%), 8.52 (7%), 9.22 (30%), 11.42 (78%), 12.69 (24%), 13 (15%), 13.41 (44%), 13.6 (26%), 14.51 (19%), 15.56 (13%), 16.25 (9%), 17.11 (13%), 17.55 (18%), 18.24 (64%), 18.59 (56%), 19.51 (33%), 19.85 (26%), 20.32 (13%), 21.49 (17%), 21.79 (13%), 22.23 (18%), 22.84 (26%), 23.72 (23%), 25.46 (74%), 26.1 (100%), 26.72 (43%), 27.94 (16%), 28.35 (8%), 34.74 (10%), 35.34 (6%), 36.72 (9%) and 38.55 (4%).

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/ enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in ref. 25.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3$+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, ref. 26.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: an C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-20}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1- methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleared by phosphotase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

General Synthesis

Compounds of formula I can be represented by Formula 1:

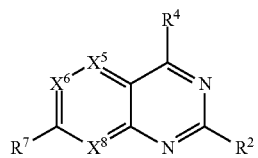

Formula 1 wherein R$^4$ represents

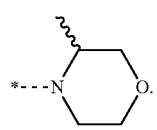

Compounds of Formula 1 can be synthesised from compounds of Formula 2:

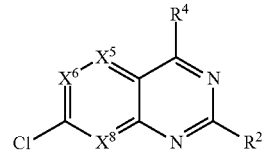

Formula 2

When R$^7$ is NR$^{N1}$R$^{N2}$, this is by reaction with R$^7$H. When R$^7$ is an amide, urea or sulfonamide group, this is by reaction with ammonia followed by reaction of the resulting primary amide with the appropriate acid chloride, isocyanate or sulfonyl chloride. When R$^7$ is OR$^{O1}$ or SR$^{S1}$, this is by reaction with potassium carbonate in the appropriate alcohol or thiol solvent. When R$^7$ is an optionally substituted C$_{3-20}$ heterocyclyl group or C$_{5-20}$ aryl group, this is by reaction with R$^7$B(OAlk)$_2$, where each Alk is independently C$_{1-7}$ alkyl or together with the oxygen to which they are attached form a C$_{5-7}$heterocyclyl group.

Compounds of Formula 2 can be synthesised from compounds of Formula 3:

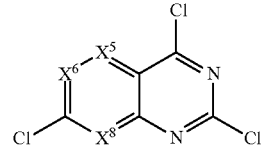

Formula 3 by reaction with HR$^4$ (eg.

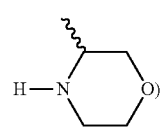

followed by reaction with HR$^2$.

Compounds of Formula 3 can be synthesised from compounds of Formula 4:

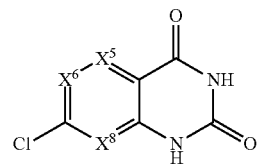

Formula 4 by treatment with POCl$_3$ and N,N-diisopropylamine, for example.

Compounds of Formula 4 can be synthesised from compounds of Formula 5:

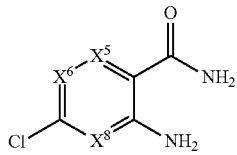

Formula 5 by treatment with oxalyl chloride, for example.

Compounds of Formula 5 can be synthesised from compounds of Formula 6, for example by reaction with liquid ammonia followed by reaction with thionyl chloride and ammonia gas:

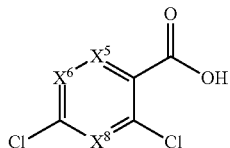

Formula 6

Alternatively compounds of Formula 1 can be synthesised from compounds of Formula 7:

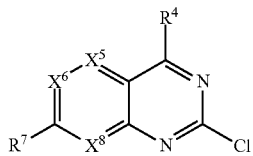

Formula 7 by reaction with $HR^2$.

Compounds of Formula 7 can be synthesised from compounds of Formula 8:

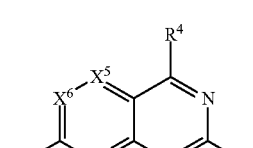

Formula 8

When $R^7$ is $NR^{N1}R^{N2}$, this is by reaction with $R^7H$. When $R^7$ is an amide, urea or sulfonamide group, this is by reaction with ammonia followed by reaction of the resulting primary amide with the appropriate acid chloride, isocyanate or sulfonyl chloride. When $R^7$ is $OR^{O1}$ or $SR^{S1}$, this is by reaction with potassium carbonate in the appropriate alcohol or thiol solvent. When $R^7$ is an optionally substituted $C_{3-20}$ heterocyclyl group or $C_{5-20}$ aryl group, this is by reaction with $R^7B(OAlk)_2$, where each Alk is independently $C_{1-7}$ alkyl or together with the oxygen to which they are attached form a $C_{5-7}$ heterocyclyl group.

Compounds of Formula 8 can be synthesised from compounds of Formula 3:

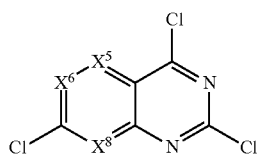

Formula 3 by reaction with $HR^4$ (eg.

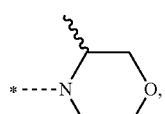

).

When $R^7$ is

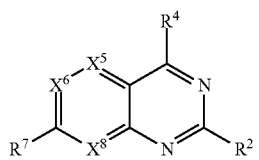

the Compound of Formula 1 can be prepared by reaction a compound of Formula 1a:

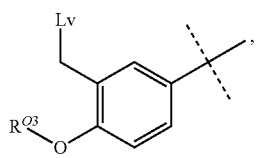

Formula 1a wherein $R^4$ represents and $R^7$ is wherein Lv is a leaving group, such as a halogen, for example chlorine, or a $OSO_2$ group, where R is alkyl or aryl, such as methyl, by reaction with $R^{N10}NH_2$.

Compounds of Formula 1a can be synthesised by reaction of a compound of Formula 1b Formula 1b

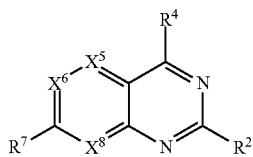

wherein $R^4$ represents

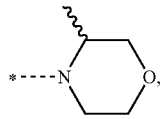

and
$R^7$ is

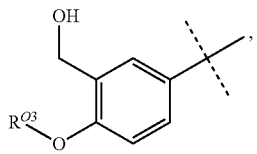

with an alkyl or aryl sulphonyl chloride in the presence of a base.

For Example:

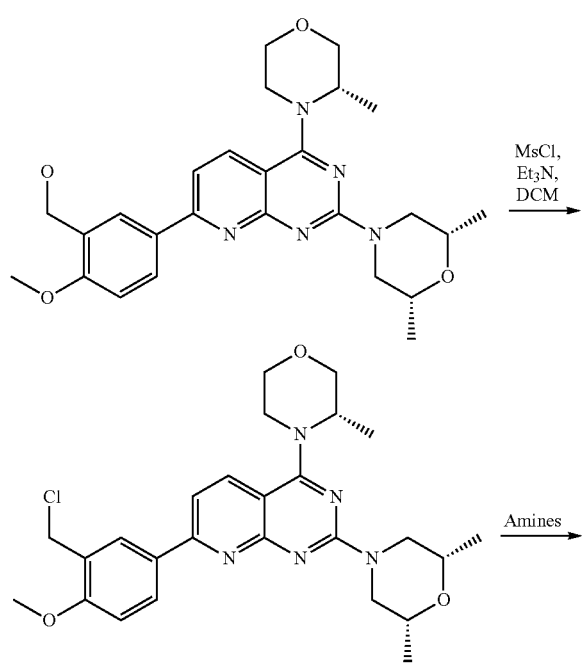

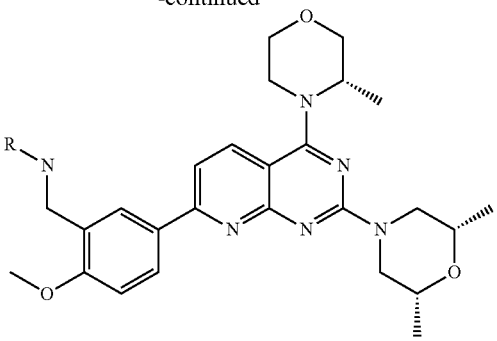

Compounds of Formula 1b can be prepared by reaction with $R^7B(OAlk)_2$, where each Alk is independently $C_{1-7}$ alkyl or together with the oxygen to which they are attached form a $C_{5-7}$heterocyclyl group.

Use

The present invention provides active compounds, specifically, active in inhibiting the activity of mTOR.

The term "active" as used herein, pertains to compounds which are capable of inhibiting mTOR activity, and specifically includes both compounds with intrinsic activity (drugs) as well as prodrugs of such compounds, which prodrugs may themselves exhibit little or no intrinsic activity.

One assay which may conveniently be used in order to assess the mTOR inhibition offered by a particular compound is described in the examples below.

The present invention further provides a method of inhibiting the activity of mTOR in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect", the inhibition of cellular growth in a certain time or the accumulation of cells in the G1 phase of the cell cycle over a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimes of drugs and/or ionising radiation as used in the treatment of different cancer types. Examples of adjunct anti-cancer agents that could be combined with compounds from the invention include, but are not limited to, the following: alkylating agents: nitrogen mustards, mechlorethamine, cyclophosphamide, ifosfamide, melphalan, chlorambucil: Nitrosoureas: carmustine (BCNU), lomustine (CCNU), semustine (methyl-CCNU), ethylenimine/methylmelamine, thriethylenemelamine (TEM), triethylene thiophosphoramide (thiotepa), hexamethylmelamine (HMM, altretamine): Alkyl sufonates; busulfan; Triazines, dacarbazine (DTIC): Antimetabolites; folic acid analogs, methotrexate, trimetrexate, pyrimidine analogs, 5-fluorouracil, fluorodeoxyuridine, gemcitabine, cytosine arabinoside (AraC, cytarabine), 5-azacytidine, 2,2'-difluorodeoxycytidine: Purine analogs; 6-mercaptopurine, 6-thioguanine, azathioprine, 2'-deoxycoformycin (pentostatin, erythrohydroxynonyladenine (EHNA), fludarabine phosphate, 2-Chlorodeoxyadenosine (cladribine, 2-CdA): Topoisomerase I inhibitors; camptothecin, topotecan, irinotecan, rubitecan: Natural products; antimitotic drugs, paclitaxel, vinca alkaloids, vinblastine (VLB), vincristine, vinorelbine, Taxotere™ (docetaxel), estramustine, estramustine phosphate; epipodophylotoxins, etoposide, teniposide: Antibiotics; actimomycin D, daunomycin (rubidomycin), doxorubicin (adriamycin), mitoxantrone, idarubicin, bleomycins, plicamycin (mithramycin), mitomycin C, dactinomycin: Enzymes; L-asparaginase, RNAse A: Biological response modifiers; interferon-alpha, IL-2, G-CSF, GM-CSF: Differentiation Agents; retinoic acid derivatives: Radiosensitizers; metronidazole, misonidazole, desmethylmisonidazole, pimonidazole, etanidazole, nimorazole, RSU 1069, EO9, RB 6145, SR4233, nicotinamide, 5-bromodeozyuridine, 5-iododeoxyuridine, bromodeoxycytidine: Platinum coordination complexes; cisplatin, carboplatin: Anthracenedione; mitoxantrone, AQ4N Substituted urea, hydroxyurea; Methylhydrazine derivatives, N-methylhydrazine (MIH), procarbazine; Adrenocortical suppressant, mitotane (o.p'-DDD), aminoglutethimide: Cytokines; interferon (α, β, γ), interleukin; Hormones and antagonists; adrenocorticosteroids/antagonists, prednisone and equivalents, dexamethasone, aminoglutethimide; Progestins, hydroxyprogesterone caproate, medroxyprogesterone acetate, megestrol acetate; Estrogens, diethylstilbestrol, ethynyl estradiol/equivalents; Antiestrogen, tamoxifen; Androgens, testosterone propionate, fluoxymesterone/equivalents; Antiandrogens, flutamide, gonadotropin-releasing hormone analogs, leuprolide; Nonsteroidal antiandrogens, flutamide; EGFR inhibitors, VEGF inhibitors; Proteasome inhibitors.

Active compounds may also be used as cell culture additives to inhibit mTOR, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Cancer

The present invention provides active compounds which are anticancer agents or adjuncts for treating cancer. One of ordinary skill in the art is readily able to determine whether or not a candidate compound treats a cancerous condition for any particular cell type, either alone or in combination.

Examples of cancers include, but are not limited to, lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma and leukemias.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

The anti cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5 fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5*-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti erbB2 antibody trastuzumab [Herceptin™], the anti-EGFR antibody panitumumab, the anti erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI 774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-yl-propoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin avb3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte macrophage colony stimulating factor, approaches to decrease T cell anergy, approaches using transfected immune cells such as cytokine transfected dendritic cells, approaches using cytokine transfected tumour cell lines and approaches using anti idiotypic antibodies.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, refs. 27 to 29.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 g/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 μg to about 250 mg per kilogram body weight of the subject per day. Where the active compound is a salt, an ester, prodrug, or the like, the amount administered is calculated on the basis of the parent compound and so the actual weight to be used is increased proportionately.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of mTor in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

General Experimental Methods

Thin Layer chromatography was carried out using Merck Kieselgel 60 $F_{254}$ glass backed plates. The plates were visualized by the use of a UV lamp (254 nm). Silica gel 60 (particle sizes 40-63 m) supplied by E.M. Merck was employed for flash chromatography. $^1$H NMR spectra were recorded at 300 MHz on a Bruker DPX-300 instrument. Chemical shifts were referenced relative to tetramethylsilane.

Purification of Samples

The samples were purified on Gilson LC units. Mobile phase A—0.1% aqueous TFA, mobile phase B—Acetonitrile; flow rate 6 ml/min; Gradient—typically starting at 90% A/10% B for 1 minute, rising to 97% after 15 minutes, holding for 2 minutes, then back to the starting conditions. Column: Jones Chromatography Genesis 4 μm, C18 column, 10 mm×250 mm. Peak acquisition based on UV detection at 254 nm.

Identification of Samples

QC Method QC2-AQ

Mass spectra were recorded on a Waters ZQ instrument in Electrospray ionisation mode. Mobile phase A—0.1% aqueous formic acid. Mobile phase B—0.1% Formic acid in acetonitrile; Flowrate 2 ml/min; Gradient—starting at 100% A/0% B for 1 minute, rising to 95% B after 7 minutes and holding for 2 minutes before returning to the starting conditions. Column: Varies, currently Genesis AQ 120A 4u 50 mm×4.6 mm, Hichrom Ltd. PDA detection Waters 996, scan range 210-400 nm.

QC Method QC2-Long

Mass spectra were recorded on a Waters ZQ instrument in Electrospray ionisation mode. Mobile phase A—0.1% aqueous formic acid. Mobile phase B—0.1% Formic acid in acetonitrile; Flowrate 2 ml/min; Gradient—starting at 95% A/5% B, rising to 95% B after 20 minutes and holding for 3 minutes before returning to the starting conditions. Column: Varies, but always C18 50 mm×4.6 mm (currently Genesis C18 4u 50 mm×4.6 mm, Hichrom Ltd). PDA detection Waters 996, scan range 210-400 nm.

QC Method QC2-QC

Mass spectra were recorded on a Waters ZQ instrument in Electrospray ionisation mode. Mobile phase A—0.1% aqueous formic acid. Mobile phase B—0.1% Formic acid in acetonitrile; Flowrate 2 ml/min; Gradient—starting at 95% A/5% B, rising to 95% B after 5 minutes and holding for 5 minutes before returning to the starting conditions. Column: Varies, but always C18 50 mm×4.6 mm (currently Genesis C18 4 μm 50×4.6 mm, Hichrom Ltd). PDA detection Waters 996, scan range 210-400 nm.

QC Method QC3-AQ-Long

Mass spectra were recorded on a Waters ZQ instrument in Electrospray ionisation mode. Mobile phase A—0.1% aqueous formic acid. Mobile phase B—0.1% Formic acid in acetonitrile; Flowrate 2 ml/min; Gradient—starting at 100% A/0% B for 1 minute, rising to 95% B after 20 minutes and holding for 5 minutes before returning to the starting conditions. Column: Varies, currently Genesis AQ 4 μm 50 mm×4.6 mm, Hichrom Ltd. PDA detection Waters 996, scan range 210-400 nm.

Examples 1u, 9a, 18bs, 18bv, 18bw, 18bx, 18by, 18bz, 18ca, 18cb, 18cc, 18cd, 18ce, 18cf, 18cg, 18ch, 18ci, 18cj, 18ck, 18cl, 18cm, 18dk, 18dl and 18dm were analysed using the QC Method QC2-AQ.

Examples 12c, 12d, 13c, 13e, 13g, 14b, 15b, 18aa, 18ab, 18ac, 18ad, 18ae, 18af, 18ag, 18ah, 18ai, 18aj, 18ak, 18al, 18am, 18an, 18ao, 18ap, 18aq, 18ar, 18as, 18at, 18au, 18az, 18bc, 18bl, 18bm, 18bt, 18bu, 18cn, 18co, 18cp, 18cq, 18cr, 18cs, 18ct, 18cu, 18cv, 18cw, 18cx, 18cy, 18cz, 18da, 18db, 18dc, 18df, 18dj, 181, 18o, 18q, 18r, 18s, 18t, 18u, 18v, 18w, 18x, 18y, 18z, 19a, 19b, 19c, 19d, 19e, 19f, 19g, 19 h, 19i, 19j, 19k, 19l, 19m, 19n, 19o, 1a, 1aa, 1ab, 1ac, 1ad, 1ae, 1af, 1ag, 1ah, 1ai, 1ak, 1as, 1au, 1az, 1bb, 1cq, 1ct, 1dg, 1ee, 1g, 1i, 1m, 1w, 1x, 1y, 1z, 21a, 3a, 3ac, 3b, 3c, 3d, 3e, 3f, 3g, 3 h, 3i, 3j, 3v, 3w, 3x, 3y, 3z, 4j, 4k, 4l, 4m, 4n, 4o, 4p, 6a, comparative of Example 1c, comparative of Example 1j and comparative of Example 1k were analysed using the QC Method QC2-Long.

Examples 10a, 11a, 12a, 12b, 12e, 13a, 13b, 13d, 13f, 14a, 15a, 15c, 16a, 17a, 18a, 18av, 18aw, 18ax, 18ay, 18b, 18ba, 18bb, 18bd, 18be, 18bf, 18bg, 18bh, 18bi, 18bj, 18bk, 18bn, 18bo, 18 bp, 18bq, 18br, 18c, 18d, 18dd, 18de, 18dg, 18dh, 18di, 18dn, 18do, 18e, 18f, 18g, 18 h, 18i, 18j, 18k, 18m, 18n, 19p, 19q, 19r, 19s, 19t, 19u, 19v, 19w, 19x, 1aj, 1al, 1am, 1an, 1ao, 1ap, 1aq, 1ar, 1at, 1av, 1aw, 1ax, 1ay, 1b, 1ba, 1bc, 1be, 1bf, 1bg, 1bh, 1bi, 1bj, 1bk, 1bl, 1bm, 1bn, 1bo, 1bp, 1bq, 1br, 1bs, 1bt, 1bu, 1bv, 1bw, 1bx, 1by, 1bz, 1c, 1ca, 1cb, 1cc, 1cd, 1ce, 1cf, 1cg, 1ch, 1ci, 1cj, 1ck, 1cl, 1cm, 1cn, 1co, 1cp, 1cr, 1cs, 1cu, 1cyv, 1cw, 1cx, 1cy, 1cz, 1d, 1da, 1db, 1dc, 1dd, 1de, 1df, 1dh, 1di, 1dj, 1dk, 1dl, 1dm, 1dn, 1do, 1dp, 1dq, 1dr, 1ds, 1dt, 1du, 1dv, 1dw, 1dx, 1dy, 1dz, 1e, 1ea, 1eb, 1ed, 1ee, 1f, 1h, 1j, 1k, 1l, 1n, 1o, 1p, 1q, 1r, 1s, 1t, 1v, 20a, 20b, 20c, 2a, 2b, 2c, 2d, 2e, 2f, 2g, 2 h, 2i, 2j, 3aa, 3ab, 3ad, 3k, 3l, 3m, 3n, 3o, 3p, 3q, 3r, 3s, 3t, 3u, 4a, 4aa, 4ab, 4ac, 4ad, 4ae, 4af, 4ag, 4ah, 4ai, 4aj, 4ak, 4al, 4am, 4an, 4ao, 4ap, 4aq, 4ar, 4as, 4at, 4au, 4av, 4aw, 4ax, 4ay, 4az, 4b, 4ba, 4bb, 4bc, 4bd, 4be, 4bf, 4c, 4d, 4e, 4f, 4g, 4 h, 4i, 4q, 4r, 4s, 4t, 4u, 4v, 4w, 4x, 4y, 4z, 5a, 5b, 5c, 5d, 5e, 5f, 5g, 5 h, 5i, 5j, 5k, 5l, 5m, 5n, 5o, 5p, 5q, 5r, 5s, 5t, 5u, 5v, 5w, 5x, 5y, 5z, 7a, 7b, 7c, 7d, 7e, 7f, 7g, 7 h, 7i, 7j, 7k, 8a, 8b, 8c, 8d, comparative of Example 1a and comparative of Example 1b were analysed using the QC Method QC2-QC.

Examples 18p and 1bd were analysed using the QC Method QC3-AQ-Long.

Microwave Synthesis

Reactions were carried out using a Personal Chemistry™ Emrys Optimiser microwave synthesis unit with robotic arm. Power range between. 0-300 W at 2.45 GHz. Pressure range between 0-20 bar; temperature increase between 2-5° C./sec; temp range 60-250° C.

General Procedure for the Synthesis of 2,4,7-Substituted Pyridopyrimidine Derivatives:

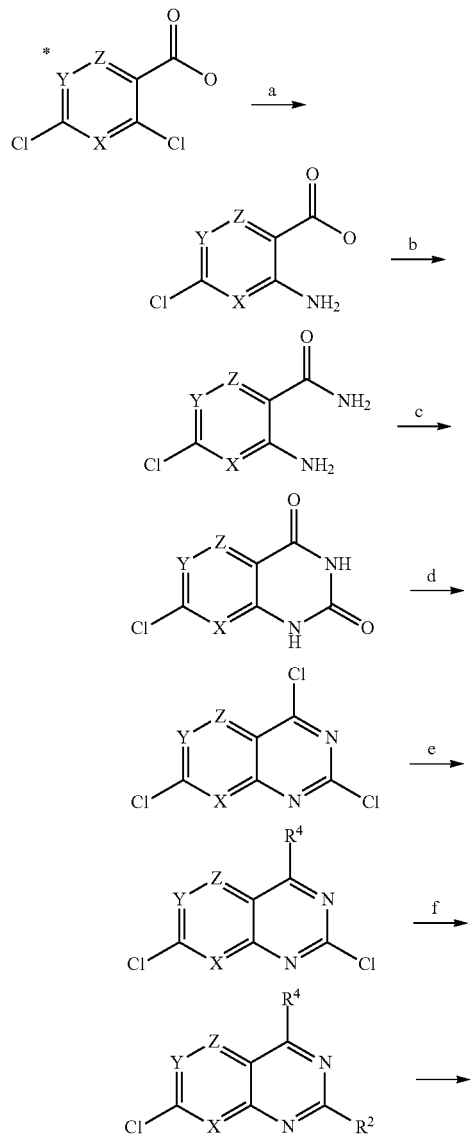

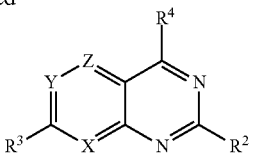

*2-amino-6-chloronicotinic acid ——X═N, Y═C, Z═C
*3-amino-6-chloroisonicotinic acid ——X═C, Y═N, Z═C
*3-Amino-chloropyridine-2-carboxylic acid ——X═C, Y═C, Z═N
a) NH₃, 14 bar;
b) (i) SOCl₂, THF, r.t., (ii) NH₃
c) Oxalyl chloride, Toluene, Δ;
d) DIPEA, POCl₃, Toluene or Anisole, Δ;
e) Appropriate amine, diisopropylethylamine, CH₂Cl₂ or Anisole;
f) Appropriate amine, diisopropyethyl amine, DMA, 70° C.;

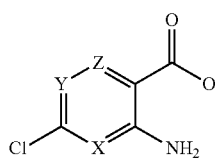

To the appropriate amino acid (1 equiv) was added liquid ammonia (sufficient to make a 0.6M solution of substrate in ammonia). The suspension was sealed in a pressure vessel which was then heated slowly to 130° C. It was noted that at this temperature a pressure of 18 bar was observed. This temperature and pressure was maintained for a further 16 hours whereupon the mixture was cooled to room temperature. The pressure vessel was opened and the reaction poured into ice cold water (1 reaction volume). The resulting solution was acidified to pH 1-2 using concentrated HCl which caused a precipitate to form. The acidic mixture was allowed to warm to room temperature and was stirred like this for a further 30 min The suspension was then extracted with diethyl ether (3×400 ml). The combined organic extracts were then filtered and the filtrate concentrated in vacuo to give a white solid which was dried further over P₂O₅ to give the title compound (typically 80-90% yield and 90%+ pure) in suitably pure form to be used without any further purification.

2-amino-6-chloronicotinic acid—X═N, Y═C, Z═C: (90% yield, 96% purity) m/z (LC-MS, ESP): 173 [M+H]⁺ R/T=3.63 min

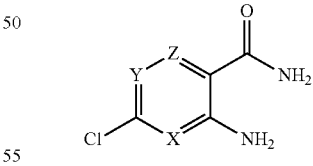

To a 0.3 M solution of amino acid (1 equiv) in anhydrous THF, under an inert atmosphere, was added thionyl chloride (3.3 equiv) in a dropwise fashion. The reaction mixture was stirred at room temperature for 2 hours. After this time the reaction was concentrated in vacuo to give a crude yellow solid residue. The crude solid was dissolved in THF (equal to initial reaction volume) and concentrated in vacuo again to give a yellow solid residue. The residue was dissolved once more in THF and concentrated as before to give a solid residue which was then dissolved in THF (to give a solution of 0.3M) and ammonia gas bubbled through the solution for 1 hour. The resultant precipitate was removed by filtration and the filtrate concentrated in vacuo to give a yellow precipitate which was triturated with water at 50° C. then dried to give the title compound (typically 90-95%) yield and suitably clean enough to be used without any further purification.

2-Amino-6-chloronicotinamide—X═N, Y═C, Z═C: (92% yield, 93% purity) m/z (LC-MS, ESP): 172 [M+H]+ R/T=3.19 min

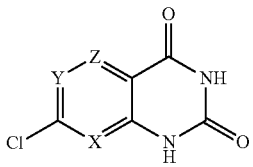

To a stirred solution (0.06 M) of substrate (1 equiv) in anhydrous toluene under an inert atmosphere was added oxalyl chloride (1.2 equiv) in a dropwise manner. The resulting mixture was then heated to reflux (115° C.) for 4 hours whereupon it was cooled and stirred for a further 16 hours. The crude reaction mixture was then concentrated to half its volume in vacuo and filtered to give the desired product in suitably pure form to be used without any further purification.

7-Chloro-1H-pyrido[2,3-d]pyrimidine-2,4-dione—X═N, Y═C, Z═C: (95% yield, 96% purity) m/z (LC-MS, ESP): 196 [M−H]− R/T=3.22 min

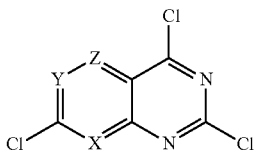

To a stirred 0.5 M suspension of the appropriate dione (1 equiv) in anhydrous toluene under an inert atmosphere was slowly added diisopropylethylamine (3 equiv). The reaction mixture was then heated to 70° C. for 30 minutes and then cooled to room temperature prior to the addition of POCl3 (3 equiv). The reaction was then heated to 100° C. for 2.5 hours before being cooled and concentrated in vacuo to give a crude slurry which was then suspended in EtOAc and filtered through a thin pad of Celite™. The filtrate was concentrated in vacuo to give a brown, oil which was dissolved in CH2Cl2 and stirred over silica gel for 30 minutes. After this time the silica was removed by filtration, the filtrate concentrated and the crude residue purified by flash chromatography (SiO2) to give the title compound in analytically pure form.

2,4,7-Trichloro-pyrido[2,3-d]pyrimidine—X═N, Y═C, Z═C: (48% yield, 96% purity) m/z (LC-MS, ESP): 234 [M+H]+ R/T=4.21 min

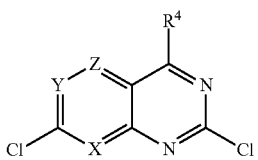

To a cooled (0-5° C.) stirred solution (0.1 M) of the appropriate trichloro-substrate (1 equiv) in CH2Cl2 was added diisopropylethylamine (1 equiv) in a dropwise fashion. The appropriate amine (1 equiv) was then added to the reaction mixture portionwise over the period of 1 hour. The solution was maintained at room temperature with stirring for a further 1 hour before the mixture was washed with water (2×1 reaction volume). The aqueous extracts were combined and extracted with CH2Cl2 (2×1 reaction volume). The organic extracts were then combined, dried (sodium sulphate), filtered and concentrated in vacuo to give an oily residue which solidified upon prolonged drying. The solid was triturated with diethylether and then filtered and the cake washed with cold diethyl ether to leave the title compound in suitable clean form to be used without any further purification.

2,7-Dichloro-4-morpholin-4-yl-pyrido[2,3-d]pyrimidine—R1=morpholine, X═N, Y═C, Z═C: (92% yield, 90% purity) m/z (LC-MS, ESP): 285 [M+H]+ R/T=3.90 min 2,7-Dichloro-4-((S)-3-methyl-morpholin-4-yl)-pyrido[2,3-d]pyrimidine—R1=(S)-3-Methyl-morpholine, X═N, Y═C, Z═C: (87% yield, 92% purity) m/z (LC-MS, ESP): 301 [M+H]+ R/T=4.13 min 2,7-Dichloro-4-((R)-3-methyl-morpholin-4-yl)-pyrido[2,3-d]pyrimidine—R1=(R)-3-Methyl-morpholine: (99% yield, 94% purity) m/z (LC-MS, ESP): 301 [M+H]+ R/T=3.49 min Alternatively, to a stirred 0.47 M suspension of the appropriate dione (1 equiv) in anhydrous anisole under an inert atmosphere was added POCl3 (2.6 equiv). The mixture was heated to 55° C. and then diisopropylethylamine (2.6 equiv) was slowly added. The reaction mixture was then heated to 85-90° C. for 30 minutes. Water was added in portions (0.15 equiv), and the reaction mixture was held at 85-90° C. for a further 30 minutes. The reaction was cooled to 50° C., and then 15% of the anisole solvent was removed by vacuum distillation. The mixture was then cooled to −5° C. and diisopropylethylamine (1.1 equiv) was added. A 4.9M solution of the appropriate amine (1.05 equiv) in anisole was then added to the reaction mixture continuously over a period of 1 hour. The solution was then warmed to 30° C. and the reaction monitored by HPLC until reaction completion.

One third of the resulting mixture from the above reaction was then added over 10 min to a stirred mixture of 1.95M aqueous potassium hydroxide (3.9 equiv) and i-butanol (6.9 equiv) at 60° C. The stirring was stopped, the phases were allowed to separate, and the aqueous phase was removed. Stirring was resumed, and 1.95M aqueous potassium hydroxide (3.9 equiv) was added to the retained organic phase. The second third of the resulting reaction mixture from the reaction above was then added over 10 min at 60° C. Again, stirring was stopped, the phases were allowed to separate, and the aqueous phase was removed. Stirring was resumed, and 1.95M aqueous potassium hydroxide (3.9 equiv) was added to the retained organic phase. The remaining third of the resulting reaction mixture from the reaction above was then added over 10 min at 60° C. Again, stirring was stopped, the phases were allowed to separate, and the aqueous phase was removed. Water was then added to the organic phase with stirring, and the stirred mixture heated to 75° C. Stirring was stopped, the phases were allowed to separate, and the aqueous phase was removed. The resulting organic phase was stirred and allowed to cool to 30° C., and then as the mixture was heated to 60° C. heptane (11.5 equiv) was added over 20 min when the mixture was around 40° C. After being heated to 60° C., the mixture was cooled over 2.5 h to 10° C. After 30 min, the resulting slurry was filtered off, washed with a 10:1 heptane:anisole mixture (2×1.4 equiv) and then washed with heptane (2×1.4 equiv). The solid was then dried in a vacuum oven at 50° C. to leave the title compound in suitable clean form to be used without any further purification.

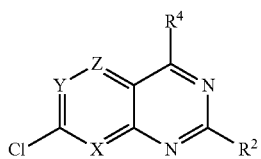

To a solution (0.2 M) of the appropriate dichloro-substrate (1 equiv) in anhydrous dimethyl acetamide under an inert atmosphere was added diisopropylethylamine (1 equiv) followed by the appropriate amine (1 equiv). The resulting mixture was heated for 48 hours at 70° C. before being cooled to ambient temperature. The reaction was diluted with $CH_2Cl_2$ (1 reaction volume) and then washed with water (3×1 reaction volumes). The organic extract was concentrated in vacuo to give a syrup which was dissolved in EtOAc (1 reaction volume) and washed with saturated brine solution before being dried (sodium sulphate) and concentrated in vacuo to give an oil. The crude residue was purified by flash chromatography ($SiO_2$, eluted with EtOAc: Hex (7:3) going to (1:1)) to give the title compound as a yellow solid that was suitably clean to be used without any further purification.

7-Chloro-2-((2S,6R)-2,6-dimethyl-morpholin-4-yl)-4-morpholin-4-yl-pyrido[2,3-d]pyrimidine—R1=morpholine, R2=cis-dimethylmorpholine, X=N, Y=C, Z=C: (45% yield, 85% purity) m/z (LC-MS, ESP): 348 [M+H]$^+$ R/T=4.16 min 7-Chloro-4-((S)-3-methyl-morpholin-4-yl)-2-((S)-3-methyl-morpholin-4-yl)-pyrido[2,3-d]pyrimidine—R1=(S)-3-Methyl-morpholine, R2=(S)-3-Methyl-morpholine, X=N, Y=C, Z=C: (71% yield, 90% purity) m/z (LC-MS, ESP): 364 [M+H]$^+$ R/T=3.52 min 7-Chloro-2-(2-ethyl-piperidin-1-yl)-4-((S)-3-methyl-morpholin-4-yl)-pyrido[2,3-d]pyrimidine—R1=(S)-3-Methyl-morpholine, R2=2-Ethyl-piperidine, X=N, Y=C, Z=C: (51% yield, 98% purity) m/z (LC-MS, ESP): 376 [M+H]$^+$ R/T=3.88 min 7-Chloro-4-((S)-3-methyl-morpholin-4-yl)-2-morpholin-4-yl-pyrido[2,3-d]pyrimidine—R1=(S)-3-Methyl-morpholine, R2=morpholine, X=N, Y=C, Z=C: (72% yield, 96% purity) m/z (LC-MS, ESP): 350 [M+H]$^+$ R/T=3.45 min 7-Chloro-2-((2S,6R)-2,6-dimethyl-morpholin-4-yl)-4-((S)-3-methyl-morpholin-4-yl-pyrido[2,3-d]pyrimidine—R1=(S)-3-Methyl-morpholine, R2=cis-dimethylmorpholine: (33% yield) m/z (LC-MS, ESP): 378 [M+H]$^+$ R/T=3.68 min 7-Chloro-4-((R)-3-methyl-morpholin-4-yl)-2-((R)-3-methyl-morpholin-4-yl)-pyrido[2,3-d]pyrimidine—R1=R2=(R)-3-Methyl-morpholine: (48% yield, 100% purity) m/z (LC-MS, ESP): 364 [M+H]$^+$ R/T=2.80 min To a 0.33 M solution of 2,7-dichloro-4-((S)-3-methyl-morpholin-4-yl)-pyrido[2,3-d]pyrimidine (1 equiv) in N,N-dimethylacetamide was added Hunig's base (1 equiv) followed by the appropriate amine (1.1 equiv). The reaction mixture was heated 40° C. for 1 hour. After this time the reaction was allowed to cool, diluted with EtOAc (1 reaction volume) and then washed with water (1 reaction volume). The aqueous fraction was removed and extracted further with EtOAc (2×1 reaction volume). The combined organic extracts were dried ($MgSO_4$), filtered and concentrated in vacuo to give a crude oily residue which was purified by flash chromatography ($SiO_2$) using EtOAc/Hexanes as eluent which furnished the desired products in a suitably clean form.

7-Chloro-4-((S)-3-methyl-morpholin-4-yl)-2-thiomorpholin-4-yl-pyrido[2,3-d]pyrimidine: (30% yield, 100% purity) m/z (LC-MS, ESP): 366.4[M+H]$^+$ R/T=3.00 min 7-Chloro-4-((S)-3-methyl-morpholin-4-yl)-2-(4-methyl-piperazin-1-yl)-pyrido[2,3-d]pyrimidine: (32% yield, 95% purity) m/z (LC-MS, ESP): 363.4[M+H]$^+$ R/T=2.37 min

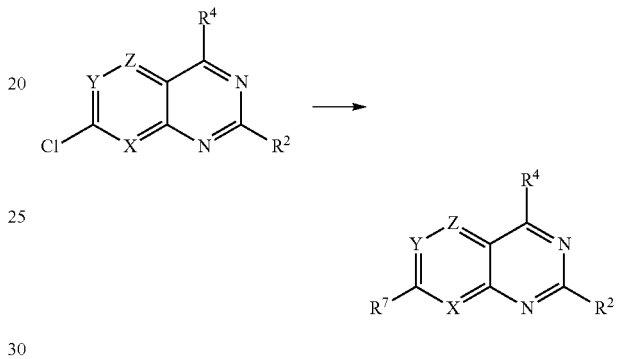

The appropriate chloro-substrate (1 equiv) was dissolved in a toluene/ethanol (1:1) solution (0.02 M). Sodium carbonate (2 equiv) and the appropriate pinacolate boron ester or boronic acid (1 equiv) were then added followed by tetrakis(triphenylphosphine)palladium$^0$ (0.1 equiv). The reaction vessel was sealed and the mixture exposed to microwave radiation (140° C., medium absorption setting) for 30 minutes. Upon completion the samples were filtered through a silica cartridge, washed with EtOAc and then concentrated in vacuo. The crude residue was then purified by preparative HPLC to give the desired products.

Example 1

Preparation of 2,4,7-substituted pyridopyrimidine Intermediates

Procedures for the synthesis of 2-Chloro-4-((S)-3-methyl-morpholin-4-yl)-7-aryl-pyrido[2,3-d]pyrimidine derivatives

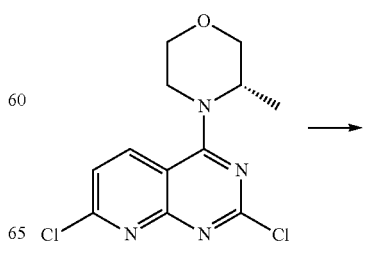

-continued

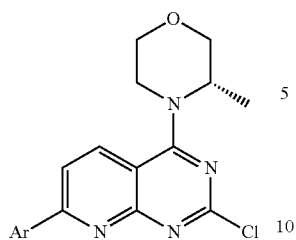

To a (0.1 M) solution of 2,7-dichloro-4-((S)-3-methyl-morpholin-4-yl)-pyrido[2,3-d]pyrimidine (1 equiv) in MeCN/H$_2$O (1:1 mixture) was added the appropriate pinacolate boron ester or boronic acid (1.1 equiv) and potassium carbonate (3 equiv). The mixture was degassed with nitrogen for 20 minutes before the addition of tetrakis(triphenylphosphine)palladium$^0$ (0.05 equiv). The reaction was degassed for a further minutes before being heated to reflux under an inert atmosphere for 3 hours. Whereupon, it was concentrated in vacuo and the crude residue partitioned between CH$_2$Cl$_2$/H$_2$O. The organic fraction was dried (MgSO$_4$), filtered and concentrated in vacuo to give an oil which was further purified by flash chromatography (SiO$_2$) using 5% MeOH in CH$_2$Cl$_2$ as eluent.

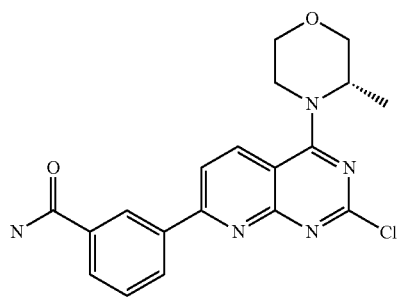 [SMILES: C[C@H]1COCCN1c1nc(Cl)nc2nc(-c3cccc(C(N)=O)c3)ccc12]

3-[2-Chloro-4-((S)-3-methyl-morpholin-4-yl)-pyrido[2,3-d]pyrimidin-7-yl]-benzamide: (27% yield, 99% purity) m/z (LC-MS, ESP): 384.3 [M+H]$^+$, R/T=3.13 min)

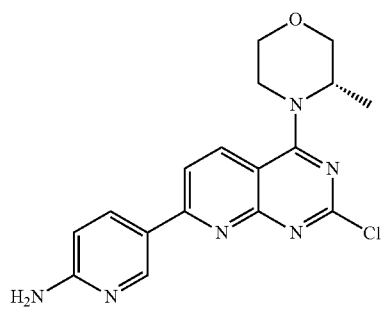 [SMILES: C[C@H]1COCCN1c1nc(Cl)nc2nc(-c3ccc(N)nc3)ccc12]

5-[2-Chloro-4-((S)-3-methyl-morpholin-4-yl)-pyrido[2,3-d]pyrimidin-7-yl]-pyridin-2-ylamine: (93% yield, 89% purity) m/z (LC-MS, ESP): 357 [M+H]$^+$, R/T=2.53 min)

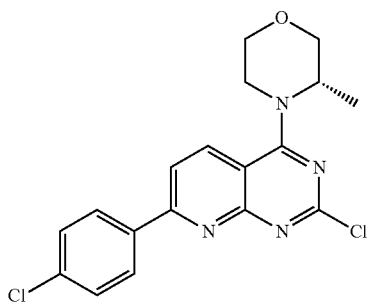 [SMILES: C[C@H]1COCCN1c1nc(Cl)nc2nc(-c3ccc(Cl)cc3)ccc12]

2-Chloro-7-(4-chloro-phenyl)-4-((S)-3-methyl-morpholin-4-yl)-pyrido[2,3-d]pyrimidine: (80% yield, 85% purity) m/z (LC-MS, ESP): 357.5 [M+H]$^+$, R/T=4.26 min)

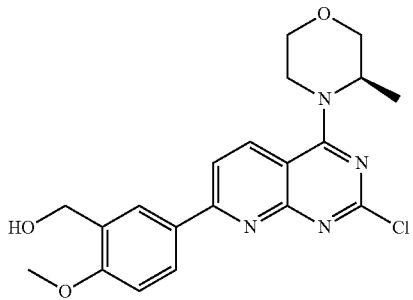

{5-[2-Chloro-4-((R)-3-methyl-morpholin-4-yl)-pyrido[2,3-d]pyrimidin-7-yl]-2-methoxy-phenyl}-methanol: (97% yield, 93% purity) m/z (LC-MS, ESP): 401 [M+H]$^+$, R/T=3.42 min)

Procedures for the Synthesis of Boronic Ester:

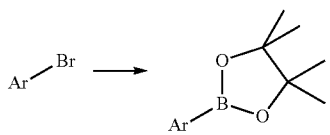

5-bromo-2-methoxybenzoic acid methyl ester (1 equiv) was dissolved in dioxane (0.1 M). Bis(pinacolato)diboron (1.1 equiv), potassium acetate (3.5 equiv) and dppf (0.05 equiv) were added and the mixture was degassed with nitrogen for 20 minutes. (1,1'-Bis(diphenylphosphino)ferrocene-dichloropalladium (0.05 equiv) was added and the mixture was degassed for a further 5 minutes. The reaction mixture was heated to 120° C. for 2 hours under nitrogen. After cooling to room temperature, the reaction mixture was diluted with CH$_2$Cl$_2$ and filtered through Celite™. The filtrate was concentrated in vacuo to give a dark oil. The residue was partitioned between EtOAc and saturated aqueous sodium bicarbonate and the aqueous layer further extracted with EtOAc. The combined organic phases were dried (MgSO$_4$), filtered and the filtrate was concentrated in vacuo to give a dark residue which was purified by flash column chromatography onto silica gel eluting with 0 to 30% ethyl acetate in hexane.

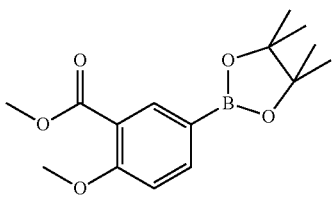

2-Methoxy-5-(4,4,5,5-tetramethyl-[1,3,2]dioxaborolan-2-yl)-benzoic acid methyl ester: (77% yield, 100% purity) m/z (LC-MS, ESP): 293.5 [M+H]$^+$ R/T=4.24 min Procedures for the Synthesis of Tetrazolyl Boronic Acids:

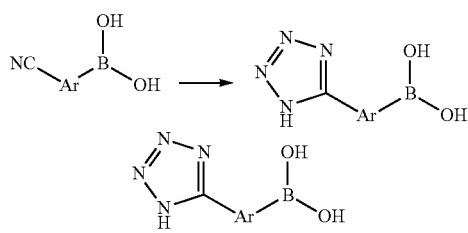

The appropriate cyanophenylpinacolate boron ester or boronic acid (1 equiv) was dissolved in DMF (0.67 M). Sodium azide (6 equiv) and ammonium chloride (6 equiv) were added. The reaction mixture was heated to 120° C. for 2.5 hours. After cooling down, the reaction mixture was poured into a mixture of ice water and EtOAc. Sodium nitrite was added and the aqueous phase was acidified by 6N HCl until pH 2. The mixture was allowed to stir at room temperature for 30 min and then was extracted with EtOAc and n-butanol. Organic fractions were collected, dried over sodium sulphate, filtered off and concentrated in vacuo, to yield a crude residue which was further purified accordingly:

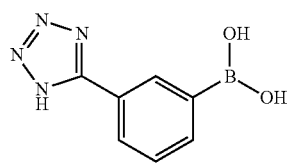 [SMILES: OB(O)c1cccc(-c2nnn[nH]2)c1]

The crude residue was recrystallized from CH$_2$Cl$_2$/hexane, obtaining the desired product as a white solid.

[3-(1H-tetrazol-5-yl)phenyl]boronic acid: (15% yield, 100% purity) m/z (LC-MS, ESP): 191 [M+H]$^+$ R/T=2.49 min

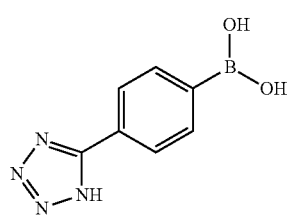 [SMILES: OB(O)c1ccc(-c2nnn[nH]2)cc1]

The crude residue was recrystallized from CH$_2$Cl$_2$/hexane, to give the desired product as a white solid.

[4-(1H-tetrazol-5-yl)phenyl]boronic acid: (64% yield, 100% purity) m/z (LC-MS, ESP): 191 [M+H]$^+$ R/T=2.49 min

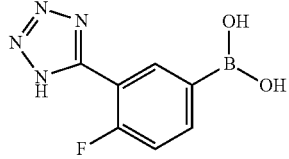 [SMILES: OB(O)c1ccc(F)c(-c2nnn[nH]2)c1]

The residue was purified by reverse phase column using a gradient from 5% to 20% acetonitrile in 0.1% formic acid/water solution, yielding the desired product. [4-fluoro-3-(1H-tetrazol-5-yl)phenyl]boronic acid: (18% yield, 100% purity) m/z (LC-MS, ESP): 207 [M−H]$^-$ R/T=2.51 min Procedure for the Synthesis of Methanesulfonylamido Boronic Acid:

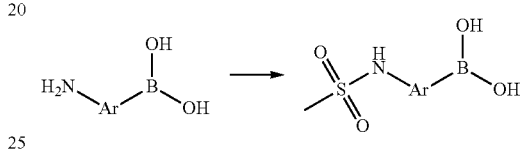

3-Amino-4-fluorophenylboronic acid (1 equiv) was dissolved in THF (0.1 M). Methane sulphonyl chloride (10 equiv) and pyridine (1 equiv) were added. The reaction mixture was heated to 70° C. for 30 minutes. After cooling down, the reaction mixture was concentrated in vacuo, to yield a crude residue which was used without further purification.

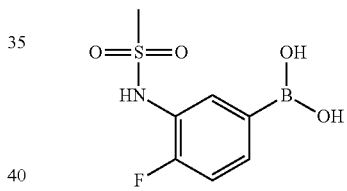

3-(Methanesulfonylamino)-4-fluoro-phenylboronic acid: (51% yield, 90% purity) m/z (LC-MS, ESP): 232 [M−H]$^-$ R/T=2.50 min Procedure for the synthesis of 3-hydroxymethyl-5-(4,4,5,5-tetramethyl-[1,3,2]dioxaborolan-2-yl)-pyridin-2-ol

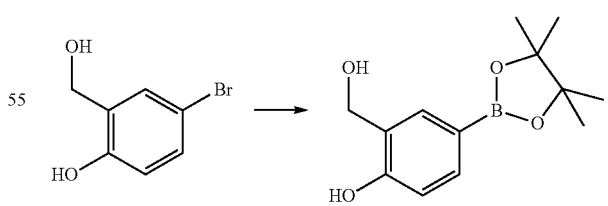

To a 0.18 M solution of 5-bromo-2-hydroxybenzyl alcohol (1 equiv) in dioxane was added bis(pinacolato)diboron (1.2 equiv) and potassium acetate (3.5 equiv) followed by 1,1'-bis(diphenylphosphino)ferrocene (0.05 equiv). The mixture was degassed with nitrogen for 20 minutes. PdCl$_2$ (dppf) (0.05 equiv) was added and the mixture degassed for a further 5 minutes. The reaction was then heated to reflux under an inert atmosphere for 2 hours. Upon completion, the reaction was cooled, filtered and concentrated in vacuo to give a crude residue which was purified by flash chromatography (SiO$_2$) using EtOAc/Hexanes—1:1 as eluent to give the desired product.

3-Hydroxymethyl-5-(4,4,5,5-tetramethyl-[1,3,2]dioxaborolan-2-yl)-pyridin-2-ol 6-Bromo-3H-pyrido[2,3-d]pyrimidin-4-one: (67% yield, 94% purity) m/z (LC-MS, ESP): 251 [M−H]⁻ R/T=3.32 minutes)

Procedure for the synthesis of 5-(4,4,5,5-Tetramethyl-[1,3,2]dioxaborolan-2-yl)-1,3-dihydro-pyrrolo[2,3-b]pyridin-2-one

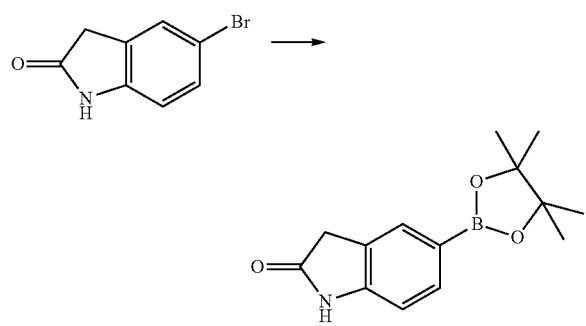

To a 0.05 M solution of 5-bromo-1,3-dihydro-pyrrolo[2,3-b]pyridin-2-one (1 equiv) in dioxane was added bis(pinacolato)diboron (1.2 equiv) and potassium acetate (1.5 equiv) followed by 1,1'-bis(diphenylphosphino)ferrocene (0.05 equiv). The mixture was degassed with nitrogen for 20 minutes. PdCl$_2$(dppf) (0.05 equiv) was added and the mixture degassed for a further 5 minutes. The reaction was then heated to 120° C. under an inert atmosphere for 8 hours. Upon completion, the reaction was cooled, filtered and concentrated in vacuo to give a crude residue which was purified by flash chromatography (SiO$_2$) using EtOAc/Hexanes—4:1 as eluent to give the desired product.

5-(4,4,5,5-Tetramethyl-[1,3,2]dioxaborolan-2-yl)-1,3-dihydro-pyrrolo[2,3-b]pyridin-2-one: (68% yield, 92% purity) m/z (LC-MS, ESP): 260 [M−H]⁻ R/T=3.52 minutes)

Procedure for the synthesis of 6-(4,4,5,5-Tetramethyl-[1,3,2]dioxaborolan-2-yl)-3H-pyrido[2,3-d]pyrimidin-4-one boronic ester

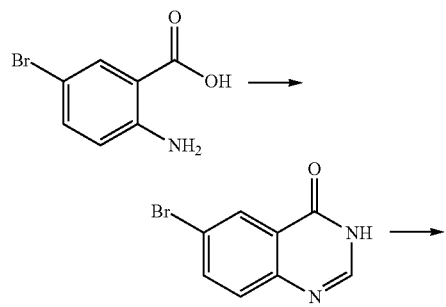

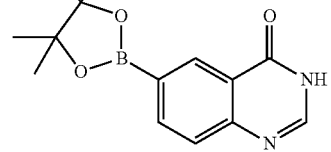

To a 1.2 M solution of 5-bromoanthranilic acid (1 equiv) in N,N-dimethylformamide was added formamidine acetate (1 equiv). The mixture was heated to reflux and stirred at this temperature for 16 hours. After this time, the reaction was cooled and NaHCO$_3$ solution (5% in H$_2$O) (3 volumes) were carefully added and the mixture stirred vigorously. The resulting precipitate was collected by filtration and then washed with water (2×1 volume) and then t-butyl methylether (2×1 volume) before being dried in a vacuum oven to give the desired product which required no further purification.

6-Bromo-3H-pyrido[2,3-d]pyrimidin-4-one: (91% yield, insert) m/z (LC-MS, ESP): 225 [M−H]⁻ R/T=2.31 minutes)

To a (0.35M) solution of 6-bromo-3H-pyrido[2,3-d]pyrimidin-4-one (1 equiv) in dioxane was added bis(pinacolato)diboron (1.2 equiv) and potassium acetate (1.5 equiv) followed by 1,1'-bis(diphenylphosphino)ferrocene (0.05 equiv). The mixture was degassed with nitrogen for 20 minutes. PdCl$_2$(dppf) (0.05 equiv) was added and the mixture degassed for a further 5 minutes. The reaction was then heated to reflux under an inert atmosphere for 16 hours. After this time, the mixture was cooled, filtered through Celite™ and then partitioned between CH$_2$Cl$_2$/NaHCO$_{3(aq)}$. The organic fraction was removed, dried (MgSO$_4$), filtered and concentrated in vacuo. The crude residue was purified by flash chromatography (SiO$_2$) 1:1-Hexanes:EtOAc going to neat EtOAc. The purified material was then dissolved in the minimum volume of CH$_2$Cl$_2$ and hexane added in order to precipitate the desired product as a whiter crystalline solid 6-(4,4,5,5-Tetramethyl-[1,3,2]dioxaborolan-2-yl)-3H-pyrido[2,3-d]pyrimidin-4-one (15% yield, 96% purity) m/z (LC-MS, ESP): Mass ion not observable, R/T=3.30 min)

Procedure for the synthesis of 7-(4,4,5,5-Tetramethyl-[1,3,2]dioxaborolan-2-yl)-1H-pyrido[2,3-b][1,4]oxazin-2-one

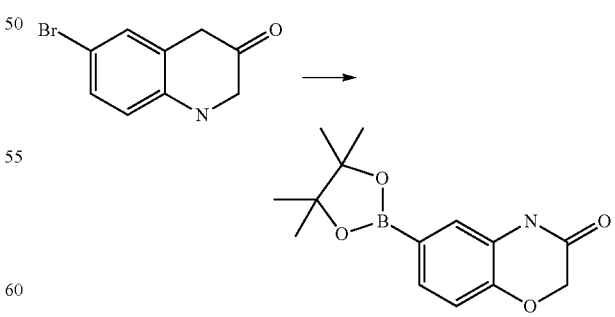

To a 0.3 M solution of 7-bromo-1H-pyrido[2,3-b][1,4]oxazin-2-one (1 equiv) were added bis(pinacolato)diboron (1.10 equiv), potassium acetate (3.5 equiv) and 1,1'-bis(diphenylphosphino)ferrocene (0.05 equiv). The mixture was degassed with nitrogen for 20 minutes before the addition of PdCl$_2$(dppf) (0.05 equiv) and degassing for a further 5 minutes. A condenser was attached to the reaction vessel and the mixture heated to reflux under an inert atmosphere for 16 hours. After this time, the reaction was cooled, filtered through Celite™. The cake was washed CH$_2$Cl$_2$ and the filtrate concentrated in vacuo before being re-dissolved in EtOAc and washed with H$_2$O and then saturated brine. The organic fraction was separated, dried (MgSO$_4$) and concentrated in vacuo to give a crude residue which was further purified by flash chromatography (SiO$_2$) using 1:1-EtOAc:Hexanes going to neat EtOAc as eluent to give the desired product.

7-(4,4,5,5-Tetramethyl-[1,3,2]dioxaborolan-2-yl)-1H-pyrido[2,3-b][1,4]oxazin-2-one: (97% yield, 90% purity) m/z (LC-MS, ESP): 317 [M+H+MeCN], R/T=3.72 min)

Procedure for the Synthesis of
2-Methoxynicotinonitrile-5-Boronic Acid

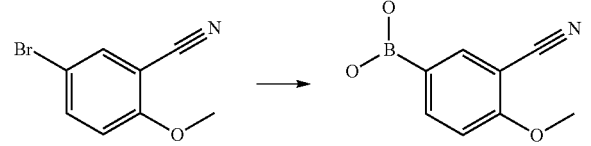

To a cooled (−78° C.) solution (0.25 M) of 5-bromo-2-methoxybenzonitrile in THF was added n-BuLi (1.10 equiv of a 2.5 M solution in hexanes) dropwise. The mixture was maintained at this temperature with stirring for 45 minutes before the addition of triisopropylborate (1.25 equiv). The reaction was then warmed to −20° C. before the addition of 1N HCl (0.5 reaction volumes). The mixture was allowed to warm to room temperature and stirred like this for a further 20 minutes. After this time the mixture was diluted with H$_2$O and then extracted with Et$_2$O (3×4 reaction volumes). The combined organic fractions were then dried (MgSO$_4$), filtered and concentrated in vacuo to give an off white solid which corresponded to the title compound 2-Methoxynicotinonitrile-5-boronic acid: (44% yield, 90% purity) m/z (LC-MS, ESP): 177.0 [M+H]$^+$, R/T=2.87 min)

Procedure for the Synthesis of
2-Ethoxynicotinonitrile-5-Boronic Acid

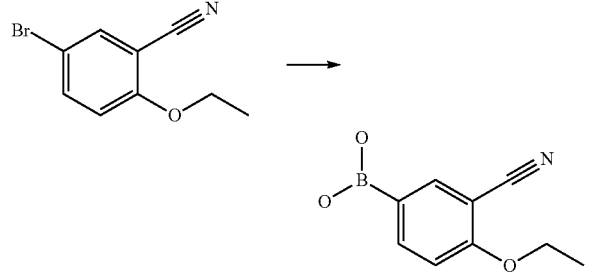

To a cooled (−78° C.) solution (0.25 M) of 5-bromo-2-ethoxybenzonitrile in THF was added n-BuLi (1.10 equiv of a 2.5 M solution in hexanes) dropwise. The mixture was maintained at this temperature with stirring for 45 minutes before the addition of triisopropylborate (1.25 equiv). The reaction was then warmed to −20° C. before the addition of 1N HCl (0.5 reaction volumes). The mixture was allowed to warm to room temperature and stirred like this for a further 20 minutes. After this time the mixture was diluted with H$_2$O and then extracted with Et$_2$O (3×4 reaction volumes). The combined organic fractions were then dried (MgSO$_4$), filtered and concentrated in vacuo to give an off white solid which corresponded to the title compound.

2-Ethoxynicotinonitrile-5-boronic acid: (23% yield, 97% purity) m/z (LC-MS, ESP): 191.0 [M+H]$^+$, R/T=3.09 min)

Procedure for the Synthesis of
2-Isopropoxynicotinonitrile-5-Boronic Acid

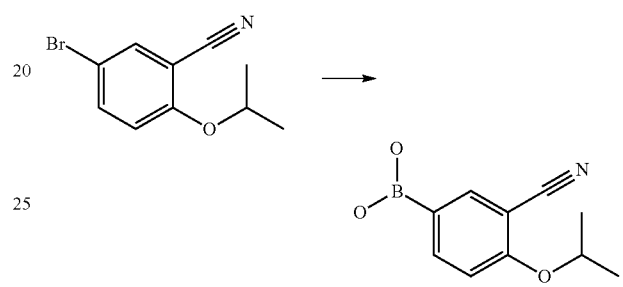

To a cooled (−78° C.) solution (0.25 M) of 5-bromo-2-isopropoxy-nicotinonitrile in THF was added n-BuLi (1.10 equiv of a 2.5 M solution in hexanes) dropwise. The mixture was maintained at this temperature with stirring for 45 minutes before the addition of triisopropylborate (1.25 equiv). The reaction was then warmed to −20° C. before the addition of 1N HCl (0.5 reaction volumes). The mixture was allowed to warm to room temperature and stirred like this for a further 20 minutes. After this time the mixture was diluted with H$_2$O and then extracted with Et$_2$O (3×4 reaction volumes). The combined organic fractions were then dried (MgSO$_4$), filtered and concentrated in vacuo to give an off white solid which which was triturated with CH$_2$Cl$_2$ to give the desired compound.

2-Isopropoxy-nicotinonitrile-5-boronic acid: (100% yield, 97% purity) m/z (LC-MS, ESP): 204.2 [M+H]$^-$, R/T=3.25 min)

Procedure for the synthesis of 7-(4,4,5,5-Tetramethyl-[1,3,2]dioxaborolan-2-yl)-2H-phthalazin-1-one

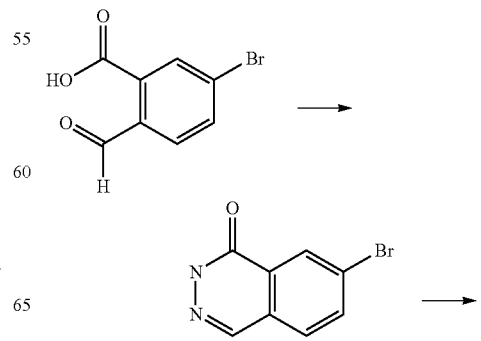

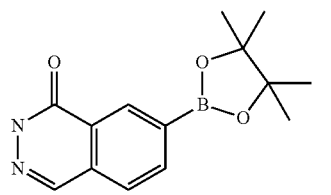

To a 3M solution of 5-bromo-2-formyl benzoic acid (1 equiv) in water was added hydrazine hydrate (5 equivs). The reaction was heated to 95° C. for 4 hours whereupon a white precipitate had formed in the mixture. The reaction was cooled, and filtered. The white solid material was washed with cold methanol and dried to give the desired product.

7-Bromo-2H-phthalazin-1-one: (73% yield, 95% purity) m/z (LC-MS, ESP): 225.2 [M+H]$^+$, R/T=2.99 min)

Bis(pinacolato)diboron (1.1 equiv), potassium acetate (3.5 equiv) and 1,1'-bis(diphenylphosphino)ferrocene (0.05 equiv) were dissolved in dioxane. The mixture was degassed with nitrogen for 20 minutes before the addition of PdCl$_2$ (dppf) (0.05 equiv). The mixture was degassed for a further 5 minutes. The mixture was heated to reflux for 16 hours and then allowed to cool to room temperature. Water was added to the mixture before it was extracted with EtOAc (2×2 reaction volumes). The combined organic fractions were dried (MgSO$_4$), filtered and concentrated in vacuo before being purified by flash chromatography (SiO$_2$) neat hexanes going to 1:1—Hexanes:EtOAc then neat EtOAc to give the desire product as a white crystalline solid.

7-(4,4,5,5-Tetramethyl-[1,3,2]dioxaborolan-2-yl)-2H-phthalazin-1-one: (86% yield, 92% purity) m/z (LC-MS, ESP): 191.3 [M+H]$^+$, R/T=2.29 min)

Procedure for the synthesis of 6-(4,4,5,5-Tetramethyl-[1,3,2]dioxaborolan-2-yl)-2,3-dihydro-isoindol-1-one

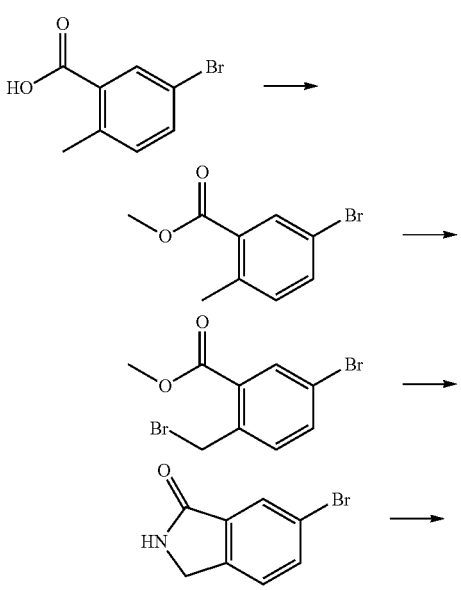

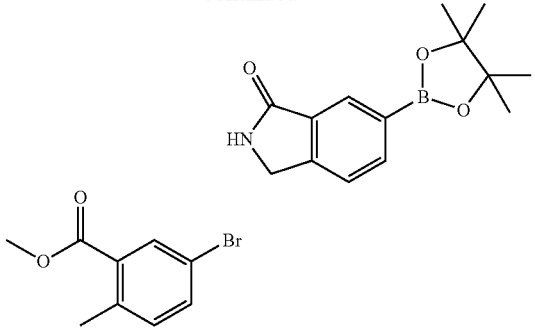

5-Bromo-2-methylbenzoic acid (1 equiv) was dissolved in a 1:9 MeOH/toluene mixture (0.1 M). The reaction mixture was cooled to 0° C. and a trimethylsilyldiazomethane (1.05 equiv) solution in diethylether (2M) was added slowly until a persistent yellow tinge was observed. The reaction mixture was stirred at room temperature for 1 hour. The reaction mixture was concentrated in vacuo. The resulting residue was sonicated in hexane, collected by vacuum filtration over a sintered funnel, dried and used without further purification.

5-Bromo-2-methyl-benzoic acid methyl ester: (99% yield, 100% purity) m/z (LC-MS, ESP): no ionisation R/T=4.43 min

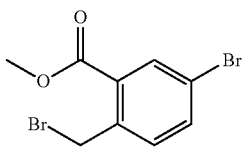

To a solution of 5-Bromo-2-methyl-benzoic acid methyl ester (1 equiv) in chloroform (0.1 M) were added N-bromosuccinimide (1.2 equiv) and benzoyl peroxide (0.05 equiv). The reaction mixture was stirred at reflux for 16 hours. It was then diluted with chloroform and a precipitate was collected by vacuum filtration on a sintered funnel. The filtrate was concentrated in vacuo. The subsequent residue was purified by flash column chromatography onto silica gel eluting with DCM in hexane (0 to 20%) to yield the desired product as a clear colourless oil.

5-Bromo-2-bromomethyl-benzoic acid methyl ester: 80% yield, 100% purity) m/z (LC-MS, ESP): no ionisation R/T=4.40 min

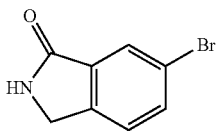 [SMILES: O=C1NCc2ccc(Br)cc21]

A solution of 5-bromo-2-bromomethyl-benzoic acid methyl ester (1 equiv) in a 1:1 THF/MeOH mixture was treated by gentle bubbling of ammonia gas for 40 minutes at room temperature. The reaction mixture was concentrated in vacuo. The residue was sonicated in CH$_2$Cl$_2$ for 15 minutes then filtered to give the desired product as a white solid.

6-Bromo-2,3-dihydro-isoindol-1-one: (98% yield, 90% purity) m/z (LC-MS, ESP): 212.3/214.3 [M+H]$^+$ R/T=2.98 min

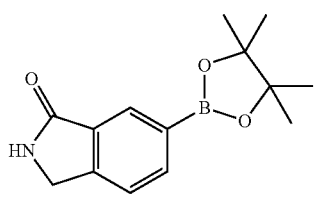 [SMILES: CC1(C)OB(c2ccc3c(c2)C(=O)NC3)OC1(C)C]

To a solution of 6-bromo-2,3-dihydro-isoindol-1-one (1 equiv) in dry dioxan (0.1 M) were added bis(pinacolato)diboron (1.1 equiv), potassium acetate (3.5 equiv) and dppf (0.05 equiv). The reaction mixture was degassed with nitrogen for 20 minutes. PdCl$_2$(dppf) (0.05 equiv) was added to the reaction mixture, which was degassed for a further 5 minutes. The reaction mixture was heated to 70° C. for 2 hours under nitrogen then heated to 120° C. for 16 hours. The reaction mixture was partitioned between EtOAc and water. The aqueous phase was further extracted with EtOAc and the combined organic phases dried (MgSO$_4$), filtered and concentrated in vacuo. The residue was sonicated in EtOAc, the suspension was filtered onto a sintered funnel and the collected grey solid was dried and used without further purification.

6-(4,4,5,5-Tetramethyl-[1,3,2]dioxaborolan-2-yl)-2,3-dihydro-isoindol-1-one: (82% yield, 29% purity, main impurity being the boronic acid 43%) m/z (LC-MS, ESP): 519.5 [2M+H] R/T=3.38 min Procedure for the synthesis of 7-(4,4,5,5-Tetramethyl-[1,3,2]dioxaborolan-2-yl)-3,4-dihydro-1H-benzo[e][1,4]diazepine-2,5-dione

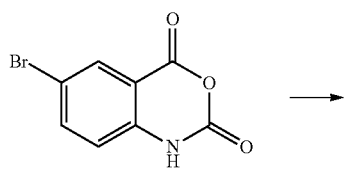

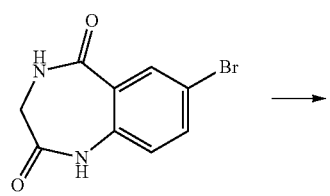

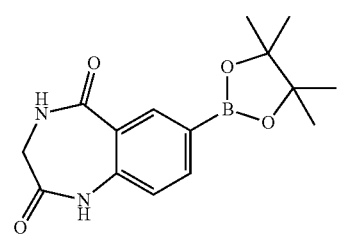

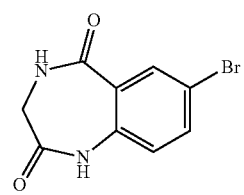 [SMILES: O=C1CNC(=O)c2cc(Br)ccc2N1]

To a solution of 5-bromoisatoic anhydride (1 equiv) in water (1 M) was added glycine (1.4 equiv) and triethylamine (1 equiv) at room temperature. The reaction mixture was stirred at room temperature for 4 hours to give a cloudy solution. The reaction mixture was concentrated in vacuo. Acetic acid was added and the reaction mixture was stirred at 140° C. for 4.5 hours. The reaction mixture was cooled down slowly to room temperature. A precipitate was formed. The reaction mixture was diluted with diethyl ether then filtered through a sintered funnel to yield the desired product.

7-Bromo-3,4-dihydro-1H-benzo[e][1,4]diazepine-2,5-dione: (75% yield, 100% purity) m/z (LC-MS, ESP): 255.2/257.2 [M+H]$^+$ R/T=2.67 min

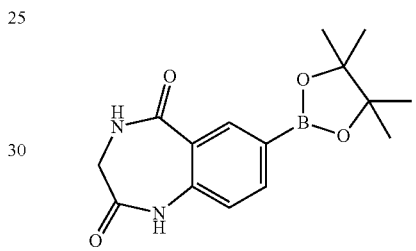

To a solution of 7-bromo-3,4-dihydro-1H-benzo[e][1,4]diazepine-2,5-dione (1 equiv) in dry dioxan (0.1 M) were added bis(pinacolato)diboron (1.1 equiv), potassium acetate (3.5 equiv) and dppf (0.05 equiv). The reaction mixture was degassed with nitrogen for 20 minutes. PdCl$_2$(dppf) (0.05 equiv) was added to the reaction mixture, which was degassed for a further 5 minutes. The reaction was heated to 120° C. for 16 hours under nitrogen. The reaction mixture was partitioned between CH$_2$Cl$_2$/MeOH and water. The aqueous phase was further extracted with CH$_2$Cl$_2$/MeOH. The combined organic phases were dried (MgSO$_4$), filtered and concentrated in vacuo. The residue was sonicated in hexane/CH$_2$Cl$_2$, filtered, sonicated in CH$_2$Cl$_2$ and filtered to yield the desired product.

7-(4,4,5,5-Tetramethyl-[1,3,2]dioxaborolan-2-yl)-3,4-dihydro-1H-benzo[e][1,4]diazepine-2,5-dione: (63% yield, 85% purity main impurity being the boronic acid 15%) m/z (LC-MS, ESP): 303.4 [M+H]$^+$ R/T=3.08 min

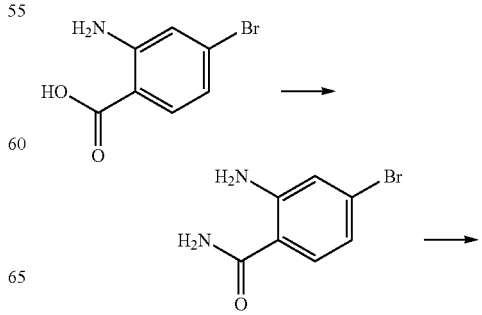

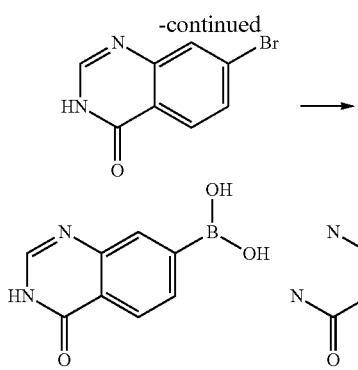

To a solution of 2-amino-4-bromobenzoic acid (1 equiv) in DMA (0.23 M), were added ammonium chloride (7 equiv), HBTU (1 equiv) and diisopropylethylamine (2 equiv). The reaction mixture was stirred for 24 hours at room temperature. DMA was evaporated and the residue was purified by flash column chromatography onto silica gel eluting with a gradient of TBME/hexane to yield the desired product as a white solid.

2-Amino-4-bromo-benzamide: 40% yield, 100% purity) m/z (LC-MS, ESP): 215 [M+H]R/T=3.00 min

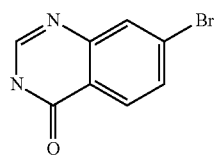 [SMILES: O=c1[nH]cnc2cc(Br)ccc12]

To a solution of 2-amino-4-bromo-benzamide (1 equiv) in DMA (0.14 M) were added triethyl orthoformate (10 equiv) and trifluoroacetic acid (1 equiv). The reaction vessel was sealed and exposed to microwave radiation (160° C., medium absorption setting) for 30 minutes. The reaction mixture was concentrated in vacuo and the residue was filtered through a silica pad with 10% methanol in ethyl acetate yielding the required product as a pale yellow solid.
7-Bromo-3H-quinazolin-4-one: (71% yield, 100% purity) m/z (LC-MS, ESP): 268 [M+H]R/T=2.94 min

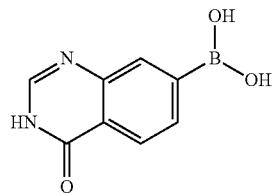 [SMILES: O=c1[nH]cnc2cc(B(O)O)ccc12]

To a solution of 7-bromo-3H-quinazolin-4-one (1 equiv) in dioxane (0.04 M) were added bispinacolato diboron (2.2 equiv), potassium acetate (1.5 equiv), dppf (0.1 equiv) and PdCl$_2$(dppf) (0.1 equiv). The reaction mixture was degassed with nitrogen for 5 minutes, sonicated and stirred at 120° C. for 3 hours. The reaction mixture was concentrated in vacuo. The residue was filtered through a Celite™ pad topped with silica with ethyl acetate. The mother liquor was concentrated in vacuo yielding a brown solid which was further purified by flash column chromatography onto silica gel eluting with a gradient of methanol/diethyl ether (0 to 5%) to yield the desired product as a white solid.

7-(4,4,5,5-Tetramethyl-[1,3,2]dioxaborolan-2-yl)-3H-quinazolin-4-one: (53% yield, 61% purity main impurity being the boronic acid 39%) m/z (LC-MS, ESP): [M+H]$^+$ R/T=min

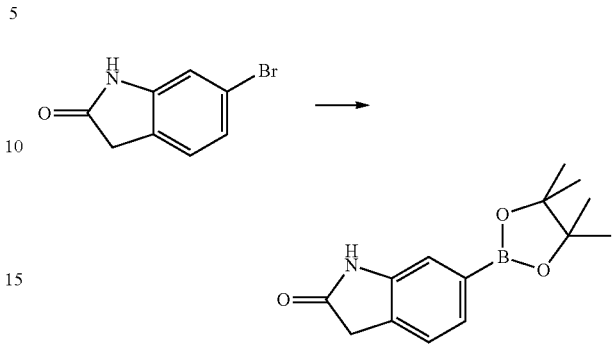

To a solution of 6-bromo-2-oxindole (1 equiv) in NMP (0.05 M) were added bispinacolato diboron (2.4 equiv), potassium acetate (1.5 equiv), dppf (0.05 equiv) and PdCl$_2$ (dppf) (0.05 equiv). The reaction mixture was stirred at 130° C. for 3 hours and then concentrated in vacuo. The residue was partitioned between water and ethyl acetate. The organic phase was dried over anhydrous sodium sulphate, filtered and concentrated in vacuo. The crude residue was purified by flash column chromatography on silica gel eluting with EtOAc/hexane (9/1), yielding the desired product as a red solid.

6-(4,4,5,5-Tetramethyl-[1,3,2]dioxaborolan-2-yl)-1,3-di-hydro-indol-2-one: (22% yield, 51% purity main impurity being the boronic acid 28%) m/z (LC-MS, ESP): 260 [M+H]$^+$ R/T=3.51 min Procedure for the synthesis of 5-(4,4,5,5-Tetram-ethyl-[1,3,2]dioxaborolan-2-yl)-2,3-dihydro-isoin-dol-1-one

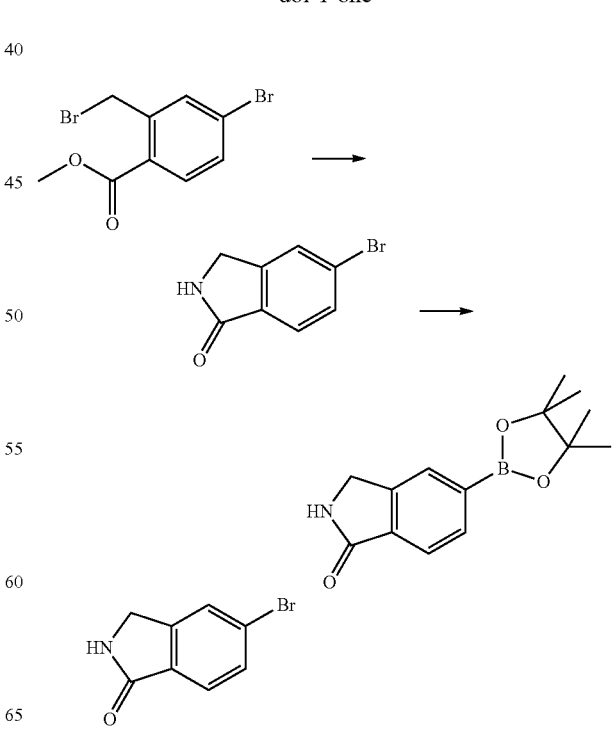

4-Bromo-2-bromomethyl-benzoic acid methyl ester was prepared according to literature. A solution of 4-bromo-2-bromomethyl-benzoic acid methyl ester (1 equiv) in a 1:1 THF/MeOH mixture was treated by gentle bubbling of ammonia gas for 4 hours at room temperature. The reaction mixture was concentrated in vacuo. The residue was sonicated in water, filtered, then sonicated in diethylether and filtered to give the desired product as a white solid.

5-Bromo-2,3-dihydro-isoindol-1-one: (81% yield, 100% purity) m/z (LC-MS, ESP): 212.3/214.3 [M+H]$^+$ R/T=3.06 min

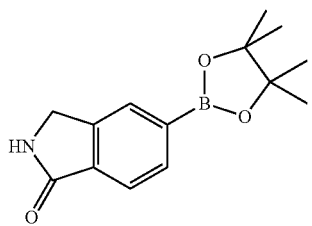 [SMILES: CC1(C)OB(c2ccc3c(c2)CNC3=O)OC1(C)C]

To a solution of 5-bromo-2,3-dihydro-isoindol-1-one (1 equiv) in dry dioxan (0.1 M) were added bis(pinacolato) diboron (1.1 equiv), potassium acetate (3.5 equiv) and dppf (0.05 equiv). The reaction mixture was degassed with nitrogen for 20 minutes. PdCl$_2$(dppf) (0.05 equiv) was added to the reaction mixture, which was degassed for a further 5 minutes. The reaction mixture was heated to 70° C. for 2 hours under nitrogen then heated to 120° C. for 16 hours. The reaction mixture was partitioned between EtOAc and water. The aqueous phase was further extracted with EtOAc and the combined organic phases dried (MgSO$_4$), filtered and concentrated in vacuo. The residue was dissolved in CH$_2$Cl$_2$ and hexane was added. The resulting suspension was filtered and the collected brown powder was dried and used without further purification.

5-(4,4,5,5-Tetramethyl-[1,3,2]dioxaborolan-2-yl)-2,3-dihydro-isoindol-1-one: (94% yield, 76% purity, main impurity being the boronic acid 13%) m/z (LC-MS, ESP): 260.4 [2M+H]$^+$ R/T=3.51 min Procedures for the Preparation of Examples 1a to 1du

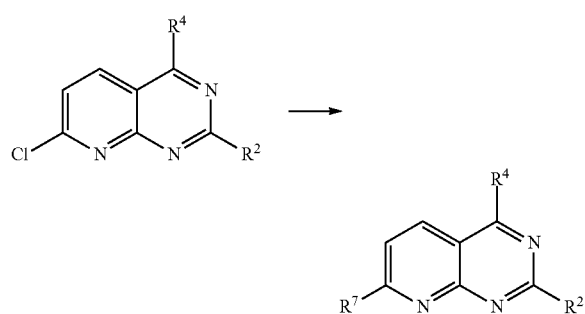

R$^4$=(S)-3-methyl-morpholine
R$^2$=(S)-3-methyl-morpholine or cis-dimethylmorpholine or 2-Ethyl-piperidine or morpholine or thiomorpholine or 4-methylpiperazine
R$^7$=aryl or heteroaryl Procedures for the Suzuki Coupling:
The synthesis of the appropriate chloro-substrate has been described in the present document as intermediates. The appropriate pinacolate boron ester or boronic acids were prepared according to synthesis described in the present document (as intermediates) or commercially available, typically from the following suppliers:

Sigma-Aldrich, Lancaster, Frontier Scientific, Boron Molecular, Interchim, Asymchem, Combi-blocks, Apollo Scientific, Fluorochem, ABCR, Digital Speciality Chemicals.

Conditions A:
The appropriate chloro-substrate (1 equiv) was dissolved in a toluene/ethanol (1:1) solution (0.02 M). Sodium carbonate (2 equiv) and the appropriate pinacolate boron ester or boronic acid (1 equiv) were then added followed by tetrakis(triphenylphosphine)palladium$^0$ (0.1 equiv). The reaction vessel was sealed and the mixture exposed to microwave radiation (140° C., medium absorption setting) for 30 minutes. Upon completion the samples were filtered through a silica cartridge, washed with EtOAc and then concentrated in vacuo. The crude residue was then purified by preparative HPLC to give the desired products.

Conditions B:
A mixture of the appropriate chloro-substrate (1 equiv), potassium carbonate (2.4 equiv), the appropriate pinacolate boron ester or boronic acid (1.1 equiv) and tetrakis(triphenylphosphine)palladium$^0$ (0.05 equiv) in n-butanol (0.03 M of chloro-substrate) was stirred at 120° C. for 2 hours. Upon completion the samples were filtered through a silica cartridge, washed through with CH$_2$Cl$_2$ and then concentrated in vacuo. The crude residue was then purified by preparative HPLC to give the desired products.

Conditions C:
To a mixture of the appropriate chloro-substrate (1 equiv), potassium carbonate (2.4 equiv), and the appropriate pinacolate boron ester or boronic acid (1.1 equiv) in acetonitrile/water (1:1) (0.041 M of chloro-substrate) was added tetrakis(triphenylphosphine)palladium$^0$ (0.05 equiv). The reaction vessel was sealed and exposed to microwave radiation (150° C., medium absorption setting) for 30 minutes under nitrogen atmosphere. Upon completion the samples were filtered through a silica cartridge, washed with CH$_2$Cl$_2$ and methanol and then concentrated in vacuo. The crude residue was then purified by preparative HPLC to give the desired products.

Conditions D:
To a mixture of the appropriate chloro-substrate (1 equiv), potassium carbonate (1.2 equiv), and the appropriate pinacolate boron ester or boronic acid (1.2 equiv) in acetonitrile/water (1:1) (0.083 M of chloro-substrate) was added tetrakis(triphenylphosphine)palladium$^0$ (0.05 equiv). The reaction vessel was sealed and exposed to microwave radiation (130° C., medium absorption setting) for 25 minutes under nitrogen atmosphere. Upon completion the sample was purified by column chromatography on silica gel using a gradient MeOH/CH$_2$Cl$_2$ to afford the desired product which was recrystallised from diethyl ether.

Conditions E:
To a mixture of the appropriate chloro-substrate (1 equiv), potassium carbonate (2.4 equiv), and the appropriate pinacolate boron ester or boronic acid (1.3 equiv) in acetonitrile/water (1:1) (0.041 M of chloro-substrate) was added tetrakis(triphenylphosphine)palladium$^0$ (0.05 equiv). The reaction vessel was sealed and heated at 95° C. for 16 hours. Upon completion the reaction mixture was partitioned between aqueous HCl and CH$_2$Cl$_2$ and washed with aqueous HCl. Combined aqueous phase were extracted with CH$_2$Cl$_2$ (2×), neutralised with aqueous NaOH (2N) to give a cloudy solution that was extracted with $CH_2Cl_2$. Combined organic phases were washed with brine, dried ($MgSO_4$), filtered and concentrated in vacuo. The crude residue was purified by column chromatography on silica gel eluting with 0 to 4% MeOH in $CH_2Cl_2$ to give the desired product.

Conditions F:

To a mixture of the appropriate chloro-substrate (1 equiv), potassium carbonate (2.0 equiv), and the appropriate pinacolate boron ester or boronic acid (1.5 equiv) in acetonitrile/water (1:1) (0.028 M of chloro-substrate) was added tetrakis(triphenylphosphine)palladium$^0$ (0.05 equiv). The reaction vessel was sealed and heated at 120° C. for 2 hours under nitrogen atmosphere. Upon completion the reaction mixture was partitioned between water and $CH_2Cl_2$ and extracted with $CH_2Cl_2$. Combined organic phases were dried ($MgSO_4$), filtered and concentrated in vacuo. The crude residue was purified by column chromatography on silica gel eluting with 0 to 4% MeOH in $CH_2Cl_2$ to give the desired product which was recrystallised from hexane/diethyl ether.

Conditions G:

To a mixture of the appropriate chloro-substrate (1 equiv), potassium carbonate (3.0 equiv), and the appropriate pinacolate boron ester or boronic acid (1.05 equiv) in acetonitrile/water (1:1) (0.068 M of chloro-substrate) was added tetrakis(triphenylphosphine)palladium$^0$ (0.05 equiv). The reaction vessel was sealed and heated at 100° C. for 5 hours under nitrogen atmosphere. Upon completion the reaction mixture was partitioned between brine and $CH_2Cl_2$ and extracted with $CH_2Cl_2$. Combined organic phases were dried ($MgSO_4$), filtered and concentrated in vacuo. The crude residue was purified by column chromatography on silica gel eluting with 0 to 4% MeOH in $CH_2Cl_2$ to give the desired products which were recrystallised from hexane/$CH_2Cl_2$.

Conditions H:

A mixture of the appropriate chloro-substrate (1 equiv), potassium carbonate (3.0 equiv), the appropriate pinacolate boron ester or boronic acid (1.1 equiv) and tetrakis(triphenylphosphine)palladium$^0$ (0.05 equiv) in acetonitrile/water (0.1 M of chloro-substrate) was stirred at 100° C. for 8 hours. Upon completion the sample was concentrated in vacuo. The crude residue was then purified by preparative HPLC to give the desired product.

Conditions I:

Conditions I were similar to conditions H apart form the heating method: 100° C. for 2 hours.

Conditions J:

A mixture of the appropriate chloro-substrate (1 equiv), potassium carbonate (1.2 equiv), the appropriate pinacolate boron ester or boronic acid (1.2 equiv) and tetrakis(triphenylphosphine)palladium$^0$ (0.05 equiv) in acetonitrile/water (0.03 M of chloro-substrate) was stirred at 100° C. for 2 hours. Upon completion the sample was concentrated in vacuo. The crude residue was then purified by preparative HPLC to give the desired product.

Conditions K:

Conditions K were similar to conditions G apart form the heating method: 100° C. for 16 hours.

Conditions L:

To a mixture of the appropriate chloro-substrate (1 equiv), potassium carbonate (2.5 equiv), and the appropriate pinacolate boron ester or boronic acid (1.10 equiv) in acetonitrile/water (1:1) (0.041 M of chloro-substrate) was added tetrakis(triphenylphosphine)palladium$^0$ (0.05 equiv). The reaction vessel was sealed and exposed to microwave radiation (100° C., medium absorption setting) for 90 minutes. Upon completion the reaction mixture was partly concentrated. The residue was partitioned between water and ethyl acetate and extracted with ethyl acetate and n-butanol. Combined organic phases were dried ($MgSO_4$), filtered and concentrated in vacuo. The crude residue was purified by column chromatography on silica gel eluting with 30 to 10% hexane in ethyl acetate to give the desired product which was recrystallised from hexane/$CH_2Cl_2$.

Conditions M:

A mixture of the appropriate chloro-substrate (1 equiv), cesium fluoride (3.0 equiv), the appropriate pinacolate boron ester or boronic acid (1.1 equiv) and tetrakis(triphenylphosphine)palladium$^0$ (0.05 equiv) in acetonitrile/water (0.09 M of chloro-substrate) was stirred at 115° C. for 48 hours. Upon completion the sample was concentrated in vacuo to half original volume. The residue was partitioned between water and $CH_2Cl_2$. Organic phase was dried ($MgSO_4$), filtered and concentrated in vacuo. The crude residue was purified by column chromatography on silica gel eluting with 0 to 100% ethyl acetate in hexane to give the desired product.

Conditions N:

A mixture of the appropriate chloro-substrate (1 equiv), tripotassium phosphate (1.5 equiv), the appropriate pinacolate boron ester or boronic acid (1.05 equiv) and bis(tri-t-butylphosphine)palladium (0.05 equiv) was suspended in dioxane (0.16 M of chloro-substrate). The reaction vessel was sealed and exposed to microwave radiation (170° C., medium absorption setting) for 45 minutes. Upon completion the sample was concentrated in vacuo. The residue was partitioned between water and $CH_2Cl_2$. The organic phase was dried ($MgSO_4$), filtered and concentrated in vacuo. The crude residue was purified by column chromatography on silica gel eluting with 40 to 100% ethyl acetate in hexane to give the desired product.

Conditions O:

A mixture of the appropriate chloro-substrate (1 equiv), potassium carbonate (2.5 equiv), the appropriate pinacolate boron ester or boronic acid (1.1 equiv) and tetrakis(triphenylphosphine)palladium$^0$ (0.05 equiv) in n-butanol (0.068 M of chloro-substrate) was stirred at 95° C. for 15 minutes. Upon completion, the residue was partitioned between ethyl acetate and brine. Organic phase was dried ($MgSO_4$), filtered and concentrated in vacuo. The crude residue was purified by column chromatography on silica gel eluting with 30 to 100% ethyl acetate in hexane to give the desired product which was recrystallised from ethyl acetate/hexane.

Conditions P:

To a mixture of the appropriate chloro-substrate (1 equiv), potassium carbonate (2.0 equiv), and the appropriate pinacolate boron ester or boronic acid (2.0 equiv) in acetonitrile/water (1:1) (0.041 M of chloro-substrate) was added tetrakis(triphenylphosphine)palladium$^0$ (0.05 equiv). The reaction vessel was sealed and exposed to microwave radiation (120° C., medium absorption setting) for 10 minutes under nitrogen atmosphere. Upon completion the samples were filtered through a silica cartridge, washed through with $CH_2Cl_2$ and the concentrated in vacuo. The crude residue was then purified by preparative HPLC to give the desired product.

Conditions Q:

A mixture of the appropriate chloro-substrate (1 equiv), potassium carbonate (2.5 equiv), the appropriate pinacolate boron ester or boronic acid (1.1 equiv) and tetrakis(triphenylphosphine)palladium$^0$ (0.05 equiv) were dissolved in n-butanol (0.056 M of chloro-substrate). The reaction vessel was sealed and exposed to microwave radiation (150° C., medium absorption setting) for 30 minutes. Upon completion the samples were filtered through a silica cartridge, washed with $CH_2Cl_2$ and methanol and then concentrated in vacuo. The crude residue was purified by column chromatography on silica gel eluting with ethyl acetate and then 5% MeOH in $CH_2Cl_2$ to give the desired product.

Conditions R:

A mixture of the appropriate chloro-substrate (1 equiv), potassium carbonate (2.5 equiv), the appropriate pinacolate boron ester or boronic acid (1.2 equiv) and tetrakis(triphenylphosphine)palladium$^0$ (0.05 equiv) in acetonitrile/water (0.05 M of chloro-substrate) was stirred at 115° C. for 1.5 hours. Upon completion the crude reaction was filtered and the filtrate was concentrated in vacuo. The crude residue was purified by column chromatography on silica gel eluting with 5 to 20% MeOH in $CH_2Cl_2$ to give the desired product.

Conditions S:

A mixture of the appropriate chloro-substrate (1 equiv), potassium carbonate (10.0 equiv), the appropriate pinacolate boron ester or boronic acid (1.2 equiv) and tetrakis(triphenylphosphine)palladium$^0$ (0.05 equiv) in acetonitrile/water (0.1 M of chloro-substrate) was stirred at 100° C. for 2 hours. Upon completion the reaction mixture was partitioned between water and $CH_2Cl_2$ and extracted with $CH_2Cl_2$. Combined organic phases were dried ($MgSO_4$), filtered and concentrated in vacuo. The crude residue was purified by column chromatography on silica gel eluting with 0 to 5% MeOH in $CH_2Cl_2$ to give the desired product which was recrystallised from hexane/$CH_2Cl_2$.

Conditions T:

A mixture of the appropriate chloro-substrate (1 equiv), potassium carbonate (2.0 equiv), the appropriate pinacolate boron ester or boronic acid (2.0 equiv) and tetrakis(triphenylphosphine)palladium$^0$ (0.05 equiv) was dissolved in acetonitrile/water (0.02 M of chloro-substrate). The reaction vessel was sealed and exposed to microwave radiation (130° C., medium absorption setting) for 30 minutes. Upon completion the sample was concentrated in vacuo. The crude residue was purified by column chromatography on silica gel eluting with 0 to 5% MeOH in $CH_2Cl_2$ to give the desired product.

Conditions U:

A mixture of the appropriate chloro-substrate (1 equiv), potassium carbonate (3.0 equiv), the appropriate pinacolate boron ester or boronic acid (1.0 equiv) and tetrakis(triphenylphosphine)palladium$^0$ (0.05 equiv) in acetonitrile/water (0.1 M of chloro-substrate) was stirred at 110° C. for 8 hours. Upon completion the reaction mixture was partitioned between water and $CH_2Cl_2$ and extracted with $CH_2Cl_2$. Combined organic phases were washed with brine, dried ($MgSO_4$), filtered and concentrated in vacuo. The crude residue was purified by column chromatography on silica gel eluting with 0 to 2% MeOH in $CH_2Cl_2$ to give the desired product which was recrystallised from hexane/$CH_2Cl_2$.

Conditions V:

A mixture of the appropriate chloro-substrate (1 equiv), cesium fluoride (3.0 equiv), the appropriate pinacolate boron ester or boronic acid (1 equiv) and tetrakis(triphenylphosphine)palladium$^0$ (0.05 equiv) in acetonitrile/water (0.1 M of chloro-substrate) was stirred at 100° C. for 16 hours. The reaction mixture was partitioned between water and $CH_2Cl_2$ and extracted with $CH_2Cl_2$. The organic phase was dried ($MgSO_4$), filtered and concentrated in vacuo. The crude residue was purified by column chromatography on silica gel eluting with 0 to 5% MeOH in $CH_2Cl_2$ to give the desired product which was recrystallised from hexane/$CH_2Cl_2$.

Conditions W:

A mixture of the appropriate chloro-substrate (1 equiv), potassium carbonate (2.5 equiv), the appropriate pinacolate boron ester or boronic acid (1 equiv) and tetrakis(triphenylphosphine)palladium$^0$ (0.05 equiv) was dissolved in acetonitrile/water (0.04 M of chloro-substrate). The reaction vessel was sealed and exposed to microwave radiation (110° C., medium absorption setting) for 10 minutes. The crude residue was purified by column chromatography on silica gel eluting with 0 to 2% MeOH in TBME to give the desired product.

TABLE 1

| | Purity (%) | Retention time (min) | m/z $[M + H]^+$ | Conditions | Example Structure |
|---|---|---|---|---|---|
| 1a | 96 | 7.66 | 466.6 | A | |

TABLE 1-continued

| | Purity (%) | Retention time (min) | m/z [M + H]⁺ | Conditions | Example Structure |
|---|---|---|---|---|---|
| 1b | 99 | 4.31 | 480.4 | A | |
| 1c | 98 | 4.67 | 478.4 | A | |
| 1d | 99 | 4.13 | 406.2 | A | |
| 1e | 99 | 3.94 | 422.3 | A | |
| 1f | 99 | 4.32 | 420.3 | A | |

TABLE 1-continued

| | Purity (%) | Retention time (min) | m/z [M + H]+ | Conditions | Example Structure |
|---|---|---|---|---|---|
| 1g | 99 | 3.83 | 436.3 | A | |
| 1h | 89 | 3.99 | 422.2 | A | |
| 1i | 96 | 3.85 | 436.3 | A | |
| 1j | 99 | 4.5 | 420.3 | A | |

TABLE 1-continued

| | Purity (%) | Retention time (min) | m/z [M + H]⁺ | Conditions | Example Structure |
|---|---|---|---|---|---|
| 1k | 98 | 4.49 | 426.3 | A | |
| 1l | 100 | 3.91 | 452.3 | A | |
| 1m | 99 | 3.99 | 437.4 | B | |
| 1n | 99 | 4.2 | 437.4 | B | |

TABLE 1-continued

| | Purity (%) | Retention time (min) | m/z [M + H]+ | Conditions | Example Structure |
|---|---|---|---|---|---|
| 1o | 99 | 4.23 | 437.4 | B | |
| 1p | 99 | 4.16 | 425.4 | B | |
| 1q | 98 | 4.1 | 492.5 | B | |
| 1r | 98 | 1.09 | 438.4 | B | |

TABLE 1-continued

| | Purity (%) | Retention time (min) | m/z [M + H]+ | Conditions | Example Structure |
|---|---|---|---|---|---|
| 1s | 99 | 3.98 | 410.4 | B | |
| 1t | 100 | 4.04 | 468.5 | B | |
| 1u | 100 | 4.95 | 422.3 | B | |
| 1v | 98 | 4.32 | 441.4 | B | |

TABLE 1-continued

| | Purity (%) | Retention time (min) | m/z [M + H]+ | Conditions | Example Structure |
|---|---|---|---|---|---|
| 1w | 91 | 6.46 | 441.3 | B | |
| 1x | 98 | 7.16 | 439.3 | B | |
| 1y | 97 | 6.54 | 441.4 | B | |
| 1z | 95 | 5.92 | 425.5 | B | |
| 1aa | 100 | 8.28 | 424.4 | B | |

TABLE 1-continued

| | Purity (%) | Retention time (min) | m/z [M + H]+ | Conditions | Example Structure |
|---|---|---|---|---|---|
| 1ab | 99 | 6.67 | 467.4 | B | |
| 1ac | 100 | 8.01 | 509.5 | B | |
| 1ad | 100 | 7.23 | 468.4 | B | |
| 1ae | 100 | 6.99 | 481.4 | B | |
| 1af | 99 | 7.55 | 495.4 | B | |

TABLE 1-continued

| | Purity (%) | Retention time (min) | m/z [M + H]+ | Conditions | Example Structure |
|---|---|---|---|---|---|
| 1ag | 100 | 6.51 | 511.4 | B | |
| 1ah | 99 | 6.95 | 425.2 | B | |
| 1ai | 89 | 7.52 | 465.2 | B | |
| 1aj | 80 | 4.5 | 459.3 | B | |

TABLE 1-continued

| | Purity (%) | Retention time (min) | m/z [M + H]+ | Conditions | Example Structure |
|---|---|---|---|---|---|
| 1ak | 97 | 6.79 | 463.2 | C | |
| 1al | 99 | 4.07 | 491.4 | C | |
| 1am | 99 | 3.94 | 484.3 | C | |
| 1an | 99 | 3.95 | 484.3 | C | |

TABLE 1-continued

| | Purity (%) | Retention time (min) | m/z [M + H]+ | Conditions | Example Structure |
|---|---|---|---|---|---|
| 1ao | 97 | 3.75 | 449.3 | C | |
| 1ap | 99 | 3.86 | 463.3 | C | |
| 1aq | 99 | 3.87 | 529.4 | D | |
| 1ar | 99 | 3.41 | 407.3 | E | |
| 1as | 98 | 6.59 | 449.4 | F | |

TABLE 1-continued

| | Purity (%) | Retention time (min) | m/z [M + H]+ | Conditions | Example Structure |
|---|---|---|---|---|---|
| 1at | 97 | 4.05 | 499.3 | G | |
| 1au | 96 | 7 | 425.3 | G | |
| 1av | 99 | 4.28 | 449.4 | H | |
| 1aw | 97 | 4.33 | 431.3 | I | |
| 1ax | 99 | 3.99 | 450.5 | J | |

TABLE 1-continued

| | Purity (%) | Retention time (min) | m/z [M + H]+ | Conditions | Example Structure |
|---|---|---|---|---|---|
| 1ay | 98 | 4.19 | 443.3 | K | |
| 1az | 100 | 8.94 | 421.2 | L | |
| 1ba | 100 | 4.28 | 464.5 | M | |
| 1bb | 98 | 8.16 | 450.3 | N | |
| 1bc | 99 | 3.99 | 454.4 | O | |

TABLE 1-continued

| | Purity (%) | Retention time (min) | m/z [M + H]+ | Conditions | Example Structure |
|---|---|---|---|---|---|
| 1bd | 90 | 8.4 | 485.3 | P | |
| 1be | 99 | 3.91 | 507.4 | C | |
| 1bf | 99 | 3.39 | 532.4 | C | |
| 1bg | 97 | 4.19 | 494.4 | M | |

TABLE 1-continued

| | Purity (%) | Retention time (min) | m/z [M + H]+ | Conditions | Example Structure |
|---|---|---|---|---|---|
| 1bh | 98 | 4.15 | 474.3 | Q | |
| 1bi | 96 | 4.13 | 474.4 | R | |
| 1bj | 94 | 3.99 | 492.3 | R | |
| 1bk | 98 | 4.04 | 517.4 | S | |
| 1bl | 98 | 4.13 | 431.2 | B | |

TABLE 1-continued

| | Purity (%) | Retention time (min) | m/z [M + H]⁺ | Conditions | Example Structure |
|---|---|---|---|---|---|
| 1bm | 98 | 4.27 | 445.3 | B | |
| 1bn | 97 | 4.27 | 451.2 | B | |
| 1bo | 99 | 4.21 | 436.3 | B | |
| 1bp | 99 | 4.40 | 440.2 | B | |

TABLE 1-continued

| | Purity (%) | Retention time (min) | m/z [M + H]⁺ | Conditions | Example Structure |
|---|---|---|---|---|---|
| 1bq | 87 | 4.22 | 420.3 | B | |
| 1br | 93 | 4.40 | 420.3 | B | |
| 1bs | 94 | 4.30 | 454.2 | B | |
| 1bt | 95 | 4.32 | 436.3 | B | |
| 1bu | 99 | 3.53 | 407.3 | B | |

TABLE 1-continued

| | Purity (%) | Retention time (min) | m/z [M + H]⁺ | Conditions | Example Structure |
|---|---|---|---|---|---|
| 1bv | 99 | 3.94 | 396.3 | B | |
| 1bw | 85 | 4.49 | 445.3 | B | |
| 1bx | 99 | 4.59 | 450.3 | B | |
| 1by | 98 | 4.20 | 450.3 | B | |

TABLE 1-continued

| | Purity (%) | Retention time (min) | m/z [M + H]+ | Conditions | Example Structure |
|---|---|---|---|---|---|
| 1bz | 87 | 4.30 | 436.3 | B | |
| 1ca | 99 | 4.62 | 434.4 | B | |
| 1cb | 99 | 4.74 | 434.4 | B | |
| 1cc | 92 | 4.67 | 463.0 | B | |

TABLE 1-continued

| | Purity (%) | Retention time (min) | m/z [M + H]⁺ | Conditions | Example Structure |
|---|---|---|---|---|---|
| 1cd | 99 | 4.63 | 450.4 | B | |
| 1ce | 85 | 3.71 | 421.3 | B | |
| 1cf | 98 | 4.35 | 410.3 | B | |
| 1cg | 97 | 4.34 | 436.3 | B | |

TABLE 1-continued

| | Purity (%) | Retention time (min) | m/z [M + H]⁺ | Conditions | Example Structure |
|---|---|---|---|---|---|
| 1ch | 98 | 4.48 | 459.3 | B | |
| 1ci | 87 | 4.49 | 465.3 | B | |
| 1cj | 100 | 4.50 | 450.3 | B | |
| 1ck | 99 | 4.14 | 466.5 | T | |

TABLE 1-continued

| | Purity (%) | Retention time (min) | m/z [M + H]+ | Conditions | Example Structure |
|---|---|---|---|---|---|
| 1cl | 100 | 3.8 | 474.4 | P | |
| 1cm | 99 | 4.01 | 477.3 | T | |
| 1cn | 99 | 4.73 | 474.3 | E | |
| 1co | 99 | 4.08 | 477.3 | D | |
| 1cp | 87 | 4.48 | 461.3 | D | |

TABLE 1-continued

| | Purity (%) | Retention time (min) | m/z [M + H]+ | Conditions | Example Structure |
|---|---|---|---|---|---|
| 1cq | 84 | 7.44 | 493.4 | L | |
| 1cr | 97 | 3.85 | 475.3 | T | |
| 1cs | 100 | 4.63 | 450.4 | D | |
| 1ct | 99 | | 464.3 | S | |
| 1cu | 100 | 3.89 | 436.2 | B | |

TABLE 1-continued

| | Purity (%) | Retention time (min) | m/z [M + H]+ | Conditions | Example Structure |
|---|---|---|---|---|---|
| 1cv | 100 | 3.89 | | J | |

Note:
The following examples were synthesized from the corresponding boronic acids: 1aa, 1ab, 1ac, 1ad, 1ae, 1af, 1ag, 1ah, 1ai, 1aj, 1ak, 1al, 1am, 1an, 1ao, 1ap, 1aq, 1as, 1at, 1au, 1av, 1aw, 1ax, 1ay, 1az, 1ba, 1bb, 1bd, 1be, 1bk, 1bl, 1bm, 1bn, 1bo, 1bp, 1bq, 1br, 1bs, 1bt, 1bu, 1bv, 1bw, 1bx, 1by, 1bz, 1ca, 1cb, 1cc, 1cd, 1cf, 1cg, 1ch, 1ci, 1cj, 1d, 1e, 1f, 1g, 1h, 1i, 1j, 1k, 1n, 1o, 1p, 1r, 1t, 1w, 1x, 1y 1cn, 1co, 1cp, 1cs, 1cy and 1z.
The following Examples were synthesized from the corresponding pinacolate boron esters: 1a-c, 1ck, 1cl, 1cm, 1cq, 1cr, 1ct, 1cu, 1ar, 1bf, 1ce, 1m, 1q, 1s, 1u and 1y.

NMR Data for Example 1n
$^1$H NMR (300 MHz, CDCl$_3$) δ ppm 8.88 (ArH, d, J=2.20 Hz, 1H), 8.55 (ArH, dd, J=8.70, 2.45 Hz, 1H), 8.04 (ArH, d, J=8.43 Hz, 1H), 7.42 (ArH, d, J=8.44 Hz, 1H), 6.88 (ArH, d, J=8.70 Hz, 1H), 5.01-4.90 (CH, m, 1H), 4.65 (CH, d, J=13.12 Hz, 1H), 4.40 (CH, d, J=6.68 Hz, 1H), 4.04 (OCH$_3$+ CH$_2$, s, 5H), 3.96-3.69 (CH$_2$, m, 7H), 3.60 (CH, dt, J=11.86, 11.60, 2.67 Hz, 1H), 3.40 (CH, dt, J=13.01, 12.73, 3.60 Hz, 1H), 1.50 (CH$_3$, d, J=6.78 Hz, 3H), 1.39 (CH$_3$, d, J=6.81 Hz, 3H)
$^{13}$C NMR (75 MHz, CDCl$_3$) δ ppm 165.41, 165.29, 162.98, 160.10, 160.01, 146.58, 138.51, 134.81, 128.05, 112.42, 110.84, 104.75, 71.29, 70.92, 67.26, 66.92, 53.75, 52.87, 46.94, 44.43, 39.33, 14.73 and 14.36.

NMR Data for Example 1u
$^1$H NMR (300 MHz, CDCl$_3$) δ ppm 8.80 (ArH, d, J=1.91 Hz, 1H), 8.39 (ArH, dd, J=8.66, 2.39 Hz, 1H), 7.96 (ArH, d, J=8.48 Hz, 1H), 7.35 (ArH, d, J=8.49 Hz, 1H), 6.59 (ArH, d, J=8.66 Hz, 1H), 4.91 (CH, dd, J=4.15, 1.62 Hz, 1H), 4.78 (NH$_2$, s, 2H), 4.67-4.55 (CH, m, 1H), 4.34 (CH, d, J=6.88 Hz, 1H), 4.04-3.91 (CH$_2$, m, 2H), 3.90-3.64 (CH$_2$, m, 7H), 3.62-3.49 (CH$_2$, m, 1H), 3.44-3.29 (CH$_2$, m, 1H), 1.45 (CH$_3$, d, J=6.77 Hz, 3H), 1.34 (CH$_3$, d, J=6.82 Hz, 3H)
$^{13}$C NMR (75 MHz, CDCl$_3$) δ ppm 165.54, 163.10, 160.45, 160.13, 159.45, 148.10, 137.82, 134.76, 125.17, 112.16, 108.45, 104.59, 71.44, 71.06, 67.41, 67.07, 52.98, 47.05, 44.56, 36.46, 14.84 and 14.75.

NMR Data for Example 1ag
$^1$H NMR (300 MHz, CDCl$_3$) δ ppm 8.59 (ArH, dd, J=7.33, 2.43 Hz, 1H), 8.40 (ArH, ddd, J=8.53, 5.03, 2.47 Hz, 1H), 7.97 (ArH, d, J=8.42 Hz, 1H), 7.42 (ArH, d, J=8.46 Hz, 1H), 7.20-7.10 (ArH, m, 1H), 4.84 (CH, dd, J=3.67, 2.96 Hz, 1H), 4.53 (CH, d, J=12.77 Hz, 1H), 4.33 (CH$_2$, d, J=6.83 Hz, 1H), 3.99-3.89 (CH$_2$, m, 2H), 3.86-3.77 (CH$_2$, m, 4H), 3.75-3.65 (CH$_2$, m, 5H), 3.67-3.32 (CH$_2$, m, 3H), 3.57-3.45 (CH$_2$, m, 1H), 3.36-3.26 (CH$_2$, m, 1H), 1.42 (CH$_3$, d, J=6.78 Hz, 3H), 1.30 (CH$_3$, d, J=6.82 Hz, 3H)
$^{13}$C NMR (75 MHz, CDCl$_3$) δ ppm 165.26, 164.26, 162.74, 160.29, 159.93, 135.52, 135.11, 133.47, 133.34, 130.89, 116.84, 116.51, 113.11, 105.11, 71.26, 70.91, 67.11, 66.91, 62.20, 52.79, 47.02, 44.46, 43.02, 39.36, 14.77 and 14.37.

NMR Data for Example 1aq
$^1$H NMR (300 MHz, CDCl$_3$) δ ppm 8.61 (ArH, t, J=1.46, 1.46 Hz, 1H), 8.33 (ArH, d, J=7.84 Hz, 1H), 8.06 (ArH, d, J=8.37 Hz, 1H), 7.90 (ArH, s, 1H), 7.62 (ArH, d, J=7.84 Hz, 1H), 7.44 (ArH, d, J=8.38 Hz, 1H), 5.30 (CH$_2$, s, 1H), 4.97-4.84 (CH$_2$, m, 1H), 4.64-4.52 (CH$_2$, m, 1H), 4.45-4.34 (CH$_2$, m, 1H), 4.06-3.94 (CH$_2$, m, 2H), 3.93-3.64 (CH$_2$, m, 8H), 3.61-3.51 (CH$_2$, m, 1H), 3.45-3.30 (CH$_2$, m, 1H), 3.19 (CH$_2$, d, J=4.84 Hz, 2H), 1.49 (CH$_3$, d, J=6.78 Hz, 3H), 1.36 (CH$_3$, d, J=6.82 Hz, 3H).
$^{13}$C NMR (75 MHz, CDCl$_3$) δ ppm 160.22, 140.70, 140.01, 134.25, 131.82, 129.24, 128.02, 126.34, 113.12, 105.41, 104.65, 71.23, 70.87, 66.88, 61.03, 52.85, 47.04, 45.34, 44.42, 39.35, 14.78 and 14.38.

NMR Data for Example 1ar
$^1$H NMR (300 MHz, CDCl$_3$) δ ppm 8.81-8.73 (ArH, m, 2H), 8.14-7.99 (ArH, m, 3H), 7.48 (ArH, d, J=8.35 Hz, 1H), 5.02-4.89 (CH, m, 1H), 4.69-4.59 (CH$_2$, m, 1H), 4.41 (CH, d, J=6.84 Hz, 1H), 4.08-3.96 (CH$_2$, m, 2H), 3.82 (H2, dddd, J=19.69, 14.05, 6.26, 3.77 Hz, 7H), 3.65-3.53 (CH$_2$, m, 1H), 3.48-3.31 (CH$_2$, m, 1H), 1.51 (CH$_3$, d, J=6.78 Hz, 3H), 1.38 (CH$_3$, d, J=6.83 Hz, 3H)
$^{13}$C NMR (75 MHz, CDCl$_3$) δ ppm 165.29, 162.96, 160.03, 159.82, 150.36, 145.80, 135.20, 121.83, 113.02, 105.93, 71.24, 70.87, 67.21, 66.87, 52.88, 46.99, 44.45, 39.35, 14.76 and 14.41.

NMR Data for Example 1as
$^1$H NMR (300 MHz, CDCl$_3$) δ ppm 8.67 (ArH, t, J=1.54, 1.54 Hz, 1H), 8.29 (ArH, dd, J=6.60, 1.28 Hz, 1H), 8.07 (ArH, d, J=8.41 Hz, 1H), 8.03-7.98 (ArH, m, 2H), 7.62-7.49 (ArH, m, 2H), 4.98-4.89 (CH, m, br, 1H), 4.67-4.59 (CH, m, br, 1H), 4.41 (CH, d, J=6.78 Hz, 1H), 4.05-3.66 (CH$_2$, m, 10H), 3.64-3.34 (CH$_2$, m, 3H), 1.75 (s, 1.5H), 1.50 (CH$_3$, d, J=6.78 Hz, 3H), 1.38 (CH$_3$, d, J=6.82 Hz, 3H).
$^{13}$C NMR (75 MHz, CDCl$_3$) δ ppm 168.86, 165.34, 162.90, 161.21, 160.01, 138 97, 135.00, 133.74, 131.09, 129.23, 128.98, 126.52, 113.20, 105.20, 100.00, 71.23, 70.89, 67.22, 66.90, 52.82, 46.97, 44.45, 39.34, 14.75 and 14.36

NMR Data for Example 1at
$^1$H NMR (300 MHz, CDCl$_3$) δ ppm 8.06 (ArH, d, J=2.05 Hz, 1H), 7.98 (ArH, d, J=8.41 Hz, 1H), 7.86-7.79 (ArH, m, 1H), 7.46-7.33 (ArH, m, 3H), 7.23 (NH, s, 1H), 4.83 (CH, dd, J=3.58, 2.50 Hz, 1H), 4.56-4.46 (CH, m, 1H), 4.32 (CH, d, J=6.74 Hz, 1H), 3.93-3.89 (CH$_2$, m, 2H), 3.88-3.77 (CH$_2$, m, 2H), 3.76-3.58 (CH$_2$, m, 5H), 3.49 (CH$_2$, dt, J=11.76, 11.38, 2.76 Hz, 1H), 3.35-3.20 (CH$_2$, m, 1H), 2.89 (SCH$_3$, s, 3H), 1.42 (CH$_3$, d, J=6.78 Hz, 3H), 1.27 (CH$_3$, d, J=5.25, Hz, 3H)

$^{13}$C NMR (75 MHz, CDCl$_3$) δ ppm 165.32, 162.87, 161.30, 159.96, 140.41, 137.57, 135.01, 129.92, 124.55, 122.25, 120.57, 113.32, 105.24, 71.25, 70.90, 67.22, 66.91, 52.86, 46.99, 44.42, 39.40, 31.60, 22.66, 14.77 and 14.12.

NMR Data for Example 1ax $^1$H NMR (300 MHz, CDCl$_3$) δ ppm 8.88 (ArH, t, J=1.52, 1.52 Hz, 1H), 8.32-8.25 (ArH, m, 1H), 8.13-8.06 (ArH, m, 1H), 7.99 (ArH, d, J=8.42 Hz, 1H), 7.53-7.39 (ArH, m, 2H), 4.90-4.80 (CH, m, 1H), 4.58-4.48 (CH, m, 1H), 4.33 (CH, d, J=6.90 Hz, 1H), 3.95-3.65 (CH$_2$, +OH m, 8H), 3.64 (CH$_2$, d, J=2.85 Hz, 2H), 3.56-3.45 (CH, m, 1H), 3.31 (CH, d, J=3.67 Hz, 1H), 1.42 (CH$_3$, d, J=6.79 Hz, 3H), 1.29 (CH$_3$, d, J=6.81 Hz, 3H)

$^{13}$C NMR (75 MHz, CDCl$_3$) δ ppm 169.20, 165.22, 161.32, 159.85, 139.91, 135.01, 131.39, 129.70, 128.71, 113.31, 70.90, 67.10, 52.80, 47.07, 44.42, 39.36, 14.77 and 14.37.

NMR Data for Example 1az $^1$H NMR (300 MHz, CDCl$_3$) δ ppm 8.04-7.95 (ArH, m, 2H), 7.87 (ArH, d, J=8.54 Hz, 1H), 7.32 (ArH, d, J=8.55 Hz, 1H), 6.71-6.64 (ArH, m, 2H), 4.92-4.81 (CH, m, 1H), 4.57 (CH, d, br, 1H), 4.29 (CH$_2$, d, J=7.10 Hz, 1H), 3.91 (CH$_2$, m, 2H), 3.82-3.58 (CH$_2$+NH$_2$, m, 9H), 3.48 (CH$_2$, dd, J=11.36, 2.76 Hz, 1H), 3.33 (CH$_2$, dd, J=13.48, 3.61 Hz, 1H), 1.39 (CH$_3$, d, J=6.78 Hz, 3H), 1.28 (CH$_3$, d, J=6.82 Hz, 3H)

$^{13}$C NMR (75 MHz, CDCl$_3$) δ ppm 165.28, 162.18, 148.68, 135.36, 129.54, 119.67, 114.75, 112.63, 104.43, 104.00, 71.29, 70.94, 67.27, 67.12, 66.95, 52.78, 44.45, 39.15, 14.74 and 14.37.

NMR Data for Example 1ba $^1$H NMR (300 MHz, CDCl$_3$) δ ppm 8.69 (ArH, t, J=1.58, 1.58 Hz, 1H), 8.44-8.33 (ArH, m, 1H), 8.11-8.03 (ArH, m, 1H), 7.99 (ArH, d, J=8.42 Hz, 1H), 7.57-7.38 (ArH, m, 2H), 4.87 (CH$_2$, dd, J=4.84, 0.43 Hz, 1H), 4.57 (CH, d, J=12.80 Hz, 1H), 4.31 (CH$_2$, t, J=6.72, 6.72 Hz, 1H), 3.94 (CH$_2$, dd, J=11.15, 3.26 Hz, 2H), 3.90 (OCH$_3$, d, J=6.23 Hz, 3H), 3.83-3.62 (CH$_2$, m, 7H), 3.57-3.45 (CH$_2$, m, 1H), 3.39-3.24 (CH$_2$, m, 1H), 1.42 (CH$_3$, d, J=6.78 Hz, 3H), 1.30 (CH$_3$, d, J=6.81 Hz, 3H)

$^{13}$C NMR (75 MHz, CDCl$_3$) δ ppm 166.92, 165.41, 162.93, 161.43, 161.01, 139.13, 134.91, 132.51, 130.87, 130.57, 128.87, 113.26, 105.16, 71.29, 70.91, 67.25, 66.91, 52.86, 52.18, 46.96, 44.45, 14.77 and 14.37.

NMR Data for Example 1bc $^1$H NMR (300 MHz, DMSO) δ ppm 8.37 (ArH, dd, J=7.40, 2.26 Hz, 1H), 8.20 (ArH, d, J=8.50 Hz, 1H), 8.14-8.05 (ArH, m, 1H), 7.62 (ArH, d, J=8.51 Hz, 1H), 7.29 (ArH, dd, J=9.77, 8.71 Hz, 1H), 5.42 (CH, t, J=5.76, 5.76 Hz, 1H), 4.77 (CH, dd, J=6.57, 1.98 Hz, 1H), 4.65 (CH$_2$OH, d, J=5.67 Hz, 2H), 4.51-4.37 (CH$_2$, m, 2H), 3.98-3.83 (CH$_2$, m, 3H), 3.80-3.70 (CH$_2$, m, 2H), 3.69-3.56 (CH$_2$, m, 4H), 3.45 (CH$_2$, dt, J=11.86, 11.77, 2.75 Hz, 1H), 3.30-3.16 (CH$_2$, m, 3H), 1.38 (CH$_3$, d, J=6.75 Hz, 3H), 1.25 (CH$_3$, d, J=6.75 Hz, 3H)

$^{13}$C NMR (75 MHz, DMSO) δ ppm 164.91, 162.60, 160.18, 159.82, 136.10, 134.86, 130.19, 129.99, 128.61, 128.27, 128.15, 115.85, 115.57, 113.00, 104.80, 70.89, 70.66, 66.84, 66.67, 52.29, 46.76, 44.34, 14.84 and 14.34.

NMR Data for Example 1bd $^1$H NMR (300 MHz, DMSO) δ ppm 8.63 (ArH, t, J=1.49, 1.49 Hz, 1H), 8.26 (ArH, d, J=7.95 Hz, 1H), 8.17 (ArH, d, J=8.46 Hz, 1H), 7.91-7.80 (ArH, m, 1H), 7.62 (ArH, dd, J=14.96, 8.10 Hz, 2H), 7.37 (NH$_2$, s, 2H), 4.69 (CH, dd, J=6.21, 1.34 Hz, 1H), 4.35 (CH$_2$, d, J=13.74 Hz, 2H), 3.91-3.74 (CH$_2$, m, 3H), 3.73-3.46 (CH$_2$, m, 6H), 3.36 (CH$_2$, dt, J=11.82, 11.71, 2.49 Hz, 1H), 2.41 (CH$_2$, td, J=3.46, 1.69, 1.69 Hz, 1H), 1.30 (CH$_3$, d, J=6.74 Hz, 3H), 1.17 (CH$_3$, d, J=6.75 Hz, 3H)

$^{13}$C NMR (75 MHz) δ ppm 164.85, 162.63, 159.86, 159.49, 145.34, 139.35, 136.44, 130.73, 129.98, 127.34, 124.96, 113.18, 105.38, 79.87, 79.43, 78.99, 70.89, 70.67, 66.85, 66.67, 52.29, 46.79, 44.37, 14.88 and 14.41.

NMR Data for Example 1bk $^1$H NMR (300 MHz, CDCl$_3$) δ ppm 8.19 (ArH, dd, J=7.62, 2.22 Hz, 1H), 8.12 (ArH, ddd, J=8.54, 5.03, 2.25 Hz, 1H), 8.01 (ArH, d, J=8.41 Hz, 1H), 7.38 (ArH, d, J=8.43 Hz, 1H), 7.24-7.19 (ArH, m, 1H), 6.83 (NH, s, br, 1H), 4.98-4.85 (CH, m, 1H), 4.67-4.55 (CH, m, 1H), 4.36 (CH$_2$, d, J=6.95 Hz, 1H), 4.06-3.93 (CH$_2$, m, 2H), 3.91-3.65 (CH$_2$, m, 1H), 3.53 (CH$_2$, dd, J=11.40, 2.69 Hz, 1H), 3.44-3.28 (CH$_2$, m, 1H), 3.07 (SCH3, s, 3H), 1.47 (CH$_3$, d, J=6.77 Hz, 3H), 1.34 (CH$_3$, d, J=6.81 Hz, 3H)

$^{13}$C NMR (75 MHz, CDCl$_3$) δ ppm 165.45, 162.93, 160.61, 160.12, 157.28, 153.99, 136.32, 135.15, 123.51, 116.31, 116.05, 113.26, 105.18, 71.39, 71.01, 67.36, 67.01, 53.00, 47.07, 44.51, 39.44, 31.71, 22.77 14.86, and 14.95.

Compounds were also synthesized according to the following procedures:

Procedure for the synthesis of 5-[2,4-bis-((S)-3-methyl-morpholin-4-yl)-pyrido[2,3-d]pyrimidin-7-yl]-2-isopropoxy-benzamide (Example 1cw)

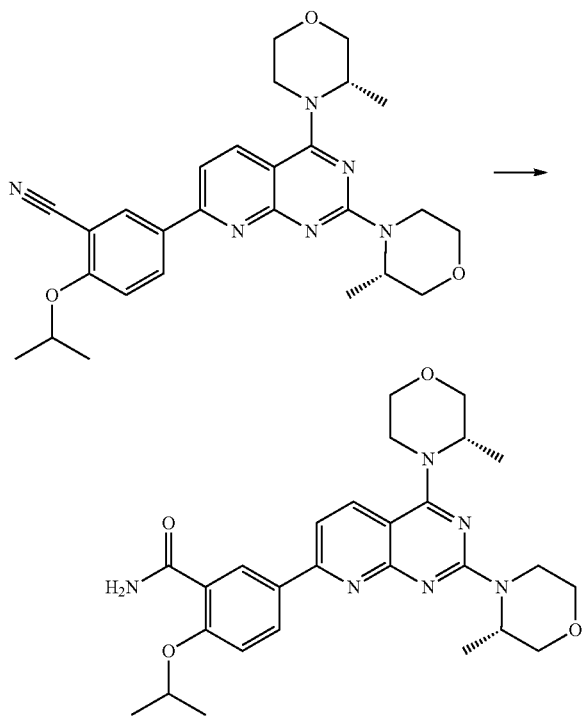

5-[2,4-Bis-((S)-3-methyl-morpholin-4-yl)-pyrido[2,3-d]pyrimidin-7-yl]-2-isopropoxy-benzonitrile (1 equiv) was added portionwise to concentrated $H_2SO_4$ (0.1 M substrate in acid). The reaction was heated to 90° C. and maintained at this temperature until all starting material had dissolved to give a bright red solution. The mixture was cooled and water (2 reaction volumes) added dropwise, then the solution was neutralized by careful addition of solid NaOH until pH 4-5 was attained. The mixture was cooled and neutralised by addition of 2N NaOH and then extracted using EtOAc (2×10 reaction volumes). The combined extracts were dried ($MgSO_4$), filtered and concentrated in vacuo to give a crude residue which was purified by flash chromatography ($SiO_2$) using MeOH/DCM—0:100 going to 5:95 as eluent to give the desire product as a yellow powder.

5-[2,4-Bis-((S)-3-methyl-morpholin-4-yl)-pyrido[2,3-d]pyrimidin-7-yl]-2-isopropoxy-benzamide: (53% yield, 100% purity) m/z (LC-MS, ESP): 507.5 [M+H]⁻, R/T=3.01 min)

Procedure for the synthesis of 5-[2,4-bis-((S)-3-methyl-morpholin-4-yl)-pyrido[2,3-d]pyrimidin-7-yl]-2-hydroxy-benzamide (Example 1cx)

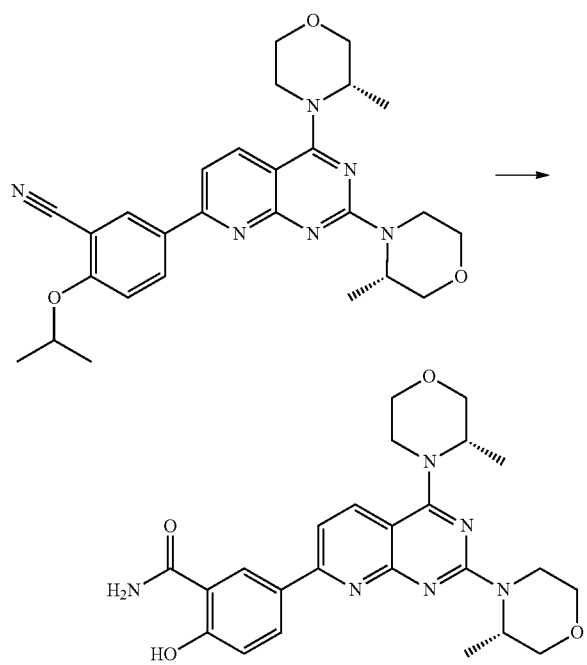

5-[2,4-Bis-((S)-3-methyl-morpholin-4-yl)-pyrido[2,3-d]pyrimidin-7-yl]-2-isopropoxy-benzonitrile (1 equiv) was added portionwise to concentrated $H_2SO_4$ (0.1 M substrate in acid). The reaction was heated to 90° C. and maintained at this temperature until all starting material had dissolved to give a bright red solution. The mixture was cooled and water (2 reaction volumes) added dropwise, then the solution was neutralized by careful addition of solid NaOH until pH 4-5 was attained. The mixture was cooled and neutralised by addition of 2N NaOH and then extracted using EtOAc (2×10 reaction volumes). The combined extracts were dried ($MgSO_4$), filtered and concentrated in vacuo to give a crude residue which was purified by flash chromatography ($SiO_2$) using MeOH/DCM—0:100 going to 5:95 as eluent to give the desire product as a yellow powder.

5-[2,4-Bis-((S)-3-methyl-morpholin-4-yl)-pyrido[2,3-d]pyrimidin-7-yl]-2-hydroxy-benzamide: (44% yield, 100% purity) m/z (LC-MS, ESP): 465.4 [M+H]⁻, R/T=2.70 min)

Procedure for the synthesis of 5-[2,4-bis-((S)-3-methyl-morpholin-4-yl)-pyrido[2,3-d]pyrimidin-7-yl]-pyridine-2-carboxylic acid amide (Example 1cy)

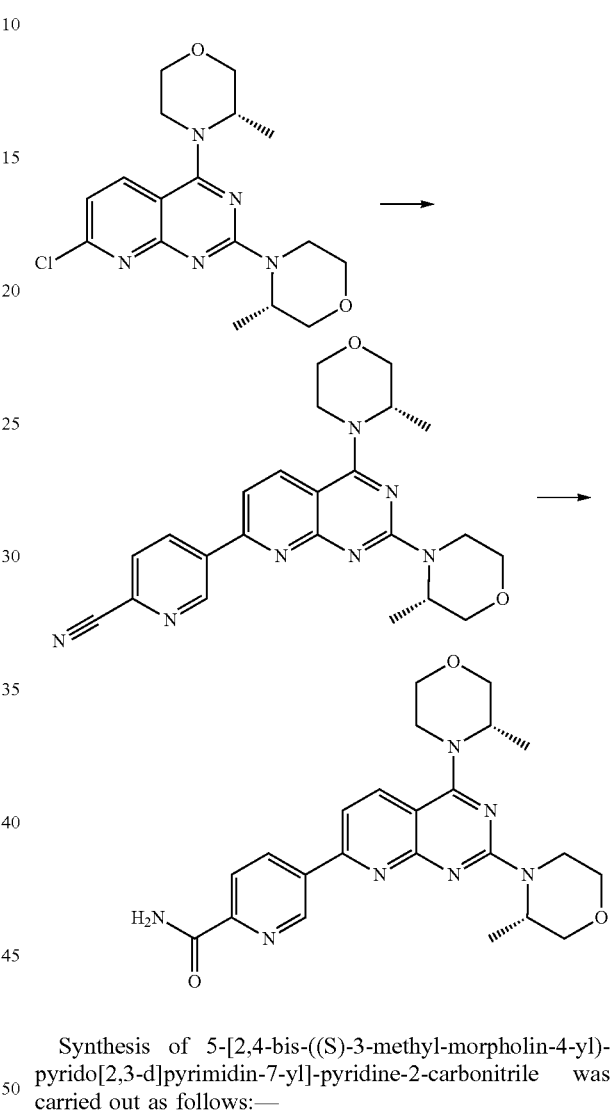

Synthesis of 5-[2,4-bis-((S)-3-methyl-morpholin-4-yl)-pyrido[2,3-d]pyrimidin-7-yl]-pyridine-2-carbonitrile was carried out as follows:—

To the appropriate chloro-substrate (1 equiv), potassium carbonate (3 equiv) and the appropriate boronic acid or pinacolate boron ester (1.1 equiv) and tetrakis(triphenylphosphine)palladium⁰ (0.05 equiv) which were dissolved in N,N-dimethylacetamide (0.17 M of chloro-substrate). The mixture was degassed with nitrogen, sealed and exposed to microwave radiation (130° C., medium absorption setting) for 15 minutes. The mixture was concentrated in vacuo and then suspended in t-butylmethyl ether, filtered and dried to give the desired product.

5-[2,4-Bis-((S)-3-methyl-morpholin-4-yl)-pyrido[2,3-d]pyrimidin-7-yl]-pyridine-2-carbonitrile: (84% yield, 93% purity) m/z (LC-MS, ESP): 191.3 [M+H]⁺, R/T=2.29 min)

To a suspension of 5-[2,4-bis-((S)-3-methyl-morpholin-4-yl)-pyrido[2,3-d]pyrimidin-7-yl]-pyridine-2-carbonitrile (1 equiv) in concentrated $H_2SO_4$. The mixture was heated to 90° C. until a pale brown solution formed. The mixture was allowed to cool and then basified with 50% w/w NaOH solution. The aqueous mixture was extracted using EtOAc (3×2 reaction volumes). The combined organic fractions were dried (MgSO₄), filtered and concentrated in vacuo to give a pale yellow solid which was triturated with EtOAc to give the desire product.

5-[2,4-Bis-((S)-3-methyl-morpholin-4-yl)-pyrido[2,3-d] pyrimidin-7-yl]-pyridine-2-carboxylic acid amide: 93% yield, 96% purity) m/z (LC-MS, ESP): 450.4 [M+H]⁺, R/T=3.72 min)

Procedure for the synthesis of 4-[2,4-bis-((S)-3-methyl-morpholin-4-yl)-pyrido[2,3-d]pyrimidin-7-yl]-pyridin-2-ylamine (Example 1cz)

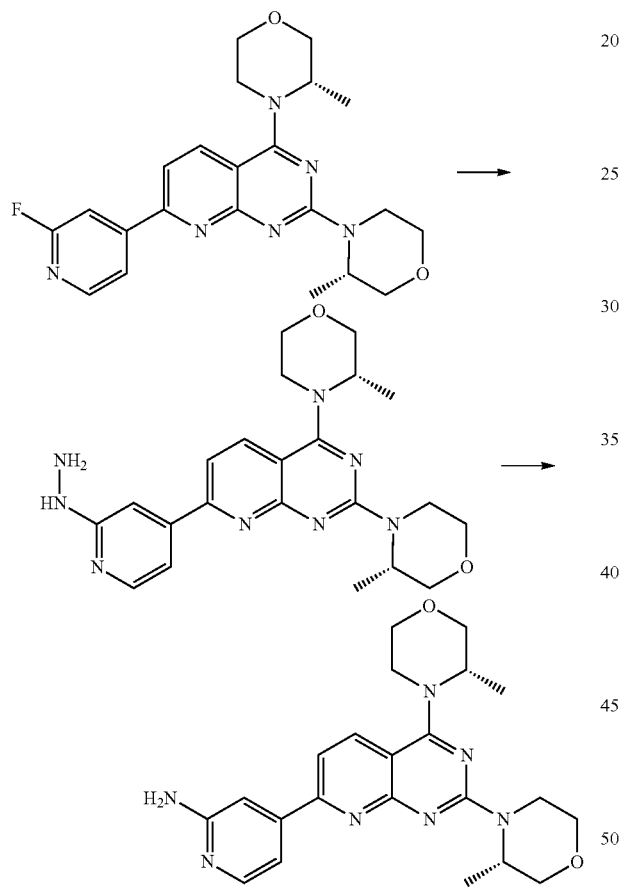

To a 1.2 M solution of compound 1au (1 equiv) in THF was added hydrazine hydrate (9 reaction volumes). The reaction vessel was sealed and exposed to microwave radiation (115° C., medium absorption setting) for 2 hours. Upon completion, the reaction mixture was extracted with EtOAc (2×1 reaction volume). The organic fractions were combined, dried (MgSO₄), filtered and concentrated in vacuo to give the desired product in suitably clean form for use in subsequent reactions.

{4-[2,4-Bis-((S)-3-methyl-morpholin-4-yl)-pyrido[2,3-d]pyrimidin-7-yl]-pyridin-2-yl}-hydrazine 7-(4,4,5,5-Tetramethyl-[1,3,2]dioxaborolan-2-yl)-2H-phthalazin-1-one: (77% yield, 84% purity) m/z (LC-MS, ESP): 437.4 [M+H]⁺, R/T=2.23 min)

A 0.12 M solution of {4-[2,4-bis-((S)-3-methyl-morpholin-4-yl)-pyrido[2,3-d]pyrimidin-7-yl]-pyridin-2-yl}-hydrazine 7-(4,4,5,5-Tetramethyl-[1,3,2]dioxaborolan-2-yl)-2H-phthalazin-1-one (1 equiv) in EtOH was added to a glass lined autoclave which contained activated Ra—Ni. The reaction was maintained under 5 bar H₂ for 30 hours. Upon completion, the mixture was filtered through a pad of Celite™ and the filtrate concentrated in vacuo. The resulting crude residue was purified by reverse phase flash chromatography using 5:95-0.1% TFA/MeCN:0.1% TFA/H₂O as eluent to give the desire product as a yellow powder.

4-[2,4-Bis-((S)-3-methyl-morpholin-4-yl)-pyrido[2,3-d]pyrimidin-7-yl]-pyridin-2-ylamine: (70% yield, 100% purity) m/z (LC-MS, ESP): 422 [M+H]⁺, R/T=2.25 min)

Procedure for the synthesis of 4-[2,4-bis-((S)-3-methyl-morpholin-4-yl)-pyrido[2,3-d]pyrimidin-7-yl]-2-fluoro-benzamide (Example 1da)

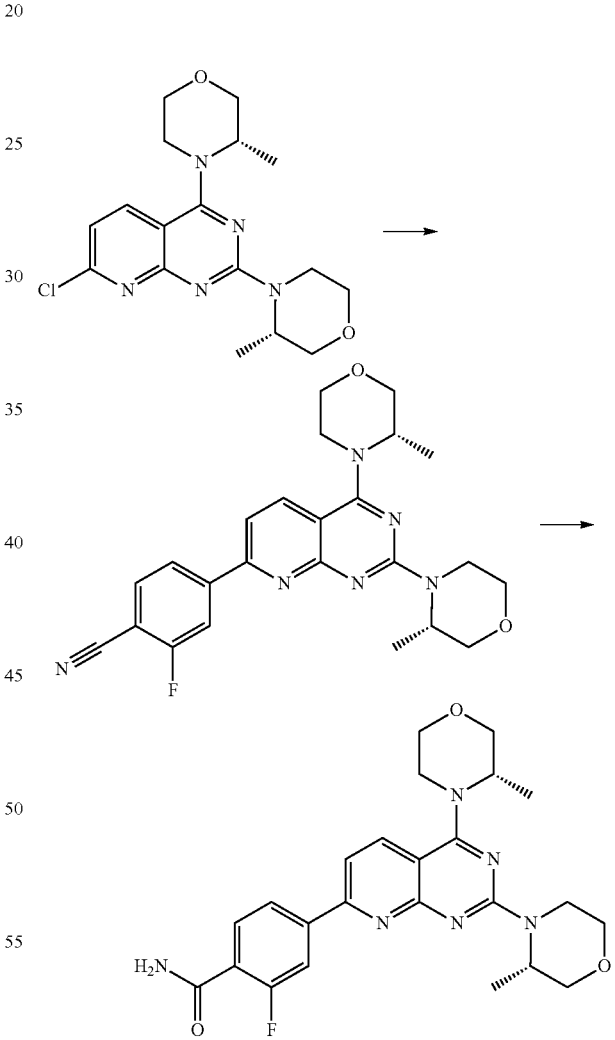

To the appropriate chloro-substrate (1 equiv), potassium carbonate (2.5 equiv) and the appropriate boronic acid or pinacolate boron ester (1.1 equiv) and tetrakis(triphenylphosphine)palladium⁰ (0.05 equiv) which were dissolved in MeCN/H₂O (0.03 M of chloro-substrate). The mixture was degassed with nitrogen, sealed and exposed to microwave radiation (110° C., medium absorption setting) for 25 minutes. The mixture filtered and the precipitate collected, and recrystallised from MeCN/H₂O to give the desired product.

4-[2,4-Bis-((S)-3-methyl-morpholin-4-yl)-pyrido[2,3-d]pyrimidin-7-yl]-2-fluoro-benzonitrile: (49% yield, 87% purity) m/z (LC-MS, ESP): 449 [M+H]⁺, R/T=2.93 min)

4-[2,4-Bis-((S)-3-methyl-morpholin-4-yl)-pyrido[2,3-d]pyrimidin-7-yl]-2-fluoro-benzonitrile (1 equiv) was dissolved concentrated sulfuric acid (0.15 M substrate in acid). The reaction was heated rapidly to 90° C. for 5 minutes before cooling the mixture and quenched, carefully, with solid NaOH until the solution was basic. The mixture was extracted with EtOAc/nBuOH (2×1 reaction volume—1:1 ratio). The organic extracts were combined, dried (MgSO₄), filtered and concentrated in vacuo to give a residue which was further purified using flash chromatography (SiO₂) with TBME going to TBME/MeOH (95:5) as eluent, the give the title compound as a yellow solid.

4-[2,4-Bis-((S)-3-methyl-morpholin-4-yl)-pyrido[2,3-d]pyrimidin-7-yl]-2-fluoro-benzamide Synthesis: (71% yield, 99% purity) m/z (LC-MS, ESP): 467 [M+H]⁺, R/T=2.60 min)

Procedure for the synthesis of 5-[2,4-bis-((S)-3-methyl-morpholin-4-yl)-pyrido[2,3-d]pyrimidin-7-yl]-1H-pyridin-2-one (Example 1db)

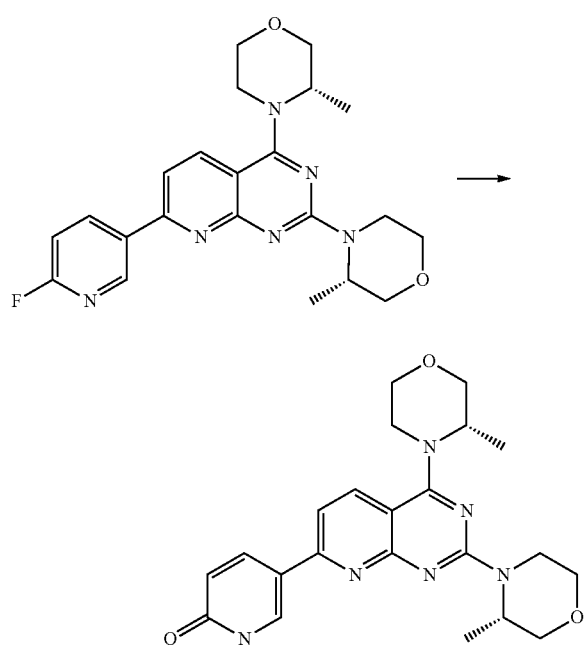

To a 0.2 M solution of compound 1ah (1 equiv) in DMA was added a 1.6 M aqueous solution of sodium hydroxide (5 equiv). The reaction vessel was sealed and exposed to microwave radiation (110° C., medium absorption setting) for 10 minutes. The reaction mixture was concentrated in vacuo. The residue was suspended in water and sonicated to give a turbid solution, washed with TBME then cooled and neutralised with 2M HCl, forming a yellow precipitate. The precipitate was filtered and washed with water and TBME and dried to give the desired product.

5-[2,4-Bis-((S)-3-methyl-morpholin-4-yl)-pyrido[2,3-d]pyrimidin-7-yl]-1H-pyridin-2-one: (69% yield, 96% purity) m/z (LC-MS, ESP): 423 [M+H]⁺, R/T=3.60 min)

Procedure for the synthesis of 5-[2,4-bis-((S)-3-methyl-morpholin-4-yl)-pyrido[2,3-d]pyrimidin-7-yl]-1H-pyridin-2-one (Example 1dc)

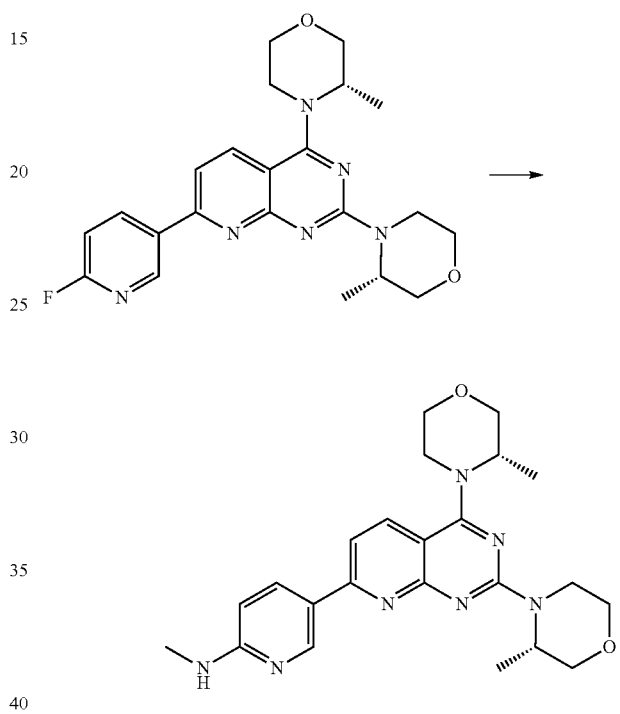

To the compound 1ah (1 equiv) was added a solution of 40% methylamine in methanol (100 equiv). The reaction vessel was sealed and exposed to microwave radiation (115° C., medium absorption setting) for 30 minutes. The solution was concentrated in vacuo to yield a yellow solid. The crude residue was then purified by preparative HPLC to give the desired product. {5-[2,4-Bis-(3-methyl-morpholin-4-yl)-pyrido[2,3-d]pyrimidin-7-yl]-pyridin-2-yl}-methyl-amine: (61% yield, 99% purity) m/z (LC-MS, ESP): 436 [M+H]⁺, R/T=3.34 min)

NMR Data for Example 1dc

¹H NMR (300 MHz, CDCl₃) δ ppm 8.69 (ArH, d, J=2.06 Hz, 1H), 8.56 (ArH, dd, J=9.02, 2.32 Hz, 1H), 7.97 (ArH, d, J=8.47 Hz, 1H), 7.33 (ArH, d, J=8.48 Hz, 1H), 6.59 (ArH, d, J=9.03 Hz, 1H), 5.92 (NH, s, br, 1H), 4.90 (CH₂, dd, J=5.85, 0.41 Hz, 1H), 4.59 (CH₂, d, J=12.53 Hz, 1H), 4.41-4.29 (CH₂, m, 1H), 4.05-3.93 (CH₂, m, 2H), 3.90-3.62 (CH₂, m, 8H), 3.62-3.50 (CH₂, m, 1H), 3.43-3.31 (CH₂, m, 1H), 3.00 (NCH₃, s, 3H), 1.47 (CH₃, d, J=6.78 Hz, 3H), 1.35 (CH₃, d, J=6.82 Hz, 3H)

¹³C NMR (75 MHz, CDCl₃) δ ppm 167.59, 165.30, 162.90, 159.99, 158.84, 144.22, 139.19, 134.85, 123.35, 111.65, 106.51, 104.57, 71.28, 70.91, 67.24, 66.92, 52.83, 46.96, 44.42, 39.34, 29.05, 14.73 and 14.34.

Procedure for the synthesis of {5-[2,4-bis-((S)-3-methyl-morpholin-4-yl)-pyrido[2,3-d]pyrimidin-7-yl]-pyridin-2-yl}-dimethyl-amine (Example 1dd)

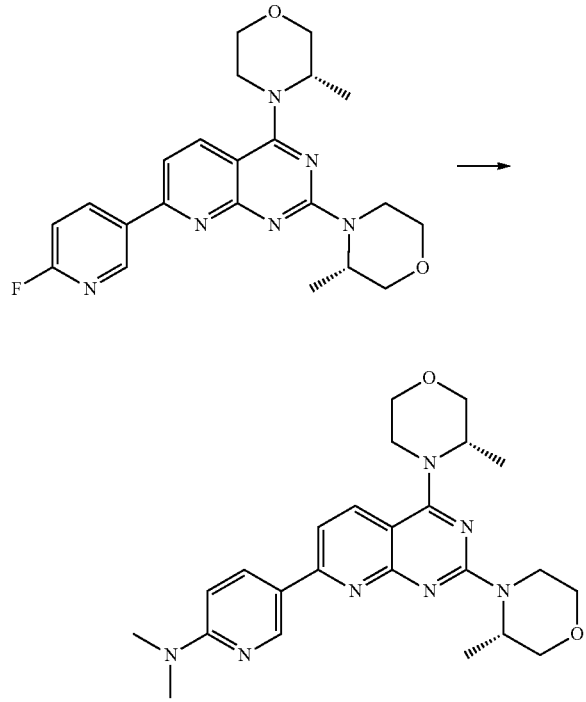

To a solution of compound 1ah (1 equiv) in THF (0.05 M) was added a solution of 33% dimethylamine in ethanol (200 equiv). The reaction vessel was sealed and exposed to microwave radiation (130° C., medium absorption setting) for 40 minutes. The solution was concentrated in vacuo to yield a yellow solid. The crude residue was then purified by preparative HPLC to give the desired product.

{5-[2,4-Bis-((S)-3-methyl-morpholin-4-yl)-pyrido[2,3-d]pyrimidin-7-yl]-pyridin-2-yl}-dimethyl-amine: (54% yield, 97% purity) m/z (LC-MS, ESP): 450 [M+H]$^+$, R/T=3.52 min)

Procedure for the synthesis of 8-[2,4-bis-((S)-3-methyl-morpholin-4-yl)-pyrido[2,3-d]pyrimidin-7-yl]-1,2,3,4-tetrahydro-benzo[e][1,4]diazepin-5-one (Example 1de)

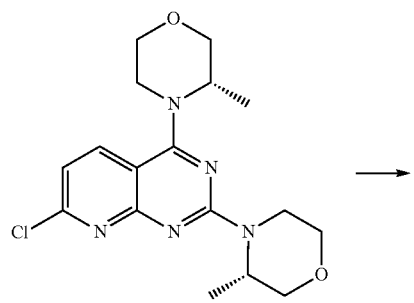

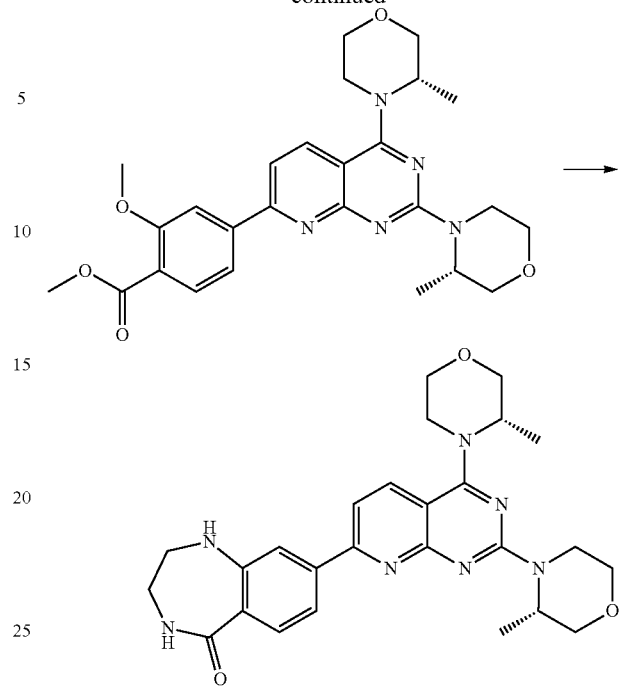

The appropriate chloro-substrate (1 equiv), potassium carbonate (2.5 equiv), 3-methoxy-4-methoxycarbonylphenylboronic acid, pinacol ester (1.1 equiv) were suspended in (1:1) acetonitrile/water (0.1 M of chloro-substrate). The mixture was sonicated and degassed for 15 minutes with nitrogen. Tetrakistriphenylphosphine (0.05 equiv) was then added and the mixture was sonicated for a further 5 minutes with nitrogen. The mixture was heated to 100° C. for 3 hours under nitrogen. The reaction was cooled and the insoluble residue was filtered off. The filtrate was concentrated to half the original volume and the remaining water mixture was extracted with CH$_2$Cl$_2$. The organic layers were washed with water and brine, combined and dried with magnesium sulphate, filtered and concentrated in vacuo to yield an oil which was purified by flash column chromatography eluting with 50% to 100% EtOAc/Hexane.

4-[2,4-Bis-((S)-3-methyl-morpholin-4-yl)-pyrido[2,3-d]pyrimidin-7-yl]-2-methoxy-benzoic acid methyl ester: (67% yield, 100% purity) m/z (LC-MS, ESP): 494 [M+H]$^+$, R/T=2.86 min)

A solution of 4-[2,4-bis-((S)-3-methyl-morpholin-4-yl)-pyrido[2,3-d]pyrimidin-7-yl]-2-methoxy-benzoic acid methyl ester (1 equiv) in ethylenediamine (0.35 M) was stirred at room temperature for 24 hours. DMA was added to the solution (ethylenediamine/DMA 1:1.25). The reaction vessel was sealed and exposed to microwave radiation (180° C., medium absorption setting) for 1 hour. The reaction mixture was diluted with CH$_2$Cl$_2$ and extracted with water and washed with brine. The organic layer was dried with magnesium sulphate, filtered and concentrated in vacuo to yield a yellow solid which was then purified by preparative HPLC to give the desired product.

8-[2,4-Bis-((S)-3-methyl-morpholin-4-yl)-pyrido[2,3-d]pyrimidin-7-yl]-1,2,3,4-tetrahydro-benzo[e][1,4]diazepin-5-one: (49% yield, 99% purity) m/z (LC-MS, ESP): 490 [M+H]$^+$, R/T=3.52 min)

161

NMR Data for Example 1de $^1$H NMR (300 MHz, CDCl$_3$) δ ppm 8.65 (NH, s, br, 1H), 8.01 (ArH, d, J=8.38 Hz, 1H), 7.78 (ArH, s, 1H), 7.68 (ArH, s, 1H), 7.44 (ArH, dd, J=18.50, 8.20 Hz, 2H), 4.93-4.77 (CH$_2$, m, 1H), 4.50 (CH$_2$, s, 1H), 4.46-4.32 (CH$_2$, m, 1H), 4.05-3.61 (CH$_2$, m, 14H), 3.53 (CH$_2$, d, J=2.04 Hz, 1H), 3.41-3.26 (CH$_2$, m, 1H), 1.47 (CH$_3$, d, J=6.76 Hz, 3H), 1.33 (CH$_3$, d, J=6.78 Hz, 3H).

$^{13}$C NMR (75 MHz, CDCl$_3$) δ ppm 165.11, 165.07, 165.00, 163.41, 162.64, 161.07, 159.90, 144.87, 135.18, 129.50, 118.02, 116.80, 113.87, 109.20, 105.45, 71.20, 70.89, 67.14, 66.89, 52.77, 47.04, 44.76, 44.40, 39.33, 14.78 and 13.32.

Procedure for the synthesis of 7-[2,4-bis-((S)-3-methyl-morpholin-4-yl)-pyrido[2,3-d]pyrimidin-7-yl]-1,2,3,4-tetrahydro-benzo[e][1,4]diazepin-5-one (Example 1df)

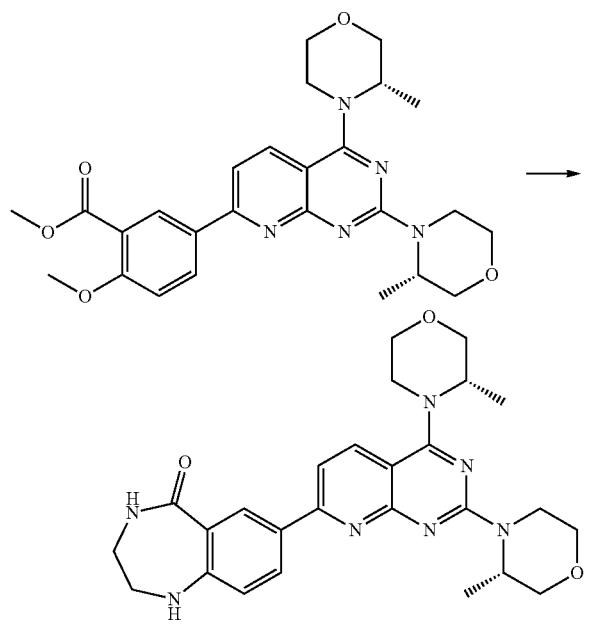

A solution of the compound 1bg (1 equiv) in ethylenediamine (0.35 M) was stirred at room temperature for 24 hours. DMA was added to the solution (ethylenediamine/DMA 1:1.25). The reaction vessel was sealed and exposed to microwave radiation (180° C., medium absorption setting) for 1 hour. The reaction mixture was diluted with ethyl acetate and extracted with water. The organic layer was dried with magnesium sulphate, filtered and concentrated in vacuo to yield a residue which was then purified by flash column chromatography eluting with 0% to 20% MeOH/CH$_2$Cl$_2$.

8-[2,4-Bis-((S)-3-methyl-morpholin-4-yl)-pyrido[2,3-d]pyrimidin-7-yl]-1,2,3,4-tetrahydro-benzo[e][1,4]diazepin-5-one: (40% yield, 100% purity) m/z (LC-MS, ESP): 490 [M+H]$^+$, R/T=3.49 min)

NMR Data for Example 1df $^1$H NMR (300 MHz, CDCl$_3$) δ ppm 8.60 (ArH, d, J=2.23 Hz, 1H), 7.93-7.83 (ArH, m, 2H), 7.34 (ArH, d, J=8.56 Hz, 1H), 6.89 (ArH, d, J=8.97 Hz, 1H), 4.82-4.71 (CH$_2$, m, 1H), 4.47 (CH$_2$, dd, J=7.28, 6.58 Hz, 1H), 4.30 (CH$_2$, d, J=6.93 Hz, 1H), 3.95-3.55 (CH$_2$, m, 13H), 3.55-3.42 (CH$_2$, m, 1H), 3.35-3.21 (CH$_2$, m, 1H), 1.40 (CH$_3$, d, J=6.77 Hz, 3H), 1.26 (CH$_3$, d, J=6.80 Hz, 3H).

162

Procedure for the synthesis of 5-[2,4-bis-((S)-3-methyl-morpholin-4-yl)-pyrido[2,3-d]pyrimidin-7-yl]-2-difluoromethoxy-benzamide (Example 1dg)

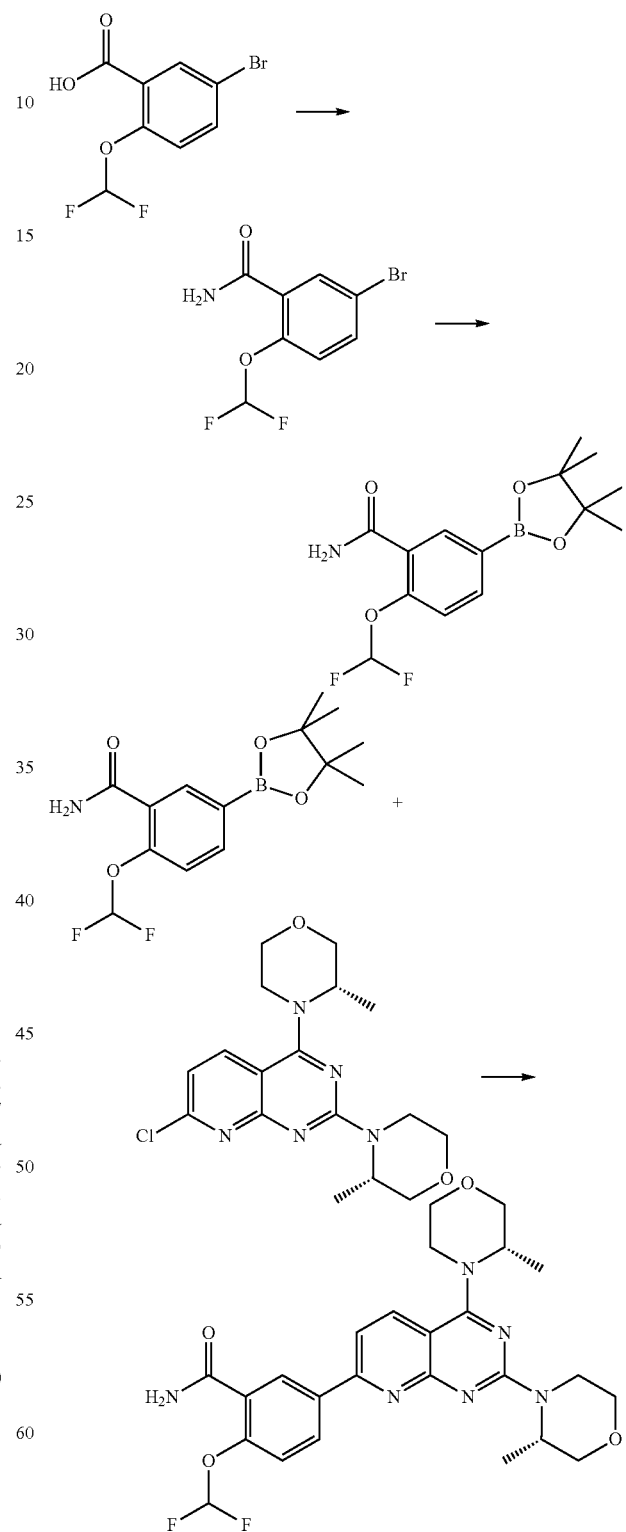

To a solution of 5-bromo-2-difluoromethoxy-benzoic acid (1 equiv) in THF (0.1 M) was added dropwise thionyl chloride (5 equiv) at room temperature. The reaction mixture was stirred at 40° C. for 2 hours. The reaction mixture was concentrated in vacuo. The residue was suspended in dry THF (0.04 M) and ammonia gas was slowly bubbled into the reaction mixture for 45 minutes. The reaction mixture was concentrated in vacuo. The residue was dissolved in minimum CH$_2$Cl$_2$ and hexane was added to give a white precipitate that was collected by vacuum filtration in suitably clean form for use in subsequent reactions.

5-Bromo-2-difluoromethoxy-benzamide: (45% yield, 73% purity) m/z (LC-MS, ESP): 266/268 [M+H]$^+$, R/T=3.42 min)

To a solution of 5-bromo-2-difluoromethoxy-benzamide (1 equiv) in dioxan (0.1 M) were added bis(pinacolato)diboron (1.1 equiv), potassium acetate (3.5 equiv) and dppf (0.05 equiv). The reaction mixture was degassed with nitrogen for 15 minutes. PdCl$_2$(dppf) (0.05 equiv) was added to the reaction mixture, which was degassed for a further 5 minutes. The reaction mixture was stirred at 110° C. for 12 hours under nitrogen. The reaction mixture was partitioned between EtOAc and water. The aqueous layer was extracted with EtOAc and the combined organic phases were washed with water, dried with magnesium sulphate, filtered and concentrated in vacuo to give the desired product for use in subsequent reactions 2-Difluoromethoxy-5-(4,4,5,5-tetramethyl-[1,3,2]dioxaborolan-2-yl)-benzamide: (71% yield, crude taken forward without further analysis)

A mixture of the appropriate chloro-substrate (1 equiv), potassium carbonate (3.0 equiv), 2-difluoromethoxy-5-(4,4,5,5-tetramethyl-[1,3,2]dioxaborolan-2-yl)-benzamide (1.1 equiv) and tetrakis(triphenylphosphine)palladium$^0$ (0.05 equiv) in acetonitrile/water (0.1 M of chloro-substrate) was stirred at 100° C. for 4 hours. Upon completion the reaction mixture was partitioned between water and CH$_2$Cl$_2$ and extracted with CH$_2$Cl$_2$. Combined organic phases were washed with brine, dried (MgSO$_4$), filtered and concentrated in vacuo. The crude residue was purified by preparative HPLC to give the desired product.

5-[2,4-Bis-((S)-3-methyl-morpholin-4-yl)-pyrido[2,3-d]pyrimidin-7-yl]-2-difluoromethoxy-benzamide: (14% yield, 100% purity) m/z (LC-MS, ESP): 515 [M+H]$^+$, R/T=7.40 min Procedure for the synthesis of 5-[2,4-bis-((S)-3-methyl-morpholin-4-yl)-pyrido[2,3-d]pyrimidin-7-yl]-2-difluoromethoxy-N-methyl-benzamide (Example 1dh)

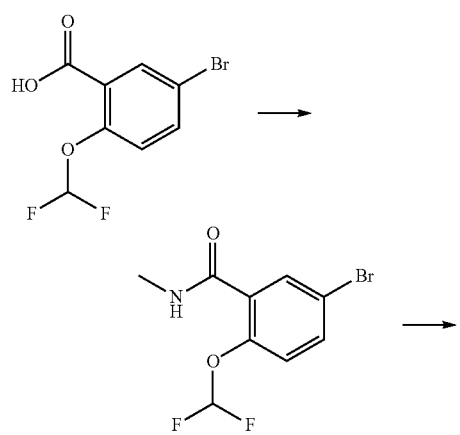

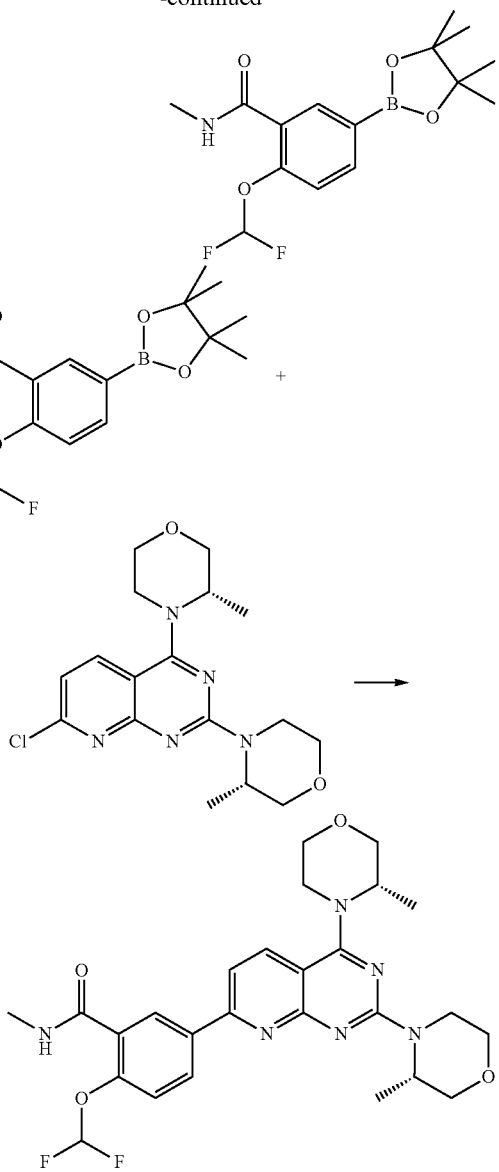

To a solution of 5-bromo-2-difluoromethoxy-benzoic acid (1 equiv) in DMF (0.1 M) was added triethylamine (4 equiv). The reaction mixture was cooled to 0° C. and HBTU (1.2 equiv) was added. The reaction mixture was allowed to reach room temperature over 1 hour and methylamine hydrochloride (2 equiv) was added. The reaction mixture was stirred at room temperature for 2 hours. The reaction mixture was partitioned between EtOAc and water and the aqueous phase was further extracted with EtOAc. The combined organic phases were washed with water, dried with magnesium sulphate, filtered and concentrated under in vacuo to give the desired product in suitably clean form for use in subsequent reactions.

5-Bromo-2-difluoromethoxy-N-methyl-benzamide: (100% yield, 75% purity) m/z (LC-MS, ESP): 280/282 [M+H]$^+$, R/T=3.55 min)

2-Difluoromethoxy-N-methyl-5-(4,4,5,5-tetramethyl-[1,3,2]dioxaborolan-2-yl)-benzamide was prepared in a similar way as 2-Difluoromethoxy-5-(4,4,5,5-tetramethyl-[1,3,2]dioxaborolan-2-yl)-benzamide using 5-bromo-2-difluoromethoxy-N-methyl-benzamide as the starting material.

2-Difluoromethoxy-N-methyl-5-(4,4,5,5-tetramethyl-[1,3,2]dioxaborolan-2-yl)-benzamide: (100% yield, crude taken forward without further analysis)

A mixture of the appropriate chloro-substrate (1 equiv), potassium carbonate (3.0 equiv), 2-difluoromethoxy-5-(4,4,5,5-tetramethyl-[1,3,2]dioxaborolan-2-yl)-benzamide (1.1 equiv) and tetrakis(triphenylphosphine)palladium⁰ (0.05 equiv) in acetonitrile/water (0.1 M of chloro-substrate) was stirred at 100° C. for 2 hours. Upon completion the reaction mixture was partitioned between water and CH$_2$Cl$_2$ and extracted with CH$_2$Cl$_2$. Combined organic phases were washed with brine, dried (MgSO$_4$), filtered and concentrated in vacuo. The crude residue was purified by preparative HPLC to give the desired product.

5-[2,4-Bis-((S)-3-methyl-morpholin-4-yl)-pyrido[2,3-d]pyrimidin-7-yl]-2-difluoromethoxy-N-methyl-benzamide: (53% yield, 87% purity) m/z (LC-MS, ESP): 421 [M+H]$^+$, R/T=4.06 min)

Procedure for the synthesis of 4-[2,4-bis-((S)-3-methyl-morpholin-4-yl)-pyrido[2,3-d]pyrimidin-7-yl]-2-methoxy-benzamide (Example 1di)

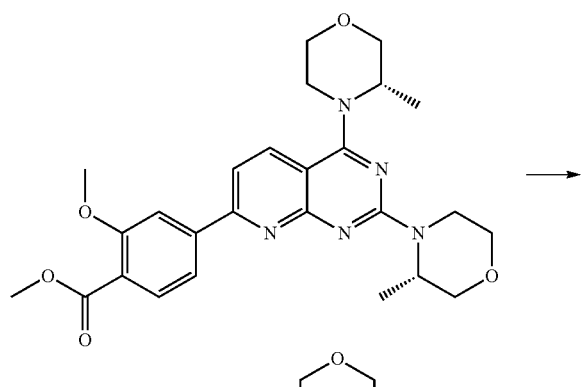

4-[2,4-Bis-((S)-3-methyl-morpholin-4-yl)-pyrido[2,3-d]pyrimidin-7-yl]-2-methoxy-benzoic acid methyl ester (1 equiv) was dissolved in methanol (0.2 M). 1M Sodium hydroxide aqueous solution (5.0 equiv) was added. The reaction mixture was stirred at room temperature for 3 hours. Upon completion the reaction mixture was neutralised with 1M aqueous HCl and concentrated in vacuo. The crude residue was purified by column chromatography on silica gel eluting with 0 to 10% MeOH in CH$_2$Cl$_2$ to give the desired product.

4-[2,4-Bis-((S)-3-methyl-morpholin-4-yl)-pyrido[2,3-d]pyrimidin-7-yl]-2-methoxy-benzoic acid: (100% yield, 100% purity) m/z (LC-MS, ESP): 480 [M+H]$^+$, R/T=2.69 min)

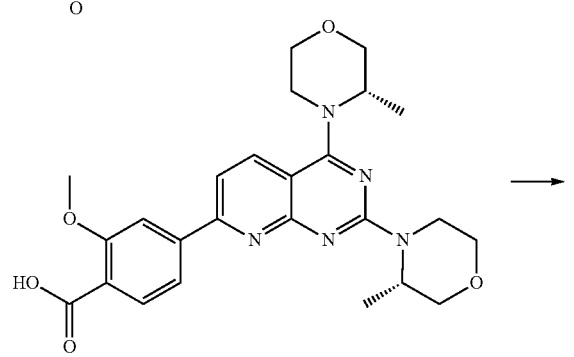

4-[2,4-Bis-((S)-3-methyl-morpholin-4-yl)-pyrido[2,3-d]pyrimidin-7-yl]-2-methoxy-benzoic acid (1 equiv) was suspended in THF (0.05 M). Thionyl chloride was added dropwise at 40° C. The reaction mixture was then heated for an hour at 40° C. Ammonia gas was then slowly bubbled into the reaction mixture. THF was then added for further dilution (0.025 M) and the reaction mixture was heated for an hour at 40° C. Upon completion the reaction mixture was cooled down and concentrated in vacuo. The residue was partitioned between water and CH$_2$Cl$_2$. The aqueous phase was extracted with CH$_2$Cl$_2$. Combined organic phases were dried (MgSO$_4$), filtered and concentrated in vacuo. The crude residue was purified by column chromatography on silica gel eluting with 0 to 5% MeOH in CH$_2$Cl$_2$ to give the desired product.

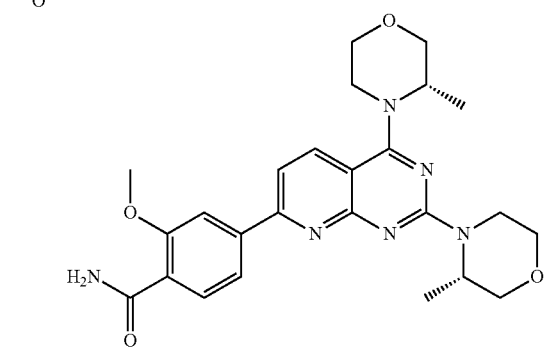

4-[2,4-Bis-((S)-3-methyl-morpholin-4-yl)-pyrido[2,3-d]pyrimidin-7-yl]-2-methoxy-benzamide: (88% yield, 99% purity) m/z (LC-MS, ESP): 479 [M+H]$^+$, R/T=3.92 min)

NMR Data for Example 1di $^1$H NMR (300 MHz, CDCl$_3$) δ ppm 8.30 (ArH, d, J=8.17 Hz, 1H), 8.04 (ArH, dd, J=6.21, 4.98 Hz, 2H), 7.80 (NH, br, s, 1H), 7.67 (ArH, dd, J=8.21, 1.49 Hz, 1H), 7.49 (ArH, d, J=8.44 Hz, 1H), 5.96 (NH, s, br, 1H), 4.98-4.85 (CH$_2$, m, 1H), 4.61 (CH$_2$, d, J=12.90 Hz, 1H), 4.39 (CH$_2$, d, J=6.89 Hz, 1H), 4.13 (OCH$_3$, s, 3H), 4.05-3.64 (CH$_2$, m, 9H), 3.64-3.51 (CH$_2$, m, 1H), 3.41 (CH$_2$, dd, J=13.34, 3.62 Hz, 1H), 1.49 (CH$_3$, d, J=6.79 Hz, 3H), 1.36 (CH$_3$, d, J=6.82 Hz, 3H).

$^{13}$C NMR (75 MHz, CDCl$_3$) δ ppm 166.78, 165.32, 162.81, 160.99, 160.02, 158.15, 143.57, 134.98, 132.76, 121.80, 120.15, 113.62, 111.30, 105.44, 71.27, 70.89, 67.23, 66.90, 56.42, 52.88, 47.01, 44.41, 39.36, 14.77 and 14.40.

Procedure for the synthesis of 4-[2,4-bis-((S)-3-methyl-morpholin-4-yl)-pyrido[2,3-d]pyrimidin-7-yl]-2-methoxy-N-methyl-benzamide (Example 1dj)

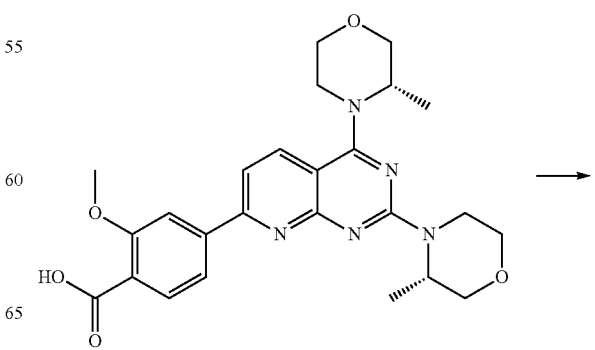

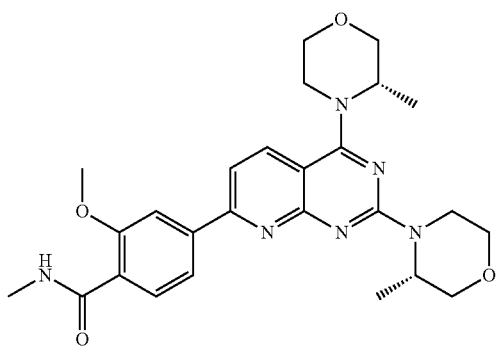 [SMILES: CNC(=O)c1ccc(-c2ccc3c(N4CCOC[C@@H]4C)nc(N4CCOC[C@@H]4C)nc3n2)cc1]

4-[2,4-Bis-((S)-3-methyl-morpholin-4-yl)-pyrido[2,3-d]pyrimidin-7-yl]-2-methoxy-benzoic acid (1 equiv) was dissolved in THF (0.1 M) and HBTU (1.5 equiv) was added. Methylamine in THF (15 equiv) was added dropwise followed by triethylamine (1.5 equiv) and the reaction mixture was stirred at room temperature for 2 hours. The reaction mixture was concentrated in vacuo. The residue was partitioned between water and $CH_2Cl_2$. The aqueous phase was extracted with $CH_2Cl_2$. Combined organic phases were dried ($MgSO_4$), filtered and concentrated in vacuo. The crude residue was purified by preparative HPLC to give the desired product.

4-[2,4-Bis-((S)-3-methyl-morpholin-4-yl)-pyrido[2,3-d]pyrimidin-7-yl]-2-methoxy-N-methyl-benzamide: (56% yield, 96% purity) m/z (LC-MS, ESP): 493 [M+H]$^+$, R/T=4.00 min)

NMR Data for Example 1dj $^1$H NMR (300 MHz, CDCl$_3$) δ ppm 8.26 (ArH, d, J=8.16 Hz, 1H), 7.98 (ArH, dd, J=8.74, 4.91 Hz, 2H), 7.91-7.81 (NH, m, br, 1H), 7.60 (ArH, dd, J=8.21, 1.52 Hz, 1H), 7.43 (ArH, d, J=8.45 Hz, 1H), 4.93-4.81 (CH$_2$, m, 1H), 4.62-4.51 (CH$_2$, m, 1H), 4.39-4.28 (CH$_2$, m, 1H), 4.07 (OCH$_3$, s, 3H), 4.00-3.58 (CH$_2$, m, 9H), 3.57-3.45 (CH$_2$, m, 1H), 3.40-3.27 (CH$_2$, m, 1H), 2.99 (NHCH$_3$, d, J=4.82 Hz, 3H), 1.43 (CH$_3$, d, J=6.78 Hz, 3H), 1.31 (CH$_3$, d, J=6.81 Hz, 3H).

Procedure for the synthesis of 2-methoxy-N-methyl-5-[4-((S)-3-methyl-morpholin-4-yl)-2-morpholin-4-yl-pyrido[2,3-d]pyrimidin-7-yl]-benzamide (Example 1 dk)

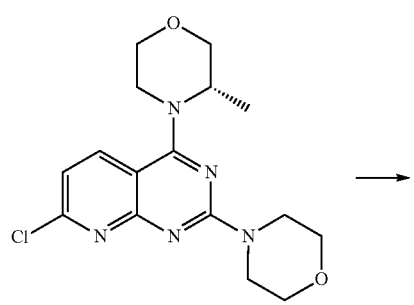

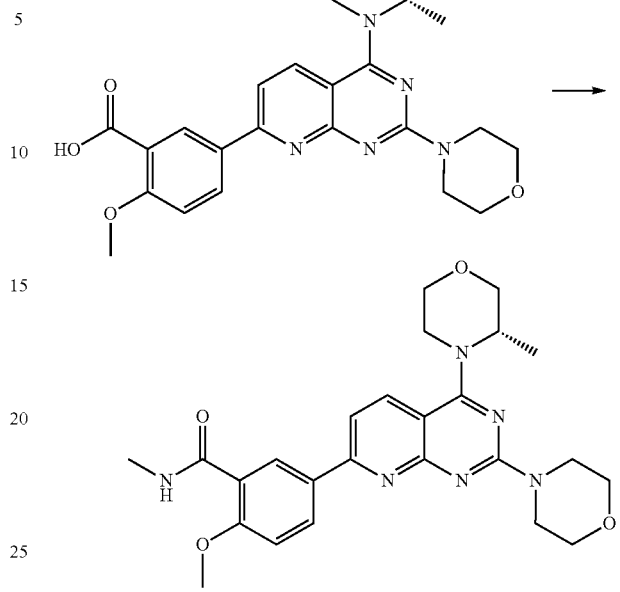

To a mixture of the appropriate chloro-substrate (1 equiv), potassium carbonate (3.0 equiv), and 2-methoxy-5-(4,4,5,5-tetramethyl-[1,3,2]dioxaborolan-2-yl)-benzoic acid methyl ester (1.05 equiv) in acetonitrile/water (1:1) (0.028 M of chloro-substrate) was added tetrakis(triphenylphosphine)palladium$^0$ (0.05 equiv). The reaction vessel was sealed and exposed to microwave radiation (130° C., medium absorption setting) for 20 minutes. Upon completion the reaction mixture was partitioned between water and $CH_2Cl_2$ and extracted with $CH_2Cl_2$. Combined organic phases were dried ($MgSO_4$), filtered and concentrated in vacuo. The crude residue was purified by column chromatography on silica gel eluting with 0 to 20% MeOH in $CH_2Cl_2$ to give the desired product.

2-Methoxy-5-[4-((S)-3-methyl-morpholin-4-yl)-2-morpholin-4-yl-pyrido[2,3-d]pyrimidin-7-yl]-benzoic acid: (91% yield, 100% purity) m/z (LC-MS, ESP): 466.4 [M+H]$^+$, R/T=2.68 min)

2-Methoxy-5-[4-((S)-3-methyl-morpholin-4-yl)-2-morpholin-4-yl-pyrido[2,3-d]pyrimidin-7-yl]-benzoic acid (1 equiv) was dissolved in DMF (0.1 M) and DIPEA (8 equiv) was added. HBTU (1.2 equiv) was added at 0° C. and the reaction mixture was stirred for 30 minutes. Methylamine hydrochloride (5 equiv) was added and the reaction mixture was stirred 0° C. for 30 minutes and at room temperature for 1 hour. The reaction mixture was partitioned between water and ethyl acetate. The aqueous phase was extracted with ethyl acetate. Combined organic phases were washed with water and brine, dried ($MgSO_4$), filtered and concentrated in vacuo. The crude residue was purified by column chromatography to give the desired product.

4-[2,4-Bis-((S)-3-methyl-morpholin-4-yl)-pyrido[2,3-d]pyrimidin-7-yl]-2-methoxy-N-methyl-benzamide: (73% yield, 97% purity) m/z (LC-MS, ESP): 479.2 [M+H]$^+$, R/T=3.97 min)

NMR Data for Example 1dk $^1$H NMR (300 MHz, CDCl$_3$) δ ppm 8.71 (ArH, d, J=2.45 Hz, 1H), 8.45 (ArH, dd, J=8.75, 2.48 Hz, 1H), 7.97 (ArH, d, J=8.52 Hz, 1H), 7.78 (NH, s, br, 1H), 7.51 (ArH, d, J=8.56

Hz, 1H), 7.01 (ArH, d, J=8.84 Hz, 1H), 4.39 (CH$_2$, d, J=6.69 Hz, 1H), 3.96 (OCH$_3$, s, 3H), 3.95-3.77 (CH$_2$, m, 7H), 3.76-3.58 (CH$_2$, m, 7H), 2.98 (NCH$_3$, d, J=4.81 Hz, 3H), 1.42 (CH$_3$, d, J=6.78 Hz, 3H).

$^{13}$C NMR (75 MHz, CDCl$_3$) δ ppm 165.74, 164.71, 161.22, 160.99, 159.11, 159.04, 135.09, 132.93, 131.23, 131.16, 121.32, 119.02, 113.63, 111.84, 104.61, 70.90, 66.90, 56.27, 52.70, 44.70, 44.48, 26.70 and 14.85.

Procedure for the synthesis of 6-[2,4-bis-((S)-3-methyl-morpholin-4-yl)-pyrido[2,3-d]pyrimidin-7-yl]-1H-indazol-3-ylamine (Example 1dl)

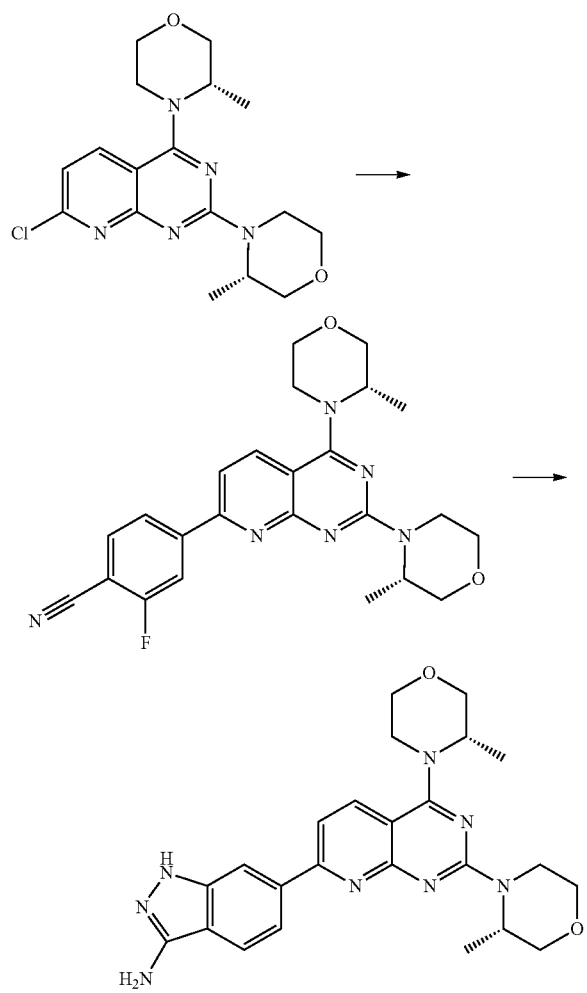

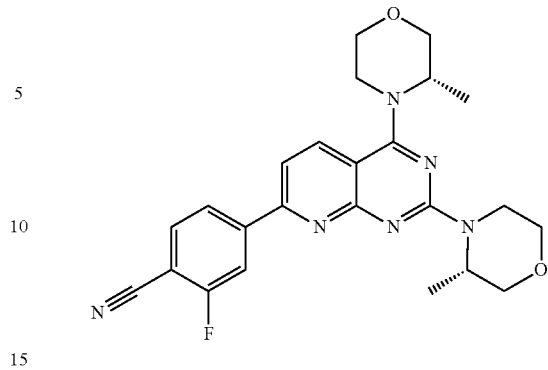

4-[2,4-Bis-((S)-3-methyl-morpholin-4-yl)-pyrido[2,3-d]pyrimidin-7-yl]-2-fluoro-benzonitrile: (49% yield, 96% purity) m/z (LC-MS, ESP): 449.2 [M+H]$^+$ R/T=2.93 min To a 0.2 M solution of 4-[2,4-bis-((S)-3-methyl-morpholin-4-yl)-pyrido[2,3-d]pyrimidin-7-yl]-2-fluoro-benzonitrile (1 equiv) in n-BuOH was added 0.2 reaction volumes of hydrazine hydrate. A reflux condenser was attached to the mixture which was then heated to 140° C. for 2 hours whereupon it was cooled, and concentrated in vacuo to give an orange residue which was purified by flash chromatography (SiO$_2$) using Et$_2$O:MeOH—94:6 as eluent which allowed a yellow solid which was then recrystallised from CH$_2$Cl$_2$/Hexanes to furnish the title compound as a yellow solid.

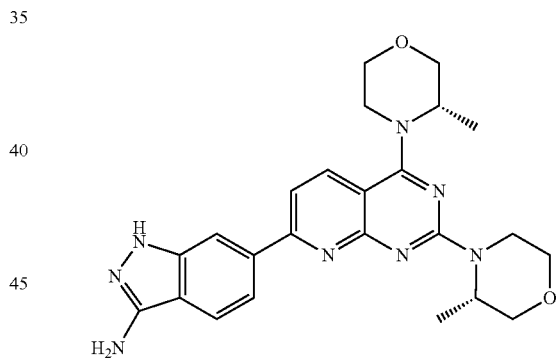

6-[2,4-Bis-((S)-3-methyl-morpholin-4-yl)-pyrido[2,3-d]pyrimidin-7-yl]-1H-indazol-3-ylamine: (90% yield, 97% purity) m/z (LC-MS, ESP): 461.2 [M+H]$^+$ R/T=3.77 min NMR Data for Example 1dl ($^1$H NMR (300 MHz, CD$_3$SOCD$_3$) δ ppm 11.6 (1H, s, formate), 8.31-8.01 (ArH, m, 2H), 7.74 (ArH, ddd, J=18.90, 15.23, 8.49 Hz, 3H), 5.42 (NH$_2$, s, 2H), 4.88-4.70 (NH, m, 1H), 4.44 (CH$_2$, d, J=10.93 Hz, 2H), 3.91 (CH$_2$, m, 3H), 3.81-3.54 (CH$_2$, m, 6H), 3.46 (CH$_2$, dt, J=11.82, 11.67, 2.52 Hz, 1H), 3.38-3.13 (CH$_2$, m, 1H), 2.51 (CH, td, J=3.52, 1.73, 1.73 Hz, 1H), 1.38 (CH$_3$, d, J=6.75 Hz, 3H), 1.26 (CH$_3$, d, J=6.79 Hz, 3H).

To a mixture of 7-chloro-4-((S)-3-methyl-morpholin-4-yl)-2-((S)-3-methyl-morpholin-4-yl)-pyrido[2,3-d]pyrimidine (1 equiv), potassium carbonate (2.5 equiv), and 4-cyano-3-fluorophenylboronic acid (1.2 equiv) in acetonitrile/water (1:1) (0.03 M of chloro-substrate) was added tetrakis(triphenylphosphine)palladium$^0$ (0.05 equiv). The reaction vessel was sealed and exposed to microwave radiation (110° C., medium absorption setting) for 25 minutes under nitrogen atmosphere. Upon completion the precipitate was collected by vacuum filtration, which was in suitably pure form to be used with no further purification.

13C NMR (75 MHz, CD$_3$SOCD$_3$) δ ppm 164.43, 162.05, 161.20, 159.29, 149.19, 141.79, 136.12, 135.32, 120.42, 116.81, 114.78, 113.13, 108.47, 104.30, 70.39, 70.15, 66.34, 66.15, 51.81, 46.24, 43.81, 30.89, 22.0, 14.31 and 13.89.

Procedure for the synthesis of N-{4-[2,4-bis-((S)-3-methyl-morpholin-4-yl)-pyrido[2,3-d]pyrimidin-7-yl]-pyridin-2-yl}-acetamide (Example 1dm)

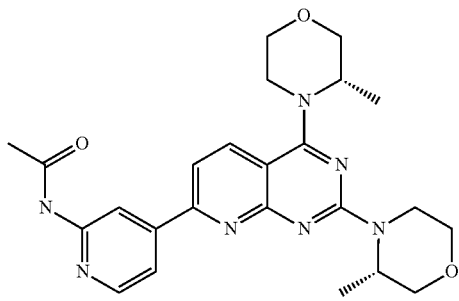 [SMILES: CC(=O)Nc1cc(-c2ccc3c(N4CCOC[C@@H]4C)nc(N4CCOC[C@@H]4C)nc3n2)ccn1]

To a 0.1 M solution of 4-[2,4-bis-((S)-3-methyl-morpholin-4-yl)-pyrido[2,3-d]pyrimidin-7-yl]-pyridin-2-ylamine (example 1cz) (1 equiv) in pyridine was added acetic anhydride (3 equiv). A reflux condenser was attached to the reaction vessel which was then heated to 70° C. for 2 days. Upon completion, the reaction was purified, in its crude for by preparative HPLC to give the title compound as a white solid.

N-{4-[2,4-Bis-((S)-3-methyl-morpholin-4-yl)-pyrido[2,3-d]pyrimidin-7-yl]-pyridin-2-yl}-acetamide: (95% yield, 99% purity) m/z (LC-MS, ESP): 464.1 [M+H]$^+$ R/T=3.77 min NMR Data for Example 1dm $^1$H NMR (300 MHz, CDCl$_3$) δ ppm 8.70 (NH, s, 1H), 8.37-8.29 (ArH, m, 2H), 8.01 (ArH, d, J=8.36 Hz, 1H), 7.94 (ArH, dd, J=5.26, 1.54 Hz, 1H), 7.49 (ArH, d, J=8.39 Hz, 1H), 4.87 (CH$_2$, ddd, J=2.90, 1.56, 0.64 Hz, 1H), 4.56 (CH$_2$, d, J=13.43 Hz, 1H), 4.33 (CH$_2$, d, J=6.86 Hz, 1H), 3.99-3.58 (CH$_2$, m, 10H), 3.57-3.45 (CH$_2$, m, 1H), 3.39-3.25 (CH$_2$, m, 1H), 2.19 (CH$_3$, s, 3H), 1.43 (CH$_3$, d, J=6.78 Hz, 3H), 1.31 (CH$_3$, d, J=6.82 Hz, 3H)

$^{13}$C NMR (75 MHz, CDCl$_3$) δ ppm 168.79, 165.32, 162.82, 160.00, 159.87, 151.94, 148.64, 148.15, 135.18, 118.86, 113.66, 111.94, 106.03, 71.27, 70.89, 67.23, 66.89, 52.89, 46.98, 44.46, 39.35, 24.81, 14.77 and 14.41.

Procedure for the Synthesis of Examples 1dn to 1dp

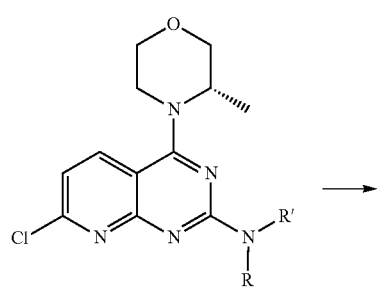

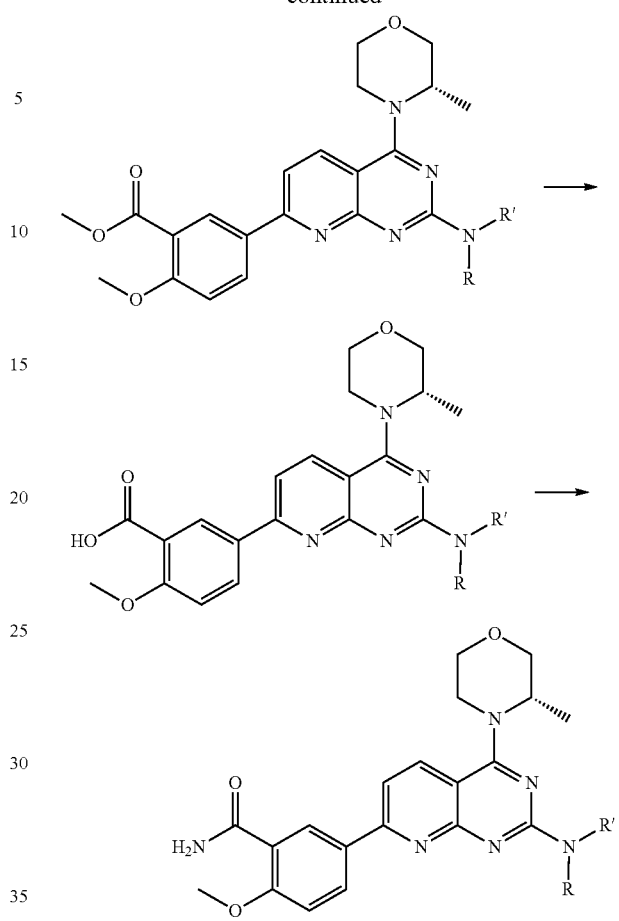

The appropriate 7-chloropyridopyrimidine was reacted with 2-methoxy-5-(4,4,5,5-tetramethyl-[1,3,2]dioxaborolan-2-yl)-benzoic acid methyl ester according to conditions E to give 2-methoxy-5-[4-((S)-3-methyl-morpholin-4-yl)-2-thiomorpholin-4-yl-pyrido[2,3-d]pyrimidin-7-yl]-benzoic acid methyl ester as the desired product (1 equiv) which was then diluted in MeOH to give a 0.03M solution. NaOH (5 equiv of 1 M solution) was then added and the resultant mixture stirred at room temperature for 5 days. After this time the reaction was filtered and neutralized with 1M HCl before being concentrated in vacuo to give a crude yellow residue which was diluted in CH$_2$Cl$_2$. The mixture was filtered and the resulting filtrate concentrated to give the desired product as an oil.

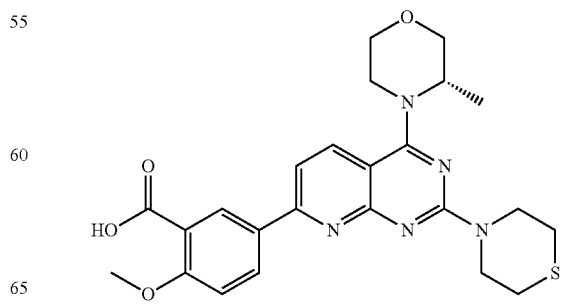

2-Methoxy-5-[4-((S)-3-methyl-morpholin-4-yl)-2-thio-morpholin-4-yl-pyrido[2,3-d]pyrimidin-7-yl]-benzoic acid: (99% yield, 95% purity) m/z (LC-MS, ESP): 482.2[M+H]+ R/T=2.78 min

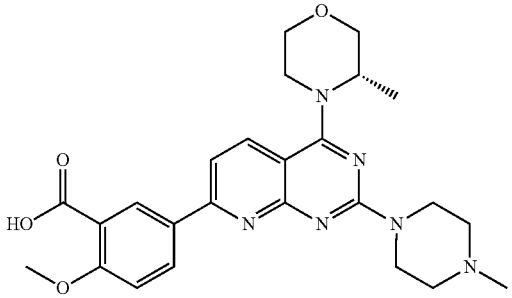

2-Methoxy-5-[4-((S)-3-methyl-morpholin-4-yl)-2-(4-methyl-piperazin-1-yl)-pyrido[2,3-d]pyrimidin-7-yl]-benzoic acid: (88% yield, 96% purity) m/z (LC-MS, ESP): 479.5[M+H]⁺ R/T=2.26 min

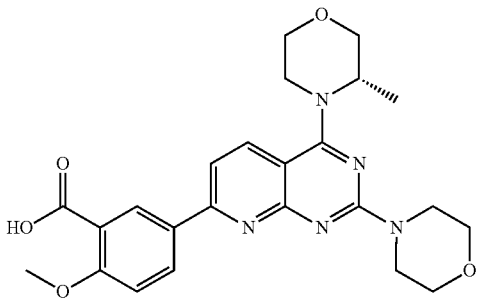 [SMILES: COc1ccc(-c2ccc3c(N4CCOC[C@@H]4C)nc(N4CCOCC4)nc3n2)cc1C(=O)O]

2-Methoxy-5-[4-((S)-3-methyl-morpholin-4-yl)-2-morpholin-4-yl-pyrido[2,3-d]pyrimidin-7-yl]-benzoic acid: (91% yield, 100% purity) m/z (LC-MS, ESP): 466.4 [M+H]⁺ R/T=2.68 min To a warmed (40° C.) 0.06 M solution of the appropriate benzoic acid derivative (1 equiv) in anhydrous THF was added thionyl chloride (2.5 equiv) in a dropwise fashion. The reaction was maintained at this temperature and stirred for a further 1 hour. After this time the mixture was evaporated to give a brown oil, which was diluted in dry THF (sufficient to make 0.06 M solution) before ammonia gas was bubble through the mixture, which was accompanied by an exotherm. Upon completion, addition of ammonia was stopped and the mixture concentrated in vacuo to give a yellow oily residue which was dissolved in $CH_2Cl_2$ (1 reaction volume) and washed with water (2×1 reaction volume). The organic extract was removed, dried ($MgSO_4$), filtered and concentrated in vacuo to give the title compound.

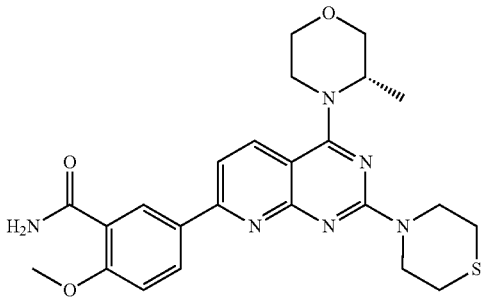 [SMILES: COc1ccc(-c2ccc3c(N4CCOC[C@@H]4C)nc(N4CCSCC4)nc3n2)cc1C(N)=O]

2-Methoxy-5-[4-((S)-3-methyl-morpholin-4-yl)-2-thio-morpholin-4-yl-pyrido[2,3-d]pyrimidin-7-yl]-benzamide: (30% yield, 97% purity) m/z (LC-MS, ESP): 481.1[M+H] R/T=4.02 min NMR Data for Example 1dn
$^1$H NMR (300 MHz, CDCl$_3$) δ ppm 8.83 (ArH, d, J=2.46 Hz, 1H), 8.61 (ArH, dd, J=8.75, 2.48 Hz, 1H), 8.00 (ArH, d, J=8.47 Hz, 1H), 7.72 (NH, d, J=0.76 Hz, 1H), 7.56 (ArH, d, J=8.50 Hz, 1H), 7.13 (ArH, d, J=8.82 Hz, 1H), 5.88 (NH, d, J=0.98 Hz, 1H), 4.42-4.23 (CH$_2$, m, 4), 4.05 (CH$_3$O, s, 3H), 4.03-3.94 (CH$_2$, m, 1H), 3.85 (CH$_2$, ddd, J=14.51, 8.58, 5.82 Hz, 2H), 3.78-3.62 (CH$_2$, m, 3H), 2.75-2.65 (CH$_2$, m, 3H), 1.46 (CH$_3$, d, J=6.76 Hz, 3H).
$^{13}$C NMR (75 MHz, CDCl$_3$) δ ppm 166.60, 165.41, 162.87, 161.09, 159.89, 159.23, 134.73, 133.71, 131.82, 131.68, 120.56, 113.16, 111.89, 104.63, 70.95, 66.91, 56.29, 52.81, 46.70, 44.54, 27.45 and 14.70.

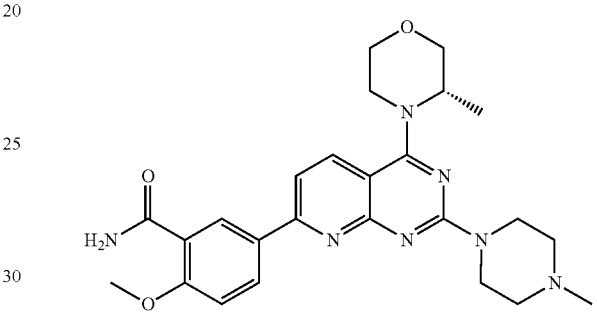

2-Methoxy-5-[4-((S)-3-methyl-morpholin-4-yl)-2-(4-methyl-piperazin-1-yl)-pyrido[2,3-d]pyrimidin-7-yl]-benzamide: (12% yield, 98% purity) m/z (LC-MS, ESP): 481.1 [M+H]+R/T=43.28 min
NMR Data for Example 1do
$^1$H NMR (300 MHz, CDCl$_3$) δ ppm 8.78 (ArH, d, J=2.48 Hz, 1H), 8.57 (ArH, dd, J=8.76, 2.52 Hz, 1H), 8.28 (NH, s, br, 1H), 7.96 (ArH, d, J=8.50 Hz, 1H), 7.68 (NH, s, br, 1H), 7.54 (ArH, d, J=8.55 Hz, 1H), 7.08 (ArH, d, J=8.84 Hz, 1H), 4.42-4.28 (CH$_2$, m, 1H), 4.09 (CH$_2$, s, br, 2H), 4.01 (OCH$_3$, s, 3H), 3.77 (CH$_2$, ddd, J=36.04, 19.80, 10.87 Hz, 9H), 2.76 (CH$_2$, t, J=5.05, 5.05 Hz, 4H), 2.47 (NCH$_3$, s, 3H), 1.42 (CH$_3$, d, J=6.77 Hz, 3H).

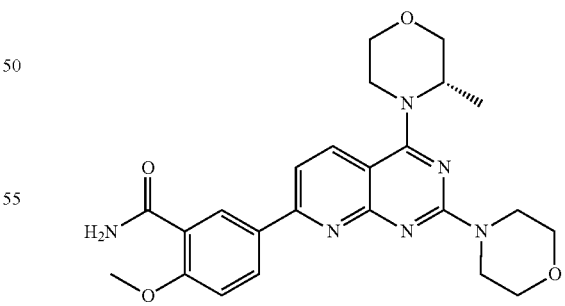

2-Methoxy-5-[4-((S)-3-methyl-morpholin-4-yl)-2-morpholin-4-yl-pyrido[2,3-d]pyrimidin-7-yl]-benzamide: (61% yield, 97% purity) m/z (LC-MS, ESP): 465.4 [M+H]⁺ R/T=2.69 min NMR Data for Example 1dp
$^1$H NMR (300 MHz, CDCl$_3$) δ ppm 8.77 (ArH, d, J=2.44 Hz, 1H), 8.58 (ArH, dd, J=8.76, 2.47 Hz, 1H), 7.94 (ArH, d, J=8.48 Hz, 1H), 7.65 (NH, s, br, 1H), 7.51 (ArH, d, J=8.53 Hz, 1H), 7.06 (ArH, d, J=8.84 Hz, 1H), 5.91 (NH, s, br, 1H), 4.32 (CH$_2$, d, J=6.79 Hz, 1H), 3.98 (OCH$_3$, s, 3H), 3.95-3.86 (CH$_2$, m, 5H), 3.84-3.55 (CH$_2$, m, 9H), 1.40 (CH$_3$, d, J=6.77 Hz, 3H)

$^{13}$C NMR (75 MHz, CDCl$_3$) δ ppm 166.63, 165.31, 162.78, 160.96, 160.31, 159.29, 134.76, 133.68, 131.69, 131.60, 120.56, 113.09, 111.88, 104.76, 70.94, 67.04, 66.91, 56.28, 52.76, 44.58, 44.45 and 14.75.

Procedure for the Synthesis of Example 1dq

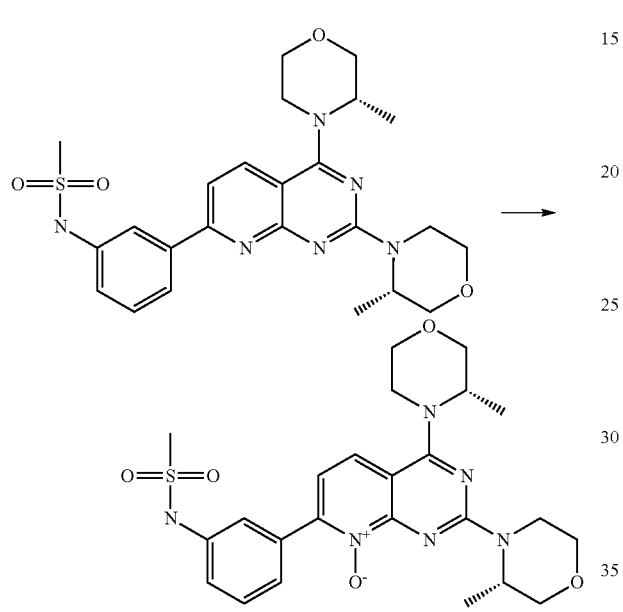

To a (0.1 M) solution of example 1at (1 equiv) in CHCl$_3$ was added m-CPBA (5.5 equiv). A reflux condenser was added to the apparatus and the mixture heated to 60° C. for 17 hours. After this time the reaction was concentrated in vacuo and purified by flash chromatography (SIO$_2$) using CH$_2$Cl$_2$:MeOH—95:5 as eluent to furnish the desired product.

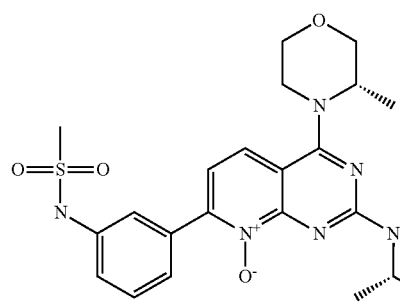

N-{3-[2,4-Bis-((S)-3-methyl-morpholin-4-yl)-8-oxy-pyrido[2,3-d]pyrimidin-7-yl]-phenyl}-methanesulfonamide: (39% yield, 100% purity) m/z (LC-MS, ESP): 515.5 [M+H]$^+$ R/T=2.95 min.

NMR Data for Example 1dq $^1$H NMR (300 MHz, CDCl$_3$) δ ppm 10.04 (NH, s, br, 1H), 8.42 (ArH, s, 1H), 7.55-7.25 (ArH, m, 4H), 6.96 (ArH, d, J=8.67 Hz, 1H), 4.80 (CH$_2$, s, br, 1H), 4.51 (CH$_2$, s, br, 1H), 4.31 (CH$_2$, d, J=6.71 Hz, 1H), 4.00-3.51 (CH$_2$, m, 9H), 3.49-3.34 (CH$_2$, m, 1H), 3.24 (CH$_2$, dd, J=13.22, 3.30 Hz, 1H), 2.80 (SCH$_3$, s, 3H), 1.42 (CH$_3$, d, J=6.78 Hz, 1H), 1.19 (CH$_3$, d, J=6.69 Hz, 3H).

$^{13}$C NMR (75 MHz, CDCl$_3$) δ ppm 165.58, 159.69, 158.28, 149.96, 138.59, 134.47, 129.53, 125.86, 123.35, 123.30, 116.17, 107.52, 71.33, 71.11, 67.32, 67.10, 53.39, 47.62, 44.87, 39.79, 38.68, 31.90, 22.97 and 15.16.

Procedure for the Synthesis of Example 1dr

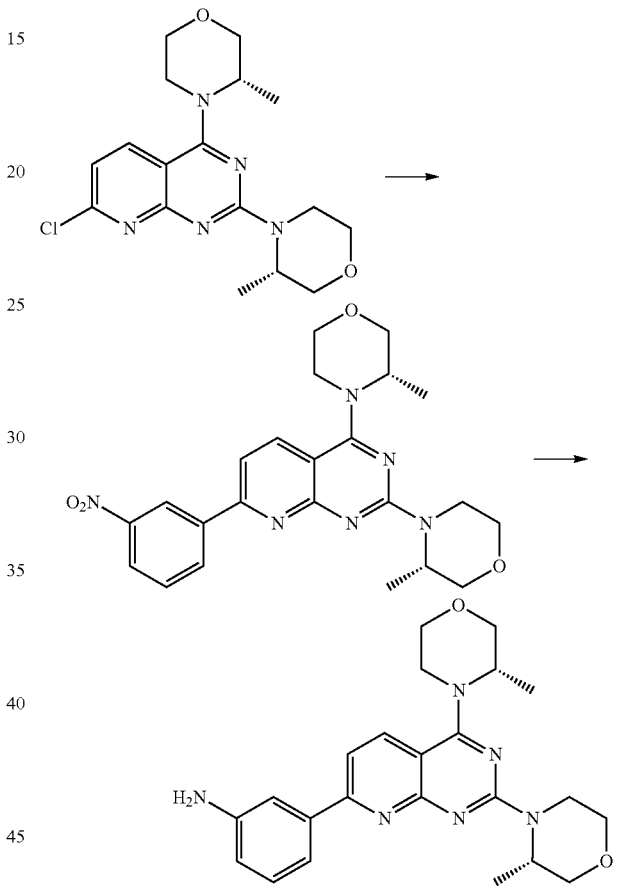

7-Chloro-2,4-bis-((S)-3-methyl-morpholin-4-yl)-pyrido[2,3-d]pyrimidine was couple with 3-nitrobenzoic acid using Suzuki conditions D to give the desire product as a yellow powder.

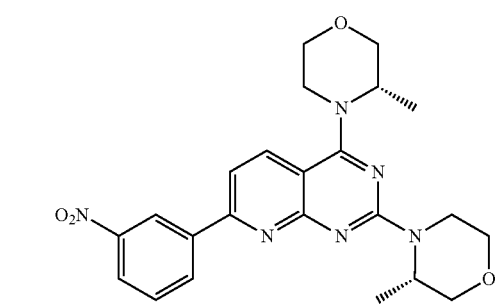 [SMILES: C[C@H]1COCCN1c1nc(N2CCOC[C@@H]2C)c2ccc(-c3cccc([N+](=O)[O-])c3)nc2n1]

2,4-Bis-((S)-3-methyl-morpholin-4-yl)-7-(3-nitro-phenyl)-pyrido[2,3-d]pyrimidine: (90% yield, 100% purity) m/z (LC-MS, ESP): 451.6[M+H]⁺ R/T=3.41 min To a 0.1M solution of 2,4-bis-((S)-3-methyl-morpholin-4-yl)-7-(3-nitro-phenyl)-pyrido[2,3-d]pyrimidine (1 equiv) in EtOH/H₂O-1:1 was added ammonium chloride (8 equiv) and iron powder (8 equiv). The reaction mixture was heated to 100° C. for 1 hour before cooling and filtering through a thin Celite™ pad. The cake was washed with EtOH (1 reaction volume). The filtrate was concentrated in vacuo and then partitioned between water and CH₂Cl₂ (1 reaction volume of each). The organic phase was removed, dried (MgSO₄), filtered and concentrated in vacuo and then purified by flash chromatography (SiO₂) using MeOH:CH₂Cl₂ (0:100-5:95-10-90) as eluent to give the title compound as a yellow solid.

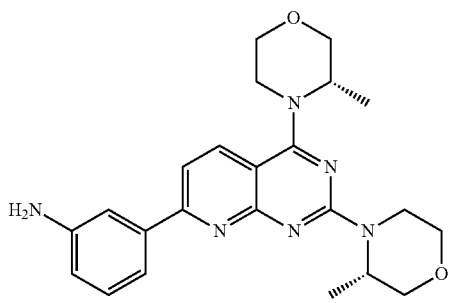

3-[2,4-Bis-((S)-3-methyl-morpholin-4-yl)-pyrido[2,3-d]pyrimidin-7-yl]-phenylamine: (88% yield, 98% purity) m/z (LC-MS, ESP): 421.1[M+H]⁺ R/T=3.76 min NMR Data for Example 1dr ¹H NMR (300 MHz, CDCl₃) δ ppm 7.93 (ArH, d, J=8.45 Hz, 1H), 7.62-7.55 (ArH, m, 1H), 7.41-7.32 (m, 1H), 7.20 (ArH, d, J=7.32 Hz, 2H), 6.71 (ArH, ddd, J=7.88, 2.40, 0.86 Hz, 1H), 4.87 (ArH, dd, J=3.54, 1.66 Hz, 1H), 4.57 (NH, d, J=13.25 Hz, 1H), 4.30 (NH, s, br, 1H), 3.98-3.56 (CH₂, m, 11H), 3.56-3.44 (CH₂, m, 1H), 3.37-3.24 (CH₂, m, 1H), 1.40 (CH₃, d, J=6.77 Hz, 3H), 1.29 (CH₃, d, J=6.81 Hz, 3H)

¹³C NMR (75 MHz, CDCl₃) δ ppm 165.46, 162.87, 162.60, 159.96, 146.80, 139.75, 134.48, 129.35, 117.99, 116.69, 114.74, 113.48, 104.92, 71.32, 70.93, 67.28, 66.94, 52.80, 46.90, 44.49, 39.33, 14.71 and 14.33.

Procedure for the Synthesis of Example 1ds

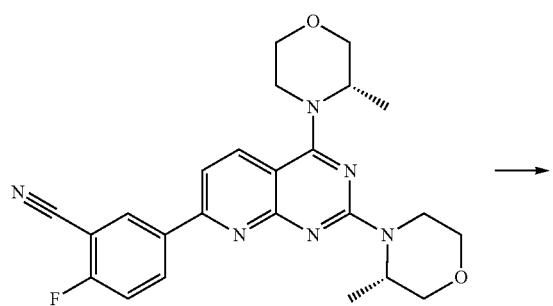

→

-continued

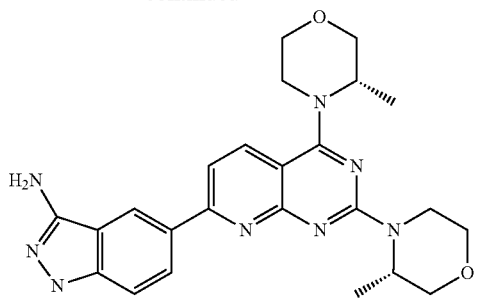

To a 0.3M solution of 5-[2,4-bis-((S)-3-methyl-morpholin-4-yl)-pyrido[2,3-d]pyrimidin-7-yl]-2-fluoro-benzonitrile (example 1av) (1 equiv) in EtOH was added hydrazine hydrate (5 equiv). The mixture was refluxed for 90 minutes whereupon it was cooled and partitioned between CH₂Cl₂ and water (1 reaction volume of each). The organic extract was removed. The aqueous phase was further extracted with CH₂Cl₂ (2×1 reaction volume). The combined organic extracts were then dried (MgSO₄), filtered and concentrated in vacuo to give a yellow slurry which was further purified by flash chromatography (SiO₂) using EtOAC/Hexanes as eluent to give the title compound as a yellow powder.

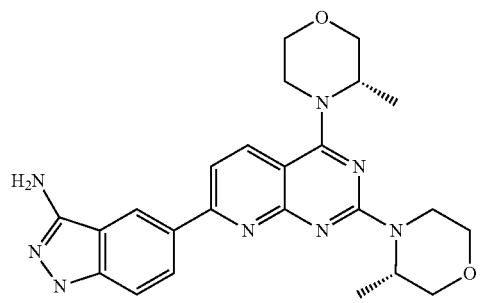 [SMILES: C[C@H]1COCCN1c1nc(N2CCOC[C@@H]2C)c2ccc(-c3ccc4[nH]nc(N)c4c3)nc2n1]

5-[2,4-Bis-((S)-3-methyl-morpholin-4-yl)-pyrido[2,3-d]pyrimidin-7-yl]-1H-indazol-3-ylamine: (52% yield, 100% purity) m/z (LC-MS, ESP): 461.6[M+H]⁺ R/T=2.85 min NMR Data for Example 1ds ¹H NMR (300 MHz, CDCl₃) δ ppm 8.52 (ArH, s, 1H), 8.06 (ArH, dd, J=8.84, 1.50 Hz, 1H), 7.94 (ArH, d, J=8.49 Hz, 1H), 7.42 (ArH, d, J=8.50 Hz, 1H), 7.29 (ArH, d, J=8.79 Hz, 2H), 4.87 (CH₂, dd, J=3.99, 1.99 Hz, 1H), 4.60 (CH₂, s, br, 1H), 4.32 (CH₂, d, J=6.78 Hz, 1H), 3.98-3.58 (CH₂, m, 9H), 3.51 (CH₂, dt, J=11.78, 11.46, 2.71 Hz, 1H), 3.39-3.25 (CH₂, m, 1H), 1.42 (CH₃, d, J=6.77 Hz, 3H), 1.29 (CH₃, d, J=6.81 Hz, 3H) (NH's not clearly seen)

¹³C NMR (75 MHz, CDCl₃) δ ppm 165.43, 162.97, 162.33, 160.01, 142.86, 134.62, 130.11, 127.06, 120.17, 115.21, 112.98, 109.71, 104.51, 71.32, 70.94, 67.28, 66.95, 52.80, 46.95, 44.48, 39.36, 27.01, 14.79 and 14.33.

| | Purity (%) | Retention time (min) | m/z [M+H]+ | Conditions | Example Structure |
|---|---|---|---|---|---|
| 1dt | 96 | 3.96 | 461.2 | U | 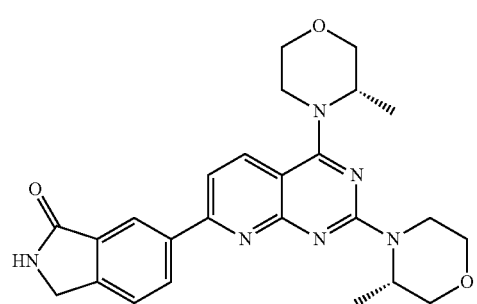 |
| 1du | 97 | 4.10 | 513.1 | I | 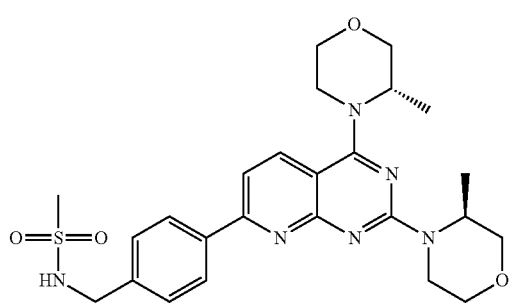 [SMILES: C[C@H]1COCCN1c1nc(N2CCOC[C@@H]2C)c2ccc(-c3ccc(CNS(C)(=O)=O)cc3)nc2n1] |
| 1dv | 99 | 4.04 | 495.0 | J | 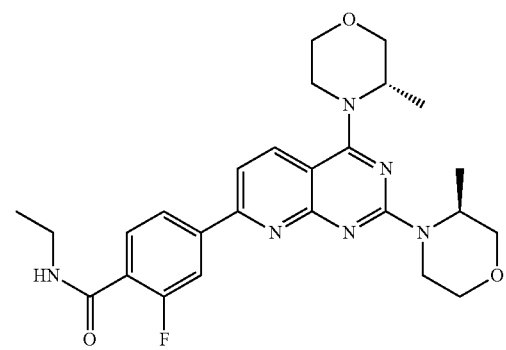 [SMILES: CCNC(=O)c1ccc(-c2ccc3c(N4CCOC[C@@H]4C)nc(N4CCOC[C@@H]4C)nc3n2)cc1F] |
| 1dw | 98 | 3.70 | 504.1 | V | 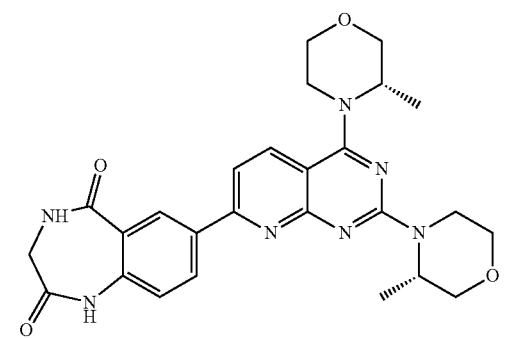 [SMILES: C[C@H]1COCCN1c1nc(N2CCOC[C@@H]2C)c2ccc(-c3ccc4c(c3)C(=O)NCC(=O)N4)nc2n1] |

-continued

| | Purity (%) | Retention time (min) | m/z [M+H]+ | Conditions | Example Structure |
|---|---|---|---|---|---|
| 1dx | 99 | 3.79 | 474.1 | I | |
| 1dy | 99 | 3.79 | 474.1 | W | |
| 1dz | 99 | 4.06 | 499.2 | D | |
| 1ea | 99 | 4.16 | 451.2 | D | |

-continued

| | Purity (%) | Retention time (min) | m/z [M+H]+ | Conditions | Example Structure |
|---|---|---|---|---|---|
| 1eb | 98 | 3.96 | 446.2 | P | |
| 1ec | 99 | 7.55 | 466.2 | J | |
| 1ed | 98 | 3.86 | 461.2 | D | |
| 1ee | 98 | 4.04 | 485.2 | D | |

Note:
The following examples were synthesized from the corresponding boronic acids: 1du, 1dv, 1dz and 1ee.
The following examples were synthesized from the corresponding pinacolate boron esters: 1dw, 1dx, 1ea, 1eb and 1ec.
The following Examples were synthesized from a mixture of the corresponding boronic acids and pinacolate boron esters: 1dt, 1dy, and 1ed.

NMR Data for Example 1ec $^1$H NMR (300 MHz, CDCl$_3$) δ ppm 8.15 (ArH, d, J=7.5 Hz, 2H), 7.97 (ArH, d, J=8.46 Hz, 1H), 7.42 (ArH, d, J=8.46 Hz, 1H), 6.98 (ArH, d, J=9.24 Hz, 1H), 4.91 (CH$_2$, d, J=5.55 Hz, 1H), 4.77 (CH$_2$OH, s, 2H), 4.61 (CH$_2$, d, J=12.42 Hz, 1H), 4.36-4.34 (CH$_2$, m, 1H), 4.00-3.70 (OCH$_3$+CH$_2$, m, 9H), 3.69-3.51 (CH$_2$, m, 1H), 3.41-3.31 (CH$_2$, m, 1H), 1.46 (CH$_3$, d, J=6.69 Hz, 3H), 1.35 (CH$_3$, d, J=6.87 Hz, 3H).

$^{13}$C NMR (75 MHz, CDCl$_3$) δ ppm 165.42, 162.88, 161.87, 159.95, 159.16, 134.54, 131.13, 129.25, 128.89, 128.44, 112.85, 110.27, 104.49, 71.30, 70.92, 67.26, 66.93, 61.98, 55.56, 52.78, 46.91, 44.45, 39.32, 14.69 and 14.31.

NMR Data for Example 1ed
$^1$H NMR (300 MHz, CDCl$_3$) δ ppm 8.34 (ArH, s, 1H), 8.11 (ArH, d, J=8.02 Hz, 1H), 8.00 (ArH, d, J=8.41 Hz, 1H), 7.90 (ArH, d, J=7.98 Hz, 1H), 7.43 (ArH, d, J=8.42 Hz, 1H), 7.10 (NH, br, s, 1H), 4.95-4.81 (CH$_2$, m, 1H), 4.57 (CH$_2$, d, J=13.37 Hz, 1H), 4.47 (NHCH$_2$, s, 2H), 4.33 (CH$_2$, d, J=6.68 Hz, 1H), 3.99-3.58 (CH$_2$, m, 9H), 3.51 (CH$_2$, dt, J=11.81, 11.45, 2.72 Hz, 1H), 3.31 (CH$_2$, dt, J=12.91, 12.52, 3.57 Hz, 1H), 1.42 (CH$_3$, d, J=6.78 Hz, 3H), 1.30 (CH$_3$, d, J=6.81 Hz, 3H).

$^{13}$C NMR (75 MHz, CDCl$_3$) δ ppm 171.32, 165.36, 162.94, 161.42, 160.04, 144.06, 142.31, 135.01, 133.20, 127.63, 123.83, 123.08, 113.49, 105.35, 71.27, 70.91, 67.24, 66.91, 52.85, 46.96, 45.70, 44.48, 39.35, 14.76 and 14.39.

NMR Data for Example 1ef
$^1$H NMR (300 MHz, CDCl$_3$) δ ppm 8.08 (ArH, d, J=1.95 Hz, 1H), 8.01-7.94 (ArH, m, 1H), 7.82 (ArH, td, J=6.63, 1.80, 1.80 Hz, 1H), 7.48 (NH, br, s, 1H), 7.39 (ArH, dd, J=12.99, 5.20 Hz, 3H), 4.34 (CH$_2$, q, J=6.63, 6.56, 6.56 Hz, 1H), 3.97-3.76 (CH$_2$, m, 7H), 3.75-3.57 (CH$_2$, m, 7H), 2.87 (SO$_2$CH$_3$, s, 3H), 1.42 (CH$_3$, d, J=6.78 Hz, 3H).

$^{13}$C NMR (75 MHz, CDCl$_3$) δ ppm 165.21, 162.77, 161.34, 160.28, 140.30, 137.69, 135.07, 129.91, 124.53, 122.37, 120.57, 113.44, 105.22, 70.91, 66.97, 66.89, 52.84, 44.58, 44.39, 39.32 and 14.79.

NMR Data for Example 1dz
$^1$H NMR (300 MHz, CDCl$_3$) δ ppm 8.11-8.03 (ArH, m, 2H), 7.96 (ArH, d, J=8.44 Hz, 1H), 7.38-7.31 (ArH, m, 1H), 7.32-7.24 (ArH, m, 2H), 4.85 (CH$_2$, d, J=5.45 Hz, 1H), 4.54 (CH$_2$, d, J=12.83 Hz, 1H), 4.32 (CH$_2$, d, J=6.78 Hz, 1H), 3.97-3.57 (CH$_2$, m, 9H), 3.50 (CH$_2$, dt, J=11.75, 11.35, 2.73 Hz, 1H), 3.37-3.24 (CH$_2$, m, 1H), 2.95 (SO$_2$CH$_3$, s, 3H), 1.42 (CH$_3$, d, J=6.78 Hz, 1H), 1.29 (CH$_3$, d, J=6.81 Hz, 3H) (NH not seen).

$^{13}$C NMR (75 MHz, CDCl$_3$) δ ppm 165.36, 162.93, 161.33, 160.00, 138.73, 135.29, 134.86, 129.34, 119.66, 112.95, 104.90, 71.27, 70.92, 67.24, 66.93, 52.82, 46.97, 44.45, 39.58, 33.35, 14.75 and 14.36.

NMR Data for Example 1ea
$^1$H NMR (300 MHz, CDCl$_3$) δ ppm 7.87 (ArH, d, J=8.55 Hz, 1H), 7.81 (ArH, d, J=1.80 Hz, 1H), 7.47 (ArH, dd, J=8.17, 1.85 Hz, 1H), 7.35 (ArH, d, J=8.57 Hz, 1H), 6.69 (ArH, d, J=8.14 Hz, 1H), 4.85 (CH$_2$, d, J=5.96 Hz, 1H), 4.62-4.52 (CH$_2$, m, 1H), 4.28 (CH$_2$, d, J=6.77 Hz, 1H), 4.02 (NH$_2$, s, br, 2H), 3.95 (d, J=6.54 Hz, 1H), 3.93 (CH$_3$, s, 3H), 3.92-3.57 (CH$_2$, m, 9H), 3.55-3.45 (CH$_2$, m, 1H), 3.38-3.25 (CH$_2$, m, 1H), 1.39 (CH$_3$, d, J=6.77 Hz, 3H), 1.29 (CH$_3$, d, J=6.81 Hz, 3H).

$^{13}$C NMR (75 MHz, CDCl$_3$) δ ppm 165.48, 162.91, 162.45, 159.98, 147.22, 138.70, 134.14, 128.92, 121.24, 113.97, 112.74, 110.15, 104.11, 71.35, 70.95, 67.32, 66.96, 55.83, 52.79, 46.89, 44.44, 39.31, 31.60, 22.66 and 14.30.

NMR Data for Example 1eb
$^1$H NMR (300 MHz, CD$_3$COCD$_3$) δ ppm 11.83 (ArH, s, 1H), 9.06 (ArH, d, J=2.07 Hz, 1H), 8.75 (ArH, d, J=2.09 Hz, 1H), 8.30-8.10 (ArH, m, 1H), 7.72 (ArH, d, J=8.55 Hz, 1H), 7.54 (ArH, s, 1H), 6.59 (NH, s, 1H), 4.77 (CH$_2$, dd, J=6.66, 1.89 Hz, 1H), 4.49-4.34 (CH$_2$, m, 2H), 4.03-3.83 (CH$_2$, m, 3H), 3.81-3.55 (CH$_2$, m, 6H), 3.54-3.38 (CH$_2$, m, 1H), 3.23 (CH$_2$, dd, J=13.19, 3.46 Hz, 1H), 1.37 (CH$_3$, d, J=6.74 Hz, 3H), 1.25 (CH$_3$, d, J=6.75 Hz, 3H).

$^{13}$C NMR (75 MHz, CD$_3$COCD$_3$) δ ppm 165.41, 163.09, 161.32, 160.22, 150.21, 143.45, 136.25, 128.14, 128.09, 126.99, 120.44, 113.54, 104.90, 101.82, 71.32, 71.09, 67.27, 67.09, 52.78, 47.17, 44.79 and 15.25.

NMR Data for Example 1dy
1H NMR (300 MHz, CD$_3$SOCD$_3$) δ ppm 8.40 (ArH, d, J=1.37 Hz, 1H), 8.33 (ArH, dd, J=8.38, 1.63 Hz, 1H), 8.25 (ArH, d, J=8.45 Hz, 2H), 8.17 (ArH, s, 1H), 7.79 (ArH, d, J=8.48 Hz, 1H), 4.84-4.73 (CH, m, 1H), 4.45 (CH$_2$, d, J=13.67 Hz, 2H), 4.00-3.84 (CH$_2$, m, 3H), 3.81-3.57 (CH$_2$, m, 6H), 3.46 (CH$_2$, dt, J=11.84, 11.73, 2.61 Hz, 1H), 3.23 (CH$_2$, dt, J=13.16, 12.92, 3.65 Hz, 1H), 1.39 (CH$_3$, d, J=6.75 Hz, 3H), 1.26 (CH$_3$, d, J=6.75 Hz, 3H)

13C NMR (75 MHz, CD$_3$SOCD$_3$) δ ppm 164.30, 162.06, 160.45, 159.32, 159.03, 149.10, 145.91, 143.53, 135.86, 126.40, 125.73, 125.30, 123.33, 113.30, 105.06, 70.35, 70.14, 66.31, 66.14, 51.79, 46.27, 43.81, 30.38, 14.35 and 13.89.

NMR Data for Example 1dv
$^1$H NMR (300 MHz, CD$_3$SOCD$_3$) δ ppm 8.39 (ArH, dd, J=5.45, 3.65 Hz, 1H), 8.23 (ArH, d, J=8.47 Hz, 1H), 8.14-8.03 (ArH, m, 2H), 7.81-7.69 (ArH+NH, m, 2H), 4.77 (CH$_2$, dd, J=6.52, 2.00 Hz, 1H), 4.43 (CH$_2$, d, J=13.75 Hz, 2H), 3.99-3.83 (CH$_2$, m, 2H), 3.80-3.56 (CH$_2$, m, 6H), 3.52-3.15 (CH$_2$, m, 5H), 2.50 (CH$_2$, td, J=3.67, 1.83, 1.83 Hz, 2H), 1.38 (CH$_3$, d, J=6.75 Hz, 3H), 1.25 (CH$_3$, d, J=6.75 Hz, 3H), 1.19-1.10 (CH$_3$, m, 3H).

$^{13}$C NMR (75 MHz, CD$_3$SOCD$_3$) δ ppm 164.80, 163.51, 162.52, 159.84, 158.73, 158.27, 142.53, 142.43, 136.38, 131.02, 125.84, 123.52, 123.48, 115.08, 114.76, 113.45, 105.57, 70.87, 70.64, 66.83, 66.65, 52.32, 46.79, 44.32, 34.59, 15.10, 14.87 and 14.42.

NMR Data for Example 1dy
$^1$H NMR (300 MHz, CD$_3$SOCD$_3$) δ ppm 10.52 (NH, s, 1H), 8.19 (ArH, d, J=8.50 Hz, 1H), 7.79-7.68 (ArH, m, 2H), 7.61 (ArH, d, J=8.52 Hz, 1H), 7.35 (ArH, d, J=7.66 Hz, 1H), 4.84-4.69 (CH$_2$, m, 1H), 4.42 (CH$_2$, dd, J=7.38, 5.30 Hz, 2H), 3.91 (CH$_2$, dd, J=14.30, 7.97 Hz, 3H), 3.82-3.52 (CH$_2$, m, 8H), 3.45 (CH$_2$, d, J=2.42 Hz, 1H), 3.26-3.15 (CH$_2$, m, 1H), 1.37 (CH$_3$, d, J=6.74 Hz, 3H), 1.25 (CH$_3$, d, J=6.76 Hz, 3H).

$^{13}$C NMR (75 MHz, CD$_3$SOCD$_3$) δ ppm 176.84, 164.89, 162.55, 160.83, 159.82, 144.90, 138.19, 135.98, 128.66, 125.02, 120.94, 113.09, 108.05, 104.92, 70.90, 70.67, 66.84, 66.67, 52.32, 46.76, 44.30, 36.29, 14.85 and 14.35.

NMR Data for Example 1dt
$^1$H NMR (300 MHz, CDCl$_3$) δ ppm 8.58 (ArH, d, J=7.97 Hz, 1H), 8.49 (ArH, d, J=45.95 Hz, 1H), 7.99 (ArH, d, J=8.42 Hz, 1H), 7.50 (ArH, dd, J=17.31, 8.21 Hz, 1H), 7.24 (ArH, d, J=17.82 Hz, 1H), 5.01-4.86 (CH$_2$, s, br, 1H), 4.65-4.39 (CH$_2$, m, 3H), 4.33 (CH$_2$, d, J=6.25 Hz, 1H), 4.04-3.58 (CH$_2$, m, 8H), 3.49 (CH$_2$, d, J=11.36 Hz, 1H), 3.31 (CH$_2$, d, J=2.99 Hz, 1H), 1.41 (CH$_3$, d, J=6.72 Hz, 3H), 1.29 (CH$_3$, d, J=6.76 Hz, 3H) (1 proton missing, lots of overlap seen, NH not seen either)

$^{13}$C NMR (75 MHz, CDCl$_3$) δ 171.52, 165.39, 162.90, 161.33, 160.01, 145.14, 139.06, 135.02, 132.17, 123.57, 122.56, 113.20, 105.21, 71.29, 70.92, 67.25, 66.93, 52.78, 46.95, 45.68, 44.51, 39.34, 27.00, 14.74 and 14.35.

NMR Data for Example 1du
$^1$H NMR (300 MHz, CDCl$_3$) δ ppm 8.12 (ArH, d, J=8.32 Hz, 2H), 8.03 (ArH, d, J=8.43 Hz, 1H), 7.51-7.39 (ArH, m, 3H), 5.08 (CH$_2$, br, s, 1H), 4.89 (CH$_2$, d, J=4.91 Hz, 1H), 4.58 (CH$_2$, d, J=12.59 Hz, 1H), 4.40 (CH$_2$NH, br, s, 2H), 4.22 (NH, br, s, 1H), 4.04-3.64 (CH$_2$, m, 9H), 3.56 (CH$_2$, dt, J=11.80, 11.45, 2.75 Hz, 1H), 3.44-3.30 (CH$_2$, m, 1H), 2.87 (SO$_2$CH$_3$s, 3H), 1.48 (CH$_3$, d, J=6.78 Hz, 3H), 1.35 (CH$_3$, d, J=6.81 Hz, 3H)

$^{13}$C NMR (75 MHz, CDCl$_3$) δ ppm 165.16, 163.70, 162.51, 159.71, 138.71, 138.33, 134.99, 128.40, 128.15, 113.45, 105.20, 71.23, 70.89, 67.18, 66.90, 52.82, 47.07, 46.90, 44.21, 41.25, 39.41, 14.78 and 14.38.

Tested in the Biological Assay: Ex. (1b) 0.00185 μM; Ex. (1c) 0.00184 μM Ex. (1d) 0.00245 μM; Ex. (1az) 0.006865 μM.

Tested in Alternative Enzyme Assay: Ex. (1a) 0.0089 μM; Ex. (1e) 0.0044 μM; Ex. (1f) 0.005 μM; Ex. (1g) 0.011 μM; Ex. (1h) 0.0021 μM; Ex. (1i) 0.0056 μM; Ex. (1j) 0.035 μM; Ex. (1k) 0.015 μM; Ex. (1l) 0.0057 μM; Ex. (1m) 0.31 μM; Ex. (1n) 0.085 μM; Ex. (1o) 0.14 μM; Ex. (1p) 0.038 μM; Ex. (1q) 0.39 μM; Ex. (1r) 0.23 μM; Ex. (1s) 0.028 μM; Ex. (1t) 0.34 μM; Ex. (1u) 0.015 μM; Ex. (1v) 0.18 μM; Ex. (1w) 0.26 μM; Ex. (1x) 0.53 μM; Ex. (1y) 0.33 μM; Ex. (1z) 0.37 μM; Ex. (1aa) 0.025 μM; Ex. (1ab) 0.029 μM; Ex. (1ac) 0.14 μM; Ex. (1ad) 0.0069 μM; Ex. (1ae) 0.38 μM; Ex. (1af) 0.054 μM; Ex. (1ag) 0.029 μM; Ex. (1ah) 0.012 μM; Ex. (1ai) 1.1 M; Ex. (1aj) 0.49 μM; Ex. (1ak) 0.017 μM; Ex. (1al) 0.23 μM; Ex. (1am) 0.21 μM; Ex. (1an) 0.14 μM; Ex. (1ao) 0.0083 μM; Ex. (1ap) 0.02 μM; Ex. (1aq) 0.084 μM; Ex. (1ar) 0.006 μM; Ex. (1as) 0.013 μM; Ex. (1at) 0.031 μM; Ex. (1au) 0.09 μM; Ex. (1av) 0.29 μM; Ex. (1aw) 0.062 μM; Ex. (1ax) 0.0092 μM; Ex. (1ay) 0.15 μM; Ex. (1ba) 0.44 μM; Ex. (1bb) 0.14 μM; Ex. (1bc) 0.083 μM; Ex. (1bd) 0.011 μM; Ex. (1be) 0.18 μM; Ex. (1bf) 0.06 μM; Ex. (1bg) 0.17 μM; Ex. (1bh) 0.014 μM; Ex. (1bi) 0.032 μM; Ex. (1bj) 0.035 μM; Ex. (1bk) 0.039 μM; Ex. (1bl) 0.0027 μM; Ex. (1bm) 0.055 μM; Ex. (1bn) 0.04 μM; Ex. (1bo) 0.018 μM; Ex. (1bp) 0.11 μM; Ex. (1bq) 0.14 μM; Ex. (1br) 0.056 μM; Ex. (1bs) 0.039 μM; Ex. (1bt) 0.11 μM; Ex. (1bu) 0.016 μM; Ex. (1bv) 0.0051 μM; Ex. (1bw) 0.036 μM; Ex. (1bx) 0.038 μM; Ex. (1by) 0.0046 μM; Ex. (1bz) 0.018 μM; Ex. (1ca) 0.35 μM; Ex. (1cb) 0.5 μM; Ex. (1cc) 0.0064 μM; Ex. (1cd) 0.46 μM; Ex. (1ce) 0.091 μM; Ex. (1cf) 0.073 μM; Ex. (1cg) 0.00026 μM; Ex. (1ch) 0.22 μM; Ex. (1ci) 0.15 μM; Ex. (1cj) 0.091 μM; Ex. (1ck) 0.065 μM; Ex. (1cl) 0.2 μM; Ex. (1cm) 0.16 μM; Ex. (1cn) 0.31 μM; Ex. (1co) 2.5 μM; Ex. (1cp) 1 μM; Ex. (1cq) 0.25 μM; Ex. (1cr) 0.69 μM; Ex. (1cs) 7.5 μM; Ex. (1ct) 0.024 μM; Ex. (1cu) 0.042 μM; Ex. (1cv) 0.3 μM; Ex. (1cw) 0.49 μM; Ex. (1cx) 0.12 μM; Ex. (1cy) 0.72 μM; Ex. (1cz) 0.066 μM; Ex. (1da) 1.8 μM; Ex. (1db) 0.031 μM; Ex. (1dc) 0.02 μM; Ex. (1dd) 0.073 μM; Ex. (1de) 0.0049 μM; Ex. (1dg) 0.014 μM; Ex. (1dh) 0.041 μM; Ex. (1di) 0.23 μM; Ex. (1dj) 0.25 μM; Ex. (1dk) 0.02 μM; Ex. (1dl) 0.018 μM; Ex. (1dm) 0.0075 μM; Ex. (1dn) 0.0055 μM; Ex. (1do) 0.03 μM; Ex. (1dp) 0.0067 μM; Ex. (1dq) 0.037 μM; Ex. (1dt) 0.0026 μM; Ex. (1du) 0.00039 μM; Ex. (1dv) 0.72 μM; Ex. (1dw) 0.021 μM; Ex. (1dx) 0.035 μM; Ex. (1dy) 0.0035 μM; Ex. (1dz) 0.099 μM; Ex. (1ea) 0.057 μM; Ex. (1eb) 0.17 μM; Ex. (1ec) 0.013 μM; Ex. (1ed) 0.016 μM; Ex. (1ee) 0.0048 μM.

Tested in phospho-Ser473 Akt assay: Ex. (1df) 0.3813 μM; Ex. (1dr) 0.01415 μM; Ex. (1ds) 0.06066 μM.

Example 2

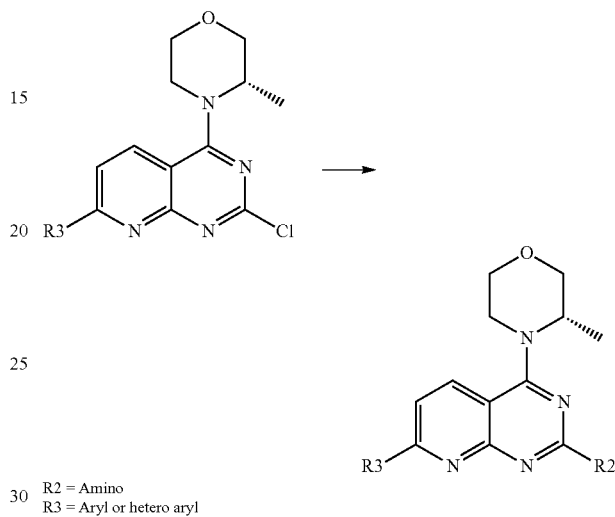

R2 = Amino
R3 = Aryl or hetero aryl

To a solution (0.2 M) of the appropriate chloro-substrate (1 equiv) in dioxane was added diisopropylethylamine (2 equiv). To this mixture was then added the appropriate amine (2 equiv). The reaction was then heated under the influence of microwave radiation (120° C., medium absorption setting) for 10 minutes. Upon completion the sample was concentrated in vacuo and the resulting residue dissolved in CH$_2$Cl$_2$ and washed with H$_2$O. The organic fraction was removed, dried (MgSO$_4$). The crude residue was purified by flash chromatography (SiO$_2$) to give the desired products.

| | Purity (%) | Retention time (min) | M/z [M+H]$^+$ | Example Structure |
|---|---|---|---|---|
| 2a | 97 | 3.28 | 448.3 | 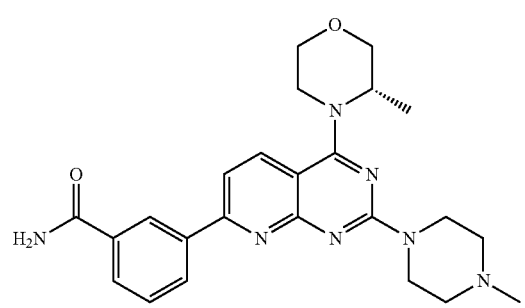 [SMILES: C[C@H]1COCCN1c1nc(N2CCN(C)CC2)nc2nc(-c3cccc(C(N)=O)c3)ccc12] |

-continued

| | Purity (%) | Retention time (min) | M/z [M+H]+ | Example Structure |
|---|---|---|---|---|
| 2b | 99 | 3.78 | 439.3 | |
| 2c | 99 | 3.31 | 462.4 | |
| 2d | 100 | 3.76 | 463.3 | |
| 2e | 99 | 3.11 | 483.3 | |

-continued

| | Purity (%) | Retention time (min) | M/z [M+H]+ | Example Structure |
|---|---|---|---|---|
| 2f | 99 | 3.82 | 463.4 | |
| 2g | 100 | 3.39 | 436.5 | |
| 2h | 100 | 3.68 | 463.4 | |
| 2i | 98 | 3.26 | 448.4 | |

-continued

| Purity (%) | Retention time (min) | M/z [M+H]+ | Example Structure |
|---|---|---|---|
| 2j | 100 | 3.38 | 450.3 |

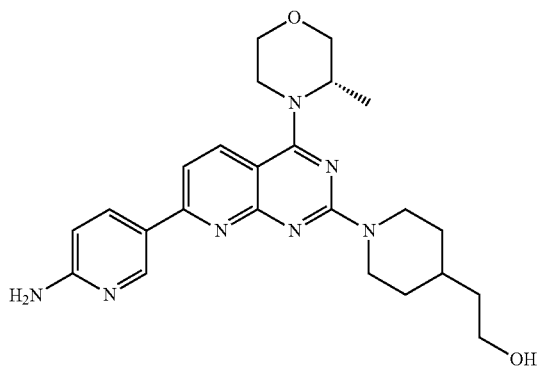 [SMILES: C[C@H]1COCCN1c1nc(N2CCC(CCO)CC2)nc2nc(-c3ccc(N)nc3)ccc12]

Tested in Alternative Enzyme Assay: Ex. (2a) 0.7 µM; Ex. (2b) 0.56 µM; Ex. (2c) 0.6 µM; Ex. (2d) 0.27 µM; Ex. (2e) 0.35 µM; Ex. (2f) 0.17 µM; Ex. (2g) 0.064 µM; Ex. (2h) 0.29 µM; Ex. (2i) 0.64 µM; Ex. (2j) 0.2 µM.

Example 3

(Compounds 3a to 3ab)
$R^4$=(S)-3-methyl-morpholine
$R^2$=(S)-3-methyl-morpholine
Ar=aryl

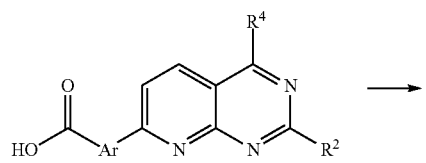 → 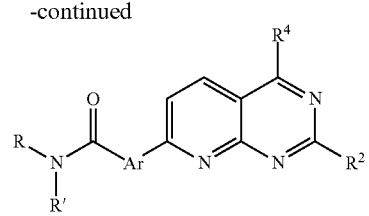

Carboxy-substrates are reported in Example 1.
Method: Amide Formation
Conditions A:

The appropriate carboxy-substrate (1 equiv) was dissolved in DMF (0.067 M). HBTU (1.2 equiv) and appropriate amines (1.05 equiv) were added along with 3 drops of triethylamine at 0° C. The reaction vessels were sealed and the mixtures were stirred between 1 and 12 hours at room temperature. Upon completion the samples were concentrated in vacuo. The crude residues were then purified by preparative HPLC to give the desired products.

TABLE 3

| Purity (%) | Retention time (min) | m/z [M+H]+ | Conditions | Example Structure |
|---|---|---|---|---|
| 3a | 98 | 7.36 | 515.3 | A |

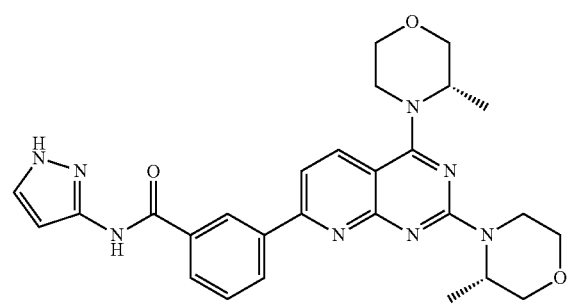 [SMILES: C[C@H]1COCCN1c1nc(N2CCOC[C@@H]2C)c2ccc(-c3cccc(C(=O)Nc4cc[nH]n4)c3)nc2n1]

TABLE 3-continued

| | Purity (%) | Retention time (min) | m/z [M+H]+ | Conditions | Example Structure |
|---|---|---|---|---|---|
| 3b | 82 | 5.31 | 518.4 | A | |
| 3c | 96 | 7.2 | 477.3 | A | |
| 3d | 96 | 6.95 | 533.4 | A | |
| 3e | 95 | 7.33 | 495.3 | A | |
| 3f | 95 | 8.34 | 531.3 | A | |

TABLE 3-continued

| | Purity (%) | Retention time (min) | m/z [M+H]+ | Conditions | Example Structure |
|---|---|---|---|---|---|
| 3g | 98 | 6.61 | 519.4 | A | |
| 3h | 98 | 6.64 | 519.4 | A | |
| 3i | 99 | 7.32 | 533.4 | A | |
| 3j | 99 | 8.19 | 505.4 | A | |
| 3k | 98 | 4.15 | 521.5 | A | |

TABLE 3-continued

| | Purity (%) | Retention time (min) | m/z [M+H]+ | Conditions | Example Structure |
|---|---|---|---|---|---|
| 3l | 99 | 4.27 | 513.4 | A | |
| 3m | 90 | 4.22 | 491.3 | A | |
| 3n | 98 | 4.35 | 505.5 | A | |
| 3o | 95 | 4.2 | 493.4 | A | |

TABLE 3-continued

| | Purity (%) | Retention time (min) | m/z [M+H]+ | Conditions | Example Structure |
|---|---|---|---|---|---|
| 3p | 98 | 4.36 | 503.4 | A | |
| 3q | 98 | 4.31 | 501.4 | A | |
| 3r | 95 | 4.62 | 519.5 | A | |
| 3s | 99 | 4.19 | 517.3 | A | |
| 3t | 99 | 3.97 | 507.4 | A | |

TABLE 3-continued

| | Purity (%) | Retention time (min) | m/z [M+H]+ | Conditions | Example Structure |
|---|---|---|---|---|---|
| 3u | 99 | 4.07 | 521.4 | A | |
| 3v | 96 | 7.38 | 495.4 | A | |
| 3w | 91 | 8.42 | 523.3 | A | |
| 3x | 97 | 8.44 | 523.4 | A | |
| 3y | 97 | 7.69 | 511.3 | A | |

TABLE 3-continued
| | Purity (%) | Retention time (min) | m/z [M+H]+ | Conditions | Example Structure |
|---|---|---|---|---|---|
| 3z | 92 | 8.33 | 521.3 | A | 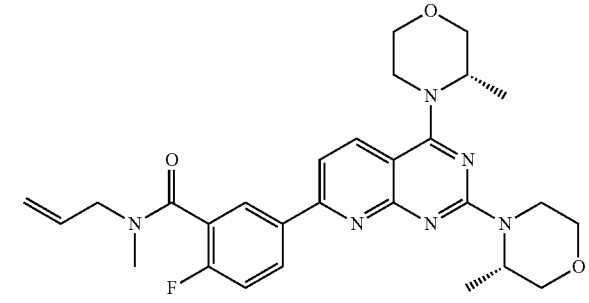 [SMILES: C=CCN(C)C(=O)c1cc(-c2ccc3c(N4CCOC[C@@H]4C)nc(N4CCOC[C@@H]4C)nc3n2)ccc1F] |
| 3aa | 86 | 4.12 | 509.3 | A | 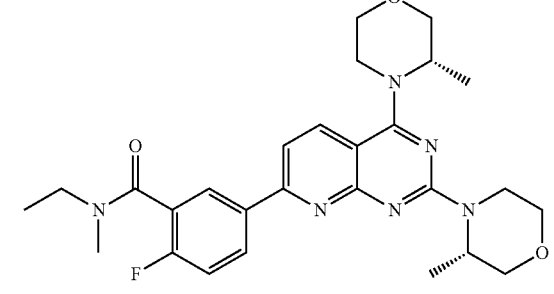 |
| 3ab | 83 | 4.19 | 519.3 | A | 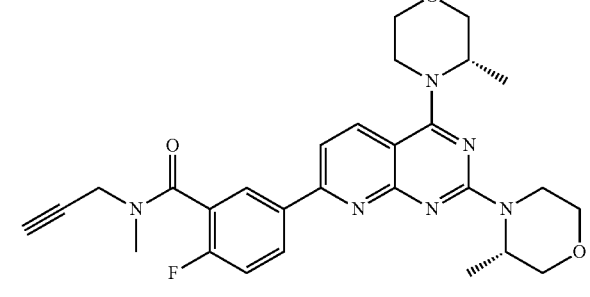 |
| 3ac | 100 | 7.13 | 477.4 | A | 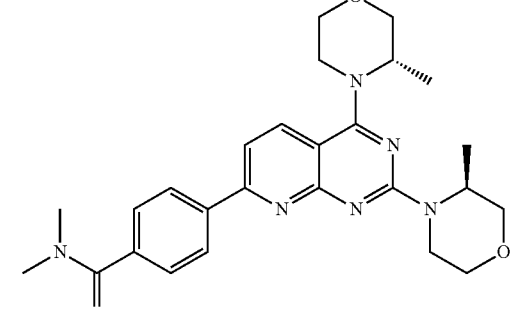 |

TABLE 3-continued

| Purity (%) | Retention time (min) | m/z [M+H]+ | Conditions | Example Structure |
|---|---|---|---|---|
| 3ad | 100 | 4.00 | 493.4 | A | 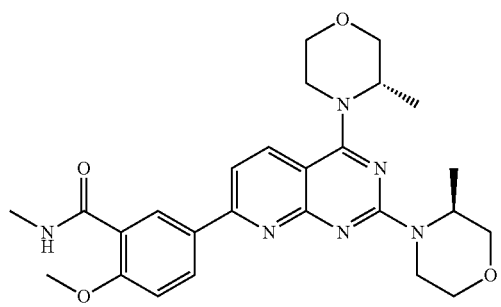 |

Tested in Alternative Enzyme Assay: Ex. (3a) 0.048 µM; Ex. (3b) 0.32 µM; Ex. (3c) 0.09 µM; Ex. (3d) 0.28 µM; Ex. (3e) 0.0047 µM; Ex. (3f) 0.28 µM; Ex. (3g) 0.0052 µM; Ex. (3h) 0.18 µM; Ex. (3i) 0.14 µM; Ex. (3j) 0.17 µM; Ex. (3k) 0.23 µM; Ex. (3l) 0.044 µM; Ex. (3m) 0.32 µM; Ex. (3n) 0.23 µM; Ex. (3O) 0.37 µM; Ex. (3p) 0.56 µM; Ex. (3q) 0.12 µM; Ex. (3r) 0.5 µM; Ex. (3s) 0.38 µM; Ex. (3t) 0.042 µM; Ex. (3u) 0.13 µM; Ex. (3v) 0.16 µM; Ex. (3w) 0.5 µM; Ex. (3x) 0.24 µM; Ex. (3y) 0.74 µM; Ex. (3z) 0.34 µM; Ex. (3aa) 0.026 µM; Ex. (3ab) 0.14 µM; Ex. (3ac) 1.6 µM; Ex. (3ad) 0.066 µM.

Example 4

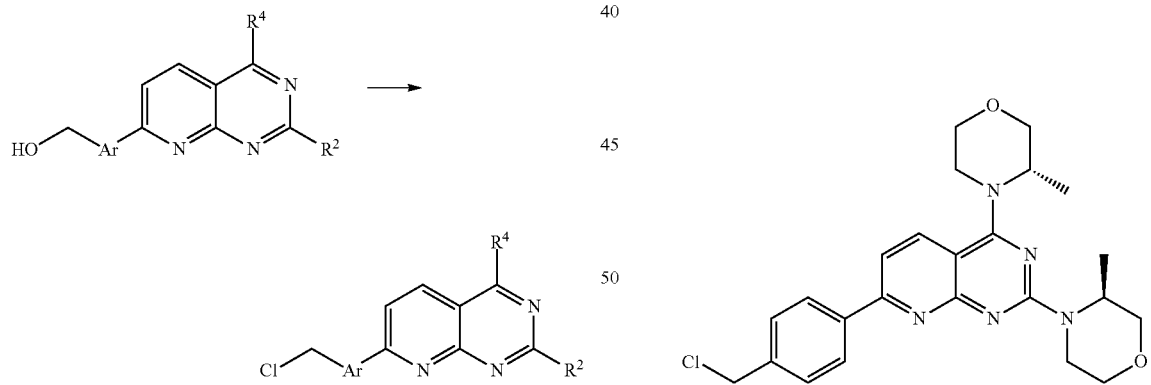

Benzyl alcohol substrates are reported in Example 1.

The appropriate benzyl alcohol (1 equiv) was dissolved in CH$_2$Cl$_2$ (0.08 M). Triethylamine (1 equiv) was added at room temperature, followed by the addition of thionyl chloride (2 equiv). The reaction mixture was stirred at 30° C. for 45 minutes. Upon completion the reaction mixture was partitioned between brine and CH$_2$Cl$_2$ and extracted with CH$_2$Cl$_2$. Combined organic phases were dried (MgSO$_4$), filtered and concentrated in vacuo. The crude residue was purified by column chromatography on silica gel eluting with 10 to 70% ethyl acetate in hexane.

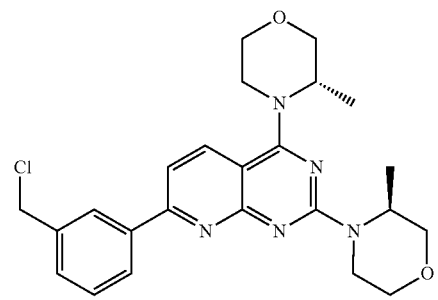 [SMILES: C[C@H]1COCCN1c1nc(N2CCOC[C@@H]2C)c2ccc(-c3cccc(CCl)c3)nc2n1]

7-(3-Chloromethyl-phenyl)-2,4-bis-((S)-3-methyl-morpholin-4-yl)-pyrido[2,3-d]pyrimidine: (72% yield, 90% purity) m/z (LC-MS, ESP): 454 [M+H]+ R/T=3.15 min The appropriate benzyl alcohol (1 equiv) was dissolved in CH$_2$Cl$_2$ (0.052 M). Thionyl chloride (3.3 equiv) was added. The reaction mixture was heated up to 55° C. and a solution of triethylamine (1.7 equiv) in CH$_2$Cl$_2$ (0.044 M) was added dropwise over 10 minutes. The reaction mixture was allowed to stir at 30° C. for 10 minutes. Upon completion the reaction mixture was partitioned between brine and CH$_2$Cl$_2$ and extracted with CH$_2$Cl$_2$. Combined organic phases were dried (MgSO$_4$), filtered and concentrated in vacuo. The crude residue was purified by column chromatography on silica gel eluting with 10 to 50% ethyl acetate in hexane.

7-(4-Chloromethyl-phenyl)-2,4-bis-((S)-3-methyl-morpholin-4-yl)-pyrido[2,3-d]pyrimidine: (65% yield, 90% purity) m/z (LC-MS, ESP): 454 [M+H]+ R/T=3.15 min

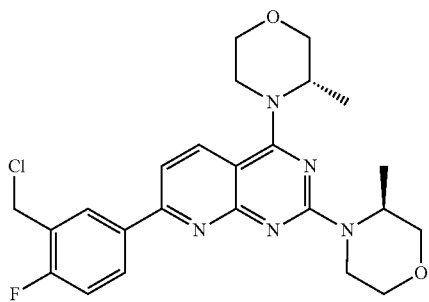 [SMILES: C[C@H]1COCCN1c1nc(N2CCOC[C@@H]2C)c2ccc(-c3ccc(F)c(CCl)c3)nc2n1]

The appropriate benzyl alcohol (1 equiv) was dissolved in CH$_2$Cl$_2$ (0.044 M). Thionyl chloride (3.3 equiv) was added. The reaction mixture was heated up to 55° C. and a solution of triethylamine (1.7 equiv) in CH$_2$Cl$_2$ (0.044 M) was added dropwise over 10 minutes. The reaction mixture was allowed to stir at 30° C. for 30 minutes. Upon completion the reaction mixture was partitioned between brine and CH$_2$Cl$_2$ and extracted with CH$_2$Cl$_2$. Combined organic phases were dried (MgSO$_4$), filtered and concentrated in vacuo. The crude residue was used without further purification.

7-(3-Chloromethyl-4-fluoro-phenyl)-2,4-bis-((S)-3-methyl-morpholin-4-yl)-pyrido[2,3-d]pyrimidine: (96% yield, 90% purity) m/z (LC-MS, ESP): 472 [M+H]+ R/T=3.96 min

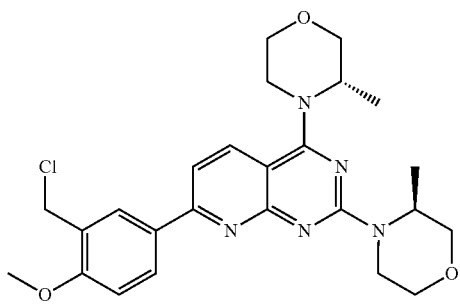 [SMILES: COc1ccc(-c2ccc3c(N4CCOC[C@@H]4C)nc(N4CCOC[C@@H]4C)nc3n2)cc1CCl]

The appropriate benzyl alcohol (1 equiv) was dissolved in CH$_2$Cl$_2$ (0.086 M). Triethylamine (2.5 equiv) and thionyl chloride (2.5 equiv) were added. The reaction mixture was heated up to 45° C. a for 3 hours. Upon completion the reaction mixture was partitioned between water and CH$_2$Cl$_2$ and extracted with CH$_2$Cl$_2$. Combined organic phases were dried (MgSO$_4$), filtered and concentrated in vacuo. The crude residue was purified by column chromatography on silica gel eluting with 10 to 50% ethyl acetate in hexane.

7-(3-Chloromethyl-4-methoxy-phenyl)-2,4-bis-((S)-3-methyl-morpholin-4-yl)-pyrido[2,3-d]pyrimidine: (37% yield, 90% purity) m/z (LC-MS, ESP): 484 [M+H]+ R/T=3.21 min (Compounds 4a to 4ak)
R$^4$=(S)-3-methyl-morpholine
R$^2$=(S)-3-methyl-morpholine
Ar=aryl

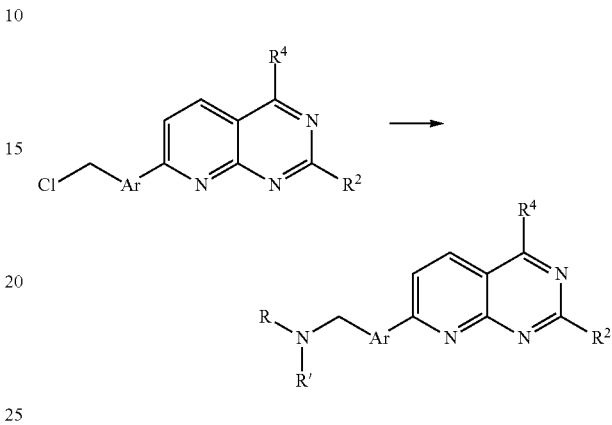

Method: Benzylamines, Benzylethers and Benzylsulfones Formation

Conditions A:

The appropriate chlorobenzyl-substrate (1 equiv) was dissolved in THF (0.067 M). The appropriate amine (80 equiv) as well as triethylamine (1 equiv) was added. The reaction vessels were sealed and the mixtures were stirred for 3 to 5 hours at 95° C. Upon completion the samples were concentrated in vacuo. The crude residues were then purified by preparative HPLC to give the desired products.

Conditions B:

The appropriate chlorobenzyl-substrate (1 equiv) was dissolved in an aqueous ammonia/n-butanol (1.5:1) solution (0.011 M). The reaction vessel was sealed and the mixture was stirred for 10 minutes at 140° C. Upon completion the sample was concentrated in vacuo. The crude residue was then purified by preparative HPLC to give the desired products.

Conditions C:

The appropriate chlorobenzyl-substrate (1 equiv) and sodium hydroxide (1 equiv) were dissolved in ethanol (0.011 M). The reaction vessel was sealed and the mixture was stirred for 3 hours at 50° C. Upon completion the sample was concentrated in vacuo. The crude residue was then purified by preparative HPLC to give the desired products.

Conditions D:

The appropriate chlorobenzyl-substrate (1 equiv) was dissolved in DMF (0.022 M). Imidazole (3 equiv) and potassium tert-butoxide (3 equiv) were added. The reaction vessel was sealed and the mixture was stirred for 2 hours at room temperature. Upon completion the sample was concentrated in vacuo. The crude residue was then purified by preparative HPLC to give the desired product.

Conditions E:

The appropriate chlorobenzyl-substrate (1 equiv) was dissolved in DMF (0.066 M). Sodium sulfinate (1.3 equiv) was added. The mixture was stirred for 2 hours at 125° C. Upon completion the sample was concentrated in vacuo. The crude residue was then purified by preparative HPLC to give the desired product.

Conditions F:

The appropriate chlorobenzyl-substrate (1 equiv), potassium carbonate (2.6 equiv) triethylamine (1 equiv) and the appropriate amine (1.1 equiv) were suspended in DMF (0.028 M). The reaction vessel was sealed and the mixture was stirred for 16 hours at 40° C. Upon completion the sample was filtered through a silica cartridge, washed with $CH_2Cl_2$ and then concentrated in vacuo. The crude residue was then purified by preparative HPLC to give the desired products.

TABLE 4

| | Purity (%) | Retention time (min) | m/z [M+H]⁺ | Conditions | Example Structure |
|---|---|---|---|---|---|
| 4a | 87 | 3.61 | 449.3 | A | |
| 4b | 95 | 3.41 | 435.2 | B | |
| 4c | 99 | 3.4 | 505.5 | A | |
| 4d | 100 | 3.42 | 505.5 | A | |

TABLE 4-continued

| | Purity (%) | Retention time (min) | m/z [M+H]+ | Conditions | Example Structure |
|---|---|---|---|---|---|
| 4e | 100 | 3.44 | 519.5 | A | |
| 4f | 100 | 3.39 | 479.4 | A | |
| 4g | 95 | 4.36 | 464.4 | C | |
| 4h | 96 | 3.4 | 479.4 | A | |
| 4i | 95 | 3.4 | 435.4 | B | |

TABLE 4-continued

| | Purity (%) | Retention time (min) | m/z [M+H]+ | Conditions | Example Structure |
|---|---|---|---|---|---|
| 4j | 92 | 5.6 | 475.4 | A | |
| 4k | 94 | 5.65 | 477.4 | A | |
| 4l | 97 | 5.39 | 449.4 | A | |
| 4m | 90 | 5.6 | 519.5 | A | |
| 4n | 96 | 5.83 | 489.5 | A | |

TABLE 4-continued

| | Purity (%) | Retention time (min) | m/z [M+H]+ | Conditions | Example Structure |
|---|---|---|---|---|---|
| 4o | 95 | 5.56 | 493.4 | A | |
| 4p | 26, 69 | 6.63, 6.78 | 501.4 | A | |
| 4q | 99 | 3.43 | 486.4 | D | |
| 4r | 94 | 3.44 | 505.5 | A | |
| 4s | 97 | 3.44 | 505.3 | A | |

TABLE 4-continued

| | Purity (%) | Retention time (min) | m/z [M+H]+ | Conditions | Example Structure |
|---|---|---|---|---|---|
| 4t | 94 | 6.06 | 498.7 | E | |
| 4u | 98 | 3.42 | 453.4 | B | |
| 4v | 99 | 3.63 | 493.4 | A | |
| 4w | 99 | 3.62 | 495.4 | A | |
| 4x | 96 | 3.55 | 467.4 | A | |

TABLE 4-continued
| | Purity (%) | Retention time (min) | m/z [M+H]+ | Conditions | Example Structure |
|---|---|---|---|---|---|
| 4y | 99 | 3.6 | 537.4 | A | 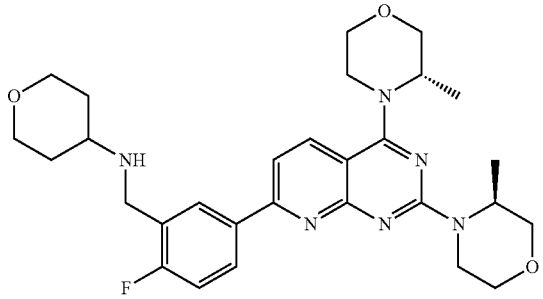 [SMILES: C[C@H]1COCCN1c1nc(N2CCOC[C@@H]2C)c2ccc(-c3ccc(F)c(CNC4CCOCC4)c3)nc2n1] |
| 4z | 99 | 3.67 | 507.4 | A | 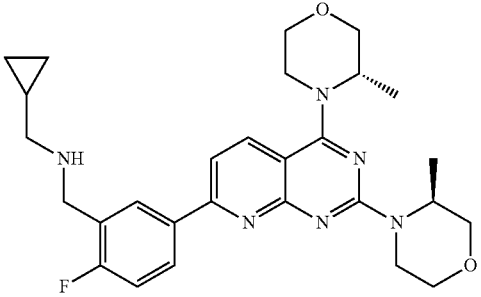 [SMILES: C[C@H]1COCCN1c1nc(N2CCOC[C@@H]2C)c2ccc(-c3ccc(F)c(CNCC4CC4)c3)nc2n1] |
| 4aa | 97 | 3.59 | 511.4 | A | 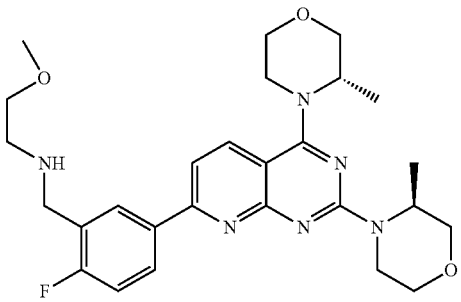 [SMILES: C[C@H]1COCCN1c1nc(N2CCOC[C@@H]2C)c2ccc(-c3ccc(F)c(CNCCO)c3)nc2n1] |
| 4ab | 91 | 3.58 | 499.4 | A | 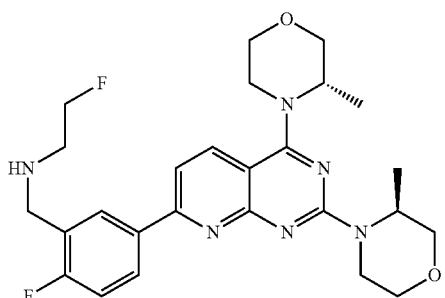 |
| 4ac | 99 | 3.55 | 497.4 | A | 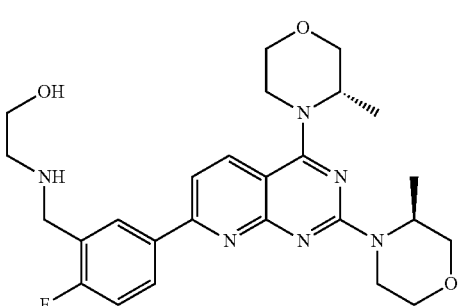 |

TABLE 4-continued

| | Purity (%) | Retention time (min) | m/z [M+H]+ | Conditions | Example Structure |
|---|---|---|---|---|---|
| 4ad | 99 | 3.4 | 523.4 | A | |
| 4ae | 99 | 3.47 | 522.4 | A | |
| 4af | 99 | 3.42 | 481.4 | A | |
| 4ag | 99 | 3.49 | 536.4 | A | |
| 4ah | 98 | 3.43 | 537.5 | A | |

TABLE 4-continued

| | Purity (%) | Retention time (min) | m/z [M+H]+ | Conditions | Example Structure |
|---|---|---|---|---|---|
| 4ai | 99 | 3.48 | 509.4 | A | |
| 4aj | 99 | 3.46 | 525.5 | A | |
| 4ak | 99 | 3.42 | 523.5 | A | |
| 4al | 99 | 3.55 | 505.4 | F | |

TABLE 4-continued
| | Purity (%) | Retention time (min) | m/z [M+H]+ | Conditions | Example Structure |
|---|---|---|---|---|---|
| 4am | 99 | 3.60 | 507.4 | F | 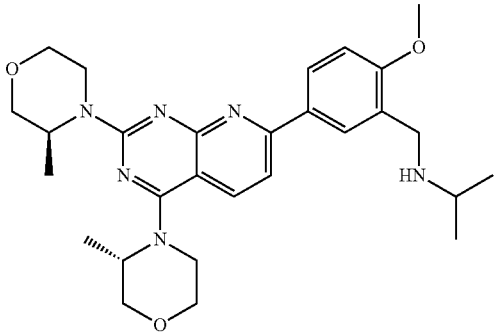 [SMILES: COc1ccc(-c2ccc3c(N4CCOC[C@@H]4C)nc(N4CCOC[C@@H]4C)nc3n2)cc1CNC(C)C] |
| 4an | 99 | 3.66 | 533.4 | F | 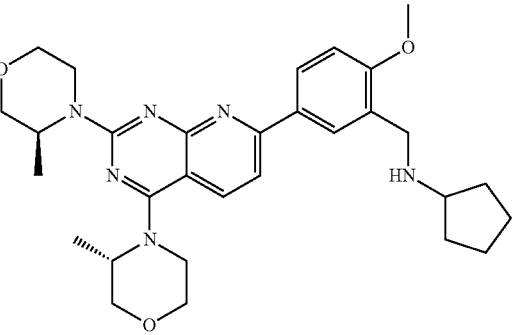 |
| 4ao | 99 | 3.77 | 547.5 | F | 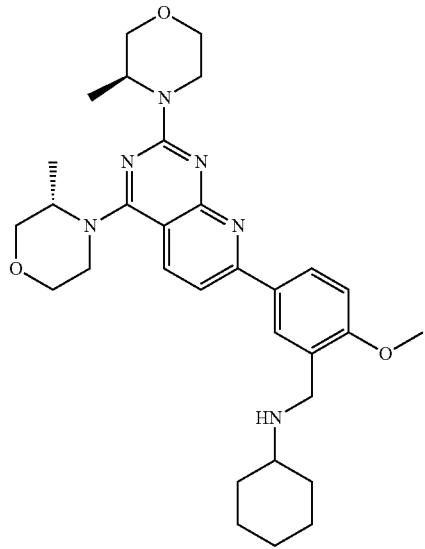 [SMILES: COc1ccc(-c2ccc3c(N4CCOC[C@@H]4C)nc(N4CCOC[C@@H]4C)nc3n2)cc1CNC1CCCCC1] |
| 4ap | 99 | 3.70 | 561.4 | F | 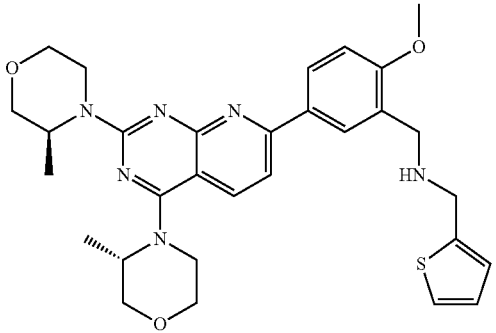 [SMILES: COc1ccc(-c2ccc3c(N4CCOC[C@@H]4C)nc(N4CCOC[C@@H]4C)nc3n2)cc1CNCc1cccs1] |

TABLE 4-continued
| | Purity (%) | Retention time (min) | m/z [M+H]+ | Conditions | Example Structure |
|---|---|---|---|---|---|
| 4aq | 99 | 3.52 | 549.5 | F | 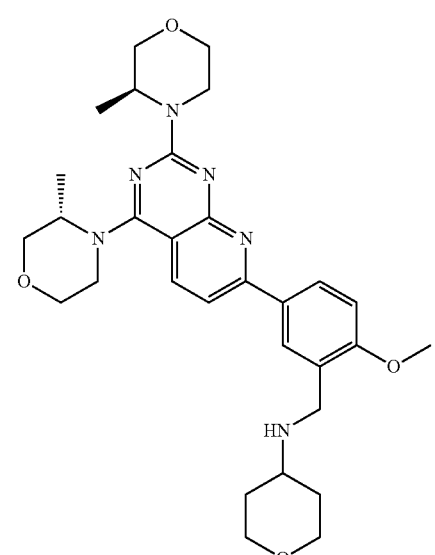 |
| 4ar | 99 | 3.85 | 571.5 | F | 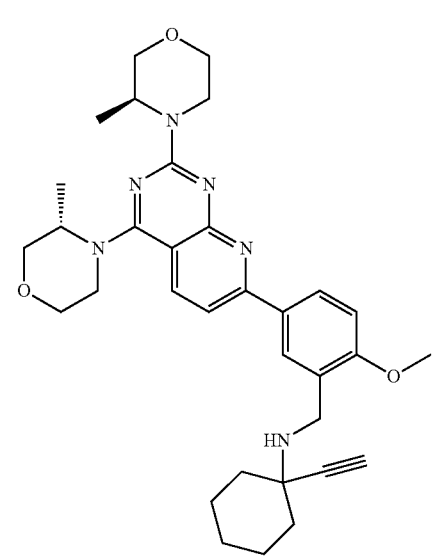 [SMILES: C#CC1(NCc2cc(-c3ccc4c(N5CCOC[C@@H]5C)nc(N5CCOC[C@@H]5C)nc4n3)ccc2OC)CCCCC1] |
| 4as | 99 | 3.85 | 549.5 | F | 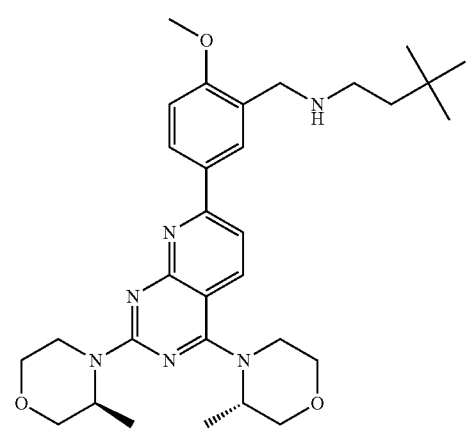 [SMILES: COc1ccc(-c2ccc3c(N4CCOC[C@@H]4C)nc(N4CCOC[C@@H]4C)nc3n2)cc1CNCCC(C)(C)C] |

TABLE 4-continued

| | Purity (%) | Retention time (min) | m/z [M+H]⁺ | Conditions | Example Structure |
|---|---|---|---|---|---|
| 4at | 99 | 3.76 | 535.5 | F | |
| 4au | 99 | 3.83 | 549.5 | F | |
| 4av | 96 | 3.32 | 578.5 | F | |

TABLE 4-continued
| | Purity (%) | Retention time (min) | m/z [M+H]+ | Conditions | Example Structure |
|---|---|---|---|---|---|
| 4aw | 99 | 3.82 | 561.5 | F | 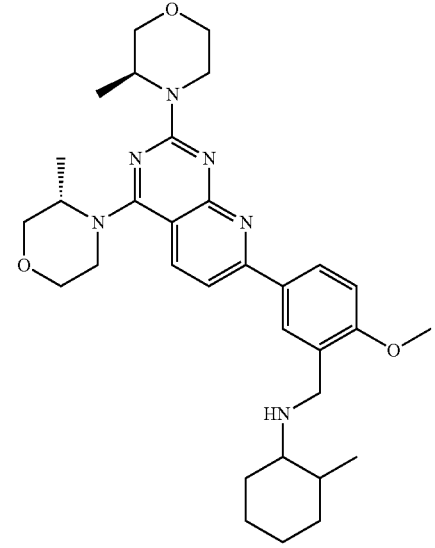 [SMILES: COc1ccc(-c2ccc3c(N4CCOC[C@@H]4C)nc(N4CCOC[C@@H]4C)nc3n2)cc1CNC1CCCCC1C] |
| 4ax | 99 | 3.59 | 519.4 | F | 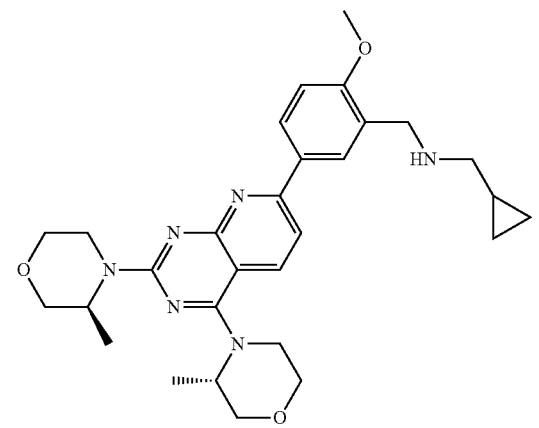 [SMILES: COc1ccc(-c2ccc3c(N4CCOC[C@@H]4C)nc(N4CCOC[C@@H]4C)nc3n2)cc1CNCC1CC1] |
| 4ay | 99 | 3.66 | 521.4 | F | 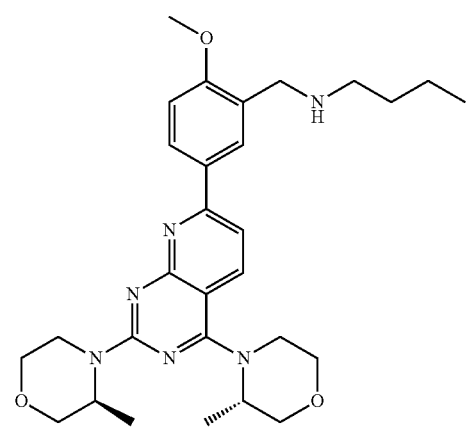 [SMILES: CCCCNCc1cc(-c2ccc3c(N4CCOC[C@@H]4C)nc(N4CCOC[C@@H]4C)nc3n2)ccc1OC] |

TABLE 4-continued

| | Purity (%) | Retention time (min) | m/z [M+H]+ | Conditions | Example Structure |
|---|---|---|---|---|---|
| 4az | 99 | 3.65 | 521.4 | F | |
| 4ba | 99 | 3.46 | 509.4 | F | |
| 4bb | 99 | 3.52 | 523.4 | F | |

TABLE 4-continued
| | Purity (%) | Retention time (min) | m/z [M+H]+ | Conditions | Example Structure |
|---|---|---|---|---|---|
| 4bc | 99 | 3.84 | 561.5 | F | 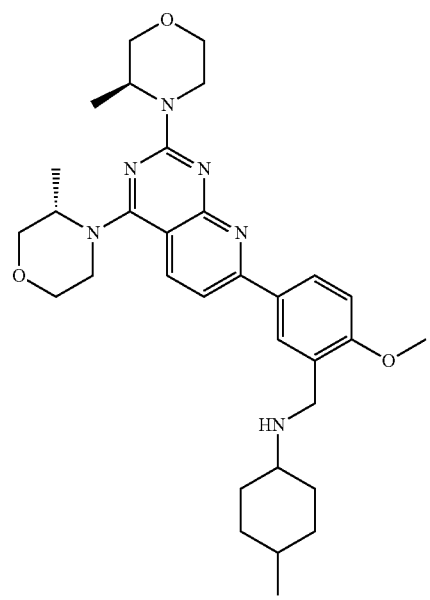 [SMILES: COc1ccc(-c2ccc3c(N4CCOC[C@@H]4C)nc(N4CCOC[C@@H]4C)nc3n2)cc1CNC1CCC(C)CC1] |
| 4bd | 99 | 3.81 | 599.5 | F | 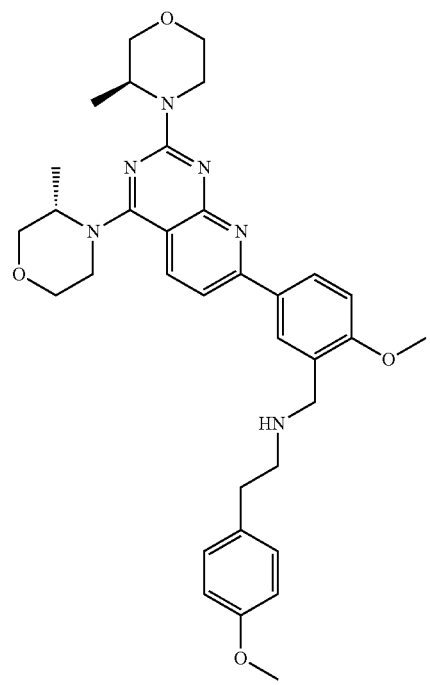 [SMILES: COc1ccc(CCNCc2cc(-c3ccc4c(N5CCOC[C@@H]5C)nc(N5CCOC[C@@H]5C)nc4n3)ccc2OC)cc1] |

TABLE 4-continued

| | Purity (%) | Retention time (min) | m/z [M+H]+ | Conditions | Example Structure |
|---|---|---|---|---|---|
| 4be | 93 | 3.29 | 559.4 | F | 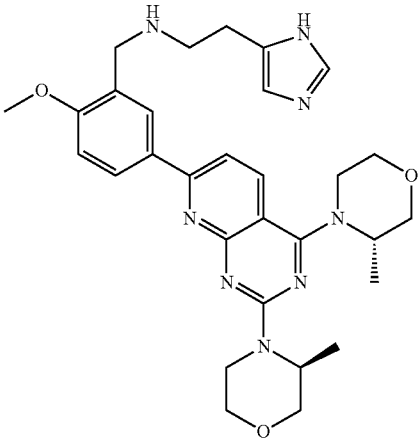 [SMILES: COc1ccc(-c2ccc3c(N4CCOC[C@@H]4C)nc(N4CCOC[C@@H]4C)nc3n2)cc1CNCCc1cnc[nH]1] |
| 4bf | 99 | 3.91 | 575.5 | F | 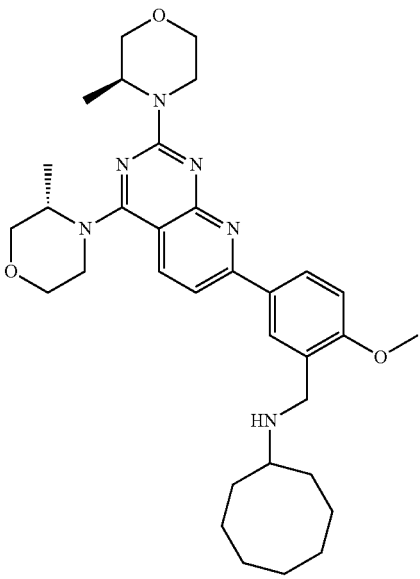 [SMILES: COc1ccc(-c2ccc3c(N4CCOC[C@@H]4C)nc(N4CCOC[C@@H]4C)nc3n2)cc1CNC1CCCCCCC1] |

NMR Data for Example 4h $^1$H NMR (300 MHz, DMSO) δ ppm 8.21 (ArH, d, J=8.39 Hz, 2H), 8.08-8.01 (ArH, m, 1H), 7.65 (ArH, d, J=8.49 Hz, 1H), 7.49 (ArH, d, J=4.85 Hz, 2H), 4.82-4.72 (CH$_2$, m, 1H), 4.45 (CH$_2$, +NH m, 3H), 3.99-3.82 (CH$_2$, m, 7H), 3.69 (CH$_2$, ddd, J=19.97, 8.86, 5.32 Hz, 8H), 3.53 (CH$_2$, t, J=5.65, 5.65 Hz, 2H), 3.29-3.15 (CH$_2$, m, 2H), 1.38 (CH$_3$, d, J=6.75 Hz, 3H), 1.25 (CH$_3$, d, J=6.75 Hz, 3H)

NMR Data for Example 4r $^1$H NMR (300 MHz, CDCl$_3$ δ ppm 8.19 (ArH, s, 1H), 8.03 (ArH, ddd, J=8.43, 5.31, 3.28 Hz, 2H), 7.54-7.37 (ArH, m, 3H), 5.00-4.85 (CH, m, 1H), 4.68-4.56 (CH$_2$, m, 1H), 4.36 (CH$_2$, ddd, J=6.83, 4.79, 2.16 Hz, 2H), 4.07-3.92 (CH$_2$, m, 2H), 3.91-3.66 (CH$_2$, m, 11H), 3.63-3.49 (CH$_2$, m, 1H), 3.39 (CH$_2$, dd, J=13.37, 3.58 Hz, 1H), 3.04-2.92 (CH$_2$, m, 1H), 2.80 (CH$_2$, d, J=10.30 Hz, 1H), 2.65 (CH$_2$, dd, J=10.23, 4.92 Hz, 1H), 2.52-2.39 (CH$_2$, m, 1H), 2.21 (CH$_2$, d, J=7.02 Hz, 1H), 1.89-1.73 (CH$_2$, m, 1H), 1.46 (CH$_3$, d, J=6.77 Hz, 3H), 1.35 (CH$_3$, d, J=6.81 Hz, 3H)

$^{13}$C NMR (75 MHz, CDCl$_3$) δ ppm 165.57, 163.03, 162.50, 160.11, 139.06, 134.83, 130.62, 128.81, 127.10, 113.70, 105.06, 71.44, 71.06, 67.41, 67.25, 67.07, 62.87, 60.08, 52.98, 52.49, 47.07, 44.58, 39.47, 35.02, 14.86 and 14.90.

NMR Data for Example 4s $^1$H NMR (300 MHz, CDCl$_3$) δ ppm 8.22 (ArH, s, 1H), 8.11-7.96 (ArH, m, 2H), 7.48 (ArH, dd, J=10.85, 7.98 Hz, 3H), 4.99-4.86 (CH, m, 1H), 4.68-4.55 (CH, m, 1H), 4.44-4.30 (CH$_2$, m, 2H), 4.06-3.92 (CH$_2$, m, 2H), 3.93-3.65 (CH$_2$, m, 10H), 3.62-3.50 (CH$_2$, m, 1H), 3.39 (CH$_2$, dd, J=13.39, 3.57 Hz, 1H), 3.14-3.01 (CH$_2$, m, 1H), 2.88 (CH$_2$, d, J=10.59 Hz, 1H), 2.77-2.67 (CH$_2$, m, 1H), 2.63-2.43 (CH$_2$, m, 1H), 2.31-2.14 (CH$_2$, m, 1H), 1.92-1.79 (CH$_2$, m, 1H), 1.47 (CH$_3$, d, J=6.77 Hz, 3H), 1.35 (CH$_3$, d, J=6.81 Hz, 3H)

$^{13}$C NMR (75 MHz, CDCl$_3$)) δ ppm 165.56, 163.03, 162.34, 160.12, 139.16, 134.89, 130.80, 128.94, 128.91, 127.39, 113.69, 105.11, 71.44, 71.21, 71.06, 67.40, 67.06, 62.61, 59.93, 52.98, 52.42, 47.08, 44.58, 39.47, 34.88, 31.73, 22.80, 14.86 and 14.91.

Tested in the Biological Assay: Ex. (4f) 0.001967 µM.

Tested in Alternative Enzyme Assay: Ex. (4a) 0.0016 µM; Ex. (4b) 0.025 µM; Ex. (4c) 0.093 µM; Ex. (4d) 0.013 µM;

Ex. (4e) 0.0019 μM; Ex. (4f)<0.0027 μM; Ex. (4g) 0.13 μM; Ex. (4h) 0.031 μM; Ex. (4i) 0.027 μM; Ex. (4j) 0.054 μM; Ex. (4k) 0.016 μM; Ex. (4l) 0.0091 μM; Ex. (4m) 0.015 μM; Ex. (4n) 0.0071 μM; Ex. (4O) 0.021 μM; Ex. (4p) 0.17 μM; Ex. (4q) 0.13 μM; Ex. (4r) 0.04 μM; Ex. (4s) 0.029 μM; Ex. (4t) 0.09 μM; Ex. (4u) 0.027 μM; Ex. (4v) 0.14 μM; Ex. (4w) 0.028 μM; Ex. (4x) 0.12 μM; Ex. (4y) 0.13 μM; Ex. (4z) 0.13 μM; Ex. (4aa) 0.21 μM; Ex. (4ab) 1.1 μM; Ex. (4ac) 0.087 μM; Ex. (4ad) 0.081 μM; Ex. (4ae) 0.16 μM; Ex. (4af) 0.58 μM; Ex. (4ag) 0.54 μM; Ex. (4ah) 0.2 μM; Ex. (4ai) 0.22 μM; Ex. (4aj) 0.46 μM; Ex. (4ak) 0.015 μM; Ex. (4al) 0.064 μM; Ex. (4am) 0.024 μM; Ex. (4an) 0.095 μM; Ex. (4ao) 0.064 μM; Ex. (4ap) 0.11 μM; Ex. (4aq) 0.012 μM; Ex. (4ar) 0.06 μM; Ex. (4as) 0.091 μM; Ex. (4at) 0.12 μM; Ex. (4au) 0.096 μM; Ex. (4av) 0.0038 μM; Ex. (4aw) 0.11 μM; Ex. (4ax) 0.1 μM; Ex. (4ay) 0.14 μM; Ex. (4az) 0.038 μM; Ex. (4ba) 0.013 μM; Ex. (4bb) 0.032 μM; Ex. (4bc) 0.076 μM; Ex. (4bd) 0.12 μM; Ex. (4be) 0.049 μM; Ex. (4bf) 0.059 μM.

Example 5

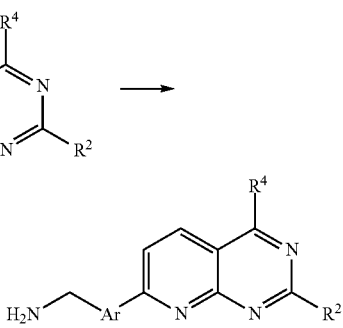

Benzyl chloride substrates are reported in Example 4.

The appropriate benzyl chloride (1 equiv) was dissolved in an ammonium hydroxide and n-butanol (1.5:1) solution (0.01 M). The reaction vessel was sealed and the mixture exposed to microwave radiation (140° C., medium absorption setting) for 10 minutes. Upon completion the reaction mixture was partitioned between brine and ethyl acetate and extracted with ethyl acetate. Combined organic phases were dried (MgSO$_4$), filtered and concentrated in vacuo. The crude residue was purified by column chromatography on silica gel eluting with 0 to 5% methanol in CH$_2$Cl$_2$.

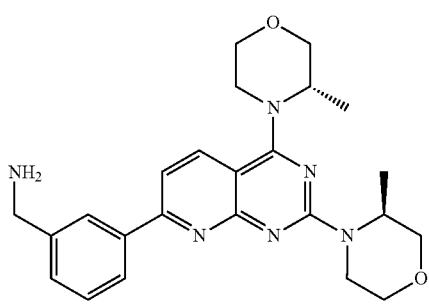 [SMILES: C[C@H]1COCCN1c1nc(N2CCOC[C@@H]2C)c2ccc(-c3cccc(CN)c3)nc2n1]

3-[2,4-Bis-((S)-3-methyl-morpholin-4-yl)-pyrido[2,3-d]pyrimidin-7-yl]-benzylamine: (81% yield, 100% purity) m/z (LC-MS, ESP): 435 [M+H]$^+$ R/T=2.44 min

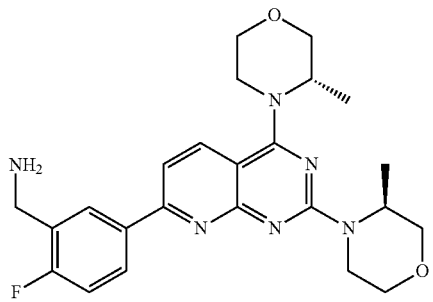 [SMILES: C[C@H]1COCCN1c1nc(N2CCOC[C@@H]2C)c2ccc(-c3ccc(F)c(CN)c3)nc2n1]

5-[2,4-Bis-((S)-3-methyl-morpholin-4-yl)-pyrido[2,3-d]pyrimidin-7-yl]-2-fluoro-benzylamine: (85% yield, 98% purity) m/z (LC-MS, ESP): 453 [M+H]R/T=3.21 min

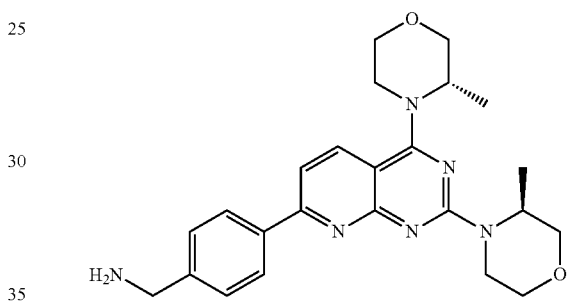

4-[2,4-Bis-(3-methyl-morpholin-4-yl)-pyrido[2,3-d]pyrimidin-7-yl]-benzylamine: (95% yield, 97% purity) m/z (LC-MS, ESP): 435 [M+H]$^+$ R/T=2.36 min

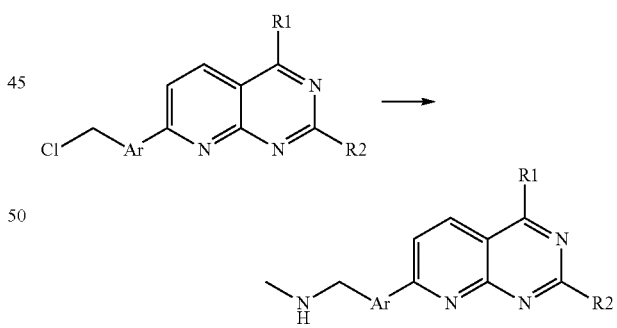

The appropriate benzyl chloride (1 equiv) was dissolved in a 2 M solution of methylamine in THF (80 equiv). Triethylamine (1 equiv) was added. The reaction mixture was stirred at 95° C. for 2.5 hours. Upon completion the reaction mixture was concentrated in vacuo and the residue was diluted with ethyl acetate and n-butanol and the organic phase was washed with brine, dried (MgSO$_4$), filtered and concentrated in vacuo. The crude residue was purified by column chromatography on silica gel eluting with 0 to 7% methanol in CH$_2$Cl$_2$.

243

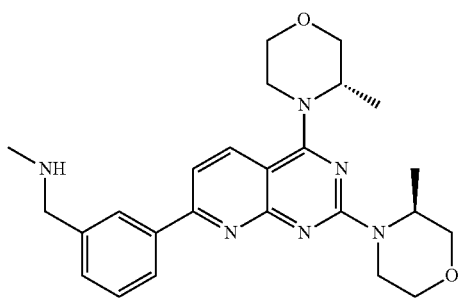 [SMILES: CNCc1cccc(-c2ccc3c(N4CCOC[C@@H]4C)nc(N4CCOC[C@@H]4C)nc3n2)c1]

{3-[2,4-Bis-((S)-3-methyl-morpholin-4-yl)-pyrido[2,3-d]pyrimidin-7-yl]-benzyl}-methyl-amine: (77% yield, 94% purity) m/z (LC-MS, ESP): 449 [M+H]+ R/T=2.44 min

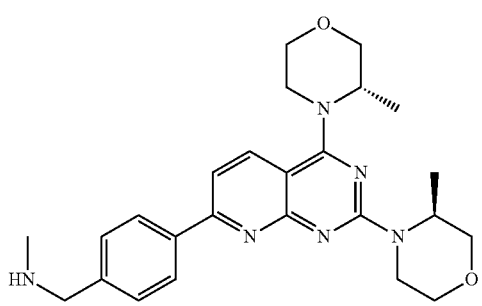

244

{4-[2,4-Bis-(3-methyl-morpholin-4-yl)-pyrido[2,3-d]pyrimidin-7-yl]-benzyl}-methyl-amine: (93% yield, 87% purity) m/z (LC-MS, ESP): 449 [M+H]+ R/T=2.40 min Procedures for the Synthesis of Examples 5a to 5z
R⁴=(S)-3-methyl-morpholine
R²=(S)-3-methyl-morpholine

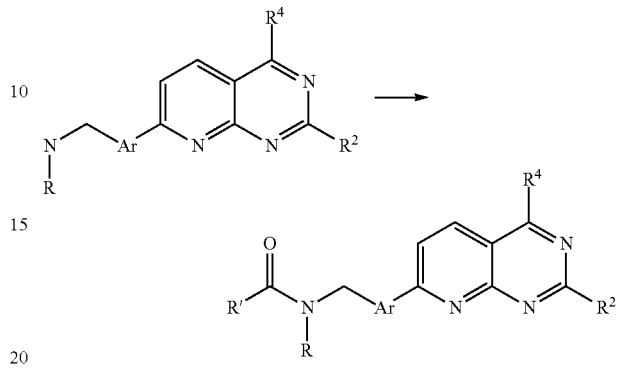

Conditions A:
The appropriate aminobenzyl-substrate (1 equiv) was dissolved in CH₂Cl₂ (0.035 M). The appropriate acyl chloride or acid anhydride (2 equiv) as well as triethylamine (1 equiv) was then added. The mixtures were stirred for 2 hours at room temperature. Upon completion the samples were concentrated in vacuo. The crude residues were then purified by preparative HPLC to give the desired products.

Conditions B:
The appropriate methylaminobenzyl-substrate (1 equiv) was dissolved in CH₂Cl₂ (0.035 M). The appropriate acyl chloride or acid anhydride (2 equiv) as well as triethylamine (1 equiv) were added. The mixtures were stirred for 12 hours at 95° C. Upon completion the samples were concentrated in vacuo. The crude residues were then purified by preparative HPLC to give the desired products.

TABLE 5

|  | Purity (%) | Retention time (min) | m/z [M+H]+ | Conditions | Example Structure |
|---|---|---|---|---|---|
| 5a | 98 | 4.02 | 477.4 | A | |
| 5b | 99 | 4.12 | 507.4 | A | |

TABLE 5-continued

| | Purity (%) | Retention time (min) | m/z [M+H]+ | Conditions | Example Structure |
|---|---|---|---|---|---|
| 5c | 99 | 4.22 | 503.4 | A | |
| 5d | 99 | 4.27 | 505.4 | A | |
| 5e | 99 | 4.34 | 517.4 | A | |
| 5f | 99 | 4.41 | 519.4 | A | |
| 5g | 99 | 4.51 | 531.3 | A | |

TABLE 5-continued

| | Purity (%) | Retention time (min) | m/z [M+H]+ | Conditions | Example Structure |
|---|---|---|---|---|---|
| 5h | 98 | 4.17 | 491.4 | B | |
| 5i | 99 | 4.17 | 521.5 | B | |
| 5j | 98 | 4.39 | 517.4 | B | |
| 5k | 98 | 4.48 | 519.5 | B | |
| 5l | 99 | 4.58 | 531.5 | B | |

TABLE 5-continued

| | Purity (%) | Retention time (min) | m/z [M+H]+ | Conditions | Example Structure |
|---|---|---|---|---|---|
| 5m | 99 | 4.64 | 533.5 | B | |
| 5n | 98 | 4.73 | 545.4 | B | |
| 5o | 100 | 4.38 | 527.4 | C | |
| 5p | 99 | 4.51 | 541.4 | C | |
| 5q | 99 | 3.8 | 477.4 | A | |

TABLE 5-continued

| | Purity (%) | Retention time (min) | m/z [M+H]+ | Conditions | Example Structure |
|---|---|---|---|---|---|
| 5r | 98 | 3.93 | 491.4 | B | |
| 5s | 99 | 3.93 | 521.4 | B | |
| 5t | 100 | 3.94 | 495.4 | A | |
| 5u | 100 | 4.02 | 525.4 | A | |

TABLE 5-continued
| | Purity (%) | Retention time (min) | m/z [M+H]+ | Conditions | Example Structure |
|---|---|---|---|---|---|
| 5v | 100 | 4.16 | 521.4 | A | 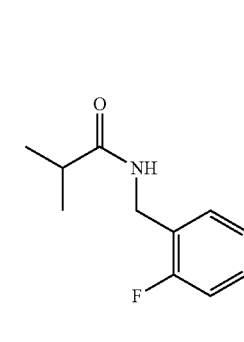 |
| 5w | 100 | 4.19 | 523.4 | A | 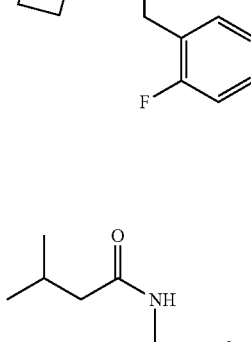 |
| 5x | 100 | 4.27 | 535.4 | A | 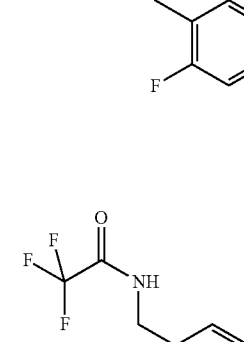 |
| 5y | 100 | 4.32 | 537.5 | A | 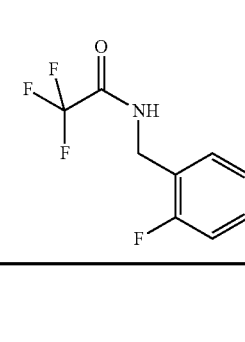 |
| 5z | 98 | 4.38 | 549.5 | A | 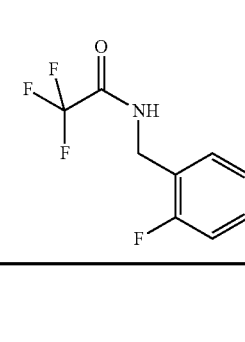 |

Tested in Alternative Enzyme Assay: Ex. (5a) 0.023 µM; Ex. (5b) 0.054 µM; Ex. (5c) 0.12 µM; Ex. (5d) 0.12 µM; Ex. (5e) 0.12 µM; Ex. (5f) 0.37 µM; Ex. (5g) 0.12 µM; Ex. (5h) 0.19 µM; Ex. (5i) 0.2 µM; Ex. (5j) 0.31 µM; Ex. (5k) 0.89 µM; Ex. (5l) 0.049 µM; Ex. (5m) 1.4 µM; Ex. (5n) 0.64 µM; Ex. (5o) 0.12 µM; Ex. (5p) 0.5 µM; Ex. (5q) 0.091 µM; Ex. (5r) 0.56 µM; Ex. (5s) 0.67 µM; Ex. (5t) 0.057 µM; Ex. (5u) 0.16 µM; Ex. (5v) 0.14 µM; Ex. (5w) 0.16 µM; Ex. (5x) 0.29 µM; Ex. (5y) 0.44 µM; Ex. (5z) 1.4 µM.

Example 6

3-[2,4-Bis-((S)-3-methyl-morpholin-4-yl)-pyrido[2,3-d]pyrimidin-7-yl]-furan-2-carbaldehyde: (26% yield, 90% purity) m/z (LC-MS, ESP): 424 [M+H]+ R/T=2.81 min (Compound 6a)

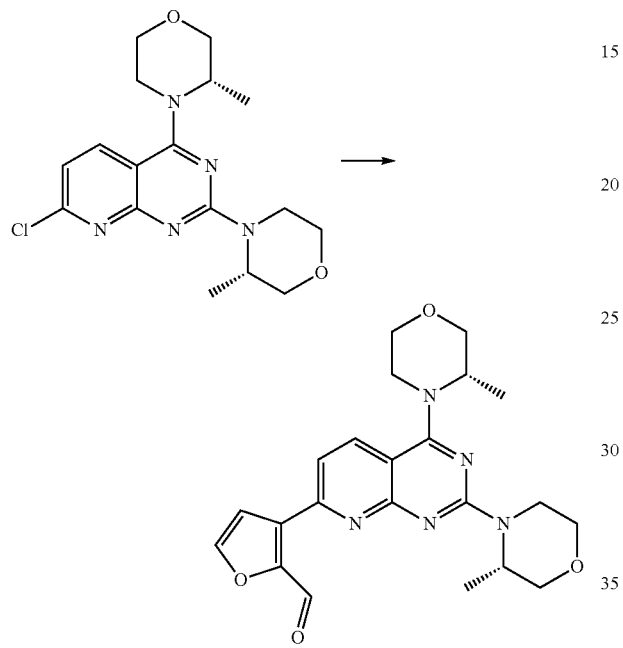
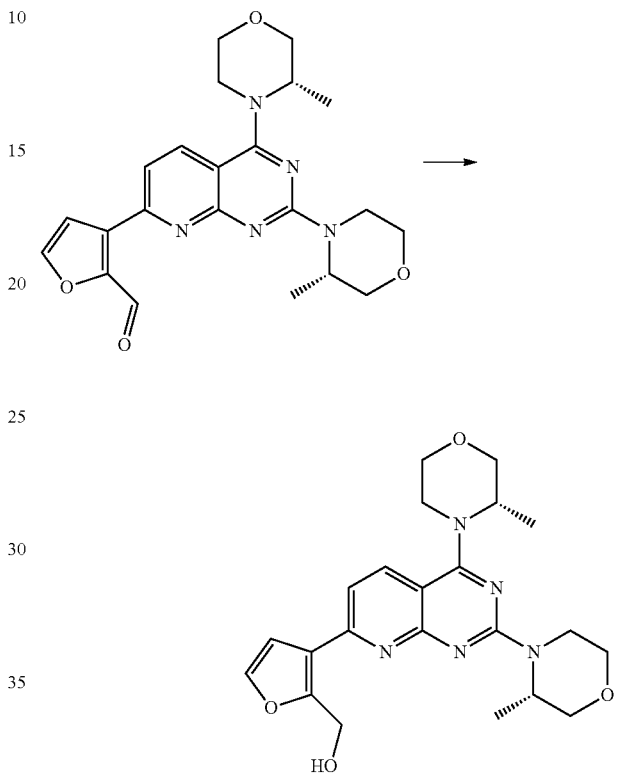

The chloro-substrate was reported in Example 1.

The appropriate chloro-substrate (1 equiv) was dissolved in n-butanol (0.055 M). 2-formylfuran-3-boronic acid (1.0 equiv), potassium carbonate (1.2 equiv), and tetrakis(triphenylphosphine)palladium⁰ (0.05 equiv) were added. The reaction vessel was sealed and exposed to microwave radiation (110° C., medium absorption setting) for 15 minutes. Upon completion the reaction mixture was filtered through a silica cartridge and the filtrate was concentrated in vacuo. The crude residue was purified by column chromatography on silica gel eluting with 40% ethyl acetate in hexane to give the desired product.

The above product was dissolved in THF (0.018 M) and sodium borohydride (2 equiv) was added. This mixture was allowed to stir at room temperature for 5 minutes. Upon completion the reaction mixture was filtered through a silica cartridge and the filtrate was concentrated in vacuo. The crude residue was purified by preparative HPLC to give the desired product.

TABLE 6

| | Purity (%) | Retention time (min) | m/z [M + H]+ | Example Structure |
|---|---|---|---|---|
| 6a | 96 | 6.89 | 426.3 | |

Tested in Alternative Enzyme Assay: Ex. (6a) 0.013 µM.

Example 7

5-[2,4-Bis-(3-methyl-morpholin-4-yl)-pyrido[2,3-d]pyrimidin-7-yl]-furan-2-carboxaldehyde: (100% yield, 100% purity) m/z (LC-MS, ESP): 424 [M+H]⁺ R/T=2.75 min (Compounds 7a to 7k)

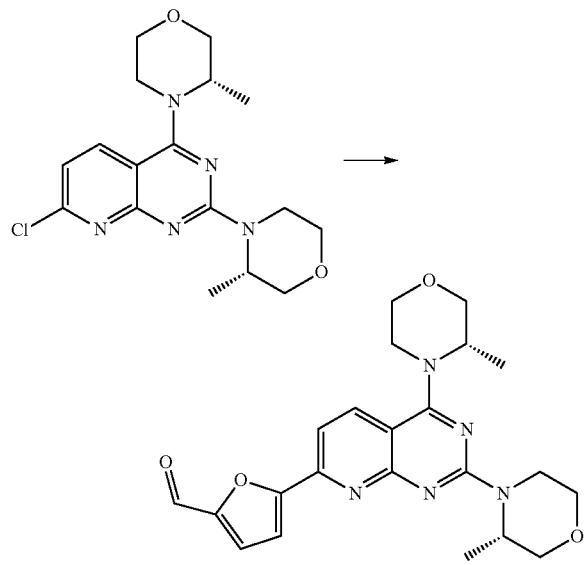

The chloro-substrate was reported in Example 1.

The appropriate chloro-substrate (1 equiv) was dissolved in dioxane (0.16 M). 5-formyl-2-furylboronic acid (1.05 equiv), tripotassium phosphate (1.5 equiv) and bis(tri-t-butylphosphine)palladium (0.05 equiv) were added. The reaction vessel was sealed and exposed to microwave radiation (170° C., medium absorption setting) for 45 minutes. Upon completion the reaction mixture was partitioned between water and CH$_2$Cl$_2$ and extracted with CH$_2$Cl$_2$. Combined organic phases were dried (MgSO$_4$), filtered and concentrated in vacuo. The crude residue was purified by column chromatography on silica gel eluting with 40 to 100% ethyl acetate in hexane to give the desired product.

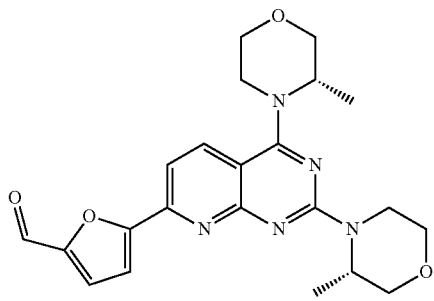 [SMILES: C[C@H]1COCCN1c1nc(N2CCOC[C@@H]2C)c2ccc(-c3ccc(C=O)o3)nc2n1]

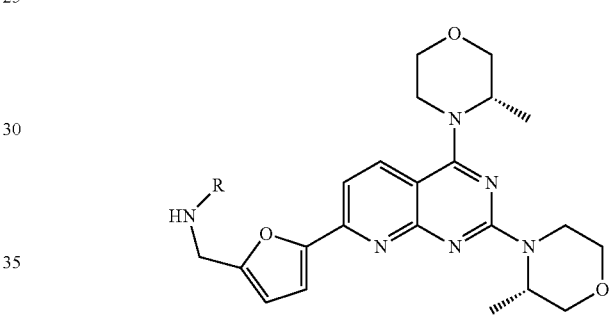

The appropriate formylfuran-substrate (1 equiv) was dissolved in a THF/CH$_2$Cl$_2$ (1:1) solution (0.036 M). The appropriate amines (2.2 equiv) sodium borohydride (2.4 equiv) and acetic acid (0.03 equiv) were added. The reaction mixture was stirred at room temperature for 24 hours. Upon completion the samples were filtered through a silica cartridge, washed with methanol and then concentrated in vacuo. The crude residue was then purified by preparative HPLC to give the desired products.

TABLE 7

| | Purity (%) | Retention time (min) | m/z [M + H]⁺ | Example Structure |
|---|---|---|---|---|
| 7a | 97 | 3.2 | 496.4 | 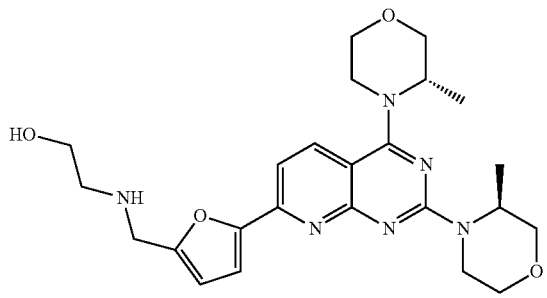 [SMILES: C[C@H]1COCCN1c1nc(N2CCOC[C@@H]2C)c2ccc(-c3ccc(CNCCO)o3)nc2n1] |

TABLE 7-continued

| | Purity (%) | Retention time (min) | m/z [M + H]+ | Example Structure |
|---|---|---|---|---|
| 7b | 99 | 3.32 | 469.4 | |
| 7c | 99 | 3.49 | 439.4 | |
| 7d | 99 | 3.51 | 453.4 | |
| 7e | 99 | 3.58 | 465.4 | |
| 7f | 97 | 3.53 | 509.4 | |

TABLE 7-continued
| | Purity (%) | Retention time (min) | m/z [M + H]+ | Example Structure |
|---|---|---|---|---|
| 7g | 98 | 3.61 | 479.4 | 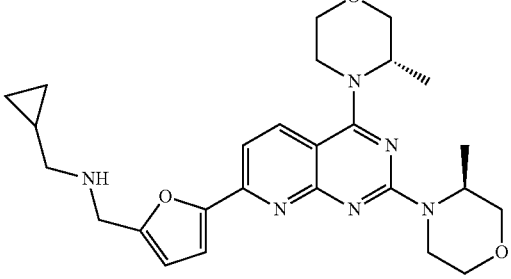 |
| 7h | 99 | 3.56 | 483.4 | 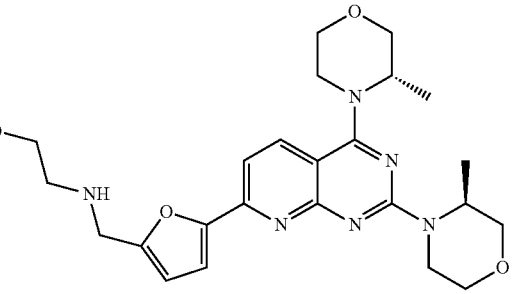 [SMILES: C[C@H]1COCCN1c1nc(N2CCOC[C@@H]2C)c2ccc(-c3ccc(CNCC4CC4)o3)nc2n1] |
| 7i | 95 | 3.86 | 491.4 | 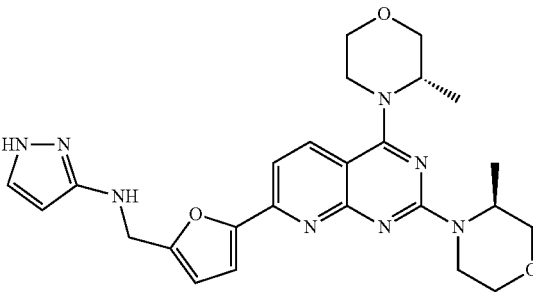 |
| 7j | 98 | 3.46 | 482.4 | 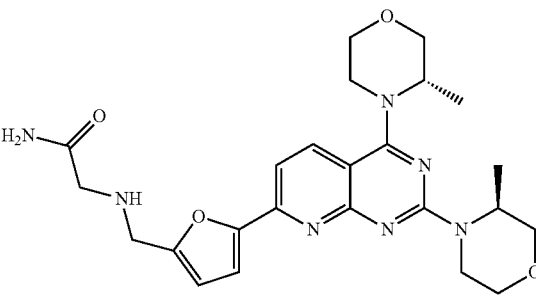 [SMILES: C[C@H]1COCCN1c1nc(N2CCOC[C@@H]2C)c2ccc(-c3ccc(CNCC(N)=O)o3)nc2n1] |
| 7k | 99 | 3.54 | 467.4 | 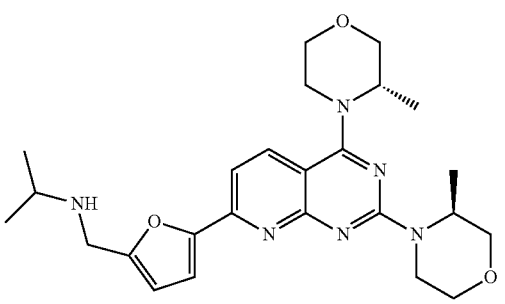 [SMILES: CC(C)NCc1ccc(-c2ccc3c(N4CCOC[C@@H]4C)nc(N4CCOC[C@@H]4C)nc3n2)o1] |

Tested in Alternative Enzyme Assay: Ex. (7a) 0.59 μM; Ex. (7b) 0.13 μM; Ex. (7c) 0.091 μM; Ex. (7d) 0.097 μM; Ex. (7e) 0.15 μM; Ex. (7f) 0.12 μM; Ex. (7g) 0.17 μM; Ex. (7h) 0.33 μM; Ex. (7i) 0.079 μM; Ex. (7j) 0.12 μM; Ex. (7k) 0.14 μM.

Example 8

(Compounds 8a to 8b)

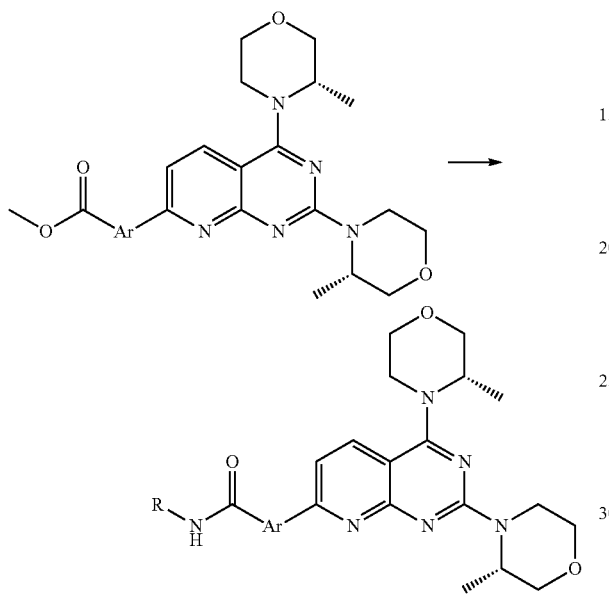

The methylbenzoic ester substrates were reported in Example 1.

Conditions A:

Example 1ba (1 equiv) was dissolved in dioxane (0.16 M). Ethanolamine (51.0 equiv) was added. The reaction vessel was sealed and exposed to microwave radiation (130° C., medium absorption setting) for 50 minutes. Upon completion the reaction mixture was concentrated in vacuo. The crude residue was then purified by column chromatography on silica gel using a gradient 0 to 5% MeOH in $CH_2Cl_2$ to afford the desired product.

Conditions B:

Example 1bg (1 equiv) was dissolved in dioxane (0.05 M). Ethanolamine (2.0 equiv) was added. The reaction vessel was sealed and exposed to microwave radiation (130° C., medium absorption setting) for 2×20 minutes. Upon completion the reaction mixture was concentrated in vacuo. The reaction mixture was partitioned between water and $CH_2Cl_2$ and extracted with $CH_2Cl_2$. Combined organic phases were dried ($MgSO_4$), filtered and concentrated in vacuo. The crude residue was then purified by column chromatography on silica gel using a gradient 0 to 5% MeOH in $CH_2Cl_2$ to afford the desired product.

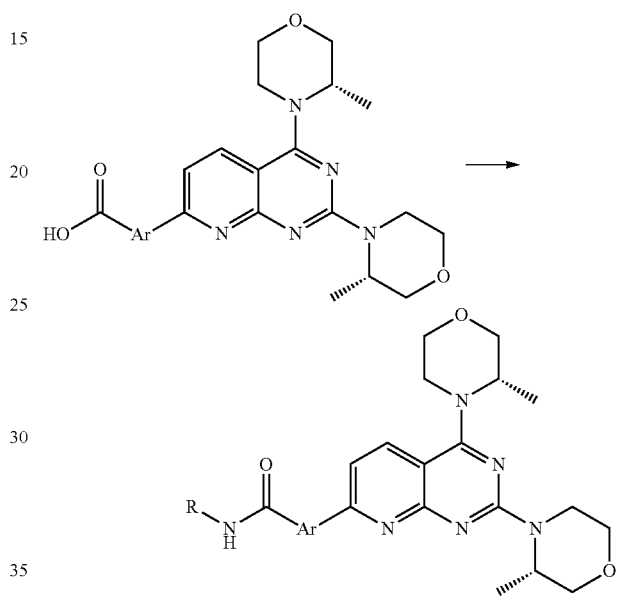

Conditions C:

To a solution of the appropriate carboxylic acid derivative (1 equiv) suspended in $CH_2Cl_2$ was added HBTU (1.3 equiv) followed by diisopropylethylamine (3 equiv). The mixture was cooled (−78° C.) and the appropriate amine added (1.1 equiv). The mixture was stirred for 3 hrs before being concentrated to dryness and purified by preparative HPLC to give the desire products.

TABLE 8

| | Purity (%) | Retention time (min) | m/z [M + H]+ | Conditions | Example Structure |
|---|---|---|---|---|---|
| 8a | 100 | 3.75 | 493.5 | A | 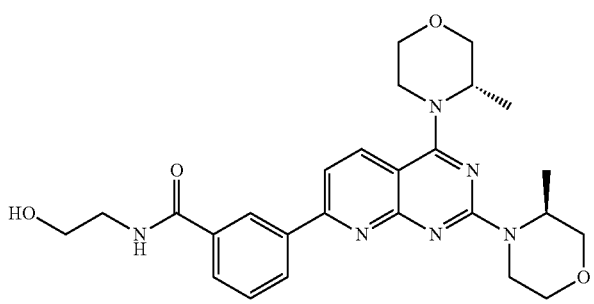 [SMILES: C[C@H]1COCCN1c1nc(N2CCOC[C@@H]2C)c2ccc(-c3cccc(C(=O)NCCO)c3)nc2n1] |

TABLE 8-continued

| Purity (%) | Retention time (min) | m/z [M + H]+ | Conditions | Example Structure |
|---|---|---|---|---|
| 8b | 99 | 3.86 | 523.5 | B |
| 8c | 97 | 3.79 | 465.3 | C |
| 8d | 98 | 3.70 | 507.4 | C |

NMR Data for Example 8a $^1$H NMR (300 MHz, CDCl$_3$) δ ppm 8.55 (ArH, s, 1H), 8.09 (ArH, d, J=7.85 Hz, 1H), 7.95 (ArH, d, J=8.42 Hz, 1H), 7.86 (ArH, d, J=7.86 Hz, 1H), 7.49-7.33 (ArH, m, 2H), 4.89-4.75 (CH, m, 1H), 4.56-4.46 (CH, m, 1H), 4.38-4.26 (CH$_2$, m, 1H), 3.97-3.87 (CH$_2$, m, 2H), 3.85-3.75 (CH$_2$, m, 4H), 3.72-3.55 (CH$_2$, m, 7H), 3.53-3.44 (CH$_2$, m, 1H), 3.34-3.24 (CH2, m, 1H), 1.41 (CH$_3$, d, J=6.77 Hz, 3H), 1.28 (CH$_3$, d, J=6.82 Hz, 3H).

Tested in Alternative Enzyme Assay: Ex. (8a) 0.028 µM; Ex. (8b) 0.079 µM; Ex. (8c) 0.13 µM; Ex. (8d) 2 µM.

Example 9

(Compound 9a)

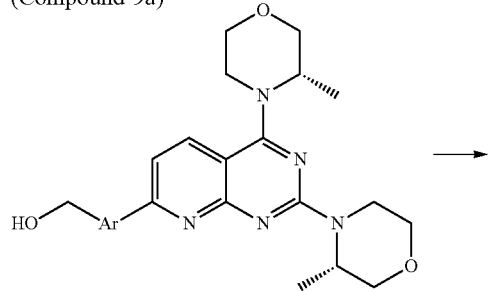

→

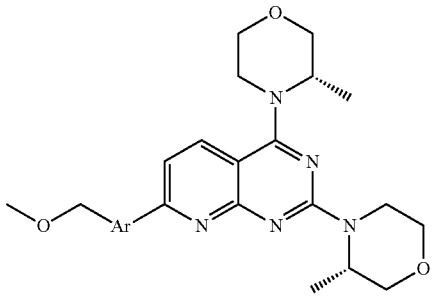

The benzyl alcohol substrate was reported in Example 1. Example 1bc (1 equiv) was dissolved in THF (0.022 M). Sodium tert-butoxide (3.0 equiv) and iodomethane (10.0 equiv) were added. The reaction vessel was stirred at room temperature for 48 hours. Upon completion the sample was filtered through a silica cartridge, washed with EtOAc and then concentrated in vacuo. The crude residue was then purified by preparative HPLC to give the desired product.

TABLE 9

| | Purity (%) | Retention time (min) | m/z [M + H]+ | Example Structure |
|---|---|---|---|---|
| 9a | 100 | 2.87 | 468.4 | |

Tested in Alternative Enzyme Assay: Ex. (9a) 0.088 µM.

Example 10

(Compound 10a)

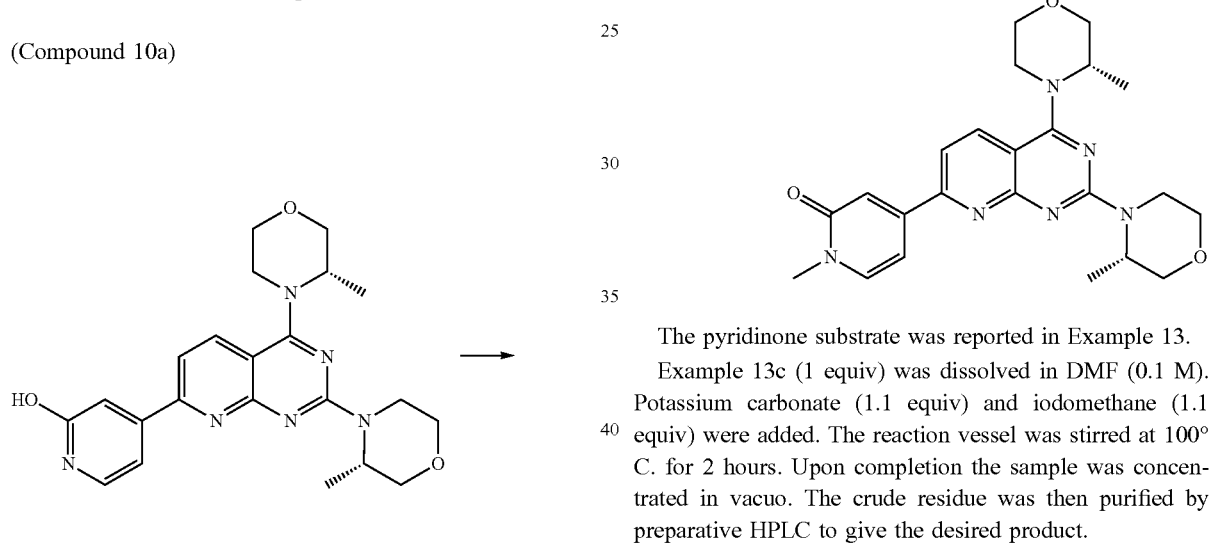

The pyridinone substrate was reported in Example 13.

Example 13c (1 equiv) was dissolved in DMF (0.1 M). Potassium carbonate (1.1 equiv) and iodomethane (1.1 equiv) were added. The reaction vessel was stirred at 100° C. for 2 hours. Upon completion the sample was concentrated in vacuo. The crude residue was then purified by preparative HPLC to give the desired product.

TABLE 10

| | Purity (%) | Retention time (min) | m/z [M + H]+ | Example Structure |
|---|---|---|---|---|
| 10a | 100 | 3.67 | 437.2 | |

Tested in Alternative Enzyme Assay: Ex. (10a) 0.11 μM.

Example 11

(Compound 11a)

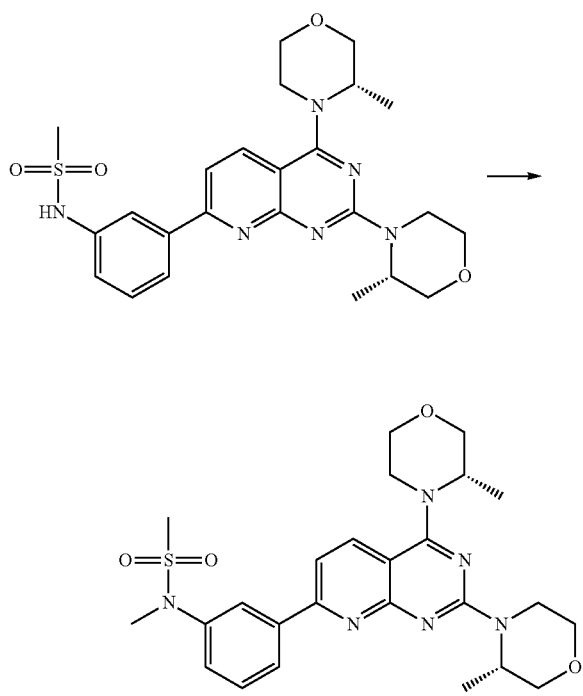

The sulfonamide substrate was reported in Example 1.

Example 1at (1 equiv) was dissolved in DMF (0.1 M). Potassium carbonate (2.0 equiv) and iodomethane (1.5 equiv) were added. The reaction vessel was heated at 100° C. for 2 hours. Upon completion the sample was concentrated in vacuo. The crude residue was then purified by preparative HPLC to give the desired product.

TABLE 11

| | Purity (%) | Retention time (min) | m/z [M + H]+ | Example Structure |
|---|---|---|---|---|
| 11a | 87 | 4.11 | 513.3 | |

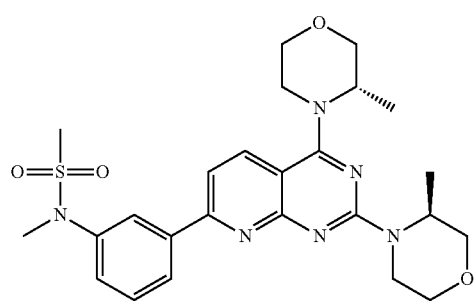 [SMILES: C[C@H]1COCCN1c1nc(N2CCOC[C@@H]2C)c2ccc(-c3cccc(N(C)S(C)(=O)=O)c3)nc2n1]

Tested in Alternative Enzyme Assay: Ex. (11a) 0.37 μM.

Example 12

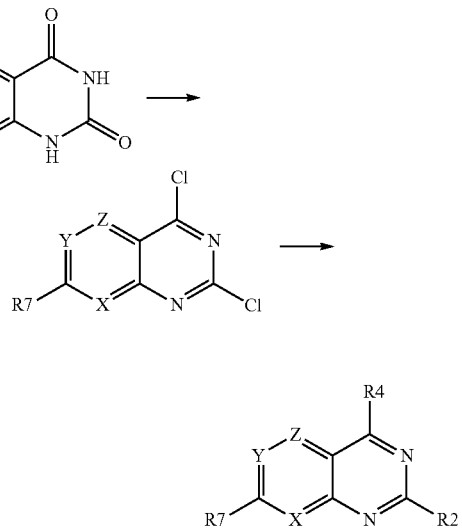

To a solution of the appropriate 7-substituted-1H-pteridine-2,4-dione (1 equiv) in anhydrous toluene (sufficient to make a 0.1 M solution) was added Hunig's base (3 equiv). A reflux condenser was attached to the reaction vessel and the mixture heated, under an inert atmosphere) to 70° C. for 30 minutes. After this time, the reaction was cooled to 40° C. whereupon $POCl_3$ (3 equiv) was added. The mixture was then heated, with stirring, to 110° C. for 3 hrs. Upon completion, the reaction was cooled and concentrated in vacuo to give a tarry residue which was dissolved in the minimum volume of $CH_2Cl_2$ and filtered through a thick silica pad. The resulting filtrate was concentrated in vacuo to give the desired 2,4-dichloro-7-substituted-pteridine product (typically 65-99% yield) in suitably pure form to be used without any further purification.

2,4-Dichloro-7-p-tolyl-pteridine; R7=toluyl, R2=Cl, R4=Cl, X═N, Y═C, Z═N: (61% yield, 99% purity) m/z (LC-MS, ESP): Did not ionize, R/T=3.27 min 2,4-Dichloro-7-phenyl-pteridine; R7=phenyl, R2=Cl, R4=Cl, X═N, Y═C, Z═N: (66% yield, 99% purity) m/z (LC-MS, ESP): Did not ionize, R/T=3.10 min

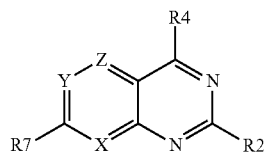

To a cooled (−5° C.) solution of the appropriate amine (1 equiv=R4) in N,N-dimethylacetamide (sufficient to make 0.2 M solution) was added the appropriate 2,4-dichloro-7-substituted-pteridine (1 equiv added as a 0.04 M solution in N,N-dimethylacetamide). After approx 10 minutes Hunig's base was added (1 equiv) and the resultant mixture stirred at −5° C. for 30 minutes. After this time, the reaction was allowed to warm to room temperature, whereupon the appropriate amine (1 equiv=R2) and Hunig's base (1 equiv) were then added. The resultant mixture was heated to 60° C. and maintained at this temperature, with stirring, for 16 hours. Upon completion, the mixture was allowed to cool to room temperature before being purified by preparative HPLC to give the desired product.

TABLE 12

| | Purity (%) | Retention time (min) | m/z [M + H]⁺ | Example Structure |
|---|---|---|---|---|
| 12a | 99 | 5.33 | 421.5 | |
| 12b | 96 | 5.55 | 435.4 | |
| 12c | 95 | 10.29 | 421.3 | |

TABLE 12-continued

| Purity (%) | Retention time (min) | m/z [M + H]+ | Example Structure |
|---|---|---|---|
| 12d | 94 | 9.48 | 407.2 |
| 12e | 94 | 9.48 | 356.2 |

Tested in Alternative Enzyme Assay: Ex. (12a) 0.02669 µM; Ex. (12b) 0.2147 µM; Ex. (12c) 0.04872 µM; Ex. (12d) 0.0263 µM; Ex. (12e) 0.5414 µM.

Example 13

(Compounds 13a to 13f)

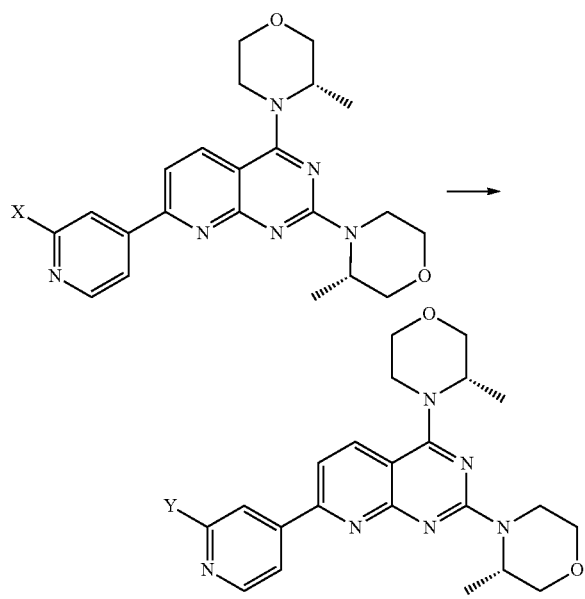

The pyridine substrates were reported in Example 1.

Conditions A:

Example 1w (1 equiv) was dissolved in a dry THF/methanol (1:1) solution (0.057 M). Sodium hydride (4.5 equiv) was added. The reaction mixture was stirred at room temperature for 15 minutes under nitrogen. The reaction vessel was sealed and the mixture exposed to microwave radiation (130° C., medium absorption setting) for 40 minutes. Upon completion the sample was concentrated in vacuo. The crude residue was then purified by preparative HPLC to give the desired product.

Conditions B:

Example 1w (1 equiv) was dissolved in dry THF (0.057 M). Dimethylethanolamine (10.0 equiv) and sodium hydride (5.0 equiv) were added. The reaction mixture was stirred at room temperature for 15 minutes under nitrogen. The reaction vessel was sealed and the mixture exposed to microwave radiation (130° C., medium absorption setting) for 20 minutes. Upon completion the sample was concentrated in vacuo. The crude residue was then purified by preparative HPLC to give the desired product.

Conditions C:

Example 1au (1 equiv) was dissolved in DMSO (0.59 M). 8N aqueous sodium hydroxide solution (50.0 equiv) was added. The reaction vessel was sealed and the mixture exposed to microwave radiation (130° C., medium absorption setting) for 20 minutes. Upon completion concentrated aqueous HCl was added carefully. The mixture was neutralized with 2N aqueous sodium hydroxide solution. The suspension was diluted with methanol then filtered through a sintered funnel. The filtrate was concentrated in vacuo. The crude residue was then purified by preparative HPLC to give the desired products.

Conditions D:

Example 1au (1 equiv) was dissolved in NMP (0.1 M). Potassium cyanide (20.0 equiv) was added. The reaction vessel was sealed and the mixture exposed to microwave radiation (130° C., medium absorption setting) for 46 hours. Upon completion the reaction mixture was partitioned between water and $CH_2Cl_2$. The aqueous phase was extracted with $CH_2Cl_2$. Combined organic phases were dried ($MgSO_4$), filtered and concentrated in vacuo. The crude residue was purified by column chromatography on silica gel eluting with 50 to 100% ethyl acetate in hexane to give the desired product.

Conditions E:

Example 1au (1 equiv) was dissolved in NMP (0.1 M). Potassium cyanide (20.0 equiv) was added. The reaction vessel was sealed and the mixture exposed to microwave radiation (130° C., medium absorption setting) for 46 hours. Upon completion the reaction mixture was partitioned between water and CH$_2$Cl$_2$. The aqueous phase was extracted with CH$_2$Cl$_2$. Combined organic phases were dried (MgSO$_4$), filtered and concentrated in vacuo. The crude residue was purified by column chromatography on silica gel eluting with 50 to 100% ethyl acetate in hexane first, then eluting with 10% methanol in CH$_2$Cl$_2$. The crude fractions were then further purified by preparative HPLC to give the desired product.

Conditions F:

Example 1ah (1 equiv) was dissolved in NMP (0.1 M). Potassium cyanide (8.0 equiv) was added. The reaction vessel was sealed and the mixture exposed to microwave radiation (180° C., medium absorption setting) for 40 minutes. Upon completion the sample was filtered through a silica cartridge, washed with EtOAc and then concentrated in vacuo. The crude residue was then purified by preparative HPLC to give the desired products.

TABLE 13

| | Purity (%) | Retention time (min) | m/z [M + H]$^+$ | Conditions | Example Structure |
|---|---|---|---|---|---|
| 13a | 99 | 4 | 437.3 | A | |
| 13b | 99 | 3.42 | 494.4 | B | |
| 13c | 97 | 5.77 | 423.4 | C | |
| 13d | 97 | 3.96 | 432.4 | D | |

TABLE 13-continued

| | Purity (%) | Retention time (min) | m/z [M + H]+ | Conditions | Example Structure |
|---|---|---|---|---|---|
| 13e | 98 | 6.62 | 450.2 | E | |
| 13f | 99 | 3.93 | 432.3 | F | |
| 13g | 89 | 5.03 | 478.4 | | |

Tested in Alternative Enzyme Assay: Ex. (13a) 0.2 μM; Ex. (13b) 0.33 μM; Ex. (13c) 0.14 μM; Ex. (13d) 0.48 μM; Ex. (13e) 0.19 μM; Ex. (13f) 0.16 μM; Ex. (13g) 0.11 μM.

Example 14

(Compounds 14a-14b)

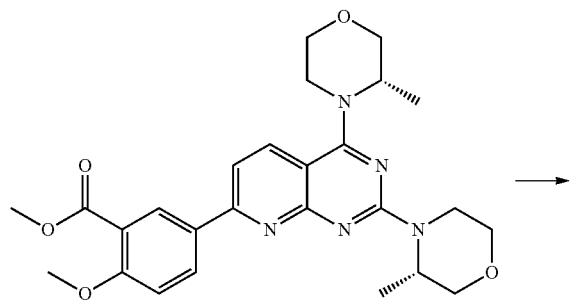

-continued

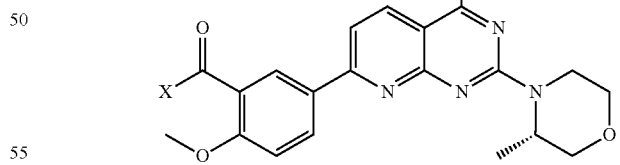

The ester substrate was reported in Example 1.
Ester Hydrolysis:
Conditions A

Example 1bg (1 equiv) was dissolved in methanol (0.2 M). 1M Sodium hydroxide aqueous solution (5.0 equiv) was added. The reaction mixture was stirred at room temperature for 3 hours. Upon completion the reaction mixture was neutralised with 1M aqueous HCl and concentrated in vacuo. The crude residue was purified by column chromatography on silica gel eluting with 0 to 10% MeOH in $CH_2Cl_2$ to give the desired product.

Amide Formation:
Conditions B

Example 1bg (1 equiv) was suspended in THF (0.05 M). Thionyl chloride (2.5 equiv) was added dropwise at 40° C. The reaction mixture was then heated for an hour at 40° C. Ammonia gas was then slowly bubbled into the reaction mixture. THF was then added for further dilution (0.025 M) and the reaction mixture was heated for an hour at 40° C. Upon completion the reaction mixture was cooled down and concentrated in vacuo. The residue was partitioned between water and $CH_2Cl_2$. The aqueous phase was extracted with $CH_2Cl_2$. Combined organic phases were dried ($MgSO_4$), filtered and concentrated in vacuo. The crude residue was purified by column chromatography on silica gel eluting with 0 to 5% MeOH in $CH_2Cl_2$ to give the desired product.

Hz, 1H), 7.13 (ArH, d, J=8.83 Hz, 1H), 5.79 (NH, s, br, 1H), 5.00-4.84 (CH, m, 1H), 4.62 (CH, dd, J=13.82, 0.70 Hz, 1H), 4.37 ($CH_2$, d, J=6.77 Hz, 1H), 4.05 ($OCH_3$, s, 3H), 4.03-3.94 ($CH_2$, m, 2H), 3.91-3.79 ($CH_2$, m, 3H), 3.79-3.63 ($CH_2$, m, 4H), 3.64-3.51 ($CH_2$, m, 1H), 3.44-3.30 ($CH_2$, m, 1H), 1.47 ($CH_3$, d, J=6.78 Hz, 3H), 1.35 ($CH_3$, d, J=6.81 Hz, 3H)

$^{13}C$ NMR (75 MHz, $CDCl_3$) δ ppm 166.58, 165.45, 162.87, 159.99, 159.22, 134.71, 133.75, 131.84, 131.65, 120.52, 113.07, 111.87, 104.80, 102.94, 71.33, 70.94, 67.29, 66.94, 56.28, 52.80, 46.93, 44.49, 39.33, 14.72 and 14.34.

Tested in Alternative Enzyme Assay: Ex. (14a) 0.00015 µM; Ex. (14b) 0.0032 µM.

TABLE 14

| | Purity (%) | Retention time (min) | m/z [M + H]+ | Conditions | Example Structure |
|---|---|---|---|---|---|
| 14a | 98 | 3.95 | 480.5 | A | |
| 14b | 98 | 7.09 | 479.4 | B | |

NMR Data for Example 14a $^1H$ NMR (300 MHz, $CDCl_3$) δ ppm 8.82-8.69 (ArH, m, 1H), 8.68-8.56 (ArH, m, 1H), 8.03-7.90 (ArH, m, 1H), 7.52-7.39 (ArH, m, 1H), 7.18-7.05 (ArH, m, 1H), 4.92-4.80 (CH, m, 1H), 4.61-4.47 (CH, m, 1H), 4.37-4.27 ($CH_2$, m, 1H), 4.07 ($OCH_3$, s, 3H), 4.00-3.87 ($CH_2$, m, 2H), 3.85-3.60 ($CH_2$, m, 6H), 3.57-3.24 ($CH_2$, m, 3H), 1.41 ($CH_3$, d, J=6.65 Hz, 3H), 1.30 ($CH_3$, d, J=6.74 Hz, 3H)

$^{13}C$ NMR (75 MHz, $CDCl_3$) δ ppm 165.33, 134.98, 134.96, 132.64, 132.61, 132.58, 119.77, 112.83, 112.11, 100.01, 71.29, 70.90, 67.24, 66.91, 52.80, 46.96, 44.44, 39.34 and 14.74.

NMR Data for Example 14b $^1H$ NMR (300 MHz, $CDCl_3$) δ ppm 8.83 (ArH, d, J=2.46 Hz, 1H), 8.64 (ArH, dd, J=8.76, 2.49 Hz, 1H), 8.01 (ArH, d, J=8.47 Hz, 1H), 7.71 (NH, s, br, 1H), 7.57 (ArH, d, J=8.50

Example 15

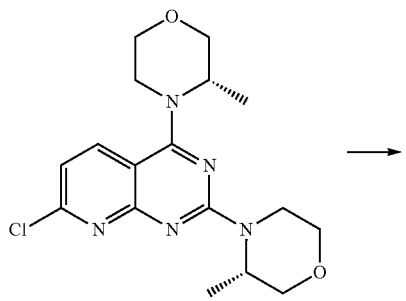

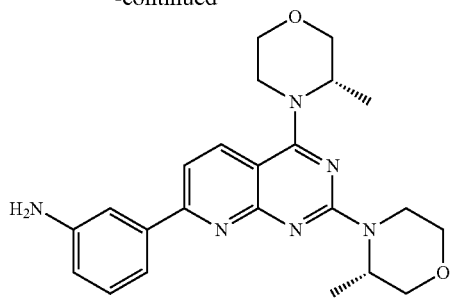

The chloro-substrate was reported in Example 1.

To a mixture of 7-chloro-4-((S)-3-methyl-morpholin-4-yl)-2-((S)-3-methyl-morpholin-4-yl)-pyrido[2,3-d]pyrimidine (1 equiv), potassium carbonate (1.2 equiv), and 3-BOC-aminophenylboronic acid (1.2 equiv) in acetonitrile/water (1:1) (0.08 M of chloro-substrate) was added tetrakis(triphenylphosphine)palladium⁰ (0.05 equiv). The reaction vessel was sealed and exposed to microwave radiation (130° C., medium absorption setting) for 10 minutes under nitrogen atmosphere. Upon completion the samples were filtered through a silica cartridge, washed with ethyl acetate and then concentrated in vacuo. The crude residue was used as such in the next reaction.

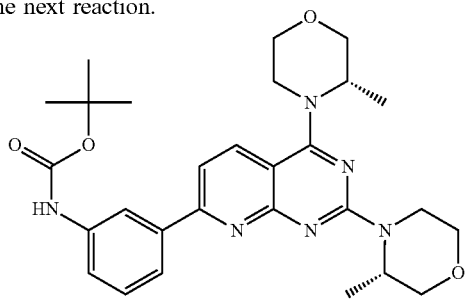

{3-[2,4-Bis-((S)-3-methyl-morpholin-4-yl)-pyrido[2,3-d]pyrimidin-7-yl]-phenyl}-carbamic acid tert-butyl ester: (95% yield, 100% purity) m/z (LC-MS, ESP): 520.9 [M+H]⁺ R/T=3.23 min The above product (1 equiv) was dissolved in a TFA/CH₂Cl₂ solution (1:20) (0.018 M). The reaction mixture was stirred at room temperature for 15 hours. The reaction mixture was then concentrated in vacuo. The residue was partitioned between water and CH₂Cl₂. The aqueous phase was neutralized with 1N aqueous sodium hydroxide. Combined organic phases were dried (MgSO₄), filtered and concentrated in vacuo. The crude residue was used as such in the next reaction.

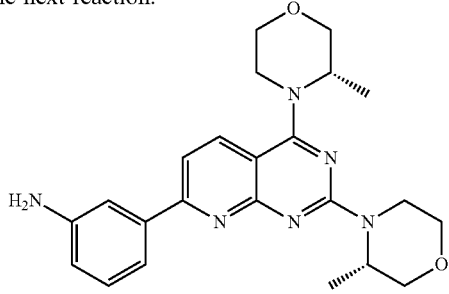

3-[2,4-Bis-((S)-3-methyl-morpholin-4-yl)-pyrido[2,3-d]pyrimidin-7-yl]-phenylamine: (100% yield, 100% purity) m/z (LC-MS, ESP): 520.9 [M+H]⁺ R/T=2.72 min (Compound 15a)

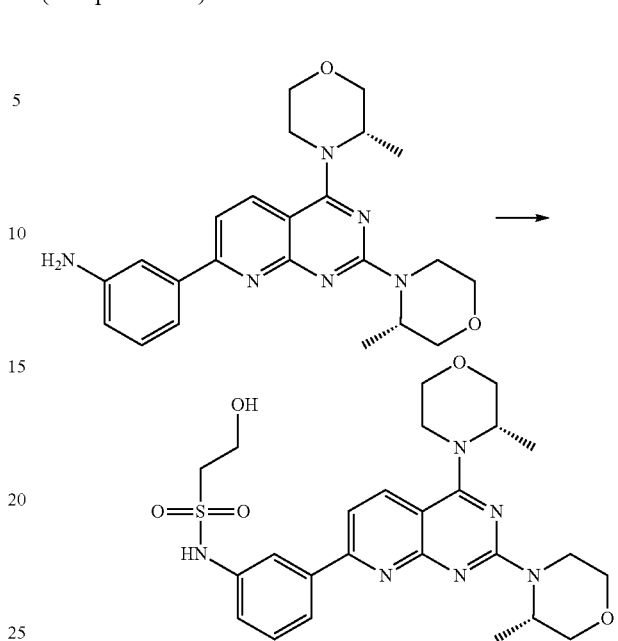

The above product (1 equiv) was dissolved in THF (0.013 M). Chloroethanesulfonyl chloride (3.5 equiv) was gently added to the reaction mixture at 0° C. and the reaction mixture was stirred at room temperature for 15 hours. 8N Aqueous sodium hydroxide (50 equiv) was then added and the reaction mixture was heated at 40° C. for 12 hours. The reaction mixture was concentrated in vacuo. The crude residue was purified by column chromatography on silica gel eluting with 0 to 5% MeOH in CH₂Cl₂ to give the desired product.

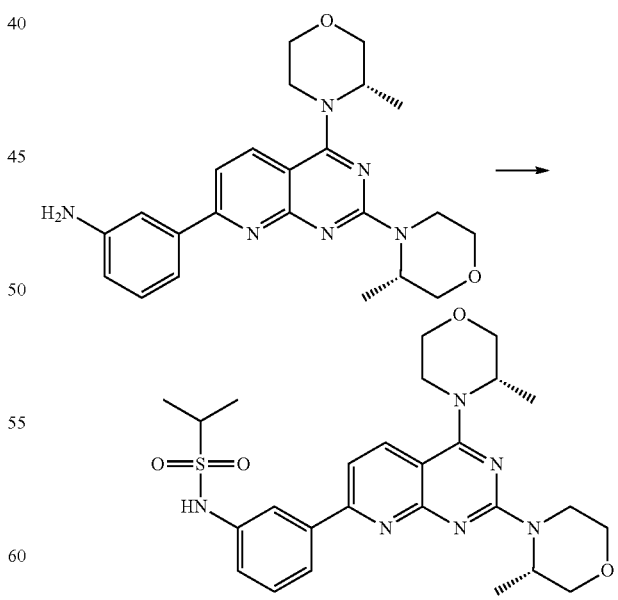

3-[2,4-Bis-((S)-3-methyl-morpholin-4-yl)-pyrido[2,3-d]pyrimidin-7-yl]-phenylamine (1 equiv) was dissolved in THF (0.1 M). Pyridine (10 equiv) and isopropylsulfonyl chloride (10 equiv) were added to the reaction mixture at room temperature. The reaction mixture was then stirred at 90° C. for 4 hours. The reaction mixture was partitioned between CH$_2$Cl$_2$ and water.

Organic phase was dried (MgSO$_4$), filtered and concentrated in vacuo. The crude residue was purified by column chromatography on silica gel eluting with 0 to 60% EtOAc in hexane to give the desired product.

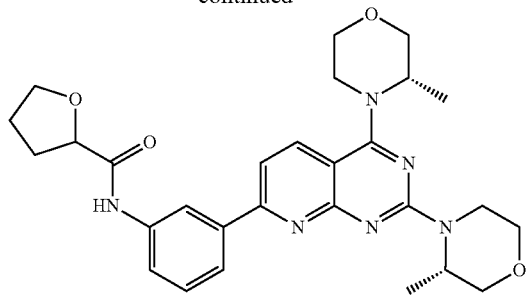

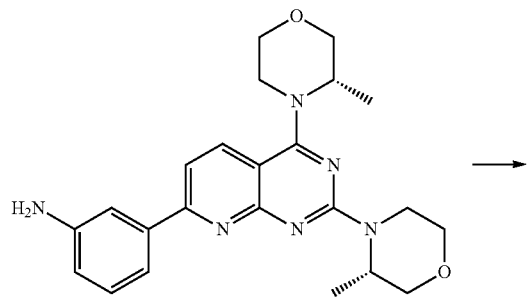

3-[2,4-Bis-((S)-3-methyl-morpholin-4-yl)-pyrido[2,3-d]pyrimidin-7-yl]-phenylamine (1 equiv) was dissolved in CH$_2$Cl$_2$ (0.24 M). Tetrahydro-2-furoic acid (1.1 equiv), HBTU (2.0 equiv) and triethylamine (2 equiv) were added and the reaction mixture was then stirred at room temperature for 3 hours. The reaction mixture was partitioned between CH$_2$Cl$_2$ and water. Organic phase was dried (MgSO$_4$), filtered and concentrated in vacuo. The crude residue was purified by column chromatography on silica gel eluting with 0 to 4% MeOH in TBME to give the desired product.

TABLE 15

| | Purity (%) | Retention time (min) | m/z [M + H]$^+$ | Example Structure |
|---|---|---|---|---|
| 15a | 98 | 3.99 | 529.4 | |
| 15b | 96 | 8.28 | 527.3 | |
| 15c | 99 | 4.19 | 519.3 | |

NMR Data for Example 15b $^1$H NMR (300 MHz), CDCl$_3$) δ ppm 8.00-7.94 (ArH, m, 2H), 7.81 (ArH, td, J=7.12, 1.52, 1.52 Hz, 1H), 7.45-7.32 (ArH, m, 3H), 6.84 (NH, s, br, 1H), 4.93-4.80 (CH$_2$, m, 1H), 4.55 (CH$_2$, d, J=12.97 Hz, 1H), 4.38-4.25 (CH$_2$, m, 1H), 4.01-3.57 (CH$_2$, m, 9H), 3.57-3.45 (CH$_2$, m, 1H), 3.36-3.32 (CH$_2$, m, 2H), 1.42 (CH$_3$, d, J=6.78 Hz, 3H), 1.37-1.26 (3×CH$_3$, m, 9H)

$^{13}$C NMR (75 MHz, CDCl$_3$) δ ppm 165.36, 162.85, 161.36, 159.98, 140.27, 137.89, 134.92, 129.80, 124.03, 121.31, 119.64, 113.30, 105.19, 71.28, 70.91, 67.25, 66.91, 52.89, 52.87, 44.42, 39.33, 31.60, 22.66, 16.60, 14.75 and 14.36.

NMR Data for Example 15c $^1$H NMR (300 MHz, CD$_3$COCD$_3$) δ ppm 8.52 (ArH, s, 1H), 8.24 (ArH, d, J=8.48 Hz, 1H), 7.91-7.80 (ArH, m, 2H), 7.62 (ArH, d, J=8.47 Hz, 1H), 7.46 (ArH, t, J=7.94, 7.94 Hz, 1H), 6.48 (NH, br, s, 1H), 4.84-4.70 (CH$_2$, m, 1H), 4.53-4.33 (CH$_2$, m, 3H), 4.09-3.79 (CH$_2$, m, 5H), 3.80-3.56 (CH$_2$, m, 5H), 3.49-3.40 (CH$_2$, m, 1H), 3.23-3.28 (CH$_2$, m, 1H), 2.20 (CH$_2$, d, J=6.66 Hz, 1H), 2.11-1.81 (CH$_2$, m, 4H), 1.39 (CH$_3$, d, J=6.75 Hz, 3H), 1.26 (CH$_3$, d, J=6.75 Hz, 3H).

$^{13}$C NMR (75 MHz, CD$_3$COCD$_3$) δ ppm 171.66, 160.37, 147.37, 145.71, 138.93, 138.46, 135.69, 128.98, 126.26, 126.11, 122.52, 121.58, 118.91, 118.37, 104.46, 77.93, 70.31, 70.13, 68.81, 66.28, 66.15, 51.77, 46.41, 43.85, 29.98, 25.06, 14.39 and 13.92.

Tested in Alternative Enzyme Assay: Ex. (15a) 0.0043 μM; Ex. (15c) 0.33 μM.

Tested in phospho-Ser473 Akt assay: Ex. (15b) 0.5051 μM.

Example 16

(Compound 16a)

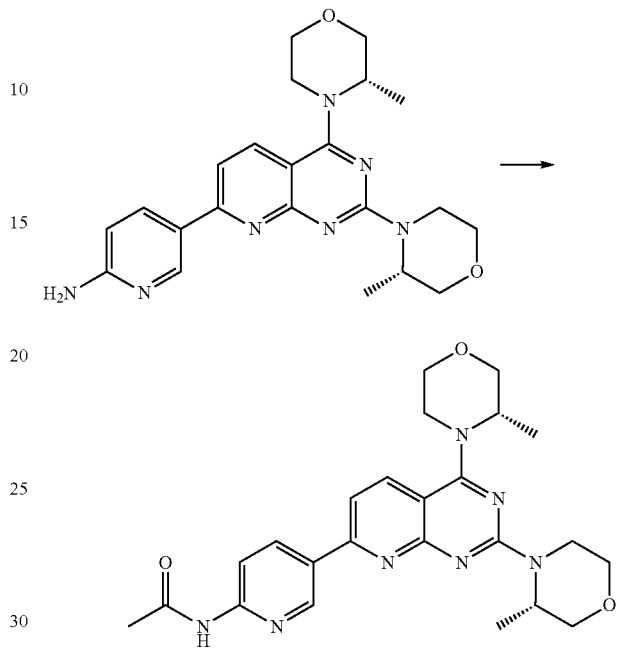

The aminopyridine substrate was reported in Example 1.

Example 1u (1 equiv) was dissolved in pyridine (0.11 M). Acetic anhydride (5.0 equiv) was added and the reaction mixture was heated at 70° C. for 6 hours. Upon completion the sample was concentrated in vacuo. The crude residue was then purified by preparative HPLC to give the desired product.

TABLE 16

| | Purity (%) | Retention time (min) | m/z [M + H]$^+$ | Example Structure |
|---|---|---|---|---|
| 16a | 100 | 3.8 | 464.4 | |

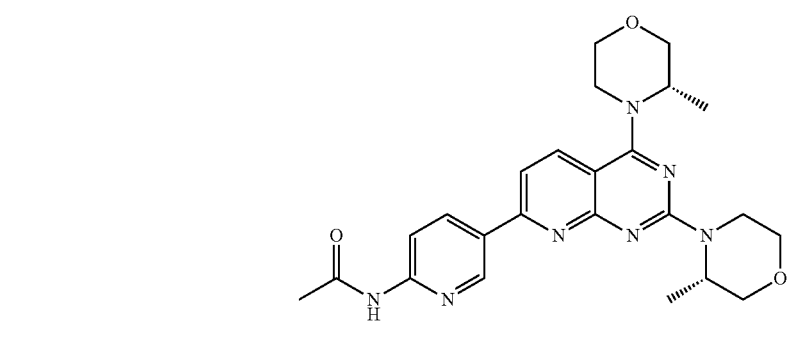 [SMILES: CC(=O)Nc1ccc(-c2ccc3c(N4CCOC[C@@H]4C)nc(N4CCOC[C@@H]4C)nc3n2)cn1]

NMR Data for Example 16a $^1$H NMR (300 MHz, CDCl$_3$) δ ppm 8.18-8.12 (ArH, m, 2H), 8.05 (ArH, d, J=8.42 Hz, 1H), 7.52-7.40 (ArH, m, 3H), 4.96 (CH, d, br, J=4.93 Hz, 1H), 4.66 (CH, d, br, J=12.90 Hz, 1H), 4.40 (d, br, J=6.71 Hz, 1H), 4.07-3.54 (CH$_2$, m, 11H), 3.47-3.35 (CH, m, 1H), 1.51 (CH$_3$, d, J=6.79 Hz, 3H), 1.39 (CH$_3$, d, J=6.82 Hz, 3H)

$^{13}$C NMR (75 MHz, CDCl$_3$) δ ppm 165.41, 162.93, 161.83, 160.02, 137.14, 136.13, 134.84, 129.19, 128.77, 112.99, 105.03, 71.29, 70.91, 67.26, 66.91, 52.85, 46.95, 44.46, 39.34, 14.73 and 14.37.

Tested in Alternative Enzyme Assay: Ex. (16a) 0.034 μM.

Example 17

(Compound 17a)

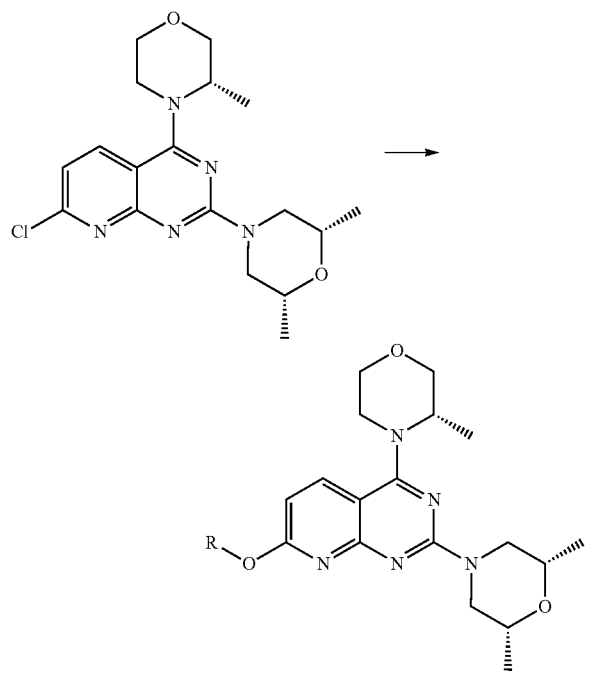

The chloro-substrate was reported in Example 1.

The appropriate chloro-substrate (1 equiv) was dissolved in toluene (0.07 M). Phenol (1.0 equiv), palladium acetate (0.05 equiv), BINAP (0.05 equiv) and tripotassium phosphate (1.0 equiv) were added. The reaction vessel was sealed and exposed to microwave radiation (140° C., medium absorption setting) for 10 minutes. Upon completion the samples was concentrated in vacuo. The crude residue was then purified by preparative HPLC to give the desired product.

TABLE 17

| | Purity (%) | Retention time (min) | m/z [M + H]$^+$ | Example Structure |
|---|---|---|---|---|
| 17a | 93 | 4.70 | 436.4 | |

Tested in Alternative Enzyme Assay: Ex. (17a) 0.52 μM.

Example 18

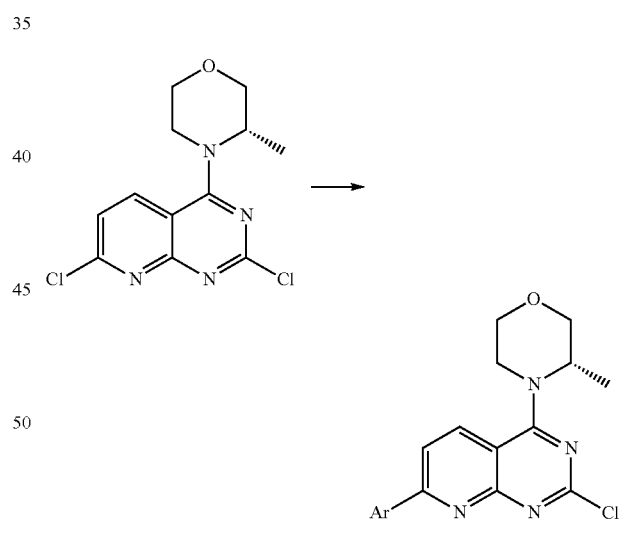

The chloro-substrate was reported in Example 1.

To a mixture of the appropriate chloro-substrate (1 equiv), potassium carbonate (2.5 equiv), and the appropriate boronic acid (1.1 equiv) in acetonitrile/water (1:1) (0.033 M of chloro-substrate) was added tetrakis(triphenylphosphine) palladium$^0$ (0.05 equiv). The suspension was sonicated while degassed with nitrogen for 5 minutes then heated to 95° C. for 2 hours. Upon completion the reaction mixture was allowed to cool down to room temperature. The reaction mixture was concentrated in vacuo to half original volume. The crude residue was extracted with CH$_2$Cl$_2$ and the combined organic phases were washed with brine, dried (MgSO₄), filtered and concentrated in vacuo to give a yellow solid. The residue was sonicated in diethyl ether, collected by vacuum filtration to give the desired product as a yellow powder.

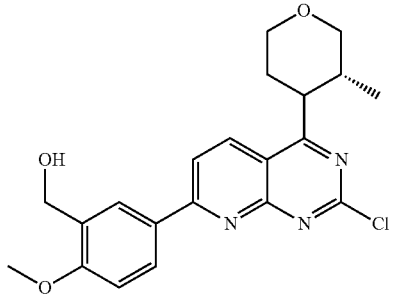

{5-[2-Chloro-4-((S)-3-methyl-morpholin-4-yl)-pyrido[2,3-d]pyrimidin-7-yl]-2-methoxy-phenyl}-methanol: (78% yield, 100% purity) m/z (LC-MS, ESP): 401 [M+H]⁺ R/T=3.47 min

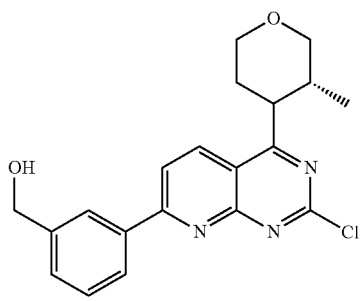 [SMILES: C[C@H]1COCCC1c1nc(Cl)nc2nc(-c3cccc(CO)c3)ccc12]

{3-[2-Chloro-4-((S)-3-methyl-morpholin-4-yl)-pyrido[2,3-d]pyrimidin-7-yl]-phenyl}-methanol: (90% yield, 90% purity) m/z (LC-MS, ESP): 371 [M+H]R/T=4.06 min Alternatively, to a stirred mixture of bis(pinacolato)diboron (1.05 equiv) and potassium acetate (3 equiv) in N-methylpyrrolidine (13.5 equiv), purged with nitrogen, was added the corresponding bromobenzylalcohol (1 equiv) followed by PdCl₂(dppf) (0.02 equiv). The mixture was then heated to 60° C. and held for 10 min, then heated to 70° C. and held for 15 min and finally heated to 80° C. and held for 1 h. The appropriate chloro-substrate (1 equiv) was then added followed by PdCl₂(dppf) (0.02 equiv) and N-methylpyrrolidine (4.5 equiv). The temperature was then held at 75° C., then 4.3M aqueous potassium carbonate (3.5 equiv) was added over 13 min, then water (12 equiv) was added and the reaction was stirred at 75° C. for 90 min. Water (144 equiv) was then added slowly over 70 min with stirring while the temperature was reduced to 66° C. The temperature of the stirred mixture was then kept at 64° C. for 30 min, then cooled to 20° C. over 2.5 h, and held at 20° C. overnight. The resulting slurry was filtered, and the solid washed first with a 3:1 water:N-methylpyrrolidone mixture (18 equiv of water), then washed with water (24 equiv) and then washed with ethyl acetate (4×4.4 equiv). The solid was then dried in a vacuum oven at 50° C. to leave the title compound in suitable clean form to be used without any further purification. For example, {5-[2-Chloro-4-((S)-3-methyl-morpholin-4-yl)-pyrido[2,3-d]pyrimidin-7-yl]-2-methoxy-phenyl}-methanol: (73% yield)

(Compounds 18a to 18do)

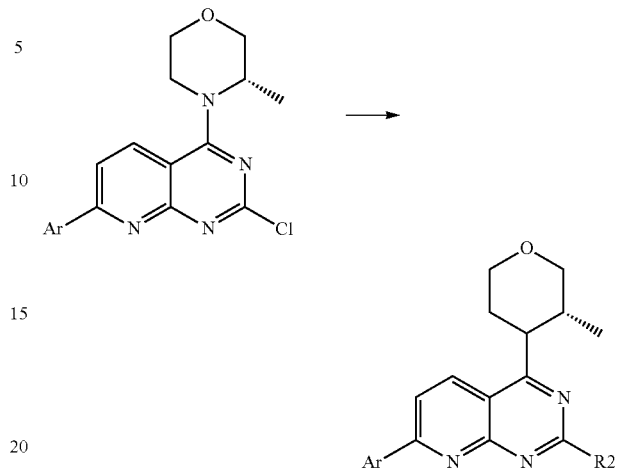

Conditions A:
The appropriate chloro-substrate (1 equiv) was dissolved in DMA (0.04 M). Tripotassium phosphate (1.5 equiv) and the appropriate nucleophile (secondary amine) (1.5 equiv) were then added. The reaction vessel was sealed and the mixture exposed to microwave radiation (200° C., medium absorption setting) for 30 minutes. Upon completion the samples were filtered through a silica cartridge, washed with EtOAc and then concentrated in vacuo. The crude residue was then purified by preparative HPLC to give the desired products.

Conditions B:
The appropriate chloro-substrate (1 equiv) was suspended in a propan-2-ol and aqueous ammonia (1:3) solution (0.02 M). The reaction vessel was sealed and the mixture exposed to microwave radiation (140° C., medium absorption setting) for 20 minutes. The crude residue was then purified by preparative HPLC to give the desired products.

Conditions C:
The appropriate chloro-substrate (1 equiv) was dissolved in dioxane (0.04 M). Diisopropylethylamine (5.0 equiv) and the appropriate nucleophile (secondary amine) (1.5 equiv) were then added. The reaction vessel was sealed and the mixture exposed to microwave radiation (130° C., medium absorption setting) for 20 minutes. Upon completion the samples were concentrated in vacuo. The crude residue was then purified by preparative HPLC to give the desired products.

Conditions D:
The appropriate chloro-substrate (1 equiv) was dissolved in dioxane (0.04 M). Tripotassium phosphate (3.0 equiv), xantphos (0.05 equiv), palladium acetate (0.05 equiv) and the appropriate nucleophile (amine) (1.5 equiv) were then added. The reaction vessel was sealed and the mixture exposed to microwave radiation (150° C., medium absorption setting) for 20 minutes. Upon completion the samples were filtered through a silica cartridge, washed with EtOAc and then concentrated in vacuo. The crude residue was then purified by preparative HPLC to give the desired products.

Conditions E:
The appropriate chloro-substrate (1.0 equiv) was dissolved in dioxane (0.04 M). Diisopropylethylamine (5.0 equiv) and the appropriate nucleophile (secondary amine, with BOC-protected amino side chain) (1.5 equiv) were then added. The reaction vessel was sealed and the mixture exposed to microwave radiation (130° C., medium absorption setting) for 20 minutes. Upon completion the samples were concentrated in vacuo. To the crude residue was then added a 4 M solution of HCl in dioxane (0.15 M). The reaction mixtures were stirred at room temperature for 3 hours. Upon completion the samples were basified with a 2 N sodium hydroxide solution. The crude residue was then purified by preparative HPLC to give the desired products.
Conditions F:
The appropriate nucleophile (substituted imidazole) (10.0 equiv) was dissolved in DMF (0.4 M). Sodium hydride (5.0 equiv) was then added. The reaction mixture was stirred at room temperature for 10 minutes under nitrogen and a solution of the appropriate chloro-substrate (1.0 equiv) in DMF (0.075 M) was added. The reaction vessel was sealed and the mixture exposed to microwave radiation (150° C., medium absorption setting) for 30 minutes. Upon completion the samples were filtered through a silica cartridge, eluted with $CH_2Cl_2$ and then concentrated in vacuo. The crude residue were then purified by preparative HPLC to give the desired products.
Conditions G:
The appropriate chloro-substrate (1 equiv) was dissolved in dioxane (0.04 M). Diisopropylethylamine (5.0 equiv) and the appropriate nucleophile (secondary amine) (4.5 equiv) were then added. The reaction vessel was sealed and the mixture exposed to microwave radiation (130° C., medium absorption setting) for 40 minutes. Upon completion the samples were concentrated in vacuo. The crude residue was then purified by preparative HPLC to give the desired products.
Conditions H:
The appropriate chloro-substrate (1 equiv) was dissolved in dioxane (0.04 M). Diisopropylethylamine (5.0 equiv) and the appropriate nucleophile (secondary amine) (10.0 equiv) were then added. The reaction vessel was sealed and the mixture exposed to microwave radiation (130° C., medium absorption setting) for 60 minutes. Upon completion the samples were concentrated in vacuo. The crude residue was then purified by preparative HPLC to give the desired products.
Conditions I:
The appropriate chloro-substrate (1 equiv) was dissolved in a solution of 1% DMA in dioxane (0.04 M). Diisopropylethylamine (5.0 equiv) and the appropriate nucleophile (secondary amine) (10.0 equiv) were then added. The reaction vessel was sealed and the mixture exposed to microwave radiation (180° C., medium absorption setting) for 60 minutes. Upon completion the samples were concentrated in vacuo. The crude residue was then purified by preparative HPLC to give the desired products.
Conditions J:
The appropriate chloro-substrate (1 equiv) was dissolved in a solution of 1% DMA in dioxane (0.04 M). Diisopropylethylamine (7.0 equiv) and the appropriate nucleophile (secondary amine) (3.0 equiv) were then added. The reaction vessel was sealed and the mixture exposed to microwave radiation (150° C., medium absorption setting) for 60 minutes. Upon completion the samples were concentrated in vacuo. The crude residue was then purified by preparative HPLC to give the desired products.
Conditions K:
The appropriate chloro-substrate (1 equiv) was dissolved in DMF (0.075 M). Potassium carbonate (5.0 equiv) and the appropriate nucleophile (alcohol) (10.0 equiv) were then added. The reaction vessel was sealed and the mixture exposed to microwave radiation (120° C., medium absorption setting) for 20 minutes. Upon completion the samples were concentrated in vacuo. The crude residue was then purified by preparative HPLC to give the desired products.
Conditions L:
The appropriate chloro-substrate (1 equiv) was dissolved in DMF (0.075 M). Potassium carbonate (5.0 equiv) and the appropriate nucleophile (alcohol) (20.0 equiv) were then added. The reaction vessel was sealed and the mixture exposed to microwave radiation (150° C., medium absorption setting) for 40 minutes. Upon completion the samples were concentrated in vacuo. The crude residue was then purified by preparative HPLC to give the desired products.
Conditions M:
The appropriate chloro-substrate (1 equiv) was dissolved in DMA (0.13 M). Diisopropylethylamine (2.0 equiv) and the appropriate nucleophile (amine) (2.0 equiv) were then added. The reaction vessel was heated to 100° C. for 3 hours. Upon completion, the reaction mixture was partitioned between dichloromethane and water and the aqueous layer further extracted with dichloromethane. The combined organic phases were dried ($MgSO_4$), filtered and the filtrate was concentrated in vacuo to give a yellow residue which was purified by recrystallisation from diethyl ether.
Conditions N:
5-[2-Chloro-4-((S)-3-methyl-morpholin-4-yl)-pyrido[2,3-d]pyrimidin-7-yl]-pyridin-2-ylamine (1 equiv) was dissolved in DMA (0.21 M). Diisopropylethylamine (1.0 equiv) and the appropriate nucleophile (amine) (1.1 equiv) were then added. The reaction vessel was sealed and the mixture exposed to microwave radiation (130° C., medium absorption setting) for 10 minutes. Upon completion, the reaction mixture was partitioned between dichloromethane and water and the aqueous layer further extracted with $CH_2Cl_2$. The combined organic phases were dried ($MgSO_4$), filtered and the filtrate was concentrated in vacuo to give a yellow residue which was purified by column chromatography on silica gel eluting with 0% to 10% MeOH in $CH_2Cl_2$ to give the desired product.
Conditions O:
The appropriate chloro-substrate (1 equiv) was dissolved in DMA (0.16 M). Diisopropylethylamine (1.0 equiv) and the appropriate nucleophile (amine) (1.2 equiv) were then added. The reaction vessel was heated to 80° C. for 48 hours. Upon completion, the reaction mixture was partitioned between ethyl acetate and water and the organic layer washed with brine. The combined organic phases were dried ($MgSO_4$), filtered and the filtrate was concentrated in vacuo to give a residue which was purified by preparative HPLC to give the desired product.
Conditions P:
The appropriate chloro-substrate (1 equiv) was dissolved in anisole (0.25 M) (10 vol). Diisopropylethylamine (1.3 equiv) and the appropriate nucleophile (amine) (1.3 equiv) were then added. The reaction vessel was heated to 125° C. and stirred for 11 h. Upon completion, the reaction mixture was allowed to cool to 50° C. Aqueous 20% citric acid solution (7 vol) was added, stirred for 5 min and then allowed to separate partitioned. The aqueous layer was removed and retained. The organic layer was then extracted with a further aliquot of aqueous 20% citric acid solution (3 vol). The organic layer discarded, and the aqueous layers combined. The combined aqueous layers were washed first with anisole (5 vol), then 50% aqueous sodium hydroxide solution (1.23 vol) was added slowly. The resulting aqueous phase was extracted with ethyl acetate (10 vol). The aqueous layer was discarded and the organic layer was washed first with 10% aqueous sodium hydroxide solution (5 vol) and then water (5 vol). The organic layer was then slurried with silicycle Si-thiourea scavenger at 50° C. for 2 h, then the scavenger was filtered off and washed with ethyl acetate (2×1 vol). The organic phase was cooled to 20° C., seeded to start crystallization and stirred until a slurry obtained. The slurry was heated to 50° C. under vacuum and ethyl acetate (3 vol) was removed by vacuum distillation. 2-Methylpentane (3.4 vol) was added and the mixture heated to 60° C. and then slowly cooled to 20° C. over 2 h. The resulting slurry was filtered, and the solid washed with 1:1 ethyl acetate:pentane (2×0.5 vol). The solid was then dried in a vacuum oven at 50° C. to leave the desired product. For example, compound 1a was obtained (50.4% yield). The crude product (1 equiv) was dissolved in DMSO (5 vol based on product weight) at 50° C. Water (2 vol) was added and the mixture stirred at 50° C. until product crystallizes. The slurry was heated to 60° C. and then water (3 vol) was added slowly over 30 min so that the temperature was maintained at 60° C. The mixture was slowly cooled to 20° C. over 2 h, and then held at 20° C. for 30 min. The resulting slurry was filtered, and the solid washed with 2:1 water: DMSO (0.5:1 vol), and then water (3×2 vol). The solid was then dried in a vacuum oven at 50° C. to leave the desired product.

TABLE 18

| | Purity (%) | Retention time (min) | m/z [M + H]+ | Conditions | Example Structure |
|---|---|---|---|---|---|
| 18a | 91 | 4.43 | 464.5 | A | |
| 18b | 98 | 3.89 | 382.4 | B | |
| 18c | 96 | 4.36 | 450.4 | C | |

TABLE 18-continued

| | Purity (%) | Retention time (min) | m/z [M + H]+ | Conditions | Example Structure |
|---|---|---|---|---|---|
| 18d | 97 | 4.48 | 464.4 | C | |
| 18e | 93 | 3.56 | 479.4 | C | |
| 18f | 97 | 4.45 | 542.4 | C | |
| 18g | 97 | 4.11 | 494.4 | C | |

TABLE 18-continued

| | Purity (%) | Retention time (min) | m/z [M + H]+ | Conditions | Example Structure |
|---|---|---|---|---|---|
| 18h | 98 | 4.60 | 518.4 | C | |
| 18i | 96 | 4.54 | 464.4 | C | |
| 18j | 98 | 4.83 | 526.4 | C | |
| 18k | 93 | 3.96 | 466.4 | C | |

TABLE 18-continued
| | Purity (%) | Retention time (min) | m/z [M + H]+ | Conditions | Example Structure |
|---|---|---|---|---|---|
| 18l | 79 | 8.73 | 559.5 | D | 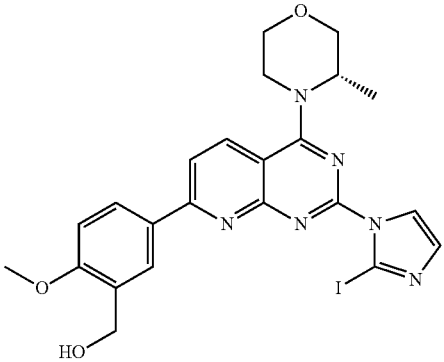 [SMILES: COc1ccc(-c2ccc3c(N4CCOC[C@@H]4C)nc(-n4ccnc4I)nc3n2)cc1CO] |
| 18m | 94 | 4.28 | 458.5 | D | 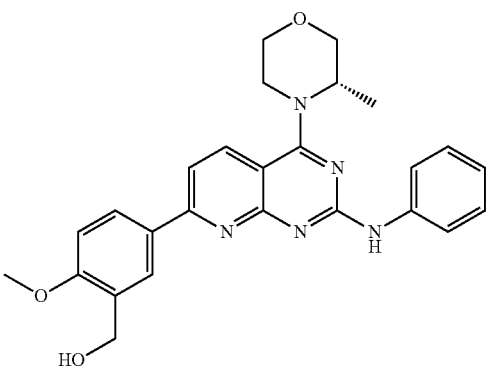 [SMILES: COc1ccc(-c2ccc3c(N4CCOC[C@@H]4C)nc(Nc4ccccc4)nc3n2)cc1CO] |
| 18n | 99 | 3.86 | 460.5 | D | 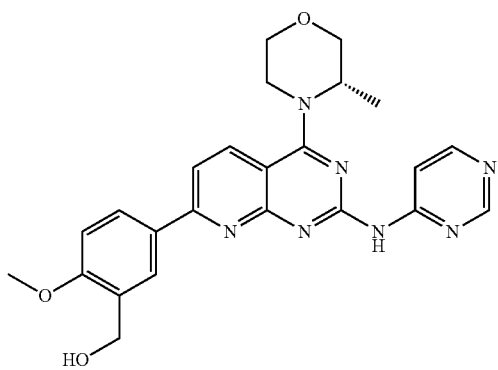 [SMILES: COc1ccc(-c2ccc3c(N4CCOC[C@@H]4C)nc(Nc4ccncn4)nc3n2)cc1CO] |
| 18o | 92 | 6.48 | 459.3 | D | 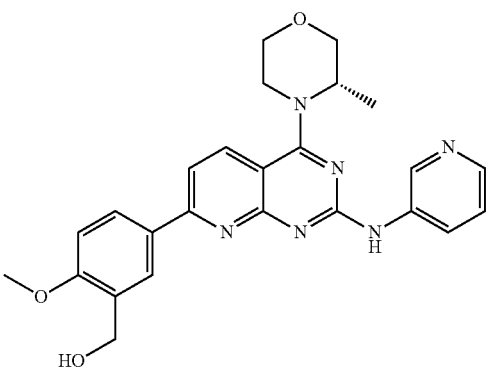 [SMILES: COc1ccc(-c2ccc3c(N4CCOC[C@@H]4C)nc(Nc4cccnc4)nc3n2)cc1CO] |

TABLE 18-continued

| | Purity (%) | Retention time (min) | m/z [M + H]+ | Conditions | Example Structure |
|---|---|---|---|---|---|
| 18p | 91 | 9.79 | 459.3 | D | |
| 18q | 91 | 8.03 | 436.3 | C | |
| 18r | 86 | 8.77 | 522.4 | C | |
| 18s | 81 | 5.59 | 479.4 | C | |

TABLE 18-continued
| | Purity (%) | Retention time (min) | m/z [M + H]+ | Conditions | Example Structure |
|---|---|---|---|---|---|
| 18t | 88 | 9.14 | 464.4 | C | 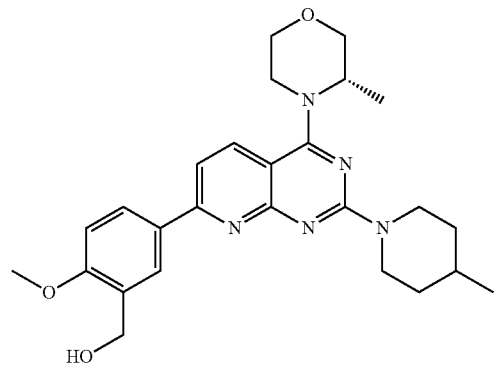 |
| 18u | 91 | 8.76 | 522.4 | C | 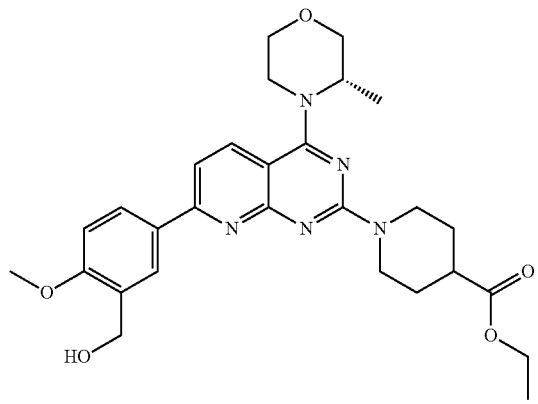 [SMILES: CCOC(=O)C1CCN(c2nc(N3CCOC[C@@H]3C)c3ccc(-c4ccc(OC)c(CO)c4)nc3n2)CC1] |
| 18v | 92 | 6.73 | 493.4 | C | 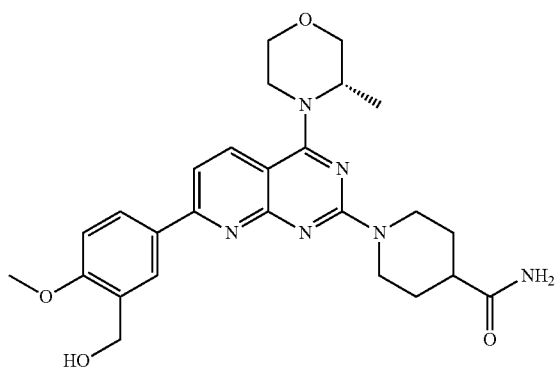 [SMILES: COc1ccc(-c2ccc3c(N4CCOC[C@@H]4C)nc(N4CCC(C(N)=O)CC4)nc3n2)cc1CO] |

TABLE 18-continued

| | Purity (%) | Retention time (min) | m/z [M + H]+ | Conditions | Example Structure |
|---|---|---|---|---|---|
| 18w | 87 | 9.69 | 584.5 | C | |
| 18x | 80 | 7.26 | 480.4 | C | |
| 18y | 85 | 7.41 | 480.4 | C | |
| 18z | 95 | 5.67 | 533.4 | C | |

TABLE 18-continued

| | Purity (%) | Retention time (min) | m/z [M + H]⁺ | Conditions | Example Structure |
|---|---|---|---|---|---|
| 18aa | 88 | 6.79 | 510.3 | C | |
| 18ab | 93 | 6.81 | 452.3 | C | |
| 18ac | 93 | 5.44 | 535.4 | C | |
| 18ad | 99 | 5.40 | 465.5 | E | |

TABLE 18-continued
| | Purity (%) | Retention time (min) | m/z [M + H]+ | Conditions | Example Structure |
|---|---|---|---|---|---|
| 18ae | 94 | 9.86 | 478.4 | C | 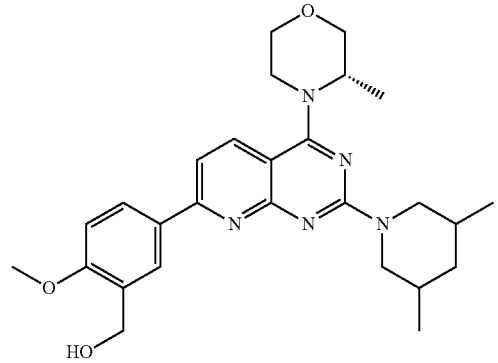 |
| 18af | 94 | 9.11 | 518.3 | C | 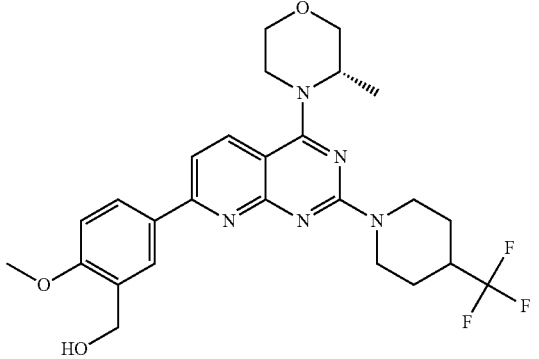 [SMILES: COc1ccc(-c2ccc3c(N4CCOC[C@@H]4C)nc(N4CCC(C(F)(F)F)CC4)nc3n2)cc1CO] |
| 18ag | 72, 25 | 10.37, 10.81 | 504.4 | C | 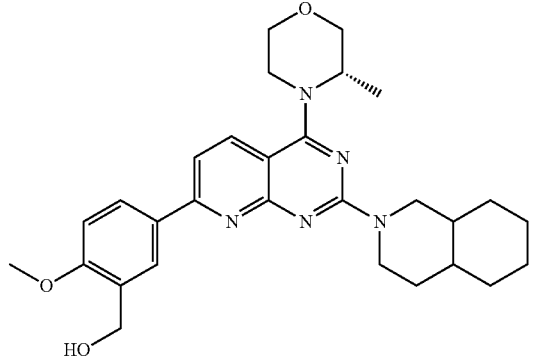 [SMILES: COc1ccc(-c2ccc3c(N4CCOC[C@@H]4C)nc(N4CCC5CCCCC5C4)nc3n2)cc1CO] |
| 18ah | 94 | 7.56 | 494.3 | C | 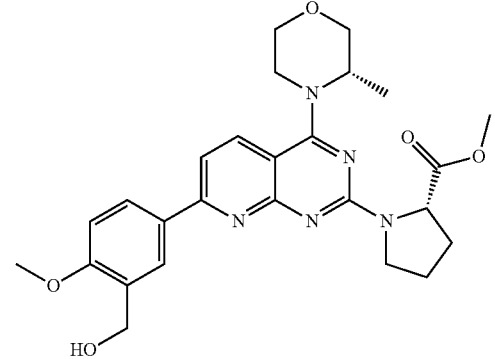 |

TABLE 18-continued

| | Purity (%) | Retention time (min) | m/z [M + H]+ | Conditions | Example Structure |
|---|---|---|---|---|---|
| 18ai | 96 | 5.55 | 519.4 | C | |
| 18aj | 99 | 7.82 | 480.4 | C | |
| 18ak | 96 | 10.49 | 588.4 | C | |

TABLE 18-continued
| | Purity (%) | Retention time (min) | m/z [M + H]+ | Conditions | Example Structure |
|---|---|---|---|---|---|
| 18al | 96 | 10.92 | 540.4 | C | 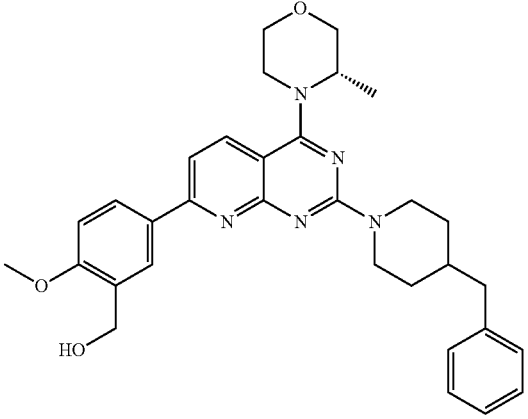 [SMILES: COc1ccc(-c2ccc3c(N4CCOC[C@@H]4C)nc(N4CCC(Cc5ccccc5)CC4)nc3n2)cc1CO] |
| 18am | 97 | 8.84 | 542.4 | C | 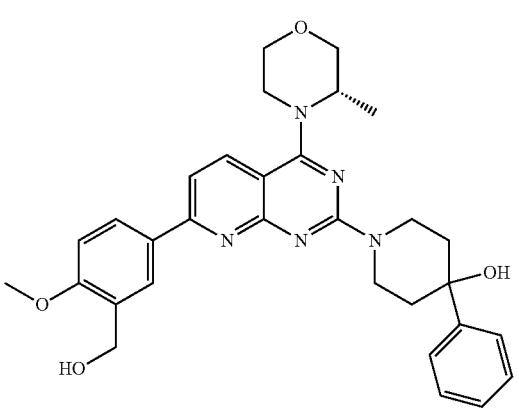 [SMILES: COc1ccc(-c2ccc3c(N4CCOC[C@@H]4C)nc(N4CCC(O)(c5ccccc5)CC4)nc3n2)cc1CO] |
| 18an | 95 | 9.74 | 551.4 | C | 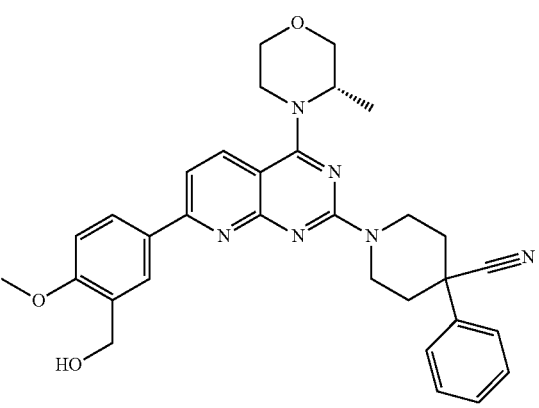 [SMILES: COc1ccc(-c2ccc3c(N4CCOC[C@@H]4C)nc(N4CCC(C#N)(c5ccccc5)CC4)nc3n2)cc1CO] |
| 18ao | 96 | 6.18 | 479.3 | C | 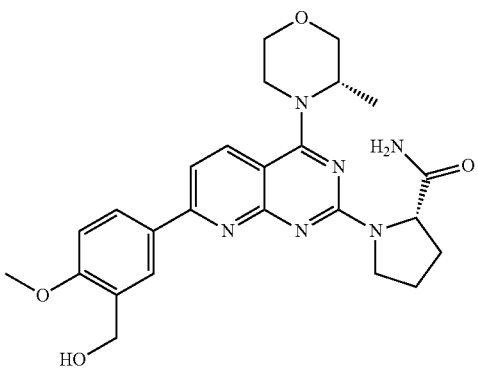 [SMILES: COc1ccc(-c2ccc3c(N4CCOC[C@@H]4C)nc(N4CCC[C@H]4C(N)=O)nc3n2)cc1CO] |

TABLE 18-continued

| | Purity (%) | Retention time (min) | m/z [M + H]+ | Conditions | Example Structure |
|---|---|---|---|---|---|
| 18ap | 92 | 8.46 | 450.3 | C | |
| 18aq | 97 | 10.99 | 560.4 | C | |
| 18ar | 89 | 8.12 | 532.4 | C | |
| 18as | 91 | 5.71 | 507.4 | C | |

TABLE 18-continued
| | Purity (%) | Retention time (min) | m/z [M + H]+ | Conditions | Example Structure |
|---|---|---|---|---|---|
| 18at | 99 | 10.88 | 679.4 | C | 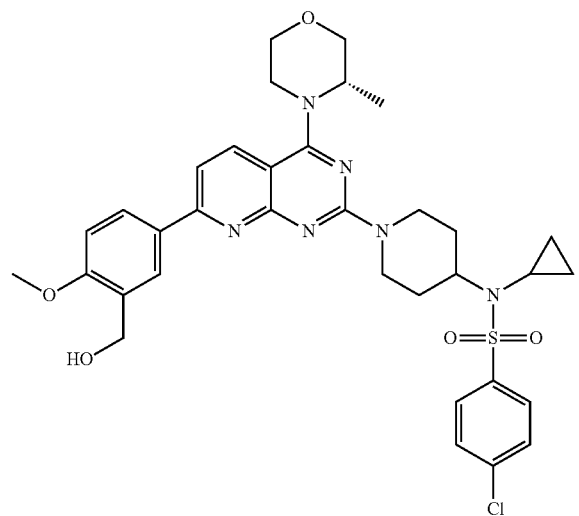 [SMILES: COc1ccc(-c2ccc3c(N4CCOC[C@@H]4C)nc(N4CCC(N(C5CC5)S(=O)(=O)c5ccc(Cl)cc5)CC4)nc3n2)cc1CO] |
| 18au | 85 | 5.37 | 465.4 | E | 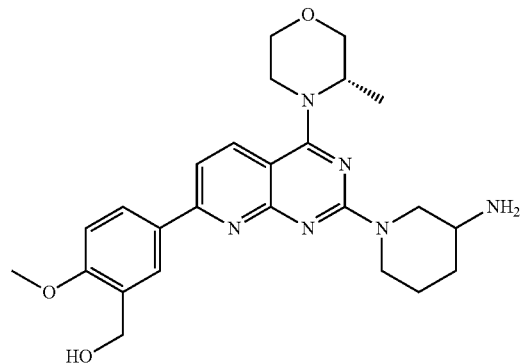 [SMILES: COc1ccc(-c2ccc3c(N4CCOC[C@@H]4C)nc(N4CCCC(N)C4)nc3n2)cc1CO] |
| 18av | 98 | 4.54 | 466.6 | C | 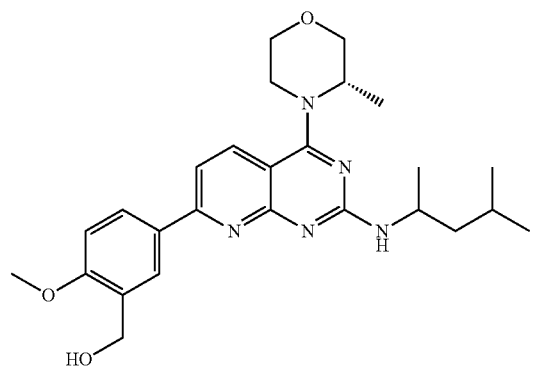 [SMILES: COc1ccc(-c2ccc3c(N4CCOC[C@@H]4C)nc(NC(C)CC(C)C)nc3n2)cc1CO] |

TABLE 18-continued
| | Purity (%) | Retention time (min) | m/z [M + H]+ | Conditions | Example Structure |
|---|---|---|---|---|---|
| 18aw | 98 | 4.30 | 450.5 | C | 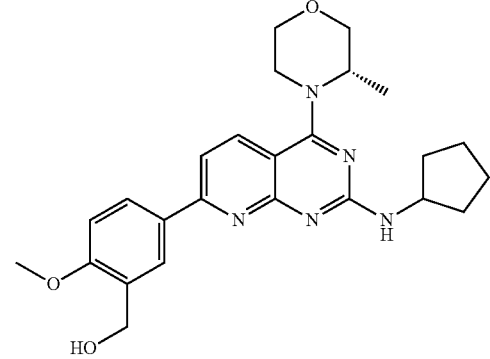 [SMILES: COc1ccc(-c2ccc3c(N4CCOC[C@@H]4C)nc(NC4CCCC4)nc3n2)cc1CO] |
| 18ax | 99 | 4.02 | 454.5 | C | 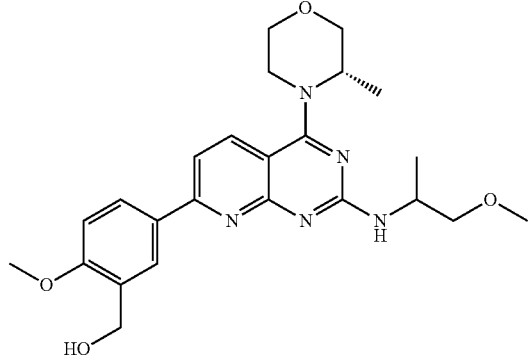 |
| 18ay | 100 | 3.83 | 433.4 | F | 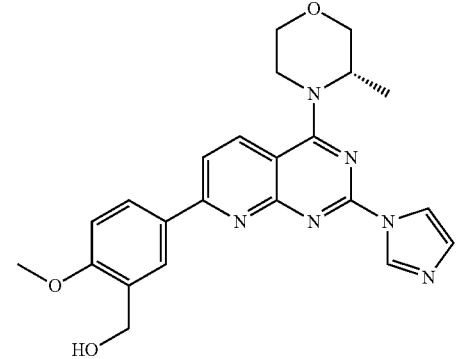 [SMILES: COc1ccc(-c2ccc3c(N4CCOC[C@@H]4C)nc(-n4ccnc4)nc3n2)cc1CO] |
| 18az | 92 | 9.32 | 491.4 | F | 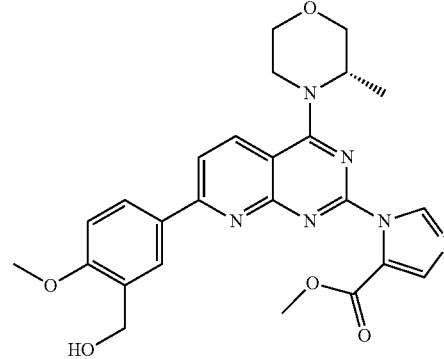 |

TABLE 18-continued
| | Purity (%) | Retention time (min) | m/z [M + H]⁺ | Conditions | Example Structure |
|---|---|---|---|---|---|
| 18ba | 93 | 4.54 | 475.4 | F | 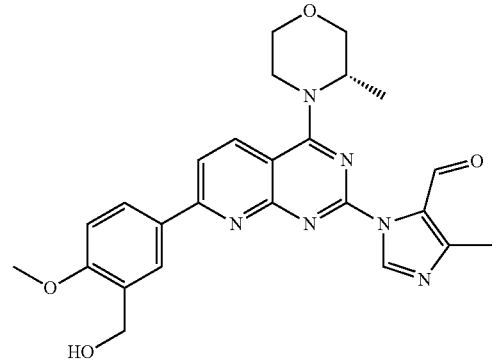 |
| 18bb | 100 | 5.06 | 511.4 | F | 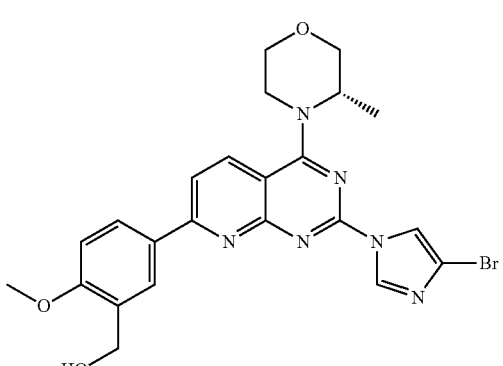 |
| 18bc | 97 | 10.48 | 525.3 | F | 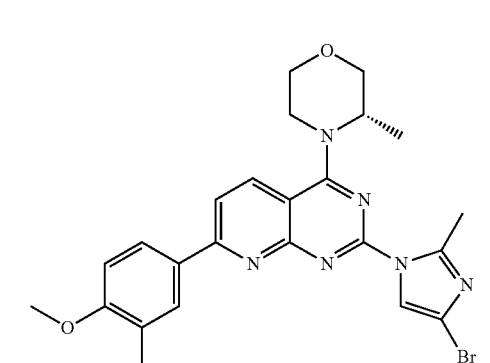 |
| 18bd | 10, 89 | 4.70, 4.77 | 492.5, 492.5 | C | 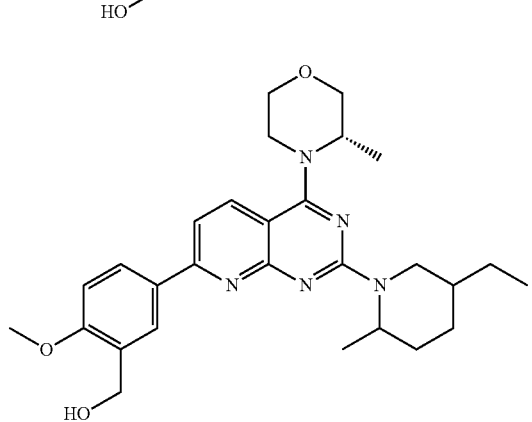 |

TABLE 18-continued
| | Purity (%) | Retention time (min) | m/z [M + H]+ | Conditions | Example Structure |
|---|---|---|---|---|---|
| 18be | 99 | 4.67 | 526.6 | C | 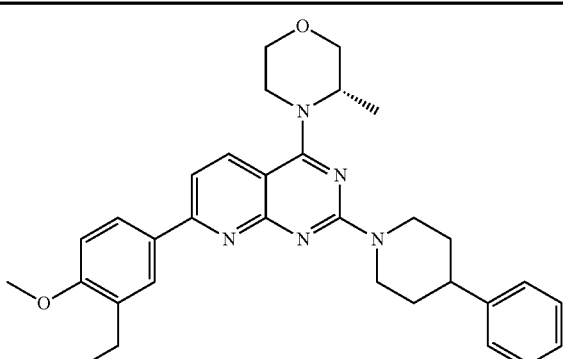 |
| 18bf | 99 | 4.48 | 528.5 | C | 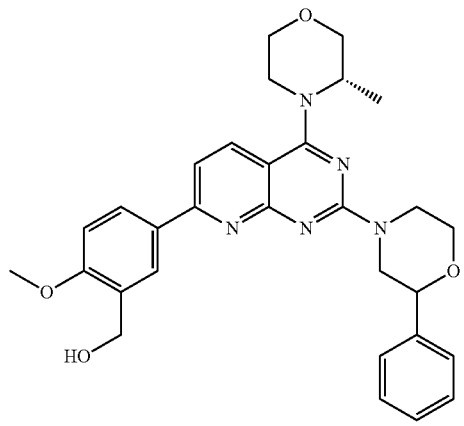 [SMILES: COc1ccc(-c2ccc3c(N4CCOC[C@@H]4C)nc(N4CCOC(c5ccccc5)C4)nc3n2)cc1CO] |
| 18bg | 98 | 4.38 | 464.5 | C | 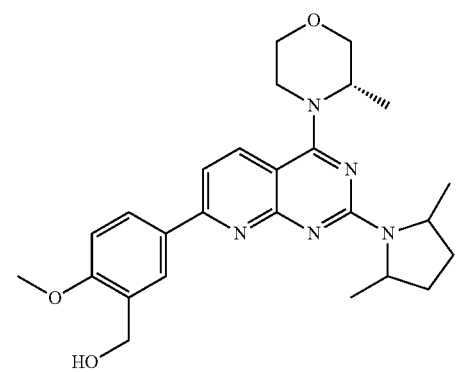 [SMILES: COc1ccc(-c2ccc3c(N4CCOC[C@@H]4C)nc(N4C(C)CCC4C)nc3n2)cc1CO] |
| 18bh | 98 | 4.37 | 464.5 | C | 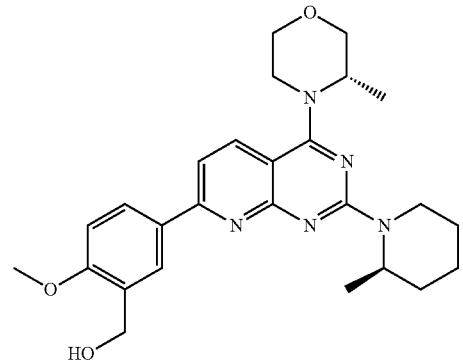 [SMILES: COc1ccc(-c2ccc3c(N4CCOC[C@@H]4C)nc(N4CCCC[C@H]4C)nc3n2)cc1CO] |

TABLE 18-continued

| | Purity (%) | Retention time (min) | m/z [M + H]+ | Conditions | Example Structure |
|---|---|---|---|---|---|
| 18bi | 100 | 3.56 | 527.5 | C | |
| 18bj | 99 | 3.84 | 466.4 | C | |
| 18bk | 99 | 3.83 | 466.4 | C | |
| 18bl | 95 | 9.06 | 500.5 | C | |

TABLE 18-continued

| | Purity (%) | Retention time (min) | m/z [M + H]+ | Conditions | Example Structure |
|---|---|---|---|---|---|
| 18bm | 98 | 7.65 | 480.5 | C | |
| 18bn | 97 | 3.78 | 452.5 | C | |
| 18bo | 95 | 4.03 | 454.4 | C | |
| 18bp | 98 | 4.01 | 396.4 | H | |

TABLE 18-continued

| | Purity (%) | Retention time (min) | m/z [M + H]+ | Conditions | Example Structure |
|---|---|---|---|---|---|
| 18bq | 99 | 4.14 | 410.4 | G | |
| 18br | 99 | 4.30 | 424.4 | H | |
| 18bs | 93 | 5.27 | 426.4 | C | |
| 18bt | 94 | 7.18 | 428.3 | H | |

TABLE 18-continued

| | Purity (%) | Retention time (min) | m/z [M + H]+ | Conditions | Example Structure |
|---|---|---|---|---|---|
| 18bu | 84 | 5.95 | 439.3 | I | |
| 18bv | 91 | 4.91 | 439.4 | C | |
| 18bw | 94 | 5.38 | 440.4 | G | |
| 18bx | 94 | 5.40 | 440.4 | G | |

TABLE 18-continued

| | Purity (%) | Retention time (min) | m/z [M + H]+ | Conditions | Example Structure |
|---|---|---|---|---|---|
| 18by | 92 | 5.44 | 440.4 | C | |
| 18bz | 97 | 5.52 | 446.3 | H | |
| 18ca | 90 | 4.92 | 451.4 | C | |
| 18cb | 93 | 4.95 | 453.4 | C | |

TABLE 18-continued

| | Purity (%) | Retention time (min) | m/z [M + H]+ | Conditions | Example Structure |
|---|---|---|---|---|---|
| 18cc | 96 | 5.50 | 454.4 | H | |
| 18cd | 92 | 5.18 | 456.4 | H | |
| 18ce | 96 | 5.37 | 463.4 | G | |
| 18cf | 91 | 5.31 | 465.4 | G | |
| 18cg | 92 | 4.95 | 465.4 | C | |

TABLE 18-continued

| | Purity (%) | Retention time (min) | m/z [M + H]+ | Conditions | Example Structure |
|---|---|---|---|---|---|
| 18ch | 93 | 5.73 | 468.3 | C | |
| 18ci | 99 | 4.95 | 495.4 | C | |
| 18cj | 97 | 5.79 | 498.4 | G | |
| 18ck | 91 | 5.28 | 470.3 | G | |

TABLE 18-continued

| | Purity (%) | Retention time (min) | m/z [M + H]+ | Conditions | Example Structure |
|---|---|---|---|---|---|
| 18cl | 93 | 5.57 | 466.3 | C | |
| 18cm | 92 | 5.58 | 466.3 | C | |
| 18cn | 97 | 6.87 | 447.3 | F | |
| 18co | 93 | 6.70 | 479.2 | C | |
| 18cp | 92 | 6.18 | 453.2 | J | |

TABLE 18-continued

| | Purity (%) | Retention time (min) | m/z [M + H]⁺ | Conditions | Example Structure |
|---|---|---|---|---|---|
| 18cq | 92 | 6.18 | 453.1 | J | |
| 18cr | 92 | 6.72 | 440.2 | C | |
| 18cs | 97 | 7.84 | 468.3 | I | |
| 18ct | 98 | 5.38 | 467.3 | I | |
| 18cu | 98 | 6.63 | 397.2 | K | |

TABLE 18-continued

| | Purity (%) | Retention time (min) | m/z [M + H]+ | Conditions | Example Structure |
|---|---|---|---|---|---|
| 18cv | 88 | 7.17 | 411.2 | L | |
| 18cw | 100 | 6.24 | 427.2 | K | |
| 18cx | 83 | 6.87 | 441.2 | L | |
| 18cy | 93 | 5.45 | 454.2 | K | |
| 18cz | 97 | 5.72 | 468.3 | K | |

TABLE 18-continued

| | Purity (%) | Retention time (min) | m/z [M + H]+ | Conditions | Example Structure |
|---|---|---|---|---|---|
| 18da | 98 | 7.96 | 489.3 | K | |
| 18db | 98 | 6.73 | 440.3 | K | |
| 18dc | 96 | 8.26 | 436.2 | K | |
| 18dd | 95 | 4.05 | 452.4 | J | |
| 18de | 93 | 5.36 | 438.2 | A | |

TABLE 18-continued

| | Purity (%) | Retention time (min) | m/z [M + H]+ | Conditions | Example Structure |
|---|---|---|---|---|---|
| 18df | 93 | 11.22 | 452.3 | A | |
| 18dg | 96 | 4.86 | 438.4 | A | |
| 18dh | 100 | 4.66 | 454.4 | A | |
| 18di | 100 | 4.37 | 426.4 | A | |

TABLE 18-continued

| | Purity (%) | Retention time (min) | m/z [M + H]⁺ | Conditions | Example Structure |
|---|---|---|---|---|---|
| 18dj | 98 | 7.86 | 467.4 | M | |
| 18dk | 97 | 4.77 | 463.2 | N | |
| 18dl | 99 | 4.78 | 408.1 | N | |
| 18dm | 97 | 4.89 | 477.3 | N | |

TABLE 18-continued

| | Purity (%) | Retention time (min) | m/z [M + H]+ | Conditions | Example Structure |
|---|---|---|---|---|---|
| 18dn | 97 | 4.03 | 466.2 | O | |
| 18do | 99 | 3.99 | 466.2 | O | |

NMR Data for Example 18b

¹H NMR (300 MHz, CDCl₃) δ ppm 8.85 (ArH, d, J=2.46 Hz, 1H), 8.64 (ArH, dd, J=8.75, 2.48 Hz, 1H), 8.30 (OH, s, br, 1H), 8.04 (ArH, d, J=8.47 Hz, 1H), 7.59 (ArH, d, J=8.54 Hz, 1H), 7.14 (ArH, d, J=8.83 Hz, 1H), 5.03-4.91 (CH₂, m, 1H), 4.66 (CH₂, dd, J=13.05, 0.77 Hz, 1H), 4.41 (CH₂, d, J=6.75 Hz, 1H), 4.07 (OCH₃, s, 3H), 4.04-3.98 (CH₂, m, 1H), 3.97-3.68 (CH₂, m, 11H), 3.60 (CH₂, d, J=2.75 Hz, 1H), 3.41 (CH₂, s, 1H), 1.50 (CH₃, d, J=6.77 Hz, 3H), 1.39 (CH₃, d, J=6.81 Hz, 3H)

NMR Data for Example 18k

¹H NMR (300 MHz, CHCl₃) δ ppm 10.59-10.51 (OH, m, 1H), 8.18 (ArH, dd, J=4.42, 2.17 Hz, 2H), 7.99 (ArH, d, J=8.45 Hz, 1H), 7.44 (ArH, d, J=8.48 Hz, 1H), 7.01 (ArH, d, J=9.22 Hz, 1H), 4.81 (CH₂OH, s, 2H), 4.37-4.11 (CH₂, m, 3H), 4.09-3.65 (OCH₃+CH₂, m, 13H), 2.02-1.94 (CH₂, m, 1H), 1.73-1.38 (CH₂, m, 1H), 1.50 (CH₃, d, J=6.77 Hz, 3H)

¹³C NMR (75 MHz, CDCl₃) δ ppm 162.05, 161.84, 161.81, 159.16, 150.47, 134.52, 129.29, 128.68, 128.43, 127.47, 117.04, 112.75, 110.28, 104.93, 104.30, 70.96, 67.12, 66.95, 66.77, 61.97, 55.57, 52.75, 50.99, 44.48 and 14.72.

NMR Data for Example 18v

¹H NMR (300 MHz, CDCl₃) δ ppm 8.07 (ArH, dd, J=7.09, 2.14 Hz, 2H), 7.89 (ArH, d, J=8.47 Hz, 1H), 7.33 (ArH, d, J=8.49 Hz, 1H), 6.91 (ArH, d, J=9.31 Hz, 1H), 6.88 (NH, S, Br, 1H), 5.34 (NH, s, Br, 1H), 4.95 (CH₂, dd, J=12.22, 0.66 Hz, 2H), 4.70 (CH₂OH, s, 2H), 4.34-4.20 (CH, m, 1H), 3.93-3.53 (OCH₃, +CH₂, m, 10H), 2.91 (CH₂, d, J=12.29 Hz, 2H), 2.38 (CH₂, s, 2H), 1.89 (CH₂, dd, J=6.92, 6.38 Hz, 2H), 1.76-1.54 (CH₂, m, 3H), 1.38 (CH₃, d, J=6.76 Hz, 3H)

¹³C NMR (75 MHz, CDCl₃) δ ppm 176.91, 165.39, 162.98, 161.80, 160.14, 159.13, 134.52, 131.20, 129.28, 128.84, 128.44, 119.99, 112.70, 110.26, 104.34, 70.97, 67.10, 66.94, 61.97, 55.57, 52.76, 44.52, 43.73, 43.69, 43.16, 26.88, and 14.70.

NMR Data for Example 18ab

¹H NMR (300 MHz, CDCl₃) δ ppm 8.19 (ArH, d, J=7.14 Hz, 2H), 8.00 (ArH, d, J=8.47 Hz, 1H), 7.43 (ArH, d, J=8.42 Hz, 1H), 7.01 (ArH, d, J=9.13 Hz, 1H), 4.82 (CH₂OH, s, 2H), 4.71-4.59 (CH₂, m, 1H), 4.47-4.35 (CH₂, m, 1H), 3.97 (OCH₃, s, 3H), 3.85 (CH₂, ddd, J=17.63, 13.74, 9.24 Hz, 8H), 2.12 (CH₂, s, Br, 5H), 1.50 (CH₃ d, J=6.75 Hz, 3H).

¹³C NMR (75 MHz, CDCl₃) ppm 159.35, 159.10, 134.61, 131.26, 129.22, 128.89, 128.54, 112.41, 110.21, 104.39, 71.06, 66.95, 61.99, 55.56, 52.80, 44.51, 27.01 and 14.78.

NMR Data for Example 18ax

¹H NMR (300 MHz, CDCl₃) δ ppm 8.27-8.17 (ArH, m, 2H), 8.00 (ArH, d, J=8.50 Hz, 1H), 7.45 (ArH, d, J=8.51 Hz, 1H), 7.01 (ArH, d, J=8.65 Hz, 1H), 5.40 (NH, br, s, 1H), 4.81 (CH₂OH, s, 2H), 4.49-4.35 (CH₂, m, 1H), 3.97 (OCH₃, s, 3H), 3.93-3.64 (CH₂, m, 6H), 3.58-3.48 (CH₂, m, 2H), 3.43 (OCH₃, s, 3H), 1.49 (CH₃, d, J=6.71 Hz, 3H), 1.34 (CH₃, d, J=6.68 Hz, 3H)

¹³C NMR (75 MHz, CDCl₃) δ ppm 165.67, 161.56, 160.64, 159.19, 134.53, 129.27, 128.83, 128.39, 112.53, 110.30, 76.23, 70.98, 67.00, 62.02, 59.18, 55.57, 52.73, 44.31, 18.23, 18.20 and 14.85.

NMR Data for Example 18bn

¹H NMR (300 MHz, CDCl₃) δ ppm 8.23-8.15 (ArH, m, 2H), 7.99 (ArH, d, J=8.45 Hz, 1H), 7.42 (ArH, d, J=8.46 Hz, 1H), 7.00 (ArH, d, J=8.35 Hz, 1H), 4.81 (CH₂OH, s, 2H), 4.65 (CH, s, br, 1H), 4.05-3.64 (OCH₃+CH₂, m, 13H), 3.24 (OH, s, 1H), 1.50 (CH₃, d, J=6.73 Hz, 3H).

¹³C NMR (75 MHz, CDCl₃) δ ppm 165.18, 162.87, 159.34, 159.06, 134.57, 131.25, 129.26, 128.84, 128.47, 112.36, 110.20, 104.35, 71.00, 70.97, 66.94, 61.91, 55.55, 52.82, 44.43, 27.01 and 14.87.

NMR Data for Example 18bo

¹H NMR (300 MHz, CDCl₃) δ ppm 8.28-8.17 (ArH, m, 2H), 8.00 (ArH, d, J=8.49 Hz, 1H), 7.45 (ArH, d, J=8.50 Hz, 1H), 7.02 (ArH, d, J=8.60 Hz, 1H), 5.51-5.34 (CH, m, 1H), 4.81 (CH₂OH, s, 2H), 4.47-4.34 (CH, m, 1H), 4.00 (CH₂, d, J=1.94 Hz, 1H), 3.97 (OCH₃, s, 3H), 3.93-3.89 (CH2, m, 2H), 3.83-3.63 (CH₂, m, 4H), 3.53 (CH₂, d, br, J=4.02 Hz, 2H), 3.43 (OCH₃, s, 3H), 1.50 (CH₃, d, J=6.73 Hz, 3H), 1.34 (CH₃, d, J=6.69 Hz, 3H)

¹³C NMR (75 MHz, CDCl₃) δ ppm 165.69, 161.55, 160.67, 159.19, 134.52, 131.15, 129.26, 128.84, 128.41, 119.72, 112.58, 110.30, 70.98, 67.12, 67.00, 62.05, 59.18, 55.58, 52.73, 44.32, 18.20 and 14.84.

NMR Data for Example 18dj

¹H NMR (300 MHz, CDCl₃) δ ppm 8.10-8.03 (ArH, m, 2H), 7.95 (ArH, d, J=8.41 Hz, 1H), 7.42-7.30 (ArH, m, 3H), 5.52-5.27 (NH₂, m, br, 2H), 4.98 (CH₂, dd, J=12.74, 0.96 Hz, 2H), 4.31-4.29 (CH, m, 1H), 3.97-3.55 (CH₂, m, 8H), 3.07-2.86 (CH₂, m, 2H), 2.45-2.35 (CH₂, m, 1H), 1.99-1.88 (CH₂, m, br, 2H), 1.70 (CH₂, m, 2H), 1.41 (CH₃, d, J=6.76 Hz, 3H)

¹³C NMR (75 MHz, CDCl₃) δ ppm 176.75, 170.03, 165.35, 162.99, 161.12, 160.17, 137.17, 136.10, 134.83, 129.19, 128.76, 112.81, 104.86, 100.00, 70.95, 67.12, 66.91, 52.83, 44.50, 43.72, 43.68, 43.10, 28.88 and 14.73.

NMR Data for Example 18dk

¹H NMR (300 MHz, CDCl₃) δ ppm 8.67 (ArH, d, J=1.86 Hz, 1H), 8.38 (ArH, dd, J=8.76, 2.36 Hz, 1H), 8.29 (NH, s, weak signal, 1H), 7.91 (ArH, d, J=8.45 Hz, 1H), 7.27 (ArH, d, J=8.46 Hz, 1H), 6.58 (ArH, d, J=8.75 Hz, 1H), 5.54-5.45 (CH₂, m, 1H), 4.97 (NH₂, br, s, 2H), 4.37-4.24 (CH₂, m, 1H), 3.97-3.54 (CH₂, m, 6H), 3.09-2.87 (CH₂, m, 2H), 2.77 (NHCH₃, d, J=4.82 Hz, 3H), 2.42-2.24 (CH₂, m, 1H), 1.87 (CH₂, d, J=0.84 Hz, 2H), 1.79-1.59 (CH₂, m, 2H), 1.40 (CH₃, d, J=6.76 Hz, 3H).

NMR Data for Example 18dl

¹H NMR (300 MHz, CDCl₃) δ ppm 8.68 (ArH, d, J=1.98 Hz, 1H), 8.49 (ArH, dd, J=8.87, 2.32 Hz, 1H), 8.38 (NH, s, br, weak signal 1H), 7.99 (ArH, d, J=8.47 Hz, 1H), 7.34 (ArH, d, J=8.49 Hz, 1H), 6.67 (ArH, d, J=8.85 Hz, 1H), 4.38 (CH₂, d, J=6.77 Hz, 1H), 4.05-3.82 (CH₂, m, 7H), 3.81-3.62 (CH₂, m, 7H), 1.47 (CH₃, d, J=6.77 Hz, 3H).

¹³C NMR (75 MHz, CDCl₃) δ ppm 165.16, 162.79, 160.31, 159.09, 158.45, 143.98, 139.12, 135.00, 124.48, 111.80, 110.03, 104.70, 70.92, 67.00, 66.90, 52.81, 44.57, 44.40 and 14.78.

NMR Data for Example 18dm

¹H NMR (300 MHz, CDCl₃) δ ppm 8.67 (ArH, d, J=2.05 Hz, 1H), 8.36 (ArH, dd, J=8.76, 2.27 Hz, 1H), 7.90 (ArH, dd, J=8.45, 2.12 Hz, 1H), 7.26 (ArH, dd, J=8.47, 0.73 Hz, 1H), 6.57 (ArH, d, J=8.76 Hz, 1H), 5.10-4.87 (NH₂, m, 2H), 4.37-4.22 (CH₂, m, 1H), 3.96-3.51 (CH₂, m, 6H), 3.08 (NCH₃+CH₂, s, 4H), 2.95-2.91 (NCH₃, s, 3H), 2.80-2.59 (CH₂, m, 1H), 1.76 (CH₂, d, J=2.61 Hz, 3H), 1.64-1.44 (CH, m, 1H), 1.38 (CH₃, t, J=6.34, 6.34 Hz, 3H).

¹³C NMR (75 MHz, CDCl₃) δ ppm 173.59, 165.46, 165.31, 163.03, 160.17, 158.89, 145.99, 138.35, 134.76, 124.89, 111.71, 109.15, 104.41, 70.96, 66.96, 52.81, 46.85, 44.38, 39.43, 37.26, 35.56, 28.06, 24.95 and 14.71.

NMR Data for Example 18dn

¹H NMR (300 MHz, CDCl₃) δ ppm 8.10 (ArH, d, J=7.89 Hz, 2H), 7.97 (ArH, d, J=8.49 Hz, 1H), 7.42 (ArH, d, J=8.46 Hz, 1H), 6.98 (ArH, d, J=8.55 Hz, 1H), 4.88 (CH₂, d, J=5.25 Hz, 1H), 4.77 (CH₂OH, s, 2H), 4.56 (CH₂, d, J=13.38 Hz, 1H), 4.38-4.36 (CH₂, m, 1H), 4.02-3.51 (OCH₃+CH₂, m, 11H), 3.43-3.33 (CH₂, m, 1H), 1.47 (CH₃, d, J=6.77 Hz, 3H), 1.35 (CH₃, d, J=6.78 Hz, 3H).

¹³C NMR (75 MHz, CD₃COCD₃) δ ppm 165.11, 162.27, 161.87, 159.54, 159.23, 134.74, 130.76, 129.41, 128.86, 128.39, 113.09, 110.32, 104.45, 71.20, 70.95, 67.17, 66.91, 61.80, 55.57, 52.82, 47.05, 44.44, 39.45, 14.74 and 14.44.

NMR Data for Example 18do

¹H NMR (300 MHz, CDCl₃) δ ppm 8.10 (ArH, d, J=8.76 Hz, 2H), 7.98 (ArH, d, J=8.49 Hz, 1H), 7.42 (ArH, d, J=8.46 Hz, 1H), 6.97 (ArH, d, J=8.37 Hz, 1H), 4.88 (CH₂, d, J=5.46 Hz, 1H), 4.77 (CH₂OH, s, 2H), 4.58-4.49 (CH₂, m, 1H), 4.39-4.36 (CH₂, d J=7.41 Hz, 1H), 4.02-3.51 (OCH₃+CH₂, m, 11H), 3.43-3.33 (CH₂, m, 1H), 1.48 (CH₃, d, J=6.78 Hz, 3H), 1.35 (CH₃, d, J=6.78 Hz, 3H).

¹³C NMR (75 MHz, CD₃COCD₃) δ ppm 165.05, 161.87, 159.45, 159.24, 134.78, 130.70, 129.44, 128.86, 128.38, 113.14, 110.33, 104.43, 71.19, 70.95, 67.16, 66.90, 61.77, 55.57, 52.82, 47.08, 44.44, 39.47, 14.76 and 14.44.

Tested in Alternative Enzyme Assay: Ex. (18a) 0.03 μM; Ex. (18b) 0.1 μM; Ex. (18c) 0.066 μM; Ex. (18d) 0.15 μM; Ex. (18e) 0.039 μM; Ex. (18f) 0.038 μM; Ex. (18g) 0.031 μM; Ex. (18h) 0.23 μM; Ex. (18i) 0.03 μM; Ex. (18j) 0.088 μM; Ex. (18k) 0.019 μM; Ex. (18l) 0.097 μM; Ex. (18m) 0.042 μM; Ex. (18n) 0.31 μM; Ex. (18o) 0.51 μM; Ex. (18p) 0.25 μM; Ex. (18q) 0.11 μM; Ex. (18r) 0.18 μM; Ex. (18s) 0.037 μM; Ex. (18t) 0.054 μM; Ex. (18u) 0.073 μM; Ex. (18v) 0.014 μM; Ex. (18w) 0.25 μM; Ex. (18x) 0.014 μM; Ex. (18y) 0.023 μM; Ex. (18z) 0.088 μM; Ex. (18aa) 0.019 μM; Ex. (18ab) 0.012 μM; Ex. (18ac) 0.014 μM; Ex. (18ad) 0.078 μM; Ex. (18ae) 0.034 μM; Ex. (18af) 0.23 μM; Ex. (18ag) 0.25 μM; Ex. (18ah) 0.03 μM; Ex. (18ai) 0.063 μM; Ex. (18aj) 0.022 μM; Ex. (18ak) 0.42 μM; Ex. (18al) 0.36 μM; Ex. (18am) 0.077 μM; Ex. (18an) 0.14 μM; Ex. (18ao) 0.073 μM; Ex. (18ap) 0.013 μM; Ex. (18aq) 0.19 μM; Ex. (18ar) 0.079 μM; Ex. (18as) 0.08 μM; Ex. (18at) 0.78 μM; Ex. (18au) 0.11 μM; Ex. (18av) 0.27 μM; Ex. (18aw) 0.058 μM; Ex. (18ax) 0.026 μM; Ex. (18ay) 0.087 μM; Ex. (18az) 0.092 μM; Ex. (18ba) 0.16 μM; Ex. (18bb) 0.65 μM; Ex. (18bc) 0.043 μM; Ex. (18bd) 0.19 μM; Ex. (18be) 0.79 μM; Ex. (18bf) 0.077 μM; Ex. (18bg) 0.047 μM; Ex. (18bh) 0.04 μM; Ex. (18bi) 0.32 μM; Ex. (18bj) 0.024 μM; Ex. (18bk) 0.022 μM; Ex. (18bl) 0.61 μM; Ex. (18bm) 0.025 μM; Ex. (18bn) 0.01 μM; Ex. (18bo) 0.058 μM; Ex. (18 bp) 0.049 μM; Ex. (18bq) 0.072 μM; Ex. (18br) 0.03 μM; Ex. (18bs) 0.042 μM; Ex. (18bt) 0.062 μM; Ex. (18bu) 0.047 μM; Ex. (18bv) 0.11 μM; Ex. (18bw) 0.031 μM; Ex. (18bx) 0.035 μM; Ex. (18by) 0.039 μM; Ex. (18bz) 0.01 μM; Ex. (18ca) 0.0026 μM; Ex. (18cb) 0.25 μM; Ex. (18cc) 0.018 μM; Ex. (18cd) 0.025 μM; Ex. (18ce) 0.37 μM; Ex. (18cf) 0.013 μM; Ex. (18cg) 0.067 μM; Ex. (18ch) 0.078 μM; Ex. (18ci) 0.068 μM; Ex. (18cj) 0.055 μM; Ex. (18ck) 0.0095 μM; Ex. (18cl) 0.023 μM; Ex. (18 cm) 0.029 μM; Ex. (18cn) 0.013 μM; Ex. (18co) 0.0052 μM; Ex. (18cp) 0.0057 μM; Ex. (18cq) 0.027 μM; Ex. (18cr) 0.0063 μM; Ex. (18cs) 0.0047 μM; Ex. (18ct) 0.097 μM; Ex. (18cu) 0.08 μM; Ex. (18cv) 0.043 μM; Ex. (18cw) 0.034 μM; Ex. (18cx) 0.024 μM; Ex. (18cy) 0.12 μM; Ex. (18cz) 0.079 μM; Ex. (18da) 0.71 μM; Ex. (18db) 0.0031 μM; Ex. (18dc) 0.21 μM; Ex. (18dd) 0.028 μM; Ex. (18de) 0.26 μM; Ex. (18df) 0.4 μM; Ex. (18dg) 0.3 μM; Ex. (18dh) 0.15 μM; Ex. (18di) 0.15 μM; Ex. (18dj) 0.052 μM; Ex. (18dm) 0.061 μM; Ex. (18dn) 0.0094 μM; Ex. (18do) 0.026 μM. Tested in phospho-Ser473 Akt assay: Ex. (18dk) 0.6821 μM; Ex. (18dl) 0.2951 μM.

Example 19

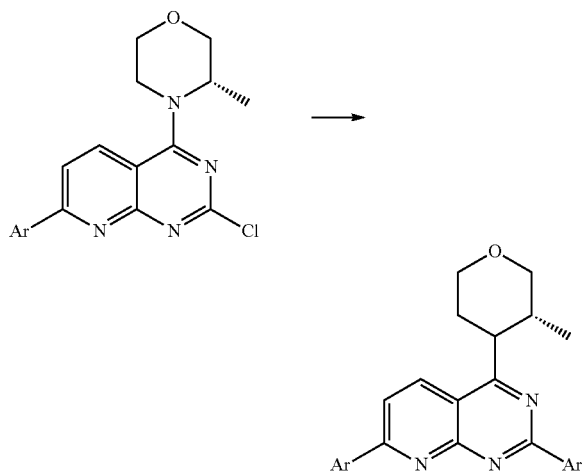

The chloro-substrates were reported in Example 18. (Compounds 19a to 19x)

Conditions A:

To a mixture of the appropriate chloro-substrate (1 equiv), potassium carbonate (3.5 equiv), and the appropriate boronic acid (1.0 equiv) in acetonitrile/water (1:1) (0.026 M of chloro-substrate) was added tetrakis(triphenylphosphine)palladium⁰ (0.05 equiv). The reaction vessel was sealed and heated at 95° C. for 2 hours. Upon completion the samples were filtered through a silica cartridge, washed with $CH_2Cl_2$ and methanol and then concentrated in vacuo. The crude residue was then purified by preparative HPLC to give the desired products.

Conditions B:

To a mixture of the appropriate chloro-substrate (1 equiv), cesium fluoride (3.5 equiv), and the appropriate boronic acid (1.0 equiv) in acetonitrile (0.026 M of chloro-substrate) was added tetrakis(triphenylphosphine)palladium⁰ (0.05 equiv). The reaction vessel was sealed and heated at 95° C. for 2 hours. Upon completion the samples were filtered through a silica cartridge, washed with $CH_2Cl_2$ and methanol and then concentrated in vacuo. The crude residue was then purified by preparative HPLC to give the desired products.

Conditions C:

To a mixture of the appropriate chloro-substrate (1 equiv), potassium carbonate (2.5 equiv), and the appropriate pinacolate boron ester or boronic acid (1.1 equiv) in acetonitrile/water (1:1) (0.041 M of chloro-substrate) was added tetrakis(triphenylphosphine)palladium⁰ (0.05 equiv). The reaction vessel was sealed and exposed to microwave radiation (150° C., medium absorption setting) for 30 minutes under nitrogen atmosphere. Upon completion the samples were concentrated in vacuo. The crude residue was then purified by preparative HPLC to give the desired products.

TABLE 19

| | Purity (%) | Retention time (min) | m/z [M + H]⁺ | Conditions | Example Structure |
|---|---|---|---|---|---|
| 19a | 93 | 7.66 | 433.2 | A | 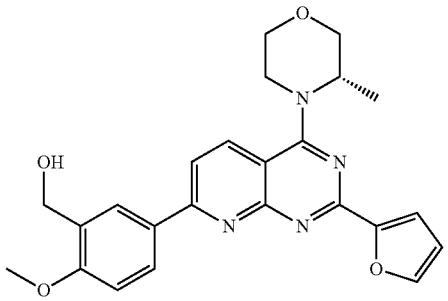 [SMILES: COc1ccc(-c2ccc3c(N4CCOC[C@@H]4C)nc(-c4ccco4)nc3n2)cc1CO] |
| 19b | 88 | 8.95 | 471.3 | A | 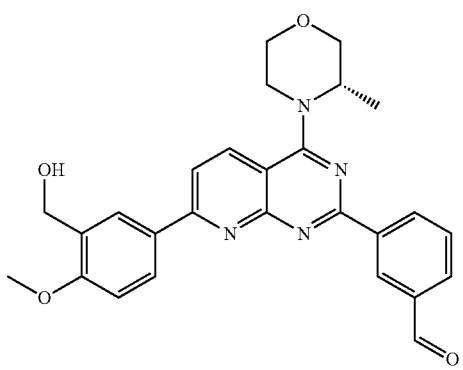 [SMILES: COc1ccc(-c2ccc3c(N4CCOC[C@@H]4C)nc(-c4cccc(C=O)c4)nc3n2)cc1CO] |

TABLE 19-continued

| | Purity (%) | Retention time (min) | m/z [M + H]+ | Conditions | Example Structure |
|---|---|---|---|---|---|
| 19c | 79 | 7.54 | 473.3 | A | |
| 19d | 92 | 11.14 | 519.3 | A | |
| 19e | 99 | 6.14 | 472.3 | A | |
| 19f | 90 | 7.43 | 458.3 | A | |

TABLE 19-continued

| | Purity (%) | Retention time (min) | m/z [M + H]+ | Conditions | Example Structure |
|---|---|---|---|---|---|
| 19g | 84 | 10.52 | 532.3 | A | |
| 19h | 75 | 9.58 | 501.3 | B | |
| 19i | 94 | 11.13 | 488.3 | A | |
| 19j | 84 | 7.36 | 444.3 | A | |
| 19k | 88 | 7.33 | 486.3 | A | |

TABLE 19-continued

| | Purity (%) | Retention time (min) | m/z [M + H]+ | Conditions | Example Structure |
|---|---|---|---|---|---|
| 19l | 88 | 8.75 | 487.3 | A | |
| 19m | 93 | 11.64 | 511.3 | A | |
| 19n | 87 | 9.26 | 457.3 | A | |
| 19o | 89 | 9.05 | 473.3 | A | |

TABLE 19-continued

| | Purity (%) | Retention time (min) | m/z [M + H]+ | Conditions | Example Structure |
|---|---|---|---|---|---|
| 19p | 97 | 4.31 | 444.3 | C | |
| 19q | 95 | 4.13 | 414.2 | C | |
| 19r | 94 | 4.14 | 414.2 | C | |
| 19s | 97 | 4.43 | 444.2 | C | |

TABLE 19-continued

| | Purity (%) | Retention time (min) | m/z [M + H]+ | Conditions | Example Structure |
|---|---|---|---|---|---|
| 19t | 98 | 4.28 | 444.2 | C | |
| 19u | 87 | 4.41 | 432.2 | C | |
| 19v | 98 | 4.07 | 417.2 | C | |
| 19w | 96 | 4.12 | 445.3 | C | |

TABLE 19-continued

| | Purity (%) | Retention time (min) | m/z [M + H]+ | Conditions | Example Structure |
|---|---|---|---|---|---|
| 19x | 99 | 5.66 | 418.2 | A | 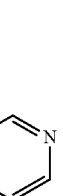 |

NMR Data for Example 19j

¹H NMR (300 MHz, DMSO) δ ppm 9.63 (ArH, d, J=1.49 Hz, 1H), 8.84-8.69 (ArH, m, 2H), 8.49-8.37 (ArH, m, 1H), 8.19 (ArH, dd, J=8.61, 2.35 Hz, 1H), 8.00 (ArH, d, J=8.76 Hz, 1H), 7.57 (ArH, ddd, J=7.99, 4.81, 0.71 Hz, 1H), 7.15 (ArH, d, J=8.71 Hz, 1H), 5.23 (ArH, dd, J=2.03, 1.13 Hz, 1H), 5.23 (CH, m, 1H), 4.78 (CH, d, J=6.83 Hz, 1H), 4.61 (CH₂OH, s, 2H), 4.22 (CH₂, d, J=13.08 Hz, 1H), 4.03-3.92 (CH₂, m, 1H), 3.98 (OCH₃, s, 3H), 3.88-3.61 (CH₂, m, 3H), 2.50 1.49 (CH₃, d, J=6.79 Hz, 3H)

¹³C NMR (75 MHz, DMSO) δ ppm 164.91, 161.77, 161.25, 160.36, 158.71, 151.75, 149.97, 136.10, 133.86, 131.45, 129.97, 127.92, 126.79, 124.08, 117.24, 110.92, 108.15, 70.77, 66.83, 66.80, 58.39, 56.04, 52.15, 44.39 and 15.24.

NMR Data for Example 19x

¹H NMR (300 MHz, CDCl₃) δ ppm 9.86-9.80 (ArH, m, 1H), 9.00-8.91 (ArH, m, 1H), 8.77 (ArH, dd, J=4.80, 1.71 Hz, 3H), 8.28 (ArH, ddd, J=9.24, 8.03, 5.57 Hz, 1H), 7.83 (ArH, d, J=8.64 Hz, 2H), 7.60-7.53 (ArH, m, 2H), 7.53-7.43 (CH, m, 1H), 4.72 (CH₂, d, J=6.93 Hz, 1H), 4.33-4.23 (CH₂, m, 1H), 4.00-3.80 (CH₂, m, 4H), 1.65 (CH₃, d, J=6.81 Hz, 3H)

¹³C NMR (75 MHz, CDCl₃) δ ppm 164.55, 161.73, 161.53, 151.52, 150.66, 136.99, 136.34, 134.91, 133.42, 129.34, 129.12, 123.19, 119.66, 117.15, 108.64, 106.49, 70.98, 67.02, 52.92, 44.49 and 15.16.

Tested in Alternative Enzyme Assay: Ex. (19a) 0.048 μM; Ex. (19b) 0.018 μM; Ex. (19c) 0.052 μM; Ex. (19d) 0.25 μM; Ex. (19e) 0.11 μM; Ex. (19f) 0.096 μM; Ex. (19g) 0.0087 μM; Ex. (19h) 0.77 μM; Ex. (19i) 0.28 μM; Ex. (19j) 0.057 μM; Ex. (19k) 0.077 μM; Ex. (19l) 0.12 μM; Ex. (19m) 0.41 μM; Ex. (19n) 0.22 μM; Ex. (19) 0.19 μM; Ex. (19p) 0.24 μM; Ex. (19q) 0.14 μM; Ex. (19r) 0.012 μM; Ex. (19s) 2 μM; Ex. (19t) 0.097 μM; Ex. (19u) 0.055 μM; Ex. (19v) 0.07 μM; Ex. (19w) 0.086 μM; Ex. (19x) 0.81 μM.

Example 20

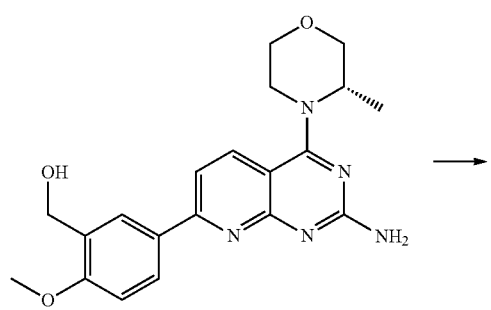

-continued

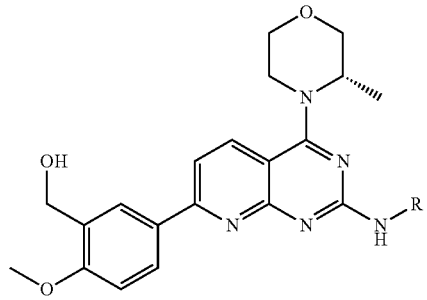

The amino substrate was reported in Example 18.

(Compounds 20a to 20c)

Conditions A:

The appropriate amino-substrate (1 equiv) was suspended in THF (0.04 M). The appropriate sulfonyl chloride (2.0 equiv) was added. The reaction vessel was sealed and exposed to microwave radiation (140° C., medium absorption setting) for 10 minutes. Upon completion the samples were concentrated in vacuo. The crude residue was then purified by preparative HPLC to give the desired products.

Conditions B:

The appropriate amino-substrate (1 equiv) was suspended in DMF (0.04 M). The appropriate acyl chloride (1.2 equiv) and potassium carbonate (2.4 equiv) were added. The reaction vessel was sealed and exposed to microwave radiation (140° C., medium absorption setting) for 10 minutes. Upon completion the samples were concentrated in vacuo. The crude residue was then purified by preparative HPLC to give the desired products.

Conditions C:

The appropriate amino-substrate (1 equiv) was suspended in DMF (0.09 M). The appropriate acyl chloride (3.0 equiv) was added. The reaction vessel was sealed and exposed to microwave radiation (130° C., medium absorption setting) for 15 minutes. Upon completion the samples were concentrated in vacuo. The crude residue was then purified by preparative HPLC to give the desired products.

TABLE 20

| | Purity (%) | Retention time (min) | m/z [M + H]+ | Conditions | Example Structure |
|---|---|---|---|---|---|
| 20a | 93 | 4.67 | 536.5 | A | |
| 20b | 97 | 4.58 | 486.4 | B | |
| 20c | 85 | 4.56 | 436.3 | C | |

Tested in Alternative Enzyme Assay: Ex. (20a) 1.4 µM; Ex. (20b) 0.67 µM; Ex. (20c) 0.024 µM.

Example 21

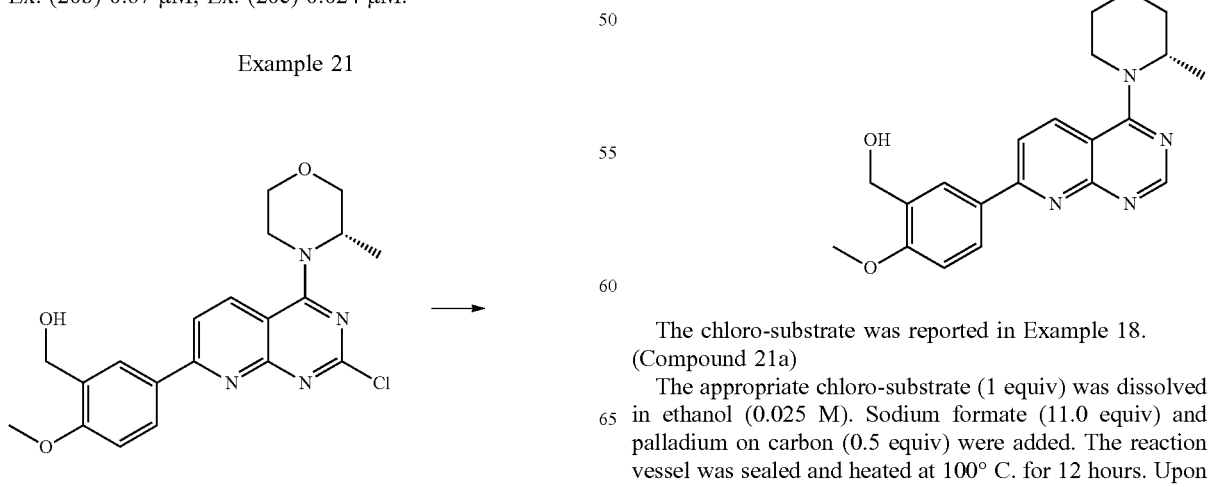

-continued

The chloro-substrate was reported in Example 18. (Compound 21a)

The appropriate chloro-substrate (1 equiv) was dissolved in ethanol (0.025 M). Sodium formate (11.0 equiv) and palladium on carbon (0.5 equiv) were added. The reaction vessel was sealed and heated at 100° C. for 12 hours. Upon completion the sample was filtered through Celite™, and the filtrate was concentrated in vacuo. The crude residue was then purified by reverse phase chromatography eluting with a gradient of 5 to 95% acetonitrile in 0.1% formic acid/water, to give the desired product.

TABLE 21

| | Purity (%) | Retention time (min) | m/z [M + H]⁺ | Example Structure |
|---|---|---|---|---|
| 21a | 97 | 5.94 | 367.3 | 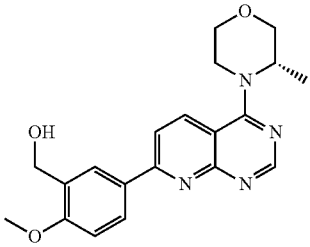 |

NMR Data for Example 21a $^1$H NMR (300 MHz, DMSO) δ ppm 8.70 (ArH, s, 1H), 8.42-8.37 (ArH, m, 2H), 8.16 (ArH, dd, J=8.59, 2.34 Hz, 1H), 8.01 (ArH, d, J=8.79 Hz, 1H), 7.14 (ArH, d, J=8.69 Hz, 1H), 5.20 (CH, t, J=5.67, 5.67 Hz, 1H), 4.59 (CH$_2$, d, J=5.61 Hz, 2H), 4.05-3.93 (CH$_2$, m, 2H), 3.89 (OCH$_3$, s, 3H), 3.80-3.59 (CH$_2$, m, 4H), 3.57 (s, 1H), 3.31 (s, 1H), 2.50 (td, J=3.64, 1.80, 1.80 Hz, 1H), 1.42 (CH$_3$, d, J=6.79 Hz, 3H)

$^{13}$C NMR (75 MHz, DMSO) δ ppm 164.04, 161.48, 160.52, 158.69, 157.38, 136.11, 131.43, 129.96, 127.87, 126.77, 117.33, 110.93, 109.11, 70.71, 66.83, 58.37, 56.03, 52.14, 44.28 and 15.17.

Tested in Alternative Enzyme Assay: Ex. (21a) 0.2 μM.

Comparative Example 1

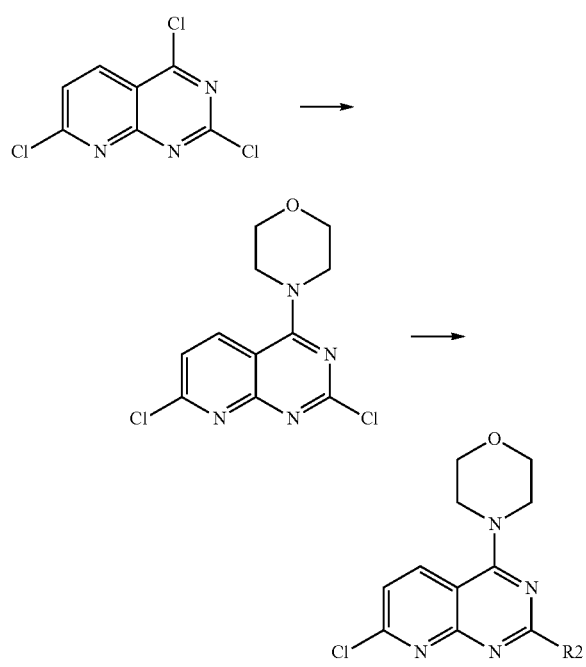

Using the method of Example 1, to a cooled (0-5° C.) stirred solution (0.1 M) of the appropriate trichloro substrate (1 equiv) in CH$_2$Cl$_2$ was added diisopropylethylamine (1 equiv) in a dropwise fashion. The appropriate amine (1 equiv) was then added to the reaction mixture portionwise over the period of 1 hour. The solution was maintained at room temperature with stirring for a further 1 hour before the mixture was washed with water (2×1 reaction volume). The aqueous extracts were combined and extracted with CH$_2$Cl$_2$ (2×1 reaction volume). The organic extracts were then combined, dried (sodium sulphate), filtered and concentrated in vacuo to give an oily residue which solidified upon prolonged drying. The solid was triturated with diethylether and then filtered and the cake washed with cold diethyl ether to leave the title compound in a suitably clean form to be used without any further purification.

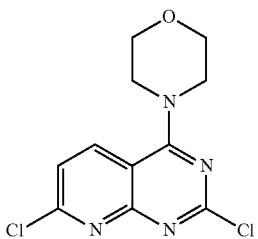 [SMILES: Clc1ccc2c(N3CCOCC3)nc(Cl)nc2n1]

2,7-Dichloro-4-morpholin-4-yl-pyrido[2,3-d]pyrimidine—R1=morpholine: (92% yield, 90% purity) m/z (LC-MS, ESP): 285 [M+H]⁺ R/T=3.90 min

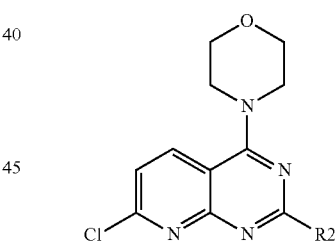

To a solution (0.2 M) of the appropriate dichloro-substrate (1 equiv) in anhydrous dimethyl acetamide under an inert atmosphere was added diisopropylethylamine (1 equiv) followed by the appropriate amine (1 equiv). The resulting mixture was heated for 48 hours at 70° C. before being cooled to ambient temperature. The reaction was diluted with CH$_2$Cl$_2$ (1 reaction volume) and then washed with water (3×1 reaction volumes). The organic extract was concentrated in vacuo to give a syrup which was dissolved in EtOAC (1 reaction volume) and washed with saturated brine solution before being dried, filtered (sodium sulphate) and concentrated in vacuo to give an oil. The crude residue was purified by flash chromatography (SiO$_2$, eluted with EtOAc:Hex (7:3) going to (1:1)) to give the title compound as a yellow solid that was suitably clean to be used without any further purification.

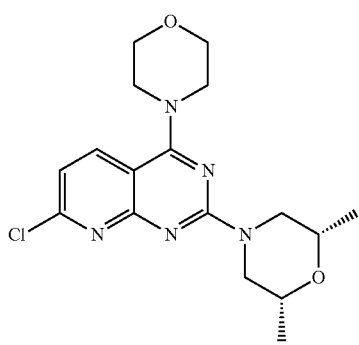 [SMILES: C[C@@H]1CN(c2nc(N3CCOCC3)c3ccc(Cl)nc3n2)C[C@H](C)O1]

7-Chloro-2-((2S,6R)-2,6-dimethyl-morpholin-4-yl)-4-morpholin-4-yl-pyrido[2,3-d]pyrimidine—R1=morpholine, R2=cis-dimethylmorpholine: (42% yield, 100% purity) m/z (LC-MS, ESP): 364 [M+H]$^+$ R/T=2.96 min

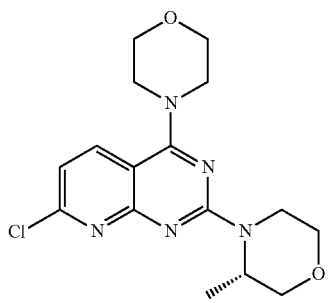 [SMILES: C[C@H]1COCCN1c1nc(N2CCOCC2)c2ccc(Cl)nc2n1]

7-Chloro-2-((S)-3-methyl-morpholin-4-yl)-4-morpholin-4-yl-pyrido[2,3-d]pyrimidine R1=morpholine, R2=(S)-3-Methyl-morpholine: (70% yield, 97% purity) m/z (LC-MS, ESP): 350 [M+H]$^+$ R/T=3.44 min

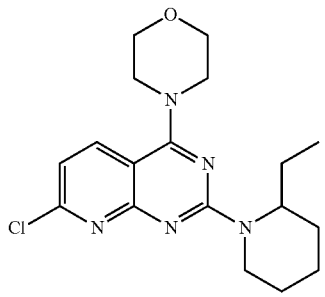 [SMILES: CCC1CCCCN1c1nc(N2CCOCC2)c2ccc(Cl)nc2n1]

7-Chloro-2-(2-ethyl-piperidin-1-yl)-4-morpholin-4-yl-pyrido[2,3-d]pyrimidine R1=morpholine, R2=2-Ethyl-piperidine: (56% yield, 95% purity) m/z (LC-MS, ESP): 362 [M+H]$^+$ R/T=3.78 min Comparative Examples 1a, 1b, 1c, 1j, and 1k R$^4$=morpholine
R$^2$=(S)-3-methyl-morpholine or cis-dimethylmorpholine or 2-Ethyl-piperidine
R$^7$=aryl or heteroaryl

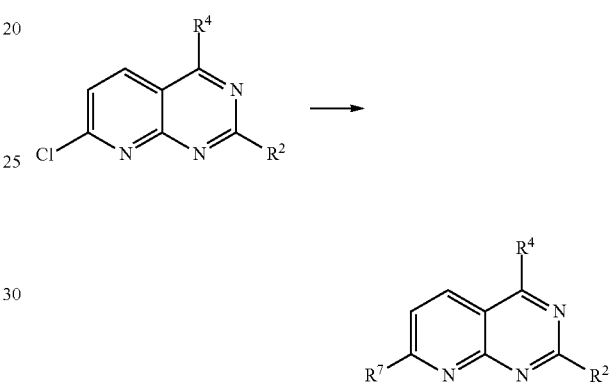

The appropriate chloro-substrate (1 equiv) was dissolved in a toluene/ethanol (1:1) solution (0.02 M). Sodium carbonate (2 equiv) and the appropriate pinacolate boron ester or boronic acid (1 equiv) were then added followed by tetrakis(triphenylphosphine)palladium$^0$ (0.1 equiv). The reaction vessel was sealed and the mixture exposed to microwave radiation (140° C., medium absorption setting) for 30 minutes. Upon completion the samples were filtered through a silica cartridge, washed with EtOAc and then concentrated in vacuo. The crude residue was then purified by preparative HPLC to give the desired comparative examples.

The following Comparative Examples were prepared

| | Purity (%) | Retention time (min) | m/z [M + H]$^+$ | Comparative Example Structure |
|---|---|---|---|---|
| 1a | 99 | 4.13 | 452.3 | |

-continued

| | Purity (%) | Retention time (min) | m/z [M + H]+ | Comparative Example Structure |
|---|---|---|---|---|
| 1b | 95 | 3.95 | 452.3 | |
| 1c | 99 | 9.01 | 464.4 | |
| 1j | 88 | 8.57 | 406.5 | |
| 1k | 93 | 8.12 | 412.3 | |

Example 22

Biological Assay

For mTOR enzyme activity assays, mTOR protein was isolated from HeLa cell cytoplasmic extract by immunoprecipitation, and activity determined essentially as described previously using recombinant PHAS-1 as a substrate (ref. 21).

Examples 1a-1l, 1ak, 1al, 1ap, 1at, 1az, 3l, 4a, 4c, 4d, 4f, 4i, 4w, 4x, 5q were tested and exhibited $IC_{50}$ values against mTOR of less than 200 nM. For example 5q was measured to have an IC50 of 46 nm.

The comparative Examples were also tested and when compared to the corresponding Examples, the exhibited $IC_{50}$ values for the Comparative Examples were higher than those of the corresponding Examples (ie IC50 Comparative Example 1a>IC50 Example 1a). For example Example 1k was measured to have an IC50 of 5 nm whereas Comparative Example 1k was measured to have an IC50 of 33 nm. Therefore, compounds of the present invention are more active in the mTOR assay.

Example 23

Alternative Enzyme Assay

The assay used AlphaScreen technology (Gray et al., Analytical Biochemistry, 2003, 313: 234-245) to determine the ability of test compounds to inhibit phosphorylation by recombinant mTOR.

A C-terminal truncation of mTOR encompassing amino acid residues 1362 to 2549 of mTOR (EMBL Accession No. L34075) was stably expressed as a FLAG-tagged fusion in HEK293 cells as described by Vilella-Bach et al., Journal of Biochemistry, 1999, 274, 4266-4272. The HEK293 FLAG-tagged mTOR (1362-2549) stable cell line was routinely maintained at 37° C. with 5% $CO_2$ up to a confluency of 70-90% in Dulbecco's modified Eagle's growth medium (DMEM; Invitrogen Limited, Paisley, UK Catalogue No. 41966-029) containing 10% heat-inactivated foetal calf serum (FCS; Sigma, Poole, Dorset, UK, Catalogue No. F0392), 1% L-glutamine (Gibco, Catalogue No. 25030-024) and 2 mg/ml Geneticin (G418 sulphate; Invitrogen Limited, UK Catalogue No. 10131-027). Following expression in the mammalian HEK293 cell line, expressed protein was purified using the FLAG epitope tag using standard purification techniques.

Test compounds were prepared as 10 mM stock solutions in DMSO and diluted into water as required to give a range of final assay concentrations. Aliquots (2 µl) of each compound dilution were placed into a well of a Greiner 384-well low volume (LV) white polystyrene plate (Greiner Bio-one). A 10 µl mixture of recombinant purified mTOR enzyme, 1 µM biotinylated peptide substrate (Biotin-Ahx-Lys-Lys-Ala-Asn-Gln-Val-Phe-Leu-Gly-Phe-Thr-Tyr-Val-Ala-Pro-Ser-Val-Leu-Glu-Ser-Val-Lys-Glu-$NH_2$; Bachem UK Ltd), ATP (20 µM) in a buffer solution [comprising Tris-HCl pH 7.4 buffer (50 mM), EGTA (0.1 mM), bovine serum albumin (0.5 mg/ml), DTT (1.25 mM) and manganese chloride (10 mM)] were added to the assay plates and incubated with compound for 2 hours at room temperature.

Each reaction was stopped by the addition of 5 µl of a mixture of EDTA (50 mM), bovine serum albumin (BSA; 0.5 mg/ml) and Tris-HCl pH 7.4 buffer (50 mM) containing p70 S6 Kinase (T389) 1A5 Monoclonal Antibody (Cell Signalling Technology, Catalogue No. 9206B) and AlphaScreen Streptavidin donor and Protein A acceptor beads (200 ng/well Perkin Elmer, Catalogue No. 6760002B and 6760137R respectively). Assay plates were left for approx 16 hours at room temperature before measurement. The resultant signals arising from laser light excitation at 680 nm were measured using a Packard Envision instrument. Phosphorylated biotinylated peptide is formed in situ as a result of mTOR mediated phosphorylation. The phosphorylated biotinylated peptide that is associated with AlphaScreen Streptavidin donor beads forms a complex with the p70 S6 Kinase (T389) 1A5 Monoclonal Antibody that is associated with Alphascreen Protein A acceptor beads. Upon laser light excitation at 680 nm, the donor bead:acceptor bead complex produces a signal that can be measured. Accordingly, the presence of mTOR kinase activity results in an assay signal. In the presence of an mTOR kinase inhibitor, signal strength is reduced.

Control wells that produced a maximum signal corresponding to maximum enzyme activity were created by using 5% DMSO instead of test compound. Control wells that produced a minimum signal corresponding to fully inhibited enzyme were created by adding EDTA (83 mM) instead of test compound.

mTOR enzyme inhibition for a given test compound was expressed as an $IC_{50}$ value.

The compounds tested in this assay exhibited $IC_{50}$ values against mTOR of less than 40 µm.

The following compounds exhibited $IC_{50}$ values against mTOR of less than 1 µm: 1bp, 1ca, 1cb, 1cd, 12e, 18df, 1m, 1q, 1r, 17, 19 h, 19m, 18n, 18o, 18ak, 18al, 18at, 1t, 18bb, 18be, 18bi, 18bl, 1x, 1y, 1ba, 1z, 20b, 1ae, 7a, 7 h, 18ce, 5f, 4af, 4ag, 4aj, 5y, 3b, 5j, 5k, 5p, 3w, 3y, 3z, 11a, 18da, 3m, 3o, 3p, 3r, 3s, 1aj, 5r, 5s, 1cn, 2a, 2b, 1cq, 1cr, 2d, 3ad, 2 h, 1cw and 1dd, with the following compounds exhibiting $IC_{50}$ values against mTOR of less than 300 nM: 1c, 1bq, 1bt, 1ch, 1ci, 4ap, 4at, 4aw, 4ax, 4ay, 4bd, 12b, 18de, 18dh, 18di, 18dg, 21a, 1o, 18b, 18d, 18 h, 19d, 19e, 19i, 19l, 19n, 19o, 18p, 18q, 18r, 18w, 18af, 18ag, 18an, 18aq, 18au, 18av, 1v, 18ay, 18ba, 18bd, 1bg, 1w, 1ac, 4p, 9a, 1bb, 1av, 7b, 7e, 7f, 7g, 7k, 7j, 5c, 5d, 5e, 5g, 4v, 4x, 4y, 4z, 4aa, 4ae, 4ah, 4ai, 5u, 5v, 5w, 5x, 3d, 3f, 18bv, 18cb, 3 h, 5 h, 5i, 5l, 5o, 3i, 3j, 3v, 3x, 3u, 3ab, 1al, 1am, 1an, 1be, 18cy, 18dc, 13a, 19p, 19q, 3k, 3n, 3q, 13f, 13b, 4g, 1au, 5q, 1ay, 18dj, 13c, 13e, 10a, 1cl, 2c, 2e, 1cs, 2i, 8d, 13g and 1cu, with the following compounds exhibiting $IC_{50}$ values against mTOR of less than 100 nM: 1b, 1a, 1d, 1bl, 1bm, 1bn, 1f, 1bo, 1i, 1g, 1h, 1br, 1bs, 1bu, 1bv, 1e, 1j, 1bw, 1bx, 1by, 1bz, 1ce, 1ce, 1k, 1cf, 1cg, 1l, 1cj, 4al, 4am, 4an, 4ao, 4aq, 4ar, 4as, 4au, 4av, 4az, 4ba, 4bb, 4bc, 4be, 4bf, 12c, 12d, 12a, 18a, 6a, 1as, 1ax, 1n, 1p, 1s, 1ck, 18c, 18e, 18f, 18g, 18i, 18j, 18k, 1ar, 19a, 19b, 19c, 19f, 19g, 19j, 19k, 18l, 18m, 1bd, 1aq, 18s, 18t, 18u, 18v, 18x, 18y, 18z, 18aa, 18ab, 18ac, 18ad, 18ae, 18ah, 18ai, 18aj, 18am, 18ao, 18ap, 18ar, 18as, 18aw, 18ax, 18az, 18bc, 18bf, 18bg, 18bk, 18bh, 18bj, 15a, 18bm, 8b, 4 h, 14a, 8a, 1aa, 1ab, 1ad, 1af, 1ag, 14b, 1bc, 4i, 1ah, 4j, 4l, 4m, 4n, 4o, 18bn, 18bo, 4u, 1bh, 16a, 1at, 7c, 7d, 7i, 3a, 3c, 5a, 5b, 4w, 4ac, 4ad, 5t, 3e, 3g, 18 bp, 18bq, 18br, 18bs, 18bt, 18bu, 18bw, 18by, 18bz, 18ca, 18cc, 18cd, 18cf, 18cg, 18ch, 18ci, 18cj, 18ck, 18cl, 4ak, 18bx, 18cm, 18cv, 1bi, 1bj, 4a, 1aw, 3t, 3aa, 1ap, 1bf, 18cn, 18co, 18cp, 18cs, 18ct, 18cu, 18cw, 18cx, 18cz, 18cq, 19r, 19t, 3l, 19u, 19v, 19w, 20c, 1u, 4b, 4q, 4t, 4c, 4e, 4f, 18dd, 4d, 1az, 4r, 4s, 2f, 2g, 2j and 1cyv. For example, Compound 4aa has an $IC_{50}$ of 151 nM.

The Comparative Examples were also tested and when compared to the corresponding Examples, the exhibited $IC_{50}$ values for the Comparative Examples were higher than those of the corresponding Examples. For example Example 1k was measured to have an IC50 of 15 nm whereas Comparative Example 1k was measured to have an IC50 of 225 nm. Therefore, compounds of the present invention are more active in reducing cell growth.

Example 24

Cell Proliferation Assay ($GI_{50}$)

Cell growth was assessed using the sulforhodamine B (SRB) assay (A). T47D (ECACC, 85102201) cells were routinely passaged in RPMI (Invitrogen, 42401018) plus 10% foetal calf serum (FCS), 1% L-glutamine (Gibco BRL, 25030) to a confluence not greater than 80%. To undertake the assay, T47D cells were seeded at $2.5 \times 10^3$ cells/well in 90 µl RPMI plus 10% foetal calf serum, 1% L-glutamine in 96 well plates (Costar, 3904) and incubated at 37° C. (+5% $CO_2$) in a humidified incubator. Once the cells had fully adhered (typically following 4-5 hours incubation) the plate was removed from the incubator and 10 μL of the diluent added to the control wells (A1-12 and B1-12). Compound was prepared in a six point semi-log dilution at 10× the final concentration required e.g. for a 6 point range of 30 μM to 100 nM in semi-log steps dilution started at 300 μM in stock plate. Dosing was completed by addition of 10 μL of compound at highest concentration to C1-12 through to the lowest concentration in H1-12. The plates were then incubated for 120 hours prior to SRB analysis.

Upon completion of incubation, media was removed and the cells fixed with 100 μl of ice cold 10% (w/v) trichloro-acetic acid. The plates were incubated at 4° C. for 20 minutes and then washed four times with water. Each well of cells was then stained with 100 μl of 0.4% (w/v) SRB (Sulforhodamine B, Sigma, Poole, Dorset, UK, Catalogue number S-9012) in 1% acetic acid for 20 minutes before washing four times with 1% acetic acid. Plates were then dried for 2 hours at room temperature. The dye from the stained cells was solubilized by the addition of 100 μl of 10 mM Tris Base into each well. Plates were gently shaken and left at room temperature for 30 minutes before measuring the optical density at 564 nM on a Microquant microtiter plate reader. The concentration of inhibitor eliciting a 50% reduction in growth ($GI_{50}$) was determined by analysis of staining intensity of the treated cells as a percentage of the vehicle control wells using Excelfit software.

(A) Skehan, P., Storung, R., Scudiero, R., Monks, A., McMahon, J., Vistica, D., Warren, J. T., Bokesch, H., Kenny, S. and Boyd, M. R. (1990) New colorimetric cytotoxicity assay for anticancer-drug screening. J. Natl. Cancer Inst. 82, 1107-1112.

Examples 1a-11 were tested and exhibited $GI_{50}$ values of less than 300 nM.

The Comparative Examples were also tested and when compared to the corresponding Examples, the exhibited $GI_{50}$ values for the Comparative Examples were higher than those of the corresponding Examples (ie $GI_{50}$ Comparative Example 1a>$GI_{50}$ Example 1a). For example Example 1k was measured to have an GI50 of 32 nm whereas Comparative Example 1k was measured to have an GI50 of 268 nm. Therefore, compounds of the present invention are more active in reducing cell growth.

Example 25

In Vitro Phospho-Ser473 Akt Assay

This assay determines the ability of test compounds to inhibit phosphorylation of Serine 473 in Akt as assessed using Acumen Explorer technology (Acumen Bioscience Limited), a plate reader that can be used to rapidly quantitate features of images generated by laser-scanning.

A MDA-MB-468 human breast adenocarcinoma cell line (LGC Promochem, Teddington, Middlesex, UK, Catalogue No. HTB-132) was routinely maintained at 37° C. with 5% $CO_2$ up to a confluency of 70-90% in DMEM containing 10% heat-inactivated FCS and 1% L-glutamine.

For the assay, the cells were detached from the culture flask using 'Accutase' (Innovative Cell Technologies Inc., San Diego, Calif., USA; Catalogue No. AT 104) using standard tissue culture methods and resuspended in media to give $1.7 \times 10^5$ cells per ml. Aliquots (90 μl) were seeded into each of the inner 60 wells of a black Packard 96 well plate (PerkinElmer, Boston, Mass., USA; Catalogue No. 6005182) to give a density of ~15000 cells per well. Aliquots (90 μl) of culture media were placed in the outer wells to prevent edge effects. The cells were incubated overnight at 37° C. with 5% $CO_2$ to allow them to adhere.

On day 2, the cells were treated with test compounds and incubated for 2 hours at 37° C. with 5% $CO_2$. Test compounds were prepared as 10 mM stock solutions in DMSO and serially diluted as required with growth media to give a range of concentrations that were 10-fold the required final test concentrations. Aliquots (10 μl) of each compound dilution were placed in a well (in triplicate) to give the final required concentrations. As a minimum response control, each plate contained wells having a final concentration of 100 μM LY294002 (Calbiochem, Beeston, UK, Catalogue No. 440202). As a maximum response control, wells contained 1% DMSO instead of test compound. Following incubation, the contents of the plates were fixed by treatment with a 1.6% aqueous formaldehyde solution (Sigma, Poole, Dorset, UK, Catalogue No. F1635) at room temperature for 1 hour.

All subsequent aspiration and wash steps were carried out using a Tecan 96 well plate washer (aspiration speed 10 mm/sec). The fixing solution was removed and the contents of the plates were washed with phosphate-buffered saline (PBS; 50 μl; Gibco, Catalogue No. 10010015). The contents of the plates were treated for 10 minutes at room temperature with an aliquot (50 μl) of a cell permeabilisation buffer consisting of a mixture of PBS and 0.5% Tween-20. The 'permeabilisation' buffer was removed and non-specific binding sites were blocked by treatment for 1 hour at room temperature of an aliquot (50 μl) of a blocking buffer consisting of 5% dried skimmed milk ['Marvel' (registered trade mark); Premier Beverages, Stafford, GB] in a mixture of PBS and 0.05% Tween-20. The 'blocking' buffer was removed and the cells were incubated for 1 hour at room temperature with rabbit anti phospho-Akt (Ser473) antibody solution (50 μl per well; Cell Signalling, Hitchin, Herts, U.K., Catalogue No 9277) that had been diluted 1:500 in 'blocking' buffer. Cells were washed three times in a mixture of PBS and 0.05% Tween-20. Subsequently, cells were incubated for 1 hour at room temperature with Alexafluor488 labelled goat anti-rabbit IgG (50 μl per well; Molecular Probes, Invitrogen Limited, Paisley, UK, Catalogue No. A11008) that had been diluted 1:500 in 'blocking' buffer. Cells were washed 3 times with a mixture of PBS and 0.05% Tween-20. An aliquot of PBS (50 μl) was added to each well and the plates were sealed with black plate sealers and the fluorescence signal was detected and analysed.

Fluorescence dose response data obtained with each compound were analysed and the degree of inhibition of Serine 473 in Akt was expressed as an $IC_{50}$ value.

The compounds tested in this assay exhibited $IC_{50}$ values against mTOR of less than 10 μm.

The following compounds exhibited $IC_{50}$ values against mTOR of less than 1 μm: 1bu, 1ce, 12b, 18de, 18dg, 18j, 1ar, 19e, 19 h, 19i, 19l, 19m, 19n, 19o, 18n, 18o, 18z, 18aa, 18ag, 18ai, 18al, 1v, 18az, 1ah, 7e, 7i, 7j, 5d, 5f, 4v, 4ab, 4aj, 5t, 5u, 5w, 5x, 5y, 5z, 3f, 3g, 18 bp, 18bs, 18bv, 18by, 18cb, 18cv, 1aw, 3u, 1bf, 18ct, 19q, 19s, 19u, 19v, 19w, 1au, 5r, 4t, 18dj, 1cl, 2d, 2e, 1cs, 2 h, 2j and 1cw, with the following compounds exhibiting $IC_{50}$ values against mTOR of less than 300 nM: 1bo, 1bp, 1j, 1bx, 1by, 1cf, 1ci, 1cj, 4an, 4ap, 4av, 12d, 18dh, 18di, 6a, 1n, 1p, 1q, 18e, 18 h, 19b, 19c, 19f, 19k, 18p, 1bd, 18w, 18ab, 18af, 18aj, 18aq, 18as, 18av, 18ay, 18bb, 18bc, 18bf, 18bl, 1ab, 4p, 9a, 1av, 3a, 5b, 5c, 5e, 5g, 4aa, 4ad, 4ah, 5v, 3e, 18bq, 18bt, 18bz, 18ca, 18cd, 18cg, 18ci, 18bx, 5n, 1am, 1ao, 18cn, 18cx, 1bk, 13b, 4g, 5s, 4q, 18dd, 1cp, 1cq, 2f, 2g, 13g, 1cyv and 1ct, with the following compounds exhibiting IC$_{50}$ values against mTOR of less than 100 nM: 1b, 1a, 1c, 1d, 1bl, 1bm, 1f, 1i, 1g, 1h, 1br, 1bs, 1bv, 1e, 1bz, 1ce, 1k, 1cg, 11, 4al, 4am, 4ao, 4aq, 4as, 4at, 4au, 4aw, 4ax, 4ay, 4az, 4ba, 4bb, 4bc, 4bd, 4be, 4bf, 12c, 12a, 18a, 1as, 1s, 18c, 18d, 18f, 18g, 18i, 18k, 19j, 18m, 18q, 18r, 18s, 18t, 18u, 18v, 18x, 18y, 18ac, 18ad, 18ae, 18ah, 18ak, 18am, 18an, 18ap, 18ar, 18au, 18aw, 18ax, 18ba, 18bd, 18be, 18bg, 18bi, 18bk, 18bh, 18bj, 18bm, 1bg, 8b, 4 h, 1ba, 8a, 1aa, 1ac, 1ae, 1af, 1ag, 14b, 1bc, 4i, 4j, 4k, 4l, 4m, 4n, 4o, 18bn, 18bo, 4u, 1bb, 1at, 7b, 7c, 7d, 7f, 7g, 7k, 5a, 4w, 4x, 4y, 4z, 4ac, 4af, 4ai, 18br, 18bw, 18cc, 18cf, 18ch, 18cj, 18ck, 18cl, 4ak, 18cm, 4a, 3i, 3y, 1ak, 1al, 1ap, 1be, 18co, 18cr, 18cs, 18db, 19p, 3l, 1u, 4b, 5q, 4c, 4e, 4f, 4d, 1az, 4r, 4s, 1cn, 1co and 3ad. For example, Compound 18di has an IC$_{50}$ of 151 nM The Comparative Examples were also tested and when compared to the corresponding Examples, the exhibited IC$_{50}$ values for the Comparative Examples were higher than those of the corresponding Examples. For example Example 1k was measured to have an IC50 of 83 nm whereas Comparative Example 1k was measured to have an IC50 of 412 nm. Therefore, compounds of the present invention are more active in reducing cell growth.

REFERENCE LIST

The following documents are all herein incorporated by reference.
1) Brown, et al., *Nature*, 369, 756-758 (1994)
2) Chiu, et al., *Proc Natl Acad Sci*, 91, 12574-12578 (1994)
3) Sabatini, et al., *Cell*, 78, 35-43, (1994)
4) Sabers, et al., *J Biol Chem*, 270, 825-822 (1995)
5) Abraham, *Curr Opin Immunol*, 8, 412-418 (1996)
6) Schmelze and Hall, *Cell*, 103, 253-262 (2000)
7) Burnett, et al., *Proc Natl Acad Sci*, 95, 1432-1437 (1998)
8) Terada, et al., *Proc Natl Acad Sci*, 91, 11477-11481 (1994)
9) Jeffries, et al., *EMBO J*, 16, 3693-3704 (1997)
10) Bjornsti and Houghton, *Nat Rev Cancer*, 4, 335-348 (2004)
11) Gingras, et al., *Genes Dev*, 13, 1422-1437 (1999)
12) Gingras, et al., *Genes Dev*, 15, 807-826 (2001)
13) Neuhaus, et al., *Liver Transplantation*, 7, 473-484 (2001)
14) Woods and Marks, *Ann Rev Med*, 55, 169-178 (2004)
15) Dahia, *Endocrine-Related Cancer*, 7, 115-129 (2000)
16) Cristofano and Pandolfi, *Cell*, 100, 387-390 (2000)
17) Samuels, et al., *Science*, 304, 554 (2004)
18) Huang and Houghton, *Curr Opin Pharmacol*, 3, 371-377 (2003)
19) Sawyers, *Cancer Cell*, 4, 343-348 (2003)
20) Huang and Houghton, *Curr Opin in Invest Drugs*, 3, 295-304 (2002)
21) Brunn, et al., *EMBO J*, 15, 5256-5267 (1996)
22) Edinger, et al., *Cancer Res*, 63, 8451-8460, (2003)
23) Lawrence, et al., *Curr Top Microbiol Immunol*, 279, 199-213 (2004)
24) Eshleman, et al., *Cancer Res*, 62, 7291-7297 (2002)
25) Berge, et al., *J. Pharm. Sci.*, 66, 1-19 (1977).
26) Green, T. and Wuts, P., "Protective Groups in Organic Synthesis", 3rd Edition, John Wiley and Sons (1999).
27) "Handbook of Pharmaceutical Additives", 2nd Edition (eds. M. Ash and I. Ash), 2001 (Synapse Information Resources, Inc., Endicott, N.Y., USA).
28) "Remington's Pharmaceutical Sciences", 20th edition, pub. Lippincott, Williams & Wilkins, 2000.
29) "Handbook of Pharmaceutical Excipients", 2nd edition, 1994.

The invention claimed is:

1. A pharmaceutical composition for treating cancer ameliorated by inhibition of mTOR in a warm blooded animal having said cancer comprising a therapeutically-effective amount of a compound of formula 1ap:

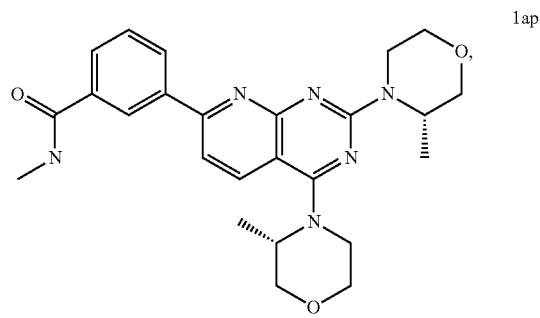 [SMILES: CNC(=O)c1cccc(-c2ccc3c(N4CCOC[C@@H]4C)nc(N4CCOC[C@@H]4C)nc3n2)c1]

1ap or a pharmaceutically acceptable salt thereof, in association with a pharmaceutically-acceptable diluent or carrier, in combination with a cytostatic agent selected from:
tamoxifen, fulvestrant, toremifene, raloxifene, droloxifene, iodoxyfene, bicalutamide, flutamide, nilutamide cyproterone acetate, goserelin, leuprorelin, buserelin, metestrol acetate, anastrozole, letrozole, vorazole, exemestane, and finasteride.

2. The pharmaceutical composition according to claim 1 wherein the cytostatic agent is fulvestrant.

3. A method of treating cancer ameliorated by inhibition of mTOR in a warm blooded animal having said cancer comprising administering to the animal an effective amount of a compound of formula 1ap:

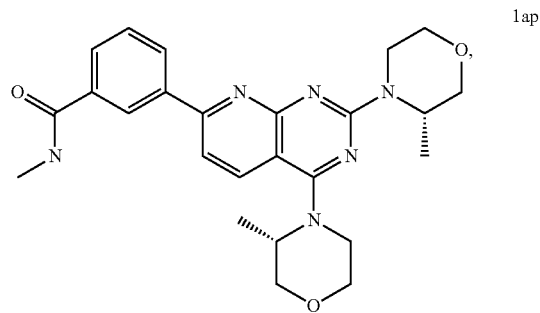 [SMILES: CNC(=O)c1cccc(-c2ccc3c(N4CCOC[C@@H]4C)nc(N4CCOC[C@@H]4C)nc3n2)c1]

1ap or a pharmaceutically acceptable salt thereof, in association with a pharmaceutically-acceptable diluent or carrier, in combination with a cytostatic agent selected from:
tamoxifen, fulvestrant, toremifene, raloxifene, droloxifene, iodoxyfene, bicalutamide, flutamide, nilutamide cyproterone acetate, goserelin, leuprorelin, buserelin, metestrol acetate, anastrozole, letrozole, vorazole, exemestane, and finasteride.

4. The method according to claim 3 wherein the cytostatic agent is fulvestrant.

* * * * *